(12) United States Patent
Hazuda et al.

(10) Patent No.: US 7,196,163 B2
(45) Date of Patent: Mar. 27, 2007

(54) ASSAYS USING AMYLOID PRECURSOR PROTEINS WITH MODIFIED β-SECRETASE CLEAVAGE SITES TO MONITOR β-SECRETASE ACTIVITY

(75) Inventors: Daria Jean Hazuda, Doylestown, PA (US); Elizabeth Chen Dodson, Souderton, PA (US); Ming-Tain Lai, Lansdale, PA (US); Min Xu, Ambler, PA (US); Xiao-Ping Shi, Warrington, PA (US); Adam J. Simon, Langhorne, PA (US); Guoxin Wu, Merion Station, PA (US); Yueming Li, New York, NY (US); Bruce Register, Berwyn, PA (US)

(73) Assignee: Merk & Co., Inc., Rahway, NJ (US)

( * ) Notice: Subject to any disclaimer, the term of this patent is extended or adjusted under 35 U.S.C. 154(b) by 304 days.

(21) Appl. No.: 10/427,208

(22) Filed: Apr. 30, 2003

(65) Prior Publication Data
US 2003/0200555 A1    Oct. 23, 2003

Related U.S. Application Data

(63) Continuation-in-part of application No. PCT/US02/15590, filed on May 17, 2002.

(60) Provisional application No. 60/316,115, filed on Aug. 30, 2001, provisional application No. 60/292,591, filed on May 22, 2001.

(51) Int. Cl.
*A61K 38/07* (2006.01)
*A61K 38/16* (2006.01)

(52) U.S. Cl. ............... 530/330; 530/350; 514/2; 514/18; 435/7.1; 424/94.63

(58) Field of Classification Search ............... 530/330; 514/18; 435/7.1
See application file for complete search history.

(56) References Cited

U.S. PATENT DOCUMENTS

| 4,666,829 | A | 5/1987 | Glenner et al. |
| 5,218,100 | A | 6/1993 | Muller-Hill et al. |
| 5,441,870 | A | 8/1995 | Seubert et al. |
| 5,593,846 | A | 1/1997 | Schenk et al. |
| 5,605,811 | A | 2/1997 | Seubert et al. |
| 6,203,979 | B1 * | 3/2001 | Bandman et al. ............ 435/6 |

FOREIGN PATENT DOCUMENTS

| EP | 0 276 723 B1 | 8/1988 |
| EP | 0 304 013 B1 | 6/1996 |
| WO | WO 00/23576 | 10/1999 |
| WO | WO 99/64587 | 12/1999 |
| WO | WO 01/00663 A2 | 6/2000 |
| WO | WO 01/31054 A1 | 10/2000 |
| WO | WO 01/42306 A2 | 12/2000 |
| WO | WO 02/06306 A2 | 7/2001 |

OTHER PUBLICATIONS

Glenner & Wong, 1984, Biochem. Biophys. Res. Comm. 120:885-890.
Ponte et al., 1988, NATURE 331:525-527.
Tanzi et al., 1988, NATURE 331:528-530.
Kitaguchi et al., 1988, NATURE 331:530-532.
Selkoe, 1998, Trends Cell Biol. 8:447-453.
Selkoe, 1994, Ann. Rev. Cell Biol. 10:373-403.
Esch et al., 1994, SCIENCE 248:1122-1124.
Masters et al., 1985, Proc. Natl. Acad. Sci. USA 82:4245-4249.
Mullan et al., 1992, Nature Genet. 1:345-347.
Citron et al., 1992, NATURE 360:672-674.
Citron et al., 1995, NEURON 14:661-670.
Sisodia, 1992, Proc. Natl. Acad. Sci. USA 89:6075-6079.
Citron, 2000, Molecular Medicine Today 6:392-397.
Esler et al., 1997, Nature Biotechnology 15:258-263.
Lin et al., 2000, Proc. Natl. Acad. Sci. USA 97:1456-1460.
Ghosh et al., 2000, J. Am. Chem. Soc. 122:3522-3523.
Genbank Accession No. Y00264.
Kang et al., 1987, NATURE 325:733-736.
Vassar et al., 1999, SCIENCE 286:735-741.
Hendriks et al., 1992, Nature Genet. 1:218-221.
Levy et al., 1990, SCIENCE 248:1124-1126.
Nilsberth et al., 2001, Nature Neuroscience 4:887-893.
Kumar-Singh et al., 2000, Hum. Mol. Genet. 9:2589-2598.
Ancolio et al., 1999, Proc. Natl. Acad.Sci. USA 96:4119-4124.
Eckman et al., 1997, Hum. Mol. Genet. 6:2087-2089.
Murrell et al., 1991, SCIENCE 254:97-99.
Chartier-Harlin et al., 1991, NATURE 353:844-846.
Goate et al., 1991, NATURE 349:704-706.
Kwok et al., 2000, American Neurol. 47:249-253.
Lichtenthaler et al., 1999, Proc. Natl. Acad.Sci. USA 96:3053-3058.
Karlstrom et al., Journal of Biological Chemistry, Mar. 1, 2002, 277(9):6763-66.
Brown, A.M. et al., "Evaluation of Cathepsins D and G and EC 3.4.24.15 As Candidate β-Secretase Proteases Using Peptide and Amyloid Precursor Protein Substrates", Journal of Neurochemistry, vol. 66, 6:2436-2445, 1996.

* cited by examiner

*Primary Examiner*—Michael Borin
(74) *Attorney, Agent, or Firm*—John E. Switzer; Joanne M. Giesser

(57) ABSTRACT

Provided are methods of identifying inhibitors of β-secretase that employ modified β-secretase substrates. The modified β-secretase substrates have β-secretase cleavage sites that are altered from wild type. The amino acid sequences of the altered β-secretase cleavage sites contain different amino acids in at least one of the positions P2-P1-P1'-P2' of the β-secretase cleavage site. Many of the modified β-secretase substrates are more efficient substrates for β-secretase than are corresponding substrates having wild-type sequences, that is, these modified substrates are more susceptible to enzymatic breakdown by β-secretase. Recombinant polynucleotide molecules encoding the modified β-secretase substrates are provided. Antibodies that recognize cleavage products of the modified β-secretase substrates are provided. Stable cell lines expressing the modified β-secretase substrates are provided. Transgenic animals expressing the modified β-secretase substrates are provided.

5 Claims, 10 Drawing Sheets

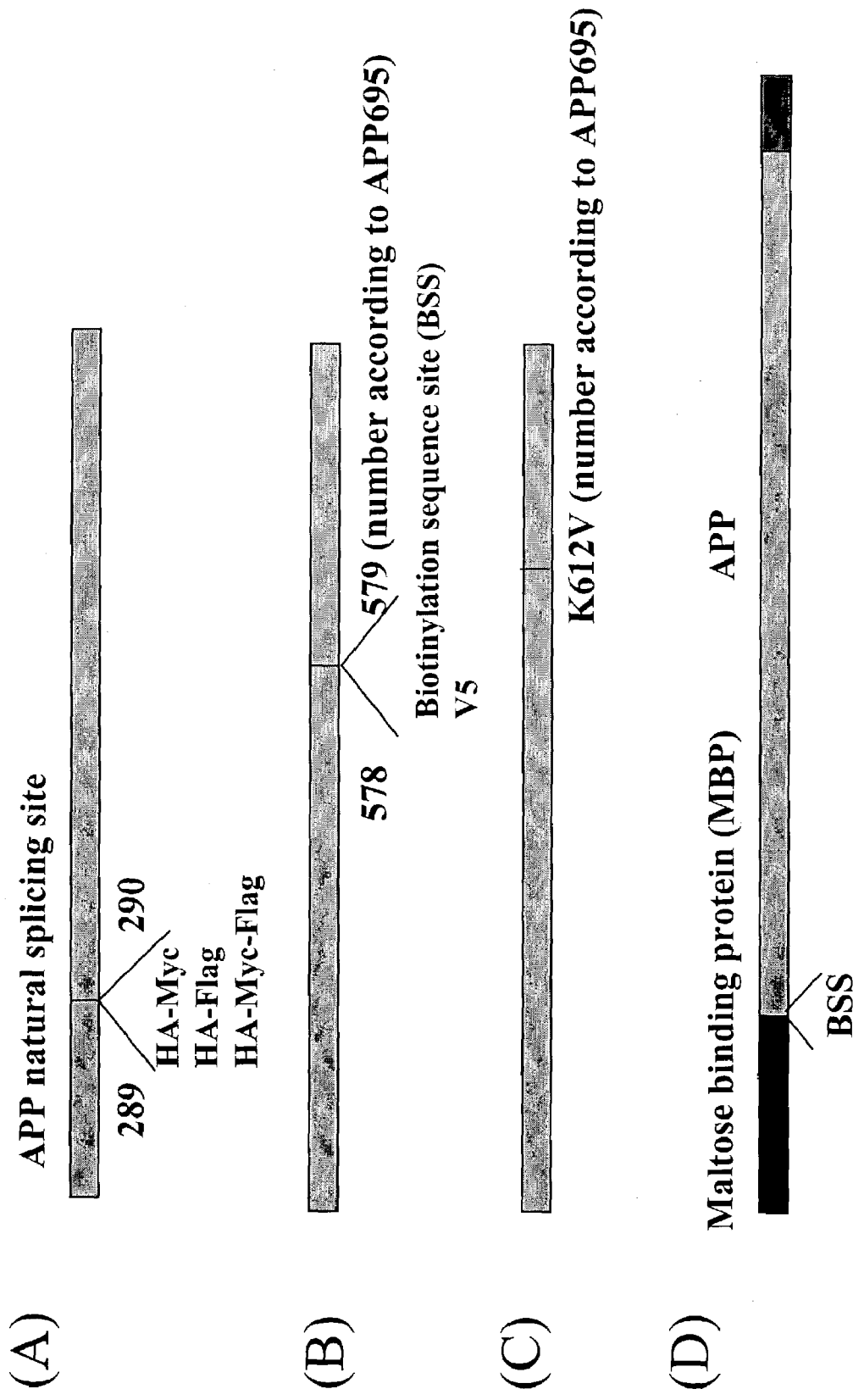
FIG.1: APP backbone constructs

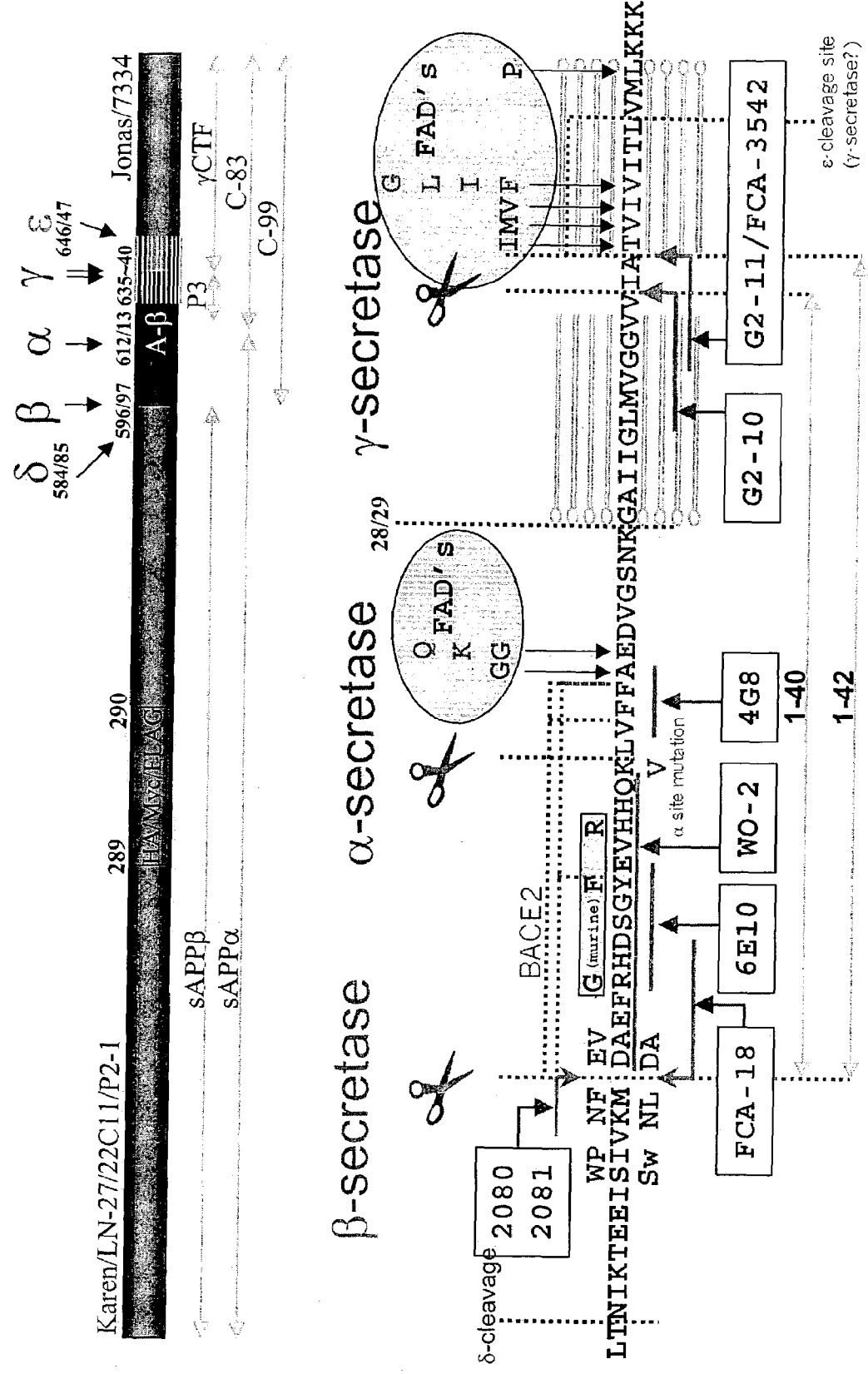
FIG. 2: Overview of APP-695: Antibodies, Cleavage Sites, and Modifications

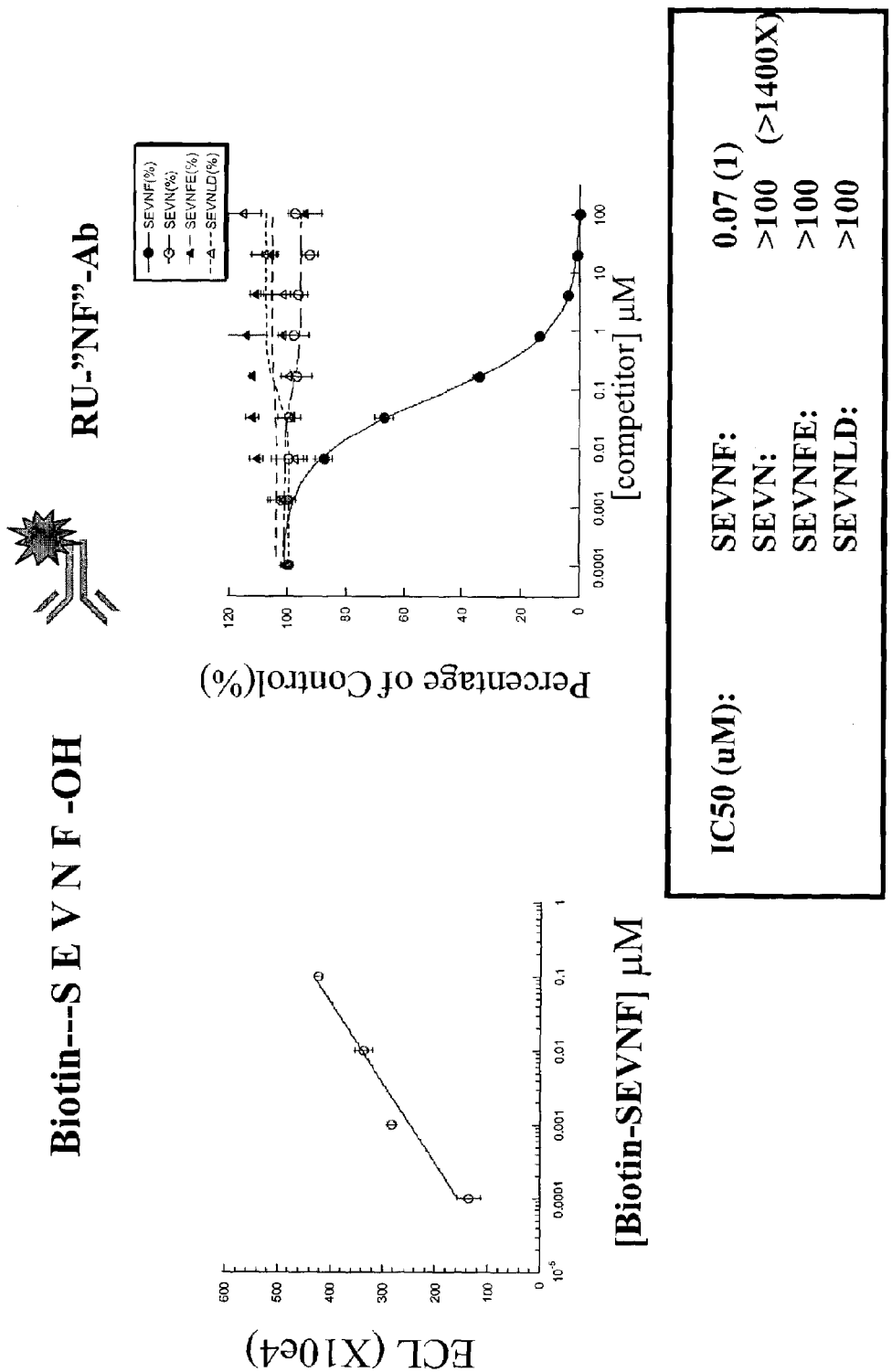
FIG. 3A: Generation and characterization of "NF"-antibodies that specifically recognize the cleaved sAPPβ C-terminus

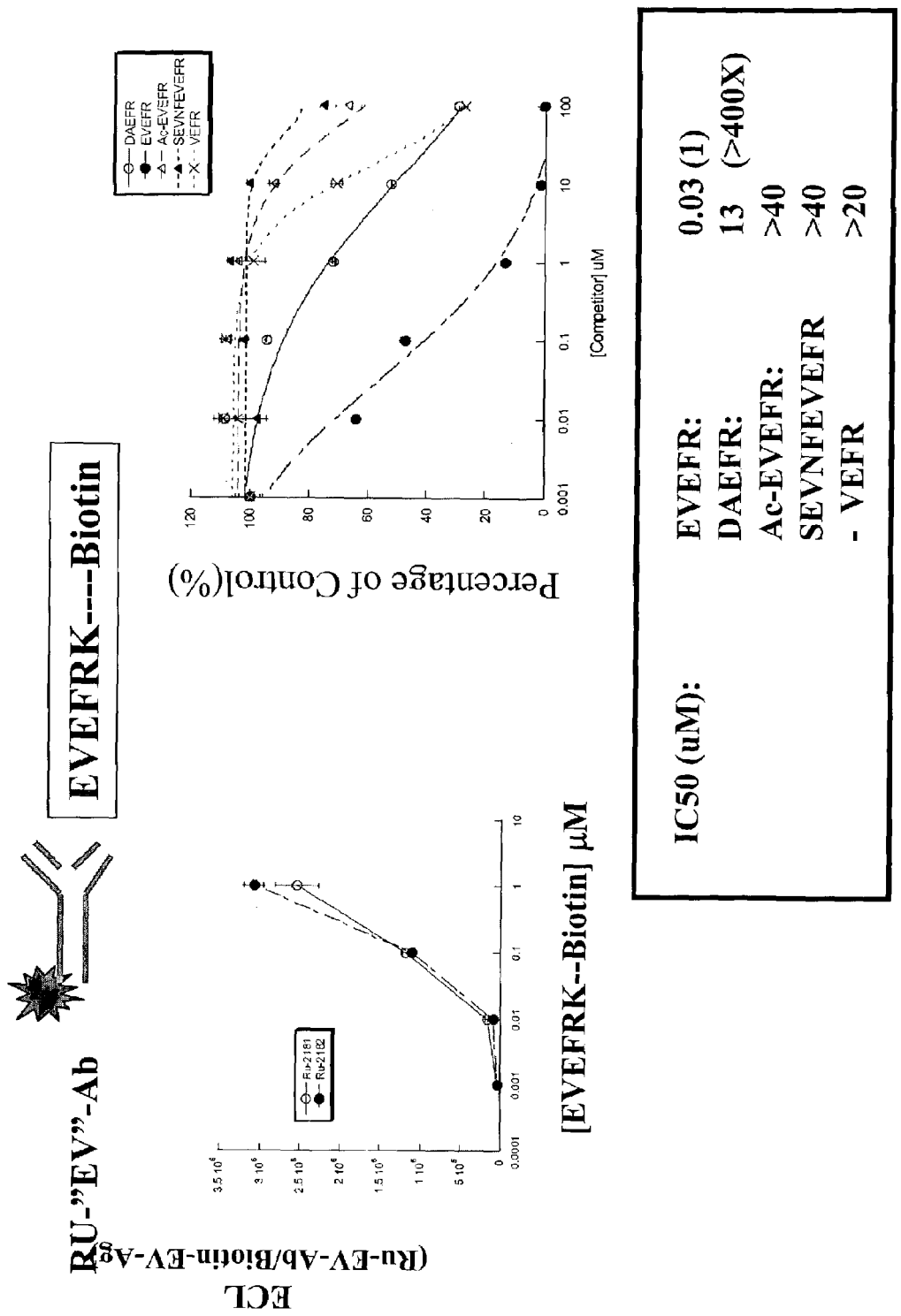
FIG. 3B: Generation and characterization of "EV"-antibodies that preferably recognize the cleaved modified "Aβ" N-terminus

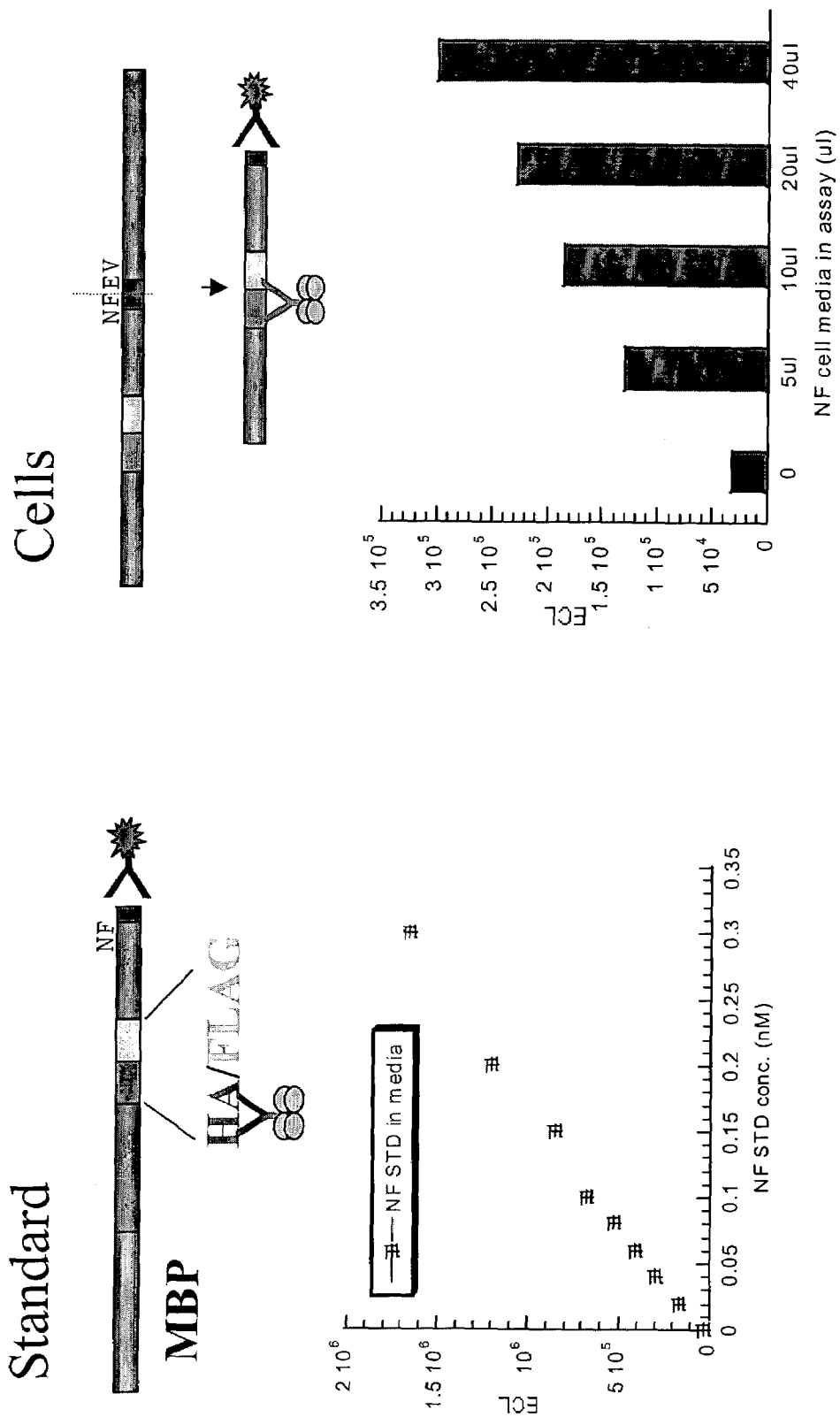
FIG. 4A: Assay of cellular BACE cleaved product in conditioned media by ECL using neo-epitope specific "NF"-antibodies

FIG. 4B: Assay of cellular BACE cleaved product in conditioned media by Western Blot, Alpha screen and ELISA using neo-epitope specific "NF"-antibodies
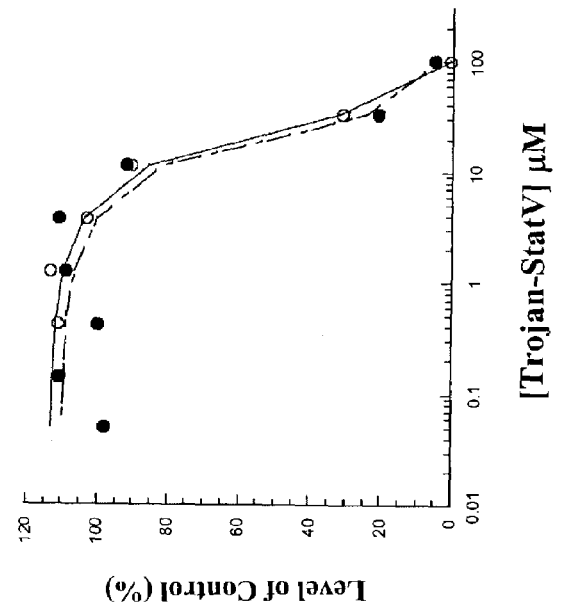
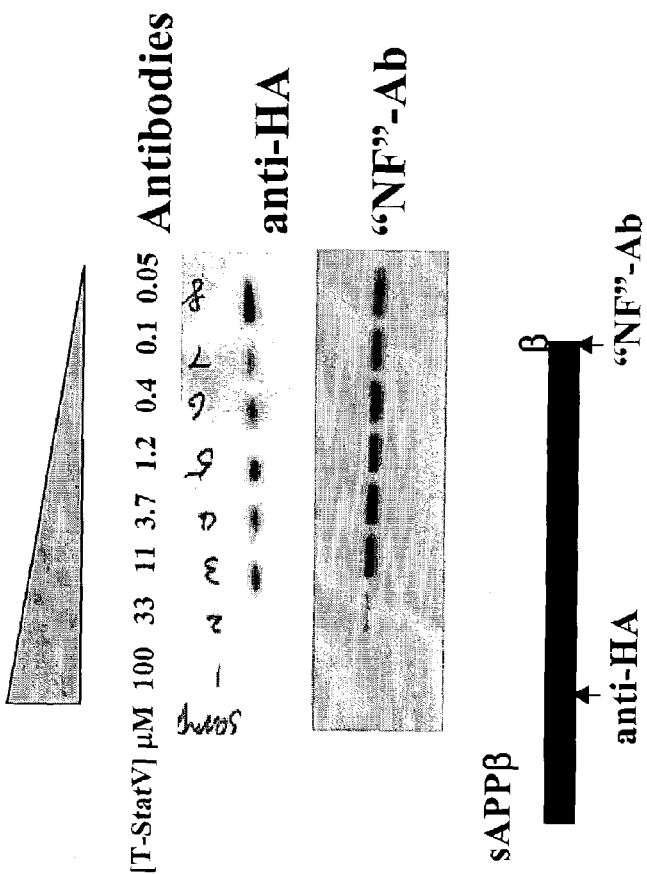

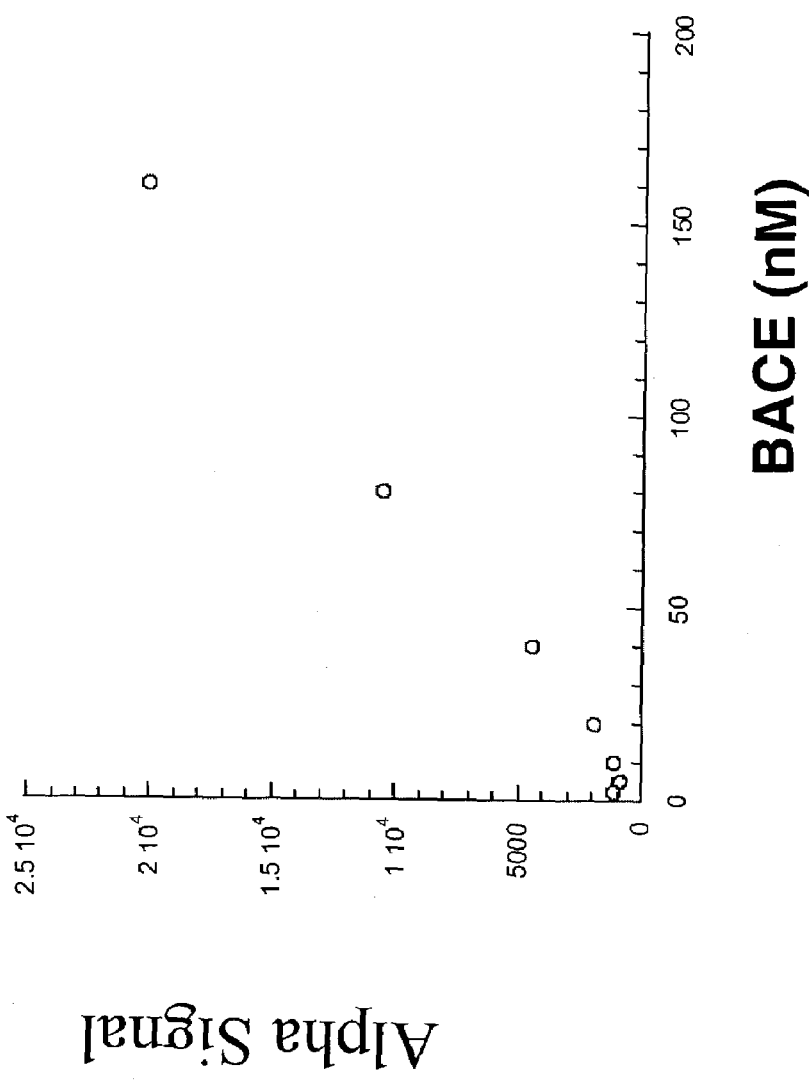
FIG. 5: Assay of in vitro BACE1 cleaved product using MBP-APP(NFEV) substrate by Alpha screen with neo-epitope specific "NF"-antibodies (Enzyme - dependence)

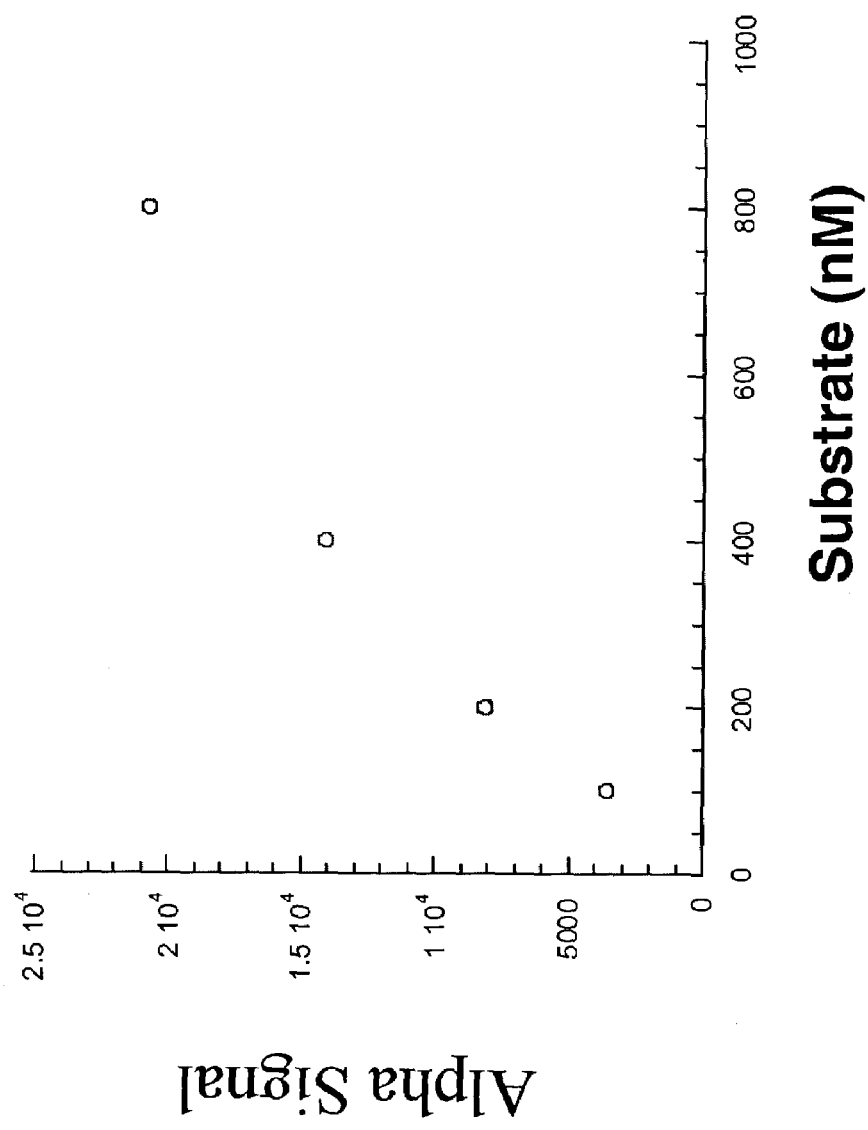
FIG. 6: Assay of in vitro BACE1 cleaved product using MBP-APP(NFEV) substrate by Alpha screen with neo-epitope specific "NF"-antibodies (Substrate - dependence)

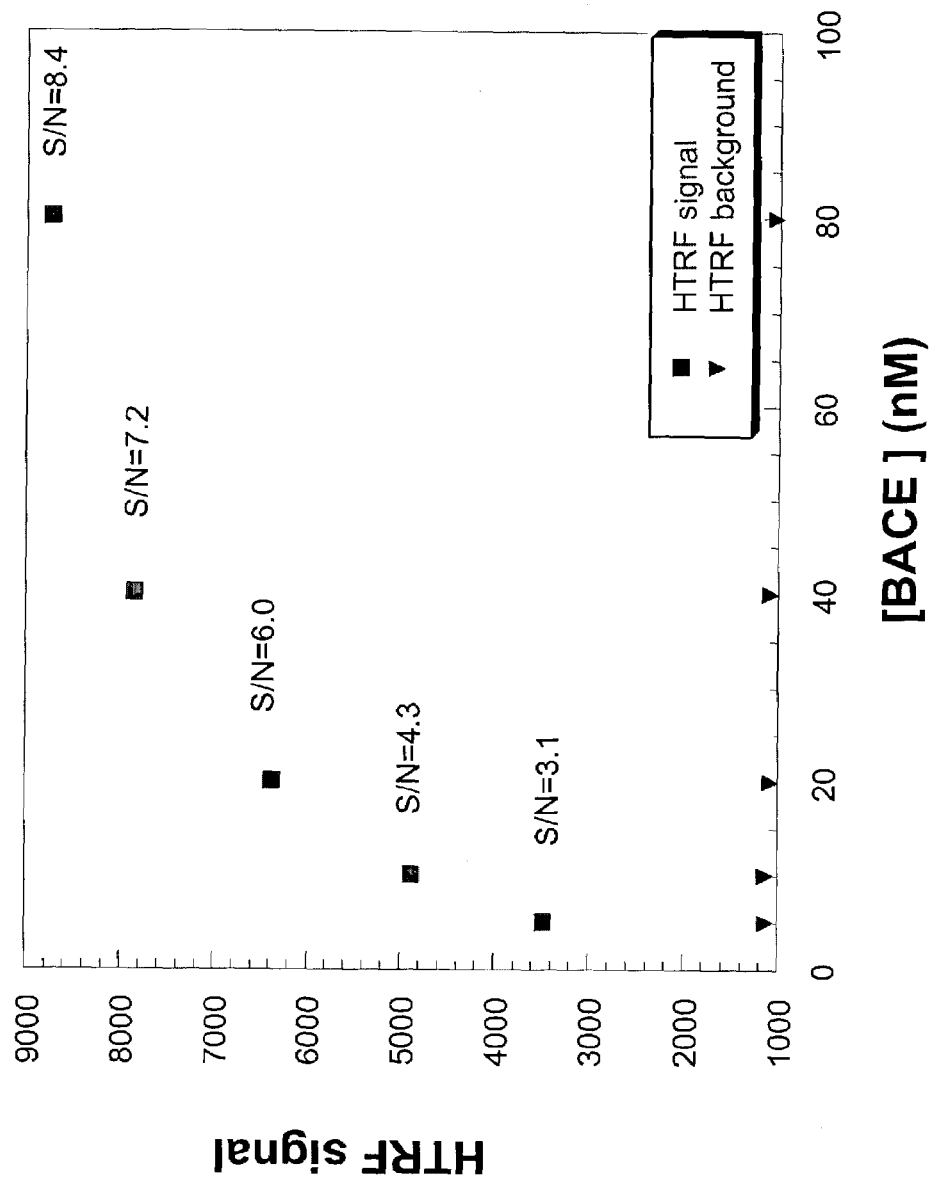
FIG. 7: Assay of in vitro BACE1 cleaved product using MBP-APP(NFEV) substrate by HTRF with neo-epitope specific "NF"-antibodies (Enzyme - dependence)

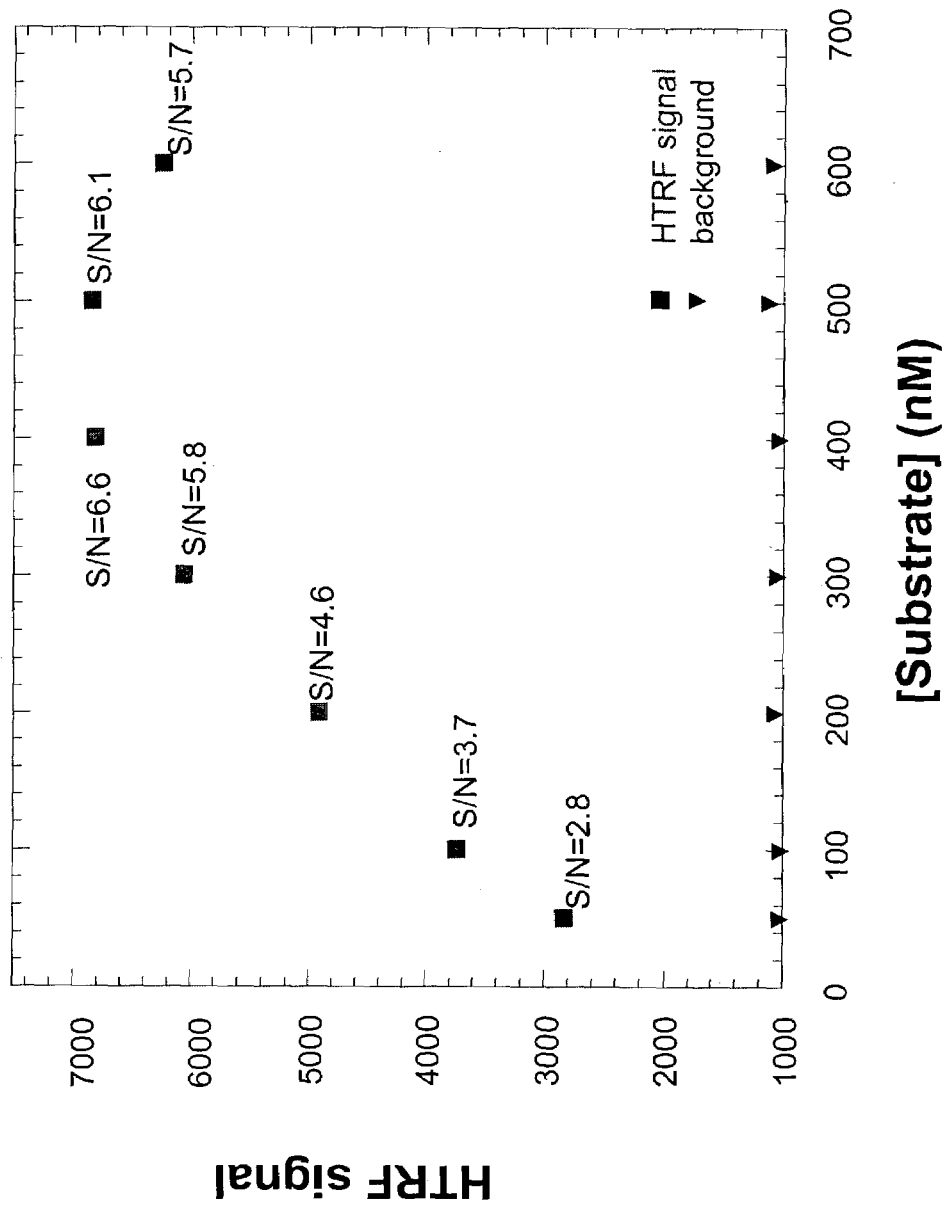
FIG. 8: Assay of in vitro BACE1 cleaved product using MBP-APP(NFEV) substrate by HTRF with neo-epitope specific "NF"-antibodies (Substrate - dependence)

ASSAYS USING AMYLOID PRECURSOR PROTEINS WITH MODIFIED β-SECRETASE CLEAVAGE SITES TO MONITOR β-SECRETASE ACTIVITY

CROSS-REFERENCE TO RELATED APPLICATIONS

This application is a continuation in part of, and claims benefit of priority under 35 U.S.C. §§120, 363, and 365(c) of International Application No. PCT/US/02/15590, filed May 17, 2002, which claims benefit of priority under 35 U.S.C. § 119(e) of U.S. Provisional Application, No. 60/316,115, filed Aug. 30, 2001, and of U.S. Provisional Application, No. 60/292,591, filed May 22, 2001. These applications, and all references cited therein, are incorporated by reference into this application.

STATEMENT REGARDING FEDERALLY SPONSORED R&D

Not applicable.

REFERENCE TO MICROFICHE APPENDIX

Not applicable.

FIELD OF THE INVENTION

The present invention is directed to the field of Alzheimer's disease. In particular, the present invention provides novel methods of identifying substances that are specific inhibitors of the cleavage of amyloid precursor protein by β-secretase where the methods employ novel polypeptides, namely, modified substrates of β-secretase.

BACKGROUND OF THE INVENTION

Alzheimer's disease is a common, chronic neurodegenerative disease, characterized by a progressive loss of memory and sometimes-severe behavioral abnormalities, as well as an impairment of other cognitive functions that often leads to dementia and death. It ranks as the fourth leading cause of death in industrialized societies after heart disease, cancer, and stroke. The incidence of Alzheimer's disease is high, with an estimated 2.5 to 4 million patients affected in the United States and perhaps 17 to 25 million worldwide. Moreover, the number of sufferers is expected to grow as the population ages.

A characteristic feature of Alzheimer's disease is the presence of large numbers of insoluble deposits, known as amyloid plaques, in the brains of those affected. Autopsies have shown that amyloid plaques are found in the brains of virtually all Alzheimer's patients and that the degree of amyloid plaque deposition correlates with the degree of dementia (Cummings & Cotman, 1995, Lancet 326:1524–1587). While some opinion holds that amyloid plaques are a late stage by-product of the disease process, the consensus view is that amyloid plaques and/or soluble aggregates of amyloid peptides are more likely to be intimately, and perhaps causally, involved in Alzheimer's disease.

A variety of experimental evidence supports this view. For example, amyloid β-protein ("Aβ"), a primary component of amyloid plaques, is toxic to neurons in culture and transgenic mice that overproduce Aβ in their brains show significant deposition of Aβ into amyloid plaques as well as significant neuronal toxicity (Yankner, 1990, Science 250:279–282; Mattson et al., 1992, J. Neurosci. 12:379–389; Games et al., 1995, Nature 373:523–527; LaFerla et al., 1995, Nature Genetics 9:21–29). Mutations in the APP gene, leading to increased Aβ production, have been linked to heritable forms of Alzheimer's disease (Goate et al., 1991, Nature 349:704–706; Chartier-Harlan et al., 1991, Nature 353:844–846; Murrel et al., 1991, Science 254:97–99; Mullan et al., 1992, Nature Genetics 1:345–347). Presenilin-1 (PS1) and presenilin-2 (PS2) related familial early-onset Alzheimer's disease (FAD) shows disproportionately increased production of Aβ1-42, the 42 amino acid isoform of Aβ, as opposed to Aβ1-40, the 40 amino acid isoform (Scheuner et al, 1996, Nature Medicine 2:864–870). The longer isoform of Aβ is more prone to aggregation than the shorter isoform (Jarrett et al, 1993, Biochemistry 32:4693–4697). Injection of the insoluble, fibrillar form of Aβ into monkey brains results in the development of pathology (neuronal destruction, tau phosphorylation, microglial proliferation) that closely mimics Alzheimer's disease in humans (Geula et al., 1998, Nature Medicine 4:827–831). See Selkoe, 1994, J. Neuropathol. Exp. Neurol. 53:438–447 for a review of the evidence that amyloid plaques have a central role in Alzheimer's disease.

Aβ, a 39–43 amino acid peptide derived by proteolytic cleavage of the amyloid precursor protein (APP), is the major component of amyloid plaques (Glenner & Wong, 1984, Biochem. Biophys. Res. Comm. 120:885–890). APP is actually a family of polypeptides produced by alternative splicing from a single gene. Major forms of APP are known as $APP_{695}$, $APP_{751}$, and $APP_{770}$, with the subscripts referring to the number of amino acids in each splice variant (Ponte et al., 1988, Nature 331:525–527; Tanzi et al., 1988, Nature 331:528–530; Kitaguchi et al., 1988, Nature 331:530–532). APP is membrane bound and undergoes proteolytic cleavage by at least two pathways. In one pathway, cleavage by an enzyme known as α-secretase occurs while APP is still in the trans-Golgi secretory compartment (Kuentzel et al., 1993, Biochem. J. 295:367–378). This cleavage by α-secretase occurs within the Aβ portion of APP, thus precluding the formation of Aβ. In another proteolytic pathway, cleavage of the $Met_{596}$-$Asp_{597}$ bond (numbered according to the 695 amino acid protein) by an enzyme known as β-secretase occurs. This cleavage by β-secretase generates the N-terminus of Aβ. The C-terminus is formed by cleavage by a second enzyme known as γ-secretase. The C-terminus is actually a heterogeneous collection of cleavage sites rather than a single site since γ-secretase activity occurs over a short stretch of APP amino acids rather than at a single peptide bond. Peptides of 40 or 42 amino acids in length (Aβ1-40 and Aβ1-42, respectively) predominate among the C-termini generated by γ-secretase. Aβ1-42 is more prone to aggregation than Aβ1-40, the major component of amyloid plaque (Jarrett et al., 1993, Biochemistry 32:4693–4697; Kuo et al., 1996, J. Biol. Chem. 271:4077–4081), and its production is closely associated with the development of Alzheimer's disease (Sinha & Lieberburg, 1999, Proc. Natl. Acad. Sci. USA 96:11049–11053). The bond cleaved by γ-secretase appears to be situated within the transmembrane domain of APP. It is unclear as to whether the C-termini of Aβ1-40 and Aβ1-42 are generated by a single γ-secretase protease with sloppy specificity or by two distinct proteases. For a review that discusses APP and its processing, see Selkoe, 1998, Trends Cell. Biol. 8:447–453.

While abundant evidence suggests that extracellular accumulation and deposition of Aβ is a central event in the etiology of AD, recent studies have also proposed that increased intracellular accumulation of Aβ or amyloid containing C-terminal fragments may play a role in the pathophysiology of AD. For example, over-expression of APP harboring mutations which cause familial AD results in the increased intracellular accumulation of C100 in neuronal cultures and Aβ42 in HEK 293 cells. Aβ42 is the 42 amino acid long form of Aβ that is believed to be more potent in forming amyloid plaques than the shorter forms of Aβ. Moreover, evidence suggests that intra- and extracellular Aβ are formed in distinct cellular pools in hippocampal neurons and that a common feature associated with two types of familial AD mutations in APP ("Swedish" and "London") is an increased intracellular accumulation of $A\beta_{42}$. Thus, based on these studies and earlier reports implicating extracellular Aβ accumulation in AD pathology, it appears that altered APP catabolism may be involved in disease progression.

APP is a ubiquitous membrane-spanning (type 1) glycoprotein that undergoes a variety of proteolytic processing events. (Selkoe, 1998, Trends Cell Biol. 8:447–453). APP is actually a family of peptides produced by alternative splicing from a single gene. Major forms of APP are known as $APP_{695}$, $APP_{751}$, and $APP_{770}$, with the subscripts referring to the number of amino acids in each splice variant (Ponte et al., 1988, Nature 331:525–527; Tanzi et al., 1988, Nature 331:528–530; Kitaguchi et al., 1988, Nature 331:530–532). APP is expressed and constitutively catabolized in most cells.

APP has a short half-life and is metabolized rapidly down two pathways in all cells. The dominant catabolic pathway appears to be cleavage of APP within the Aβ sequence by α-secretase, resulting in the constitutive secretion of a soluble extracellular domain (sAPPα) and the appearance of a nonamyloidogenic intracellular fragment (approximately 9 kD), referred to as the constitutive carboxy-terminal fragment (cCTFα). cCTFα is a suitable substrate for cleavage by γ-secretase to yield the p3 fragment. This pathway appears to be widely conserved among species and present in many cell types (Weidemann et al., 1989, Cell 57:115–126; Oltersdorf et al., 1990, J. Biol. Chem. 265:4492–4497; and Esch et al., 1990, Science 248:1122–1124). In this pathway, processing of APP involves proteolytic cleavage at a site between residues $Lys_{16}$ and $Leu_{17}$ of the Aβ region while APP is still in the trans-Golgi secretory compartment (Kang et al., 1987, Nature 325:773–776). Since this cleavage occurs within the Aβ portion of APP, it precludes the formation of Aβ. sAPPα has neurotrophic and neuroprotective activities (Kuentzel et al., 1993, Biochem. J. 295: 367–378).

In contrast to this non-amyloidogenic pathway involving α-secretase described above, proteolytic processing of APP by β-secretase exposes the N-terminus of Aβ, which after γ-secretase cleavage at the variable C-terminus, liberates Aβ. This Aβ-producing pathway involves cleavage of the $Met_{671}$-$Asp_{672}$ bond (numbered according to the 770 amino acid isoform) by β-secretase. The C-terminus is actually a heterogeneous collection of cleavage sites rather than a single site since γ-secretase activity occurs over a short stretch of APP amino acids rather than at a single peptide bond. In the amyloidogenic pathway, APP is cleaved by β-secretase to liberate sAPPβ and CTFβ, which CTFβ is then cleaved by γ-secretase to liberate the harmful Aβ peptide.

Of key importance in this Aβ-producing pathway is the position of the γ-secretase cleavage. If the γ-secretase cut is at residue 711–712, short Aβ (Aβ40) is the result; if it is cut after residue 713, long Aβ (Aβ42) is the result. Thus, the γ-secretase process is central to the production of Aβ peptide of 40 or 42 amino acids in length (Aβ40 and Aβ42, respectively). For a review that discusses APP and its processing, see Selkoe, 1998, Trends Cell. Biol. 8:447–453; Selkoe, 1994, Ann. Rev. Cell Biol. 10:373–403. See also, Esch et al., 1994, Science 248:1122.

Aβ, the principal component of amyloid plaques, is a 39–43 amino acid peptide which is capable of forming β-pleated sheet aggregates. These aggregating fibrils are subsequently deposited in the brain parenchyma or in the cerebrovasculature of the Alzheimer's disease victim (Glenner et al., 1984, Biochem. Biophys. Res. Comm. 120: 885–890; Masters et al., 1985, Proc. Natl. Acad. Sci. USA 82:4245–4249).

Reports show that soluble β-amyloid peptide is produced by healthy cells into culture media (Haass et al., 1992, Nature 359:322–325) and in human and animal CSF (Seubert et al., 1992, Nature 359:325–327).

Cleavage of APP can be detected in a number of convenient manners, including the detection of polypeptide or peptide fragments produced by proteolysis. Such fragments can be detected by any convenient means, such as by antibody binding. Another convenient method for detecting proteolytic cleavage is through the use of a chromogenic β-secretase substrate whereby cleavage of the substrate releases a chromogen, e.g., a colored or fluorescent, product.

As noted above, various naturally occurring mutations in APP have been identified that lead to familial, early-onset Alzheimer's disease. Once such mutation, known as the "Swedish" mutation, consists of a double change in the amino acid sequence of $APP_{695}$ at the β-secretase cleavage site: $K^{595}$, $M^{596}$ to $N^{595}$, $L^{596}$ (Mullan et al., 1992, Nature Genet. 1:345; Citron et al., 1992, Nature 360:672). Cultured cells that express a cDNA encoding APP bearing the Swedish version of the β-secretase cleavage site produce about 6–8 fold more Aβ than cells expressing wild-type APP (Citron et al., 1992, Nature 360:672–674).

Citron et al., 1995. Neuron 14:661–670 varied the amino acid sequence at the β-secretase cleavage site of APP (positions Val594-Ala598 of $APP_{695}$) and found that most substitutions in this sequence strongly decreased or eliminated cleavage by β-secretase. Only the Swedish mutation was found to strongly increase cleavage.

Sisodia, 1992, Proc. Natl. Acad. Sci. USA 89:6975–6979 described experiments in which various changes in the amino acid sequence of APP in the region of the α-secretase cleavage site were made and the effect of those changes on cleavage by α-secretase were measured. A change of K to V at position 612 of the 695 amino acid version of APP led to reduced cleavage by α-secretase. The K612V change has been built into a vector encoding the carboxy terminal 99 amino acids of APP and transgenic mice expressing this construct have been obtained. Such mice develop a myopathy similar to human inclusion body myositis (Jin et al., 1998, Am. J. Pathol. 153:1679–1686).

Much interest has focused on the possibility of inhibiting the development of amyloid plaques as a means of preventing or ameliorating the symptoms of Alzheimer's disease. To that end, a promising strategy is to inhibit the activity of β- and γ-secretase, the two enzymes that together are responsible for producing Aβ. This strategy is attractive because, if the formation of amyloid plaques is a result of the deposition of Aβ is a cause of Alzheimer's disease, inhibiting the activity of one or both of the two secretases would intervene in the disease process at an early stage, before late-stage events such as inflammation or apoptosis occur. Such early stage intervention is expected to be particularly beneficial (see, e.g., Citron, 2000, Molecular Medicine Today 6:392–397).

To that end, various assays have been developed that are directed to the identification of substances that may interfere with the production of Aβ or its deposition into amyloid plaques. U.S. Pat. No. 5,441,870 is directed to methods of monitoring the processing of APP by detecting the production of amino terminal fragments of APP. U.S. Pat. No. 5,605,811 is directed to methods of identifying inhibitors of the production of amino terminal fragments of APP. U.S. Pat. No. 5,593,846 is directed to methods of detecting soluble Aβ by the use of binding substances such as antibodies. Esler et al., 1997, Nature Biotechnology 15:258–263 described an assay that monitored the deposition of Aβ from solution onto a synthetic analogue of an amyloid plaque. The assay was suitable for identifying substances that could inhibit the deposition of Aβ. However, this assay is not suitable for identifying substances, such as inhibitors of β- or γ-secretase, that would prevent the formation of Aβ.

Various groups have cloned and sequenced cDNA encoding a protein that is believed to be β-secretase (Vassar et al., 1999, Science 286:735–741; Hussain et al., 1999, Mol. Cell. Neurosci. 14:419–427; Yan et al., 1999, Nature 402:533–537; Sinha et al., 1999, Nature 402:537–540; Lin et al., 2000, Proc. Natl. Acad. Sci. USA 97:1456–1460). Hong et al., 2000, Science 290:150–153 determined the crystal structure of the protease domain of human β-secretase complexed with an eight-residue peptide-like inhibitor at 1.9 angstrom resolution. Compared to other human aspartic proteases, the active site of human β-secretase is more open and less hydrophobic, contributing to the broad substrate specificity of human β-secretase (Lin et al., 2000, Proc. Natl. Acad. Sci. USA 97:1456–1460).

Ghosh et al., 2000, J. Am. Chem. Soc. 122:3522–3523 disclosed two inhibitors of β-secretase, OM99-1 and OM99-2, that are modified peptides based on the β-secretase cleavage site of the Swedish mutation of APP (SEVNL/DAEFR, with "/" indicating the site of cleavage). OM99-1 has the structure VNL*AAEF (with "L*A" indicating the uncleavable hydroxyethylene transition-state isostere of the LA peptide bond) and exhibits a $K_i$ towards recombinant β-secretase produced in $E.\ coli$ of $6.84 \times 10^{-8}$ M±$2.72 \times 10^{-9}$ M. OM99-2 has the structure EVNL*AAEF (with "L*A" indicating the uncleavable hydroxyethylene transition-state isostere of the LA peptide bond) and exhibits a $K_i$ towards recombinant β-secretase produced in $E.\ coli$ of $9.58 \times 10^{-9}$ M±$2.86 \times 10^{-10}$ M. OM99-1 and OM99-2, as well as related substances, are described in International Patent Publication WO 01/00665.

Despite some progress in identifying β-secretase inhibitors, there are currently no approved pharmaceuticals for the treatment or prevention of Alzheimer's disease that are believed to exert their therapeutic effect through the inhibition of β-secretase. Thus, there remains a need for additional assays that can be used to identify additional inhibitors of β-secretase.

SUMMARY OF THE INVENTION

The present invention is based, in part, on the discovery of modified β-secretase substrates comprising a novel cleavage site designated P1-P1'-P2', which is altered from the wild-type. As well, the invention features methods of identifying inhibitors of β-secretase where such methods employ modified β-secretase substrates that have β-secretase cleavage sites that are altered from wild type. The amino acid sequences of the altered β-secretase cleavage sites contain different amino acids in at least one of the positions P2-P1-P1'-P2' of the β-secretase cleavage site. Rather than the wild-type KMDA (SEQ.ID.NO.:1) or the Swedish NLDA (SEQ.ID.NO.:2) sequences at these positions, the altered sequences of the present invention contain a variety of different amino acids at one or more positions at P2-P1-P1'-P2' sequences. A striking feature of the novel discovery disclosed herein is that the novel sequences derived from the novel cleavage site designated P1-P1'-P2' are better substrates than the wild type substrate in that the modifications disclosed herein results in a markedly improved β-secretase substrates such that the modified substrate is cleaved by β-secretase at a rate higher than that attending the wild-type or other substrates missing the novel cleavage site. That is, the modified β-secretase substrates (containing altered P2-P1-P1'-P2' sequences) are cleaved at a higher rate and thus produce more product in a given time than similar substrates having the wild-type sequence. For example, when present in an APP backbone and expressed in tissue culture cells, an altered substrate containing the sequence NFEV (SEQ.ID.NO.:3) in the P2-P1-P1'-P2' position is cleaved at a rate about 15–20 times faster than a similar substrate having the wild-type KMDA (SEQ.ID.NO.:1) sequence.

The present invention provides recombinant DNA molecules encoding the modified β-secretase substrates. Such recombinant DNA molecules can be used to express the modified β-secretase substrates in tissue culture cells. This allows for the use of the modified β-secretase substrates in methods of identifying inhibitors of β-secretase. The methods can be carried out in a cell-based manner, using tissue culture cells (a) that endogenously express β-secretase or (b) that have been engineered to express β-secretase.

Alternatively, the recombinant DNA molecules can be used to produce RNA encoding polypeptides that function as modified β-secretase substrates. Such RNA can be used in known in vitro translation systems to produce the polypeptides, which can then be used in methods of identifying inhibitors of β-secretase that can be carried out in a cell-free manner, using purified β-secretase.

Alternatively, the recombinant DNA molecules can be expressed in bacteria, yeast, insect cells or mammalian cells. The expressed protein polypeptide can be purified and used as substrate for in vitro biochemical assays in combination with purified β-secretase.

Methods to identify the products of cleavage at the β-secretase cleavage site, which indicates, inter alia, the relative lability of the modified β-secretase substrates, may be done by a number of methods as described herein. Among such methods are various assays based on immunological detection by specific polyclonal or monoclonal antibodies and, alternatively, the use of peptide aptamers or single-chain monoclonal antibodies (which may be identified using phage display technologies). For instance, such immunological reagents are and can be identified which specifically bind to either the novel carboxyl terminal or amino terminal epitopes at the end of the processed amyloid β-protein products, where such terminal epitopes are generated by β-secretase cleavage of any of the modified β-secretase substrates of the present invention.

Methods of identifying inhibitors of β-secretase provided by the present invention can be carried out in transgenic animals that are engineered to express the modified β-secretase substrates. Such transgenic animals can also serve as useful animal models for Alzheimer's disease.

In addition to having changes at the β-secretase cleavage site, the modified β-secretase substrates may be engineered to have several further changes from wild-type APP. Among such further changes are:
the inclusion of one or more epitope tags;
a K612V change; and
N-terminal or C-terminal peptide extensions.

Antibodies that recognize epitopes formed by cleavage of the modified β-secretase substrates are also provided by the present invention.

BRIEF DESCRIPTION OF THE DRAWINGS

FIGS. 1A–D shows various modifications to an APP backbone that are suitable for use in the present invention. FIG. 1A shows the insertion of epitope tags into the natural splice site of APP. FIG. 1B shows the insertion of a V5 or a biotinylation sequence site ("BSS") upstream of the β-secretase cleavage site. FIG. 1C shows the K612V change. FIG. 1D shows the use of N-terminal or C-terminal fusions.

FIG. 2 shows a more detailed overview of the APP backbone, particularly detailing cleavage sites for β-secretase, Δ-secretase, and γ-secretase. The figure also indicates epitope sites along the APP backbone cleavage area for several known antibodies.

FIGS. 3A and 3B provide data summaries of competition of selected antibodies against peptides that represent different cleavages of a modified β-secretase substrate. These data are discussed in Example 2.

FIGS. 4A and 4B provide data regarding, and diagrammatic representations of, BACE-cleaved product as detected utilizing neo-epitope specific "NF"-antibodies.

FIG. 5 shows the increase in signal observed with a titration of BACE cleaving 400 nM MBP-biotinylation sequence site ("BSS")-APP(NFEV) with identification of the cleavage product carried out using AlphaScreen as described in Example 9.

FIG. 6 shows the increase in signal observed with a titration of MBP-BSS-APP(NFEV) cleaved with 20 nM BACE, with identification of the cleavage product carried out in AlphaScreen as described in Example 9.

FIG. 7 shows the increase in signal observed with a titration of BACE cleaving 400 nM MBP-BSS-APP(NFEV) with identification of the cleavage product carried out in HTRF as described in Example 10. S/N refers to the signal/noise ratio at each concentration of BACE.

FIG. 8 shows the increase in signal observed with a titration of MBP-BSS-APP(NFEV) cleaved with 20 nM BACE, with identification of the cleavage product carried out in HTRF as described in Example 10. S/N refers to the signal/noise ratio at each concentration of MBP-BSS-APP (NFEV).

DETAILED DESCRIPTION OF THE INVENTION

For the purposes of this invention:

"$APP_{695}$" refers to the 695 amino acid splice variant of APP (see GenBank accession no. Y00264 and Kang et al., 1987, Nature 325:733–736).

"$APP_{751}$" refers to the 751 amino acid splice variant of APP (see Ponte et al., 1988, Nature 331:525–527).

"$APP_{770}$" refers to the 770 amino acid splice variant of APP (see Kitaguchi et al., 1988, Nature 331:530–532).

"β-secretase" refers to an enzyme that is sometimes known in the literature as "BACE" or "BACE1" (see, e.g., Vassar et al., 1999, Science 286:735–741). As used herein, the term β-secretase is taken to include all mammalian forms of the naturally occurring enzyme(s) with ability to cleave at the β-site in APP. The term as used herein also includes all recombinant forms, mutations, and other variants of such enzyme so long as these maintain a functional capability to catalyze the cleavage of molecules bearing P2-P1-P1'-P2' β-secretase cleavage sites disclosed herein at a level of at least about five percent of the effectiveness of a naturally occurring β-secretase on the same substrate.

As used herein, "substance" may be any molecule, compound, mixture of molecules or compounds, or any other composition which is suspected of being capable of inhibiting β-secretase activity in vivo or in vitro. "Substances" that are screened in the present invention can be any substances that are generally screened in the pharmaceutical industry during the drug development process. The substances may be macromolecules, such as biological polymers, including proteins, polysaccharides, nucleic acids, or the like. More usually, a substance will be a small molecule having a molecular weight below about 2 kD, more usually below 1.5 kD, frequently below 1 kD, and usually in the range from 100 Da to 1,000 Da, and even more usually in the range from 200 Da to 750 Da. One or more substances may be pre-selected based on a variety of criteria. For example, suitable substances may be selected as having known proteolytic inhibitory activity. Alternatively, the substances may be selected randomly and tested by the screening methods of the present invention. Substances which are able to inhibit β-secretase cleavage of the invention peptide substrates in vitro are considered as candidates for further screening of their ability to decrease Aβ production in cells and/or animals. Substances are often tested in the methods of the present invention as large collections of substances, e.g. libraries of low molecular weight organic compounds, peptides, or natural products.

A "conservative amino acid substitution" refers to the replacement of one amino acid residue by another, chemically similar, amino acid residue. Examples of such conservative substitutions are: substitution of one hydrophobic residue (isoleucine, leucine, valine, or methionine) for another; substitution of one polar residue for another polar residue of the same charge (e.g., arginine for lysine; glutamic acid for aspartic acid); substitution of one aromatic amino acid (tryptophan, tyrosine, or phenylalanine) for another.

A "conservative amino acid substitution" as defined above is but one type of variation of an amino acid sequence listing encompassed by the broader term, "conservatively modified variants thereof." For instance, the latter is taken to have the meaning ascribed to the term in M.P.E.P. § 2422.03, Eighth Edition, 2001, which can include, without being limited to this example, deletions such as "at the C-terminus by 1, 2, 3, 4, or 5 residues." Where appropriate within this specification, conservative amino acid substitutions that are known or reasonably predicted to not adversely alter the desired functionality of the novel sequences disclosed herein are disclosed. Such disclosed conservative amino acid substitutions are considered to fall within the scope of the sequence listings that include the novel β-secretase cleavage area sequences disclosed and claimed herein.

For instance, but not meant to be limiting, an amino acid sequence or a nucleotide sequence is considered "identical" to a reference sequence if the two sequences are the same when aligned for maximum correspondence over a comparison window. Optimal alignment of nucleotide and amino acid sequences for aligning comparison window may be conducted by the local homology algorithm of Smith &

Waterman, 1981, Adv. Appl. Math. 2:482, by the homology alignment algorithm of Needleman & Wunsch, 1970, J. Mol. Biol. 48:443, by the search for similarity method of Pearson & Lipman, 1988, Proc. Natl. Acad. Sci., U.S.A. 85:2444–2448, by computerized implementations of these algorithms (GAP, BESFIT, FASTA, and TFASTA in the Wisconsin Genetics Software Package Release 7.0, Genetics Computer Group, 575 Science Dr., Madison, Wis.), or by inspection. Such determination of identity can be considered to indicate a "conservatively modified variant" of a particular amino acid sequence or nucleotide sequence so long as the variant continues to function as a β-secretase substrate.

In the alternative, comparative similarity of a variant, for purposes of invention and claim scope, is defined by the "relative sequence identity" of that variant to a novel protein or polypeptide sequence specifically disclosed and claimed herein, so long as the comparative similarity falls within a specified boundary and the variant continues to be a substrate for the β-secretase enzyme. For instance, and as described elsewhere in this specification, a particular APP backbone (or polypeptide regions thereof) can have any or all of the following: substitutions, deletions, insertions, and additions. Certain approaches and specific methods for making variants with substitutions, deletions, insertions, and/or additions are described herein. Also, the references cited herein, and the knowledge of those skilled in the art, provide for the a multitude of other possible substitutions, deletions, insertions, and/or additions that must be considered routine in the art. Thus, in certain embodiments, a protein or polypeptide variant of a specified claimed sequence number that is at least 95 percent identical to that sequence number (based on amino acid sequence homology, i.e., the "relative sequence identity"), where that variant is demonstrated to be a substrate for the β-secretase enzyme, is within the scope of the present invention. In other embodiments, a protein or polypeptide variant of a specified claimed sequence number that is at least 85 percent identical to that sequence number (based on amino acid sequence homology), where that variant is demonstrated to be a substrate for the β-secretase enzyme, is within the scope of the present invention. In yet other embodiments, a protein or polypeptide variant of a specified claimed sequence number that is at least 65 percent identical to that sequence number (based on amino sequence homology), where that variant is demonstrated to be a substrate for the β-secretase enzyme, is within the scope of the present invention. For all such variants, it is noted that the functional ability to serve as a "suitable substrate" for the β-secretase enzyme, such as in test systems described herein, or also in other methods now known in the art, or, optionally, also including methods later known in the art, is essential to the inclusion of any such variant within the operation of the invention, and the scope of any relevant claim.

"Consists essentially," with respect to a β-secretase substrate, indicates that the reference sequence can be modified by N-terminal and/or C-terminal additions or deletions that do not cause a substantial decrease in the ability of the β-secretase substrate to be cleaved compared to the reference sequence. An example of a deletion is the removal of an N-terminal methionine.

A "substantial decrease" in the ability of the β-secretase substrate to be cleaved is a decrease of at least about 25% inhibition, more usually at least about 50% inhibition, preferably at least about 75% inhibition, and often at least about 90% inhibition or higher compared to activity observed using a reference substrate incubated with appropriate buffers and suitable reagents.

The term "antibody" refers to a polypeptide substantially encoded by an immunoglobulin gene or immunoglobulin genes, or fragments thereof, which specifically bind and recognize an analyte (antigen). The recognized immunoglobulin genes include the kappa, lambda, alpha, gamma, delta, epsilon and mu constant region genes, as well as the myriad immunoglobulin variable region genes. Antibodies exist, e.g., as intact immunoglobulins or as a number of well-characterized fragments produced by digestion with various peptidases. These include, e.g., Fab' and F(ab)'$_2$ fragments. The term "antibody" also includes antibody fragments either produced by the modification of whole antibodies or those synthesized de novo using recombinant DNA methodologies, and further includes "humanized" antibodies made by conventional techniques.

The term "immunoassay" is an assay that utilizes an antibody to specifically bind an analyte. The immunoassay is characterized by the use of specific binding properties of a particular antibody to isolate, target, and/or quantify the analyte.

An antibody "specifically binds to" or "is specifically immunoreactive with" a protein, polypeptide, or peptide when the antibody functions in a binding reaction which is determinative of the presence of the protein, polypeptide, or peptide in the presence of a heterogeneous population of proteins and other biologics. Thus, under designated immunoassay conditions, the specified antibodies bind preferentially to a particular protein, polypeptide, or peptide and do not bind in a significant amount to other proteins, polypeptides, or peptides present in the sample. Specific binding to a protein, polypeptide, or peptide under such conditions requires an antibody that is selected for specificity for a particular protein, polypeptide, or peptide. As used herein, the term "recognize" as it regards an antibody's association to an a particular protein, polypeptide, or peptide, or an epitope therein, is taken to mean that said antibody "specifically binds to" or "is specifically immunoreactive with" that protein, polypeptide, or peptide.

The protein, polypeptide, or peptide that combines specifically with antibodies, and the processed peptides that combine specifically with cell-surface receptors of immune cells, are referred to as "antigens."

An "immunogenic peptide" is defined as a peptide sequence that is of sufficient length and amino acid composition to induce an immune response (humoral and/or cell-mediated) in a suitable host animal when injected therein with a suitable range of concentrations. Within the context of the present invention, an immunogenic peptide that includes all or part of a novel β-secretase cleavage site of the present invention results in production in said host animal of an antibody which ultimately recognizes the peptide sequence as a free peptide and also when at an end of the β-secretase processed APP and APP variants. Immunogenic peptides of the present invention also possess the property of antigens, i.e., such immunogenic peptides are antigens in that each such immunogenic peptide combines specifically with particular antibodies raised against such specific peptide.

A variety of immunoassay formats may be used to select antibodies specifically immunoreactive with a particular protein, polypeptide, or peptide. For example, solid-phase ELISA immunoassays are routinely used to select monoclonal antibodies specifically immunoreactive with a protein, polypeptide, or peptide. See Harlow & Lane, 1988, Antibodies, A Laboratory Manual, Cold Spring Harbor Publications, New York, for a description of immunoassay formats and conditions that can be used to determine specific immunoreactivity.

"Transfection" refers to any of the methods known in the art for introducing DNA into a cell, for example, but not limited to, the methods of calcium phosphate or calcium chloride mediated transfection, electroporation, and infection with a retroviral vector.

"sAPPβ fragment" refers to an approximately 100 kD amino terminal fragment produced when APP is cleaved by β-secretase.

A "modified β-secretase substrate" refers to any polypeptide molecule that contains any of the novel β-secretase P2-P1-P1'-P2' cleavage sites disclosed herein, whether or not such molecules also are comprised of additional epitopes to facilitate analysis. For instance, polypeptides that are comprised of 2, 3, 4, 5 or 6 amino acids attached either to one or both sides of a novel β-secretase P2-P1-P1'-P2' cleavage site are modified β-secretase substrates. Modified β-secretase substrates include non-naturally occurring peptides, each of which comprises a contiguous sequence fragment of at least 8 amino acids, such fragment comprising a synthetic β-secretase cleavage site, where the at least 8 amino acids have a sequence selected from the group of sequences disclosed in International Application No. PCT/US/02/15590, filed May 17, 2002. As similarly noted therein, fragments and homologs of such non-naturally occurring peptides also are encompassed by the present invention. Full-length APP molecules, whether of 695, 751 or 770 amino acid lengths, and such molecules with additional amino acids added to either or both ends, are modified β-secretase substrates so long as they possess a novel β-secretase P2-P1-P1'-P2' cleavage site. Also, intermediate-sized polypeptides smaller than the full-length APP molecules of 695, 751 or 770 amino acid lengths but larger than the aforementioned multimers up to 16 polypeptides in length, which are substantially comprised of the APP sequence and which are cleavable by β-secretase, are modified β-secretase substrates so long as they possess a novel β-secretase P2-P1-P1'-P2' cleavage site. Such intermediate-sized polypeptides are also referred to as "biologically active fragments" or "biologically active amino acid fragments" of APP, "APP biologically active fragments," or "APP biologically active amino acid fragments." Reference to such intermediate-sized polypeptide is limited to these terms, to avoid confusion with the use of the term "fragment" when referring, infra, to peptides and polypeptides that result from enzymatic cleavage by β-secretase alone or in conjunction with other enzymes, such as γ-secretase.

Also, it is noted that certain modified β-secretase substrates are shown to be "positive" substrates in that the observed reaction rates in testing with β-secretase is greater with such substrates than with a substrate of similar overall structure but having the wild-type KMDA cleavage site. That is, these modified substrates, when tested in model systems, appear more susceptible to enzymatic breakdown by β-secretase. However, other modified β-secretase substrates are believed to be "negative" substrates in that the observed reaction rates in testing is lower with such substrates compared to a substrate having the wild-type KMDA cleavage site. That is, the rate of cleavage of some modified β-secretase substrates was shown to be below the detection limit of the assay. One or more of such modified β-secretase substrates are usable as "negative controls" that, on further testing, can be confirmed to have substantially lower reaction rates as substrates for β-secretase.

All of the above defined forms and variations of modified β-secretase substrates alternately may be referred to as a "β-secretase cleavable substrate," provided, however, that the use of such term is associated with the inclusion of the novel amino acid sequences at the P2-P1-P1'-P2' cleavage site as disclosed herein, and further provided that such form or variation is a substrate for the β-secretase enzyme under appropriate test conditions such as those described herein. Alternately, a modified β-secretase substrate may be referred to herein as a "mutant" or "variant." An APP molecule that contains any such novel P2-P1-P1'-P2' cleavage site, optionally (and typically) with other modifications (such as a second polypeptide and/or an epitope tag), which comprises a sub-group of modified β-secretase substrates, also is referred to herein as an "$APP_{695}$-derived polypeptide" (where the APP is the 695 amino acid form/splice variant).

A "fusion protein" is a protein that contains at least two polypeptide regions and, optionally, a linking peptide to operatively link the two polypeptides into one continuous polypeptide. The at least two polypeptide regions in a fusion protein are derived from different sources, and therefore a fusion protein comprises two polypeptide regions not normally joined together in nature.

A "linking sequence (or linker peptide)" contains one or more amino acid residues joined in peptide bonds. A linking sequence serves to join two polypeptide regions of differing origins in a fusion protein via a peptide bond between the linking sequence and each of the polypeptide regions.

Typically, a fusion protein is synthesized as a continuous polypeptide in a recombinant host cell which contains an expression vector comprising a nucleotide sequence encoding the fusion protein where the different regions of the fusion protein are fused in frame on either side of a linker peptide's coding sequence. The chimeric coding sequence (encoding the fusion protein) is operatively linked to expression control sequences (generally provided by the expression vector) that are functional in the recombinant host cell. Alternatively, a fusion protein may be synthesized in vitro, by methods of solid-state peptide synthesis that are well known in the art.

In Example 9, below, maltose binding protein ("MBP") is fused to an APP backbone that comprises a modified β-secretase substrate of the present invention. However, it is appreciated by those skilled in the art that polypeptides other than MBP are fused to modified β-secretase substrates of the present invention to form various fusion proteins that facilitate detection in assays that utilize modified β-secretase substrates of the present invention. Some such polypeptides are reporter genes, while other such polypeptides are epitope tags that facilitate separation and/or identification immunologically. The following listing of such reporter gene and epitope tag polypeptides is meant to be illustrative and not limiting, and there is a large and ever-increasing selection of such reporter gene and epitope polypeptides that are substitutable for those specifically described in the examples below. One skilled in the art is capable of making desired substitutions without undue experimentation.

Green fluorescent protein ("GFP"), or functional protein/polypeptide derivatives thereof, comprise one group of suitable reporter genes. The GFP gene was originally cloned from the jellyfish Aequorea victoria. It encodes a protein of 238 amino acids which absorbs blue light (major peak at 395 nm) and emits green light (major peak at 509 nm) (Prasher et al., Gene 15:229–223, 1992). GPF genes and functional proteins have been identified in a variety of organisms in the phyla hydrozoa, cnidaria, anthozoa and ctenophora. Both wild-type GFP and mutated GFP from Aequorea victoria can be used as a reporter gene. The mutation of GFP (e.g., the substitution of certain amino acids in the GFP polypeptide) has been reported to yield GFP proteins with improved spectral properties. For example, mutating serine 65 to a threonine generates a GFP variant which has about sixfold greater brightness than wild-type GFP (Heim et al., Nature 372:663–664, 1995). The coding sequence for an enhanced GFP can be purchased commercially (Clontech, Palo Alto, Calif.). In some embodiments a mammalian-optimized version of a GFP cDNA is used.

Blue fluorescent protein ("BPF") can also be used as a reporter gene. To obtain BFP, tyrosine 66 of GFP is mutated to a histidine. This mutated GFP protein fluoresces bright blue, in contrast to the green of the wild-type protein. Other variants of GFP include yellow fluorescent protein (YFP), and cyan fluorescent protein (CFP). Other suitable fluorescent proteins include those described by Matz et al., 1999, Nature Biotechnology 17:969–973. For the purposes of this disclosure, the above variants of GFP, as well as functional (fluorescing) derivatives of these, whether classified as a protein or a polypeptide, are collectively referred to as "GFP variants."

Other suitable reporter genes include chloramphenicol acetyl transferase ("CAT"; Alton and Vapnek (1979), Nature 282:864–869), and other enzyme detection systems, such as beta-galactosidase ("β-gal"); firefly luciferase (deWet et al. (1987), Mol. Cell. Biol. 7:725–737); bacterial luciferase (Engebrecht and Silverman (1984), PNAS 1:4154–4158; Baldwin et al. (1984), Biochemistry 23:3663–3667) (for luciferases, collectively "luc"); phycobiliproteins (especially phycoerythrin) (for phycobiliproteins, collectively "pbp"; alkaline phosphates (Toh et al. (1989) Eur. J Biochem. 182:231–238, Hall et al. (1983) J. Mol. Appl. Gen. 2:101), or secreted alkaline phosphate (Cullen and Malim (1992) Methods in Enzymol. 216:362–368) (for alkaline phosphatases collectively, "AP"). Other examples of suitable reporter genes include those which encode proteins conferring drug/antibiotic resistance to the host mammalian cell.

The amount of transcription from the reporter gene may be measured using any suitable method. Various suitable methods are known in the art. For example, specific RNA expression may be detected using Northern blots, or specific protein product may be identified by a characteristic stain or an intrinsic activity.

In preferred embodiments, the protein encoded by the reporter is detected by an intrinsic activity associated with that protein. For instance, the reporter gene may encode a gene product that, by enzymatic activity, gives rise to a detection signal based on, fluorescence, colour, or luminescence.

In other preferred embodiments, the reporter gene provides a selection method such that cells in which the reporter gene is activated have a growth advantage. For example the reporter could enhance cell viability, e.g., by relieving a cell nutritional requirement, and/or provide resistance to a drug. Another class of useful reporter genes encode cell surface proteins for which antibodies or ligands are available. Expression of the reporter gene allows cells to be detected or affinity purified by the presence of the surface protein.

Alternatively, the fused polypeptide is an epitope tag, examples of which include but are not limited to a Myc tag, a Flag tag, a His tag, a Leucine tag, an IgG tag, a biotinylation sequence site ("BSS," i.e., a streptavidin tag) and the like.

In particular embodiments, as described in examples below, two or more reporter gene constructs and/or epitope tags are fused to a polypeptide (e.g., an APP backbone) that comprises a modified β-secretase substrate of the present invention. For instance, in Example 7, a three-component fused protein is comprised of maltose binding protein (MBP) fused to biotinylation sequence site ("BSS") sequence (to facilitate intracellular biotinylation of the expressed protein), and these are fused to an APP backbone comprising the NFEV modified β-secretase cleavage site.

The present invention relates to the discovery that the P2-P1-P1'-P2' amino acids at the β-secretase cleavage site of amyloid precursor protein (APP) can be varied from their previously known wild-type, Swedish and other sequence variants to produce sequences that are much more efficient substrates for β-secretase that the wild-type sequence. Peptides containing such more efficient substrates are disclosed in co-pending U.S. Provisional Patent Application Serial No. 60/316,115, filed Aug. 30, 2001, entitled "BETA-SECRETASE SUBSTRATES AND USES THEREOF," the disclosure of which is incorporated herein, in its entirety. In particular, the sequence NFEV (SEQ.ID.NO.:3) and other novel β-secretase cleavage sites are disclosed in this application. The P2-P1-P1'-P2' amino acids at the β-secretase cleavage site of APP correspond to positions 595-596-597-598 of the 695 amino acid version of APP, positions 651-652-653-654 of the 751 amino acid version of APP, and positions 670-671-672-673 of the 770 amino acid version of APP. In the wild-type version of APP, these amino acids are KMDA (SEQ.ID.NO.:1); in the Swedish version, they are NLDA (SEQ.ID.NO.:2).

The present invention also relates to the discovery that the P2-P1-P1'-P2' amino acids at the β-secretase cleavage site of amyloid precursor protein (APP) also can be varied from the previously known wild-type sequence variant to produce sequences that are less efficient substrates for β-secretase than the wild-type sequence. This has been shown by testing modified β-secretase substrates which demonstrate reaction rates below the detection limit in an analysis in which the wild-type KMDA APP did provide a detectable response (see Example 4 for latter). These are referred to as "negative" modified β-secretase substrates. Peptides containing such less efficient substrates, and corresponding nucleic acid sequences, are useful in the overall development of methods, kits, and systems that screen for inhibitors of β-secretase activity. For instance, as a null control on the validity of an inhibitor screening system, when evaluating a putative effective β-secretase inhibitor in a treatment (negative control) having as its APP a sequence variant less effective than the wild-type sequence, one would expect a slower production of Aβ to be even slower. If results do not show this, then the mechanism and scope of effectiveness of such inhibitor might be questioned. Thus, among other applications, the use of such negative modified β-secretase substrates can increase the robustness of an inhibitor screening system of the present invention. Other embodiments of the present invention include recombinant DNA molecules encoding for negative modified β-secretase substrates, without and with the various changes engineered into it besides the coding for such novel P2-P1-P1'-P2' amino acid sequences, as are described immediately below for the P2-P1-P1'-P2' amino acid sequences that result in more efficient β-secretase activity.

The present invention provides recombinant DNA molecules encoding polypeptides that are modified β-secretase substrates. The polypeptides comprise amino acid sequences at the P2-P1-P1'-P2' positions at the β-secretase cleavage site of APP that differ from the wild type or Swedish sequences and that confer on the encoded polypeptides the property of being cleaved more efficiently by β-secretase than similar polypeptides containing the wild-type sequence at the corresponding positions.

The modified P2-P1-P1'-P2' amino acids are generally engineered into a larger polypeptide derived from APP. This "APP backbone" can have various changes engineered into it besides the modified P2-P1-P1'-P2' amino acids. FIG. 1 illustrates some of these additional changes. FIG. 1A shows the insertion of numerous epitopes such as Hemagglutinin, Myc, Flag, or combinations thereof, into the natural splicing site of APP (i.e., between amino acids 289 and 290 of $APP_{695}$). FIG. 1B shows the insertion of V5 or Biotinylation sites at a site 18 amino acid residues upstream from the β-secretase cleavage site (i.e., between positions 578 and 579 of $APP_{695}$). FIG. 1C shows a mutation (V612K) at the P1 position of the α-secretase cleavage site (i.e., position 612 of $APP_{695}$), to reduce α-secretase cleavage. This modification in the modified β-secretase substrate allows for the monitoring of β-secretase activity with less interference from α-secretase activity. FIG. 1D shows an APP backbone with fusion partners either at its N-terminal or C-terminals. As examples, maltose-binding protein ("MBP") and a biotinylation sequence site ("BSS") are shown. These modifications facilitate the purification of recombinant modified β-secretase substrates and allow the measurement of β-secretase cleaved modified β-secretase substrate N-terminal or C-terminal products without using any antibodies against APP.

Each APP backbone modification can be used alone or in combination with other modifications. The modifications can be used in all 3 differentially spliced forms of APP (i.e., the 770, 751 and 695 amino acid versions). APP β-secretase cleavage site changes can be incorporated either into all 3 unmodified APP splice variants or into the modified APP backbones, or into any combinations of these backbone modifications.

Preferred combinations of backbone modifications include (numbering is from $APP_{695}$):

(1) an epitope tag between positions 289 and 290 plus the insertion of V5 or Biotinylation sites between positions 578 and 579;

(2) an epitope tag between positions 289 and 290 plus the K612V change;

(3) the insertion of V5 or Biotinylation sites between positions 578 and 579 plus the K612V change;

(4) an epitope tag between positions 289 and 290 plus the insertion of V5 or Biotinylation sites between positions 578 and 579 plus the K612V change.

All of these backbone modifications are suitable for combination with any of the modified P2-P1-P1'-P2' amino acids, whether the resulting modified β-secretase substrates have a positive or a negative effect on the rate of catalysis by a β-secretase.

FIG. 2 provides a more detailed view of the region of $APP_{695}$ that is between and includes amino acids 596–639. Shown are the cleavage sites for the β-secretase, Δ-secretase, and γ-secretase enzymes. Also shown is a hemagluttin ("HA")/Myc/Flag combined epitope flag insert between amino acids 289 and 290. Also shown are sites of binding of certain antibodies known in the art, i.e., 6E10, 4G8, G2-10, and G2-11. Antibodies specific for said site may be used for diagnostic and prognostic purposes, which are well known to a skilled artisan.

The recombinant DNA molecules encoding modified β-secretase substrates may be transfected into a cell line that processes APP into Aβ, and stable clones may be generated. Alternatively, the recombinant DNA molecules may be utilized in transient transfections to express the modified β-secretase substrates in transfected cells.

A variety of cells are suitable for use in the methods of the present invention. Particularly preferred are eukaryotic, especially mammalian, cell lines. In particular embodiments, the cells are selected from the group consisting of: L cells L-M(TK$^-$) (ATCC CCL 1.3), L cells L-M (ATCC CCL 1.2), HEK293 (ATCC CRL 1573), HEK293T, Raji (ATCC CCL 86), CV-1 (ATCC CCL 70), COS-1 (ATCC CRL 1650), COS-7 (ATCC CRL 1651), CHO-K1 (ATCC CCL 61), 3T3 (ATCC CCL 92), NIH/3T3 (ATCC CRL 1658), HeLa (ATCC CCL 2), C1271 (ATCC CRL 1616), BS-C-1 (ATCC CCL 26), T24 (ATCC HTB-4), PC12 cells, Jurkat cells, H4 cells (ATCC HTB-148), and MRC-5 (ATCC CCL 171).

To make the assay more amenable for ultra-high throughput screening, a non-adherent cell line, such as Jurkat, can be used.

Generally, the assays of the present invention employ cells that naturally express β-secretase and, optionally, γ-secretase. However, it is possible to practice the invention in cells that lack the expression of one, or both, of these enzymes. In such cases, β-secretase and, if desired, γ-secretase activity can be provided by the recombinant expression of these enzymes in the cells.

In one embodiment, the present invention provides a recombinant cell, preferably a eukaryotic cell, even more preferably a mammalian cell, and most preferably a human cell, where the cell expresses a modified substrate of β-secretase where the modified substrate is a polypeptide comprising the amino acid sequence of APP in the region of the β-secretase cleavage site where the P2-P1-P1'-P2' positions of the β-secretase cleavage site differ from both the wild-type (KMDA (SEQ.ID.NO.:1)) and the Swedish (NLDA ((SEQ.ID.NO.:2)) sequences and the modified substrate is a more efficient substrate for β-secretase than a corresponding polypeptide that has the same amino acid sequence as the modified substrate except that the corresponding polypeptide contains the wild-type sequence at the P2-P1-P1'-P2' positions of the β-secretase cleavage site.

The present invention further provides assays for detecting β-secretase mediated cleavage of peptide substrates such as those exemplified in Table 1 (discussed in Example 4, infra). The methods utilize a reaction system which includes (i) aβ-secretase component and (ii) a substrate component, preferably the invention modified β-secretase substrate molecule, where the β-secretase cleaves the substrate over time to produce cleavage products. Thus, β-secretase activity can be observed and monitored over time as the amount of cleavage product(s) increases. The amount of cleavage product(s) in the reaction system can be measured in a variety of ways, including immunologic, chromatographic, electrophoretic, and the like.

Such β-secretase cleavage detection methods are particularly useful for screening test substances to determine their ability to inhibit β-secretase mediated cleavage of APP. In such cases, a test substance is first identified by the methods described herein using invention polypeptide modified β-secretase substrate molecules. Those test substances that have the ability to inhibit the β-secretase-mediated cleavage of invention polypeptides may be further tested for the ability to inhibit β-secretase-mediated cleavage of wtAPP as confirmatory testing. In general, the test substance is added to a reaction system where the substrate component is modified or wtAPP and the effect of the test substance on production of cleavage product is observed. In certain embodiments, those substances which inhibit the production of cleavage product(s) from modified and wtAPP are considered to be potential therapeutic agents for treatment of conditions associated with increased Aβ production such as Alzheimer's disease.

The reaction system will usually comprise β-secretase that will be either a purified or partially purified native β-secretase obtained from a cellular source. The cellular source may be a recombinant host cell that expresses β-secretase by virtue of having been transfected with an expression vector encoding β-secretase. Alternatively, β-secretase may be obtained from a cellular source that naturally (i.e., non-recombinantly) expresses β-secretase. Such a non-recombinant source could be a cell line having a sufficiently high level of expression of native β-secretase. Such a non-recombinant source could be endogenous β-secretase in animal models. The invention peptide substrate may include any one of the peptides exemplified in Table 2. The peptide substrate may be recombinant or synthetically derived. The reaction system can employ a wide variety of solid phase detection systems which permit observance of the production of β-secretase cleavage products over time or the disappearance of substrate over time. The methods will be particularly useful for determining the ability of test substances to inhibit β-secretase mediated cleavage.

The assay may be performed by combining an at least partially purified β-secretase with at least one invention modified β-secretase substrate or polypeptide in the presence of the test substance. Conditions are maintained such that the β-secretase cleaves the invention peptide substrate into an amino-terminal fragment and a carboxy-terminal fragment in the absence of a substance which inhibits such cleavage. Cleavage of the peptide substrate in the presence of the test substance is compared with that in the absence of the test substance, and those test substances which provide significant inhibition of the cleavage activity (usually at least about 25% inhibition, more usually at least about 50% inhibition, preferably at least about 75% inhibition, and often at least about 90% inhibition or higher) are considered to be β-secretase inhibitors. Such β-secretase inhibitors may then be subjected to further in vitro and/or in vivo testing to determine if they inhibit the production of Aβ in cellular and animal models. As well, the cleavage products thus produced can be purified and used as immunogens to provide for antibodies specific for each of the "amino terminal" and "carboxy terminal" fragments, which, in turn, can be used to identify such fragments in other assays.

It is noted that although most research may be directed to identifying inhibitors of β-secretase, such as described immediately above, the same methods also may be used to identify substances that otherwise modulate the activity of β-secretase. For instance, for certain research, such as that directed to determining the role(s) of specific chemical structures or moieties on a molecule identified as having a role in β-secretase regulation, it may be desirable to identify substances that accelerate β-secretase. Accordingly, the term "modulate" is taken to mean to increase or accelerate and/or to decrease or delay, the catalysis or effect of a particular reaction.

The screening assays of β-secretase and the invention peptide substrate are conveniently performed using "sandwich" assays where the amino-terminal or the carboxy-terminal fragment produced by cleavage is captured on a solid phase. The captured fragment may then be detected using an antibody specific for the end of the fragment exposed by β-secretase cleavage. An exemplary antibody is an antibody raised against any cleavage products produced as a result of β-secretase activity. The binding of the antibody to the cleaved cleavage product is detected using conventional labeling systems, such as horseradish peroxidase or other detectable enzyme labels, which are bound to the antibody directly (covalently), or indirectly through intermediate linking substances, such as biotin and avidin. Such "sandwich" assay can be performed in various formats. For example, IGEN based technology, HTRF, Alpha Screen technology, and other technologies known to those of ordinary skill in the art.

In cells or animal models, following β-secretase cleavage, the carboxy-terminal fragment of modified β-secretase substrate described in this patent, βCTF with modified β-cleavage P1' and P2' sites, can be further processed to generate various Aβ peptides. These Aβ peptides with modified β-cleavage P1' and P2' sites secreted in the media or body fluid can be detected by "sandwich" assays using an antibody specific for the N-terminal end of the modified Aβ peptides and an antibody specific for the C-terminal end of the modified Aβ peptides. The antibody specific for the N-terminal end of the modified Aβ peptides can be those that recognize any of the modifications described in this application, such as "EVEFR". The antibody specific for the C-terminal end of the modified Aβ peptides can be those that recognize Aβ peptide species ending after the amino acid residues 29, including 34, 37, 38, 39, 40, 42, 43 or 49.

Also, peptide aptamers or single chain monoclonal antibodies identified using phage display technologies that specifically bind to either the carboxyl terminal (e.g., —NF—COOH) or amino terminal (e.g., NH2-EV) neo epitopes generated by BACE cleavage of any of the modified BACE substrates can be prepared and used in an assay in which these novel epitopes are generated. Methods for identifying peptide aptamers that specifically bind to a protein of interest are described in the scientific literature. Essentially, a library of filamentous phage containing an insertion of random nucleotide sequences of a fixed length in the gene for the pIII or pVIII coat protein. Transformation of bacteria with this phage library leads to expression of the phage, which display the altered protein. A target molecule that is biotinylated, or labeled in such a manner that it can be captured by a bead, or affixed to a surface, may then be used to capture phage displaying a coat protein that contains a specific sequence capable of binding the target molecule. See, for example, Smith, G. P, Science (1985) 228:1315–1317; Scott, J. K., and Smith, G. P., Science (1990) 249: 386–390; and Cwirla, S. E., et al., Proc. Acad. Sci. U.S.A., (1990) 87:6378–6382. The affinity of peptides that are identified as binding one of the cleavage products of BACE cleavage of APP using this technology can be improved by affinity maturation procedures. Additionally, higher affinity binding proteins may be identified by screening a phage library that expresses single chain antibodies. These technologies are described in Abelson, J. N. (ed) Methods in Enzymology (1996) vol. 267, pp. 3–149, Academic Press and in Barbas, C. F. et al., Phage Display: A laboratory Manual (2001) Cold Spring Harbor Laboratory Press. Thus, apatamers or single chain antibodies that are specific to novel epitopes based on the novel endings formed by β-secretase cleavage of the modified β-secretase substrates of the present invention are considered part of the invention described herein.

Pharmaceutical Compositions and Therapeutic Methods

The present invention further comprises methods for inhibiting the β-secretase mediated cleavage of APP to APP cleavage products in cells, where the method comprises administering to the cells substances selected by the method described herein. The substances may be added to cell culture in order to inhibit APP cleavage which results in Aβ production. The substances may also be administered to a patient in order to inhibit β-secretase mediated APP cleavage which results in pathogenic Aβ production and the deposition of amyloid β-plaque associated with Alzheimer's Disease and other Aβ-related conditions.

The present invention further comprises pharmaceutical compositions incorporating a substance selected by the herein-described methods and including a pharmaceutically acceptable carrier. Such pharmaceutical compositions should contain a therapeutic or prophylactic amount of at least one substance identified by the method of the present invention. The pharmaceutically acceptable carrier can be any compatible, non-toxic substance suitable to deliver the substances to an intended host. Sterile water, alcohol, fats, waxes, and inert solids may be used as the carrier. Pharmaceutically acceptable adjuvants, buffering agents, dispersing agents, and the like may also be incorporated into the pharmaceutical compositions. Preparation of pharmaceutical conditions incorporating active agents is well described in the medical and scientific literature. See, for example, Remington's Pharmaceutical Sciences, Mack Publishing Company, Easton, Pa., 16th Ed., 1982, the disclosures of which are incorporated herein by reference.

Frequently, it will be desirable or necessary to introduce the pharmaceutical compositions directly or indirectly to the brain. Direct techniques usually involve placement of a drug delivery catheter into the host's ventricular system to bypass the blood-brain barrier. Indirect techniques, which are generally preferred, involve formulating the compositions to provide for drug latentiation by the conversion of hydrophilic drugs into lipid-soluble drugs. Latentiation is generally achieved through blocking of the hydroxyl, carboxyl, and primary amine groups present on the drug to render the drug more lipid-soluble and amenable to transportation across the blood-brain barrier. Alternatively, the delivery of hydrophilic drugs can be enhanced by intra-arterial infusion of hypertonic solutions which can transiently open the blood-brain barrier.

The concentration of the substance in the pharmaceutical carrier may vary widely, i.e., from less than about 0.1% by weight of the pharmaceutical composition to about 20% by weight, or greater. Typical pharmaceutical composition for intramuscular injection would be made up to contain, for example, one to four ml of sterile buffered water and one μg to one mg of a substance identified by the methods of the present invention. A typical composition for intravenous infusion could be made up to contain 100 to 500 ml of sterile Ringer's solution and about 1 to 100 mg of the substance.

The pharmaceutical compositions of the present invention can be administered for prophylactic and/or therapeutic treatment of diseases related to the deposition of Aβ, such as Alzheimer's disease, Down's syndrome, and advanced aging of the brain. In therapeutic applications, the pharmaceutical compositions are administered to a subject in need thereof already suffering from the disease. The pharmaceutical compositions will be administered in an amount sufficient to inhibit further neurodegeneration or deposition and/or accumulation of Aβ peptides. An amount adequate to accomplish any of these is a "therapeutically effective dose" for that respective result of a treatment or treatment regime. Such a therapeutically effective dose will depend on the extent of the disease, the size of the host, and the like, but will generally range from about 1 μg to 100 mg of the substance per kilogram of body weight of the host, with dosages of 10 μg to 1 mg/kg being more commonly employed.

For prophylactic applications, the pharmaceutical compositions of the present invention are administered to a host susceptible to the Aβ-related disease, but not already suffering from such disease. Such hosts may be identified by genetic screening and clinical analysis, as described in the medical literature (e.g. Goate, 1991, Nature 349:704–706). The pharmaceutical compositions will be able to inhibit neurodegeneration or prevent deposition of Aβ plaque at a symptomatically early stage, preferably preventing even the initial stages of the β-amyloid disease. The amount of the substance required for such prophylactic treatment, referred to as a prophylactically effective dosage, is generally the same as described above for therapeutic treatment.

In certain embodiments, the modified β-secretase substrate is a polypeptide comprising the following amino acids derived from APP in the region of the β-secretase cleavage site:

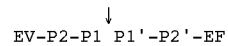

EV-P2-P1 P1'-P2'-EF where the above represents positions 593–600 of $APP_{695}$ and the arrow indicates the β-secretase cleavage site;

where P2-P1-P1'-P2' is selected from the group consisting of:

| | |
|---|---|
| NFEV; | (SEQ.ID.NO.:3) |
| NFDA; | (SEQ.ID.NO.:4) |
| NFEA; | (SEQ.ID.NO.:5) |
| NLEA; | (SEQ.ID.NO.:6) |
| NLDV; | (SEQ.ID.NO.:7) |
| NFDV; | (SEQ.ID.NO.:8) |
| NFTV; | (SEQ.ID.NO.:9) |
| NYDA; | (SEQ.ID.NO.:10) |
| NYEA; | (SEQ.ID.NO.:11) |
| NYDV; | (SEQ.ID.NO.:12) |
| FFAV; | (SEQ.ID.NO.:13) |
| FFEV; | (SEQ.ID.NO.:14) |
| NLAA; | (SEQ.ID.NO.:15) |
| NFAA; | (SEQ.ID.NO.:16) |
| NYAA; | (SEQ.ID.NO.:17) |
| KFAA; | (SEQ.ID.NO.:18) |
| KMAA; | (SEQ.ID.NO.:19) |
| KMDV; | (SEQ.ID.NO.:20) |
| KFEA; | (SEQ.ID.NO.:21) |
| KYAA; and | (SEQ.ID.NO.:22) |
| NFAV. | (SEQ.ID.NO.:23) |

In other embodiments, the modified β-secretase substrate is a polypeptide comprising the following amino acids derived from APP in the region of the β-secretase cleavage site:

EV-P2-P1 P1'-P2'-EF where the above represents positions 593–600 of $APP_{695}$ and the arrow indicates the β-secretase cleavage site;
where P2 is selected from the group consisting of: N, K, and F;
where P1 is selected from the group consisting of: F, L, Y, and M;
where P1' is selected from the group consisting of: E, D, and A; and
where P2' is selected from the group consisting of: V and A;
with the proviso that P2, P1, P1', and P2' are not selected such that P2-P1-P1'-P2' is KMDA (SEQ.ID.NO.:1), NLDA (SEQ.ID.NO.:2), KYAA (SEQ.ID.NO.:22), NFAV (SEQ.ID.NO.:23), KMEA (SEQ.ID.NO.:47), KFDA (SEQ.ID.NO.:48), KLDA (SEQ.ID.NO.:49), KYDA (SEQ.ID.NO.:50), or NMDA (SEQ.ID.NO.:51).

In certain embodiments, the modified β-secretase substrate is a polypeptide comprising the following amino acids derived from APP in the region of the β-secretase cleavage site:

EV-P2-P1 P1'-P2'-EF where the above represents positions 593–600 of $APP_{695}$ and the arrow indicates the β-secretase cleavage site; and where the polypeptide results in at least five times more Aβ being produced when expressed in HEK293T cells than a corresponding polypeptide having the sequence EVKMDAEF (SEQ.ID.NO.:52) instead of EV-P2-P1-P1'-P2'-EF, wherein P2-P1-P1'-P2' is selected from the group consisting of:

| | |
|---|---|
| NFEV; | (SEQ.ID.NO.:3) |
| NLEA; and | (SEQ.ID.NO.:6) |
| NLDV. | (SEQ.ID.NO.:7) |

In other embodiments, the modified β-secretase substrate is a polypeptide comprising the following amino acids derived from APP in the region of the β-secretase cleavage site:

EV-P2-P1 P1'-P2'-EF where the above represents positions 593–600 of $APP_{695}$ and the arrow indicates the β-secretase cleavage site; and where the polypeptide results in at least five times more Aβ being produced when expressed in HEK293T cells than a corresponding polypeptide having the sequence EVKMDAEF (SEQ.ID.NO.:52) instead of EV-P2-P1-P1'-P2'-EF, and where P2 is N;
where P1 is selected from the group consisting of: F and L;
where P1' is selected from the group consisting of: E and D; and
where P2' is selected from the group consisting of: V and A;
with the proviso that P2, P1, P1', and P2' are not selected such that P2-P1-P1'-P2' is NLDA (SEQ.ID.NO.:2).

In certain embodiments, the modified β-secretase substrate is a polypeptide comprising the following amino acids derived from APP in the region of the β-secretase cleavage site:

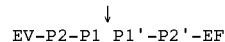
EV-P2-P1 P1'-P2'-EF where the above represents positions 593–600 of $APP_{695}$ and the arrow indicates the β-secretase cleavage site; where the polypeptide results in at least ten times more Aβ being produced when expressed in HEK293T cells than a corresponding polypeptide having the sequence EVKMDAEF (SEQ.ID.NO.:52) instead of EV-P2-P1-P1'-P2'-EF, and where P2-P1-P1'-P2' is selected from the group consisting of:

| | |
|---|---|
| NFEV; and | (SEQ.ID.NO.:3) |
| NLDV. | (SEQ.ID.NO.:7) |

In other embodiments, the modified β-secretase substrate is a polypeptide comprising the following amino acids derived from APP in the region of the β-secretase cleavage site:

EV-P2-P1 P1'-P2'-EF where the above represents positions 593–600 of $APP_{695}$ and the arrow indicates the β-secretase cleavage site; where the polypeptide results in at least ten times more Aβ being produced when expressed in HEK293T cells than a corresponding polypeptide having the sequence EVKMDAEF (SEQ.ID.NO.:52) instead of EV-P2-P1-P1'-P2'-EF, and where P2 is N;
where P1 is selected from the group consisting of: F and L;
where P1' is selected from the group consisting of: E and D; and
where P2' is V;
with the proviso that P2, P1, P1', and P2' are not selected such that P2-P1-P1'-P2' is NLDA (SEQ.ID.NO.:2).

In certain embodiments, the modified β-secretase substrate is a polypeptide comprising the following amino acids derived from APP in the region of the β-secretase cleavage site:

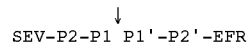
SEV-P2-P1 P1'-P2'-EFR where the above represents positions 592–601 of $APP_{695}$ and the arrow indicates the β-secretase cleavage site;
where P2-P1-P1'-P2' is selected from the group consisting of:

| | |
|---|---|
| NFEV; | (SEQ.ID.NO.:3) |
| NFDA; | (SEQ.ID.NO.:4) |
| NFEA; | (SEQ.ID.NO.:5) |
| NLEA; | (SEQ.ID.NO.:6) |
| NLDV; | (SEQ.ID.NO.:7) |
| NFDV; | (SEQ.ID.NO.:8) |
| NFTV; | (SEQ.ID.NO.:9) |

```
        NYDA;         (SEQ.ID.NO.:10)
        NYEA;         (SEQ.ID.NO.:11)
        NYDV;         (SEQ.ID.NO.:12)
        FFAV;         (SEQ.ID.NO.:13)
        FFEV;         (SEQ.ID.NO.:14)
        NLAA;         (SEQ.ID.NO.:15)
        NFAA;         (SEQ.ID.NO.:16)
        NYAA;         (SEQ.ID.NO.:17)
        KFAA;         (SEQ.ID.NO.:18)
        KMAA;         (SEQ.ID.NO.:19)
        KMDV;         (SEQ.ID.NO.:20)
        KFEA;         (SEQ.ID.NO.:21)
        KYAA; and     (SEQ.ID.NO.:22)
        NFAV.         (SEQ.ID.NO.:23)
```

In other embodiments, the modified β-secretase substrate is a polypeptide comprising the following amino acids derived from APP in the region of the β-secretase cleavage site:

$$\text{SEV-P2-P1}\downarrow\text{P1'-P2'-EFR}$$

where the above represents positions 592–601 of $APP_{695}$ and the arrow indicates the β-secretase cleavage site;
where P2 is selected from the group consisting of: N, K, and F;
where P1 is selected from the group consisting of: F, L, Y, and M;
where P1' is selected from the group consisting of: E, D, and A;
where P2' is selected from the group consisting of: V and A;

with the proviso that P2, P1, P1', and P2' are not selected such that P2-P1-P1'-P2' is KMDA (SEQ.ID.NO.:1), NLDA (SEQ.ID.NO.:2), KYAA (SEQ.ID.NO.:22), NFAV (SEQ.ID.NO.:23), KMEA (SEQ.ID.NO.:47), KFDA (SEQ.ID.NO.:48), KLDA (SEQ.ID.NO.:49), KYDA (SEQ.ID.NO.:50), or NMDA (SEQ.ID.NO.:51).

In certain embodiments, the modified β-secretase substrate is a polypeptide comprising the following amino acids derived from APP in the region of the β-secretase cleavage site:

$$\text{SEV-P2-P1}\downarrow\text{P1'-P2'-EFR}$$

where the above represents positions 593–600 of $APP_{695}$ and the arrow indicates the β-secretase cleavage site; where the polypeptide results in at least five times more Aβ being produced when expressed in HEK293T cells than a corresponding polypeptide having the sequence SEVKMDAEFR (SEQ.ID.NO.:53) instead of SEV-P2-P1-P1'-P2'-EFR, and where P2-P1-P1'-P2' is selected from the group consisting of:

```
        NFEV;         (SEQ.ID.NO.:3)
        NLEA; and     (SEQ.ID.NO.:6)
        NLDV.         (SEQ.ID.NO.:7)
```

In other embodiments, the modified β-secretase substrate is a polypeptide comprising the following amino acids derived from APP in the region of the β-secretase cleavage site:

$$\text{SEV-P2-P1}\downarrow\text{P1'-P2'-EFR}$$

where the above represents positions 593–600 of $APP_{695}$ and the arrow indicates the β-secretase cleavage site; where the polypeptide results in at least five times more Aβ being produced when expressed in HEK293T cells than a corresponding polypeptide having the sequence SEVKMDAEFR (SEQ.ID.NO.:53) instead of SEV-P2-P1-P1'-P2'-EFR, and where P2 is N;
where P1 is selected from the group consisting of: F and L;
where P1' is selected from the group consisting of: E and D; and
where P2' is selected from the group consisting of: V and A;

with the proviso that P2, P1, P1', and P2' are not selected such that P2-P1-P1'-P2' is NLDA (SEQ.ID.NO.:2).

In certain embodiments, the modified β-secretase substrate is a polypeptide comprising the following amino acids derived from APP in the region of the β-secretase cleavage site:

$$\text{SEV-P2-P1}\downarrow\text{P1'-P2'-EFR}$$

where the above represents positions 593–600 of $APP_{695}$ and the arrow indicates the β-secretase cleavage site; where the polypeptide results in at least ten times more Aβ being produced when expressed in HEK293T cells than a corresponding polypeptide having the sequence SEVKMDAEFR (SEQ.ID.NO.:53) instead of SEV-P2-P1-P1'-P2'-EFR, and where P2-P1-P1'-P2' is selected from the group consisting of:

```
        NFEV; and     (SEQ.ID.NO.:3)
        NLDV.         (SEQ.ID.NO.:7)
```

In other embodiments, the modified β-secretase substrate is a polypeptide comprising the following amino acids derived from APP in the region of the β-secretase cleavage site:

$$\text{SEV-P2-P1}\downarrow\text{P1'-P2'-EFR}$$

where the above represents positions 593–600 of $APP_{695}$ and the arrow indicates the β-secretase cleavage site; where the polypeptide results in at least ten times more Aβ being produced when expressed in HEK293T cells than a corresponding polypeptide having the sequence SEVKMDAEFR (SEQ.ID.NO.:53) instead of SEV-P2-P1-P1'-P2'-EFR, and where P2 is N;
where P1 is selected from the group consisting of: F and L;
where P1' is selected from the group consisting of: E and D; and
where P2' is V;

with the proviso that P2, P1, P1', and P2' are not selected such that P2-P1-P1'-P2' is NLDA (SEQ.ID.NO.:2).

In certain embodiments, the modified β-secretase substrate is a polypeptide comprising the following amino acids derived from APP in the region of the β-secretase cleavage site:

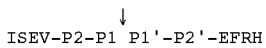
ISEV-P2-P1 P1'-P2'-EFRH where the above represents positions 591–602 of $APP_{695}$ and the arrow indicates the β-secretase cleavage site; and where P2-P1-P1'-P2' is selected from the group consisting of:

| | |
|---|---|
| NFEV; | (SEQ.ID.NO.:3) |
| NFDA; | (SEQ.ID.NO.:4) |
| NFEA; | (SEQ.ID.NO.:5) |
| NLEA; | (SEQ.ID.NO.:6) |
| NLDV; | (SEQ.ID.NO.:7) |
| NFDV; | (SEQ.ID.NO.:8) |
| NFTV; | (SEQ.ID.NO.:9) |
| NYDA; | (SEQ.ID.NO.:10) |
| NYEA; | (SEQ.ID.NO.:11) |
| NYDV; | (SEQ.ID.NO.:12) |
| FFAV; | (SEQ.ID.NO.:13) |
| FFEV; | (SEQ.ID.NO.:14) |
| NLAA; | (SEQ.ID.NO.:15) |
| NFAA; | (SEQ.ID.NO.:16) |
| NYAA; | (SEQ.ID.NO.:17) |
| KFAA; | (SEQ.ID.NO.:18) |
| KMAA; | (SEQ.ID.NO.:19) |
| KMDV; | (SEQ.ID.NO.:20) |
| KFEA; | (SEQ.ID.NO.:21) |
| KYAA; and | (SEQ.ID.NO.:22) |
| NFAV. | (SEQ.ID.NO.:23) |

In other embodiments, the modified β-secretase substrate is a polypeptide comprising the following amino acids derived from APP in the region of the β-secretase cleavage site:

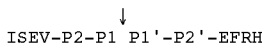
ISEV-P2-P1 P1'-P2'-EFRH where the above represents positions 591–602 of $APP_{695}$ and the arrow indicates the β-secretase cleavage site; and
where P2 is selected from the group consisting of: N, K, and F;
where P1 is selected from the group consisting of: F, L, Y, and M;
where P1' is selected from the group consisting of: E, D, and A; and
where P2' is selected from the group consisting of: V and A;
with the proviso that P2, P1, P1', and P2' are not selected such that P2-P1-P1'-P2' is KMDA (SEQ.ID.NO.:1), NLDA (SEQ.ID.NO.:2), KYAA (SEQ.ID.NO.:22), NFAV (SEQ.ID.NO.:23), KMEA (SEQ.ID.NO.:47), KFDA (SEQ.ID.NO.:48), KLDA (SEQ.ID.NO.:49), KYDA (SEQ.ID.NO.:50), or NMDA (SEQ.ID.NO.:51).

In certain embodiments, the modified β-secretase substrate is a polypeptide comprising the following amino acids derived from APP in the region of the β-secretase cleavage site:

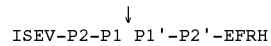
ISEV-P2-P1 P1'-P2'-EFRH where the above represents positions 593–600 of $APP_{695}$ and the arrow indicates the β-secretase cleavage site; where the polypeptide results in at least five times more Aβ being produced when expressed in HEK293T cells than a corresponding polypeptide having the sequence ISEVKMDAEFRH (SEQ.ID.NO.:54) instead of ISEV-P2-P1-P1'-P2'-EFRH, and
where P2-P1-P1'-P2' is selected from the group consisting of:

| | |
|---|---|
| NFEV; | (SEQ.ID.NO.:3) |
| NLEA; and | (SEQ.ID.NO.:6) |
| NLDV. | (SEQ.ID.NO.:7) |

In other embodiments, the modified β-secretase substrate is a polypeptide comprising the following amino acids derived from APP in the region of the β-secretase cleavage site:

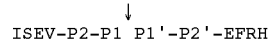
ISEV-P2-P1 P1'-P2'-EFRH where the above represents positions 593–600 of $APP_{695}$ and the arrow indicates the β-secretase cleavage site; where the polypeptide results in at least five times more Aβ being produced when expressed in HEK293T cells than a corresponding polypeptide having the sequence ISEVKMDAEFRH (SEQ.ID.NO.:54) instead of ISEV-P2-P1-P1'-P2'-EFRH, and
where P2 is N;
where P1 is selected from the group consisting of: F and L;
where P1' is selected from the group consisting of: E and D; and
where P2' is selected from the group consisting of: V and A;
with the proviso that P2, P1, P1', and P2' are not selected such that P2-P1-P1'-P2' is NLDA (SEQ.ID.NO.:2).

In certain embodiments, the modified β-secretase substrate is a polypeptide comprising the following amino acids derived from APP in the region of the β-secretase cleavage site:

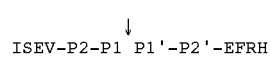
ISEV-P2-P1 P1'-P2'-EFRH where the above represents positions 593–600 of $APP_{695}$ and the arrow indicates the β-secretase cleavage site;

where the polypeptide results in at least ten times more Aβ being produced when expressed in HEK293T cells than a corresponding polypeptide having the sequence ISEVKMDAEFRH (SEQ.ID.NO.:54) instead of ISEV-P2-P1-P1'-P2'-EFRH, and where P2-P1-P1'-P2' is selected from the group consisting of:

```
NFEV; and       (SEQ.ID.NO.:3)
NLDV.           (SEQ.ID.NO.:7)
```

In other embodiments, the modified β-secretase substrate is a polypeptide comprising the following amino acids derived from APP in the region of the β-secretase cleavage site:

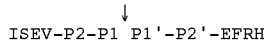
ISEV-P2-P1 P1'-P2'-EFRH where the above represents positions 593–600 of APP$_{695}$ and the arrow indicates the β-secretase cleavage site; where the polypeptide results in at least ten times more Aβ being produced when expressed in HEK293T cells than a corresponding polypeptide having the sequence ISEVKMDAE-FRH (SEQ.ID.NO.:54) instead of ISEV-P2-P1-P1'-P2'-EFRH, and
where P2 is N;
where P1 is selected from the group consisting of: F and L;
where P1' is selected from the group consisting of: E and D; and
where P2' is V;
with the proviso that P2, P1, P1', and P2' are not selected such that P2-P1-P1'-P2' is NLDA (SEQ.ID.NO.:2).

In certain embodiments, the modified β-secretase substrate is a polypeptide comprising the following amino acids derived from APP in the region of the β-secretase cleavage site:

EISEV-P2-P1 P1'-P2'-EFRHD where the above represents positions 590–603 of APP$_{695}$ and the arrow indicates the β-secretase cleavage site;
where P2-P1-P1'-P2' is selected from the group consisting of:

```
NFEV;           (SEQ.ID.NO.:3)
NFDA;           (SEQ.ID.NO.:4)
NFEA;           (SEQ.ID.NO.:5)
NLEA;           (SEQ.ID.NO.:6)
NLDV;           (SEQ.ID.NO.:7)
NFDV;           (SEQ.ID.NO.:8)
NFTV;           (SEQ.ID.NO.:9)
NYDA;           (SEQ.ID.NO.:10)
NYEA;           (SEQ.ID.NO.:11)
NYDV;           (SEQ.ID.NO.:12)
FFAV;           (SEQ.ID.NO.:13)
FFEV;           (SEQ.ID.NO.:14)
NLAA;           (SEQ.ID.NO.:15)
NFAA;           (SEQ.ID.NO.:16)
NYAA;           (SEQ.ID.NO.:17)
KFAA;           (SEQ.ID.NO.:18)
KMAA;           (SEQ.ID.NO.:19)
KMDV;           (SEQ.ID.NO.:20)
KFEA;           (SEQ.ID.NO.:21)
KYAA; and       (SEQ.ID.NO.:22)
NFAV.           (SEQ.ID.NO.:23)
```

In other embodiments, the modified β-secretase substrate is a polypeptide comprising the following amino acids derived from APP in the region of the β-secretase cleavage site:

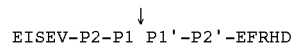
EISEV-P2-P1 P1'-P2'-EFRHD where the above represents positions 590–603 of APP$_{695}$ and the arrow indicates the β-secretase cleavage site;
where P2 is selected from the group consisting of: N, K, and F;
where P1 is selected from the group consisting of: F, L, Y, and M;
where P1' is selected from the group consisting of: E, D, and A; and
where P2' is selected from the group consisting of: V and A;
with the proviso that P2, P1, P1', and P2' are not selected such that P2-P1-P1'-P2' is KMDA (SEQ.ID.NO.:1), NLDA (SEQ.ID.NO.:2), KYAA (SEQ.ID.NO.:22), NFAV (SEQ.ID.NO.:23), KMEA (SEQ.ID.NO.:47), KFDA (SEQ.ID.NO.:48), KLDA (SEQ.ID.NO.:49), KYDA (SEQ.ID.NO.:50), or NMDA (SEQ.ID.NO.:51).

In certain embodiments, the modified β-secretase substrate is a polypeptide comprising the following amino acids derived from APP in the region of the β-secretase cleavage site:

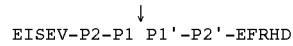
EISEV-P2-P1 P1'-P2'-EFRHD where the above represents positions 593–600 of APP$_{695}$ and the arrow indicates the β-secretase cleavage site;
where the polypeptide results in at least five times more Aβ being produced when expressed in HEK293T cells than a corresponding polypeptide having the sequence EISEVK-MDAEFRHD (SEQ.ID.NO.:55) instead of EISEV-P2-P1-P1'-P2'-EFRHD,
where P2-P1-P1'-P2' is selected from the group consisting of:

```
NFEV;           (SEQ.ID.NO.:3)
NLEA; and       (SEQ.ID.NO.:6)
NLDV.           (SEQ.ID.NO.:7)
```

In other embodiments, the modified β-secretase substrate is a polypeptide comprising the following amino acids derived from APP in the region of the β-secretase cleavage site:

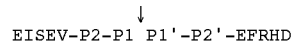
EISEV-P2-P1 P1'-P2'-EFRHD where the above represents positions 593–600 of APP$_{695}$ and the arrow indicates the β-secretase cleavage site;

where the polypeptide results in at least five times more Aβ being produced when expressed in HEK293T cells than a corresponding polypeptide having the sequence EISEVK-MDAEFRHD (SEQ.ID.NO.:55) instead of EISEV-P2-P1-P1'-P2'-EFRHD,
where P2 is N;
where P1 is selected from the group consisting of: F and L;
where P1' is selected from the group consisting of: E and D; and
where P2' is selected from the group consisting of: V and A;
with the proviso that P2, P1, P1', and P2' are not selected such that P2-P1-P1'-P2' is NLDA (SEQ.ID.NO.:2).

In certain embodiments, the modified β-secretase substrate is a polypeptide comprising the following amino acids derived from APP in the region of the β-secretase cleavage site:

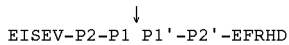
EISEV-P2-P1 P1'-P2'-EFRHD where the above represents positions 593–600 of APP$_{695}$ and the arrow indicates the β-secretase cleavage site;

where the polypeptide results in at least ten times more Aβ being produced when expressed in HEK293T cells than a corresponding polypeptide having the sequence EISEVK-MDAEFRHD (SEQ.ID.NO.:55) instead of EISEV-P2-P1-P1'-P2'-EFRHD,
where P2-P1-P1'-P2' is selected from the group consisting of:

| | |
|---|---|
| NFEV; and | (SEQ.ID.NO.:3) |
| NLDV. | (SEQ.ID.NO.:7) |

In other embodiments, the modified β-secretase substrate is a polypeptide comprising the following amino acids derived from APP in the region of the β-secretase cleavage site:

EISEV-P2-P1 P1'-P2'-EFRHD where the above represents positions 593–600 of APP$_{695}$ and the arrow indicates the β-secretase cleavage site;

where the polypeptide results in at least ten times more Aβ being produced when expressed in HEK293T cells than a corresponding polypeptide having the sequence EISEVK-MDAEFRHD (SEQ.ID.NO.:55) instead of EISEV-P2-P1-P1'-P2'-EFRHD,
where P2 is N;
where P1 is selected from the group consisting of: F and L;
where P1' is selected from the group consisting of: E and D; and
where P2' is V;
with the proviso that P2, P1, P1', and P2' are not selected such that P2-P1-P1'-P2' is NLDA (SEQ.ID.NO.:2).

In certain embodiments, the modified β-secretase substrate is a polypeptide comprising the following amino acids derived from APP in the region of the β-secretase cleavage site:

EEISEV-P2-P1 P1'-P2'-EFRHDS where the above represents positions 589–604 of APP$_{695}$ and the arrow indicates the β-secretase cleavage site;
where P2-P1-P1'-P2' is selected from the group consisting of:

| | |
|---|---|
| NFEV; | (SEQ.ID.NO.:3) |
| NFDA; | (SEQ.ID.NO.:4) |
| NFEA; | (SEQ.ID.NO.:5) |
| NLEA; | (SEQ.ID.NO.:6) |
| NLDV; | (SEQ.ID.NO.:7) |
| NFDV; | (SEQ.ID.NO.:8) |
| NFTV; | (SEQ.ID.NO.:9) |
| NYDA; | (SEQ.ID.NO.:10) |
| NYEA; | (SEQ.ID.NO.:11) |
| NYDV; | (SEQ.ID.NO.:12) |
| FFAV; | (SEQ.ID.NO.:13) |
| FFEV; | (SEQ.ID.NO.:14) |
| NLAA; | (SEQ.ID.NO.:15) |
| NFAA; | (SEQ.ID.NO.:16) |
| NYAA; | (SEQ.ID.NO.:17) |
| KFAA; | (SEQ.ID.NO.:18) |
| KMAA; | (SEQ ID.NO.:19) |
| KMDV; | (SEQ.ID.NO.:20) |
| KFEA; | (SEQ.ID.NO.:21) |
| KYAA; and | (SEQ.ID.NO.:22) |
| NFAV. | (SEQ.ID.NO.:23) |

In other embodiments, the modified β-secretase substrate is a polypeptide comprising the following amino acids derived from APP in the region of the β-secretase cleavage site:

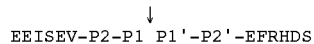
EEISEV-P2-P1 P1'-P2'-EFRHDS where the above represents positions 589–604 of APP$_{695}$ and the arrow indicates the β-secretase cleavage site;
where P2 is selected from the group consisting of: N, K, and F;
where P1 is selected from the group consisting of: F, L, Y, and M;
where P1' is selected from the group consisting of: E, D, and A; and
where P2' is selected from the group consisting of: V and A;

with the proviso that P2, P1, P1', and P2' are not selected such that P2-P1-P1'-P2' is KMDA (SEQ.ID.NO.:1), NLDA (SEQ.ID.NO.:2), KYAA (SEQ.ID.NO.:22), NFAV (SEQ.ID.NO.:23), KMEA (SEQ.ID.NO.:47), KFDA (SEQ.ID.NO.:48), KLDA (SEQ.ID.NO.:49), KYDA (SEQ.ID.NO.:50), or NMDA (SEQ.ID.NO.:51).

In certain embodiments, the modified β-secretase substrate is a polypeptide comprising the following amino acids derived from APP in the region of the β-secretase cleavage site:

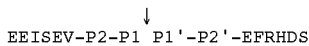

where the above represents positions 593–600 of APP$_{695}$ and the arrow indicates the β-secretase cleavage site;

where the polypeptide results in at least five times more Aβ being produced when expressed in HEK293T cells than a corresponding polypeptide having the sequence EEISEVK-MDAEFRHDS (SEQ.ID.NO.:56) instead of EEISEV-P2-P1-P1'-P2'-EFRHDS, where P2-P1-P1'-P2' is selected from the group consisting of:

| NFEV; | (SEQ.ID.NO.:3) |
| NLEA; and | (SEQ.ID.NO.:6) |
| NLDV. | (SEQ.ID.NO.:7) |

In other embodiments, the modified β-secretase substrate is a polypeptide comprising the following amino acids derived from APP in the region of the β-secretase cleavage site:

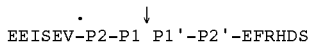

where the above represents positions 593–600 of APP$_{695}$ and the arrow indicates the β-secretase cleavage site;

where the polypeptide results in at least five times more Aβ being produced when expressed in HEK293T cells than a corresponding polypeptide having the sequence EEISEVK-MDAEFRHDS (SEQ.ID.NO.:56) instead of EEISEV-P2-P1-P1'-P2'-EFRHDS, where P2 is N;
where P1 is selected from the group consisting of: F and L;
where P1' is selected from the group consisting of: E and D; and
where P2' is selected from the group consisting of: V and A;

with the proviso that P2, P1, P1', and P2' are not selected such that P2-P1-P1'-P2' is NLDA (SEQ.ID.NO.:2).

In certain embodiments, the modified β-secretase substrate is a polypeptide comprising the following amino acids derived from APP in the region of the β-secretase cleavage site:

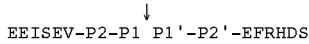

where the above represents positions 593–600 of APP$_{695}$ and the arrow indicates the β-secretase cleavage site;

where the polypeptide results in at least ten times more Aβ being produced when expressed in HEK293T cells than a corresponding polypeptide having the sequence EEISEVK-MDAEFRHDS (SEQ.ID.NO.:56) instead of EEISEV-P2-P1-P1'-P2'-EFRHDS, where P2-P1-P1'-P2' is selected from the group consisting of:

| NFEV; and | (SEQ.ID.NO.:3) |
| NLDV. | (SEQ.ID.NO.:7) |

In other embodiments, the modified β-secretase substrate is a polypeptide comprising the following amino acids derived from APP in the region of the β-secretase cleavage site:

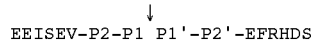

where the above represents positions 593–600 of APP$_{695}$ and the arrow indicates the β-secretase cleavage site;

where the polypeptide results in at least ten times more Aβ being produced when expressed in HEK293T cells than a corresponding polypeptide having the sequence EEISEVK-MDAEFRHDS (SEQ.ID.NO.:56) instead of EEISEV-P2-P1-P1'-P2'-EFRHDS, where P2 is N;
where P1 is selected from the group consisting of: F and L;
where P1' is selected from the group consisting of: E and D; and
where P2' is V;

with the proviso that P2, P1, P1', and P2' are not selected such that P2-P1-P1'-P2' is NLDA (SEQ.ID.NO.:2).

In certain embodiments, the modified β-secretase substrate is a polypeptide comprising the following amino acids derived from APP that include the region of the β-secretase cleavage site, the APP transmembrane region, and the region of the γ-secretase cleavage site:

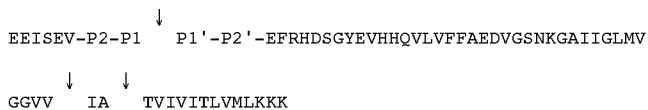

where the above represents positions 589–651 of APP$_{695}$ and the first arrow indicates the β-secretase cleavage site while the second two arrows indicate the predominant sites of γ-secretase cleavage;

where the above contains the K612V change;

where P2-P1-P1'-P2' is selected from the group consisting of:

| NFEV; | (SEQ.ID.NO.:3) |
| NFDA; | (SEQ.ID.NO.:4) |
| NFEA; | (SEQ.ID.NO.:5) |
| NLEA; | (SEQ.ID.NO.:6) |
| NLDV; | (SEQ.ID.NO.:7) |
| NFDV; | (SEQ.ID.NO.:8) |
| NFTV; | (SEQ.ID.NO.:9) |
| NYDA; | (SEQ.ID.NO.:10) |

```
NYEA;             (SEQ.ID.NO.:11)
NYDV;             (SEQ.ID.NO.:12)
FFAV;             (SEQ.ID.NO.:13)
FFEV;             (SEQ.ID.NO.:14)
NLAA;             (SEQ.ID.NO.:15)
NFAA;             (SEQ.ID.NO.:16)
NYAA;             (SEQ.ID.NO.:17)
KFAA;             (SEQ.ID.NO.:18)
KMAA;             (SEQ ID.NO.:19)
KMDV;             (SEQ.ID.NO.:20)
KFEA;             (SEQ.ID.NO.:21)
KYAA; and         (SEQ.ID.NO.:22)
NFAV.             (SEQ.ID.NO.:23)
```

In other embodiments, the modified β-secretase substrate is a polypeptide comprising the following amino acids derived from APP that include the region of the β-secretase cleavage site, the APP transmembrane region, and the region of the γ-secretase cleavage site:

```
                ↓
EEISEV-P2-P1  P1'-P2'-EFRHDSGYEVHHQVLVFFAEDVGSNKGAIIGLMV

↓    ↓
GGVV  IA   TVIVITLVMLKKK
``` where the above represents positions 589–651 of $APP_{695}$ and the first arrow indicates the β-secretase cleavage site while the second two arrows indicate the predominant sites of γ-secretase cleavage;
where the above contains the K612V change;
where P2 is selected from the group consisting of: N, K, and F;
where P1 is selected from the group consisting of: F, L, Y, and M;
where P1' is selected from the group consisting of: E, D, and A; and
where P2' is selected from the group consisting of: V and A;
with the proviso that P2, P1, P1', and P2' are not selected such that P2-P1-P1'-P2' is KMDA (SEQ.ID.NO.:1), NLDA (SEQ.ID.NO.:2), KYAA (SEQ.ID.NO.:22), NFAV (SEQ.ID.NO.:23), KMEA (SEQ.ID.NO.:47), KFDA (SEQ.ID.NO.:48), KLDA (SEQ.ID.NO.:49), KYDA (SEQ.ID.NO.:50), or NMDA (SEQ.ID.NO.:51).

In certain embodiments, the modified β-secretase substrate is a polypeptide comprising the following amino acids derived from APP that include the region of the β-secretase cleavage site, the APP transmembrane region, and the region of the γ-secretase cleavage site:

where the above represents positions 589–651 of $APP_{695}$ and the first arrow indicates the β-secretase cleavage site while the second two arrows indicate the predominant sites of γ-secretase cleavage;
where P2-P1-P1'-P2' is selected from the group consisting of:

```
NFEV;             (SEQ.ID.NO.:3)
NFDA;             (SEQ.ID.NO.:4)
NFEA;             (SEQ.ID.NO.:5)
NLEA;             (SEQ.ID.NO.:6)
NLDV;             (SEQ.ID.NO.:7)
NFDV;             (SEQ.ID.NO.:8)
NFTV;             (SEQ.ID.NO.:9)
NYDA;             (SEQ.ID.NO.:10)
NYEA;             (SEQ.ID.NO.:11)
NYDV;             (SEQ.ID.NO.:12)
FFAV;             (SEQ.ID.NO.:13)
FFEV;             (SEQ.ID.NO.:14)
```

```
                    -continued
NLAA;             (SEQ.ID.NO.:15)
NFAA;             (SEQ.ID.NO.:16)
NYAA;             (SEQ.ID.NO.:17)
KFAA;             (SEQ.ID.NO.:18)
KMAA;             (SEQ.ID.NO.:19)
KMDV;             (SEQ.ID.NO.:20)
KFEA;             (SEQ.ID.NO.:21)
KYAA; and         (SEQ.ID.NO.:22)
NFAV.             (SEQ.ID.NO.:23)
```

In other embodiments, the modified β-secretase substrate is a polypeptide comprising the following amino acids derived from APP that include the region of the β-secretase cleavage site, the APP transmembrane region, and the region of the γ-secretase cleavage site:

```
                ↓
EEISEV-P2-P1  P1'-P2'-EFRHDSGYEVHHQKLVFFAEDVGSNKGAIIGLMV

↓    ↓
GGVV  IA   TVIVITLVMLKKK
```

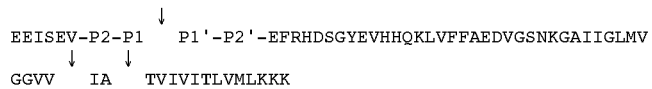

where the above represents positions 589–651 of $APP_{695}$ and the first arrow indicates the β-secretase cleavage site while the second two arrows indicate the predominant sites of γ-secretase cleavage;
where P2 is selected from the group consisting of: N, K, and F;
where P1 is selected from the group consisting of: F, L, Y, and M;
where P1' is selected from the group consisting of: E, D, and A; and
where P2' is selected from the group consisting of: V and A;
with the proviso that P2, P1, P1', and P2' are not selected such that P2-P1-P1'-P2' is KMDA (SEQ.ID.NO.:1), NLDA (SEQ.ID.NO.:2), KYAA (SEQ.ID.NO.:22), NFAV (SEQ.ID.NO.:23), KMEA (SEQ.ID.NO.:47), KFDA (SEQ.ID.NO.:48), KLDA (SEQ.ID.NO.:49), KYDA (SEQ.ID.NO.:50), or NMDA (SEQ.ID.NO.:51).

In the above examples, where the modified β-secretase substrates of the present invention are compared with, for example the wild type KMDA cleavage site (SEQ.ID.NO.: 1), the comparative results are based on data obtained in Example 4, below. It is noted that such in vitro data may vary depending on reagents used, purity of or choice of reagents, and other factors. Accordingly, it must be appreciated that the relative results, for example (and not meant to be limiting), "at least five times more Aβ being produced . . ." compared to a substrate comprising the wild type KMDA cleavage site (SEQ.ID.NO.:1), are expected to fluctuate depending on the specific experimental protocol and materials selected by a researcher. Nonetheless, modified β-secretase substrates of the present invention that are shown to consistently exceed the performance of the KMDA cleavage site (SEQ.ID.NO.:1), whether tested repeatedly in one laboratory and/or via different test protocols or in different laboratories, are utilizable as effective β-secretase substrates for new compound screening and other purposes. Also, modified β-secretase substrates that demonstrate performance approximately equivalent to substrates comprising the wild type KMDA cleavage site (SEQ.ID.NO.:1), or that on further testing demonstrate less performance, nonetheless may be used for protocol verification, as negative controls, or for other purposes in certain new compound screening.

Also, it is appreciated by those skilled in the art that the above-noted modified β-secretase substrates need not be used exclusively in the complete $APP_{695}$ polypeptide and conservatively modified variants thereof. For instance, the polypeptide chains described above are utilized independently, at the lengths specified, or, alternatively, linked to other peptides as are suitable for a desired system (whether cell free or cellular assays, or for production of antibodies). Also, it is appreciated that the above-noted modified β-secretase substrates are also implemented in $APP_{751}$ and $APP_{770}$ polypeptides and conservatively modified variants thereof. Any one of these peptide, polypeptide or protein forms and variants is included within the scope of the invention so long as β-secretase is able to catalyze a modified β-secretase cleavage site in such molecule. In alternate embodiments, sequence identity to forms of $APP_{695}$, $APP_{751}$ and $APP_{770}$ that comprise any of SEQ.ID.NOs.: 3–23 in their respective P2-P1-P1'-P2' β-secretase cleavage sites, is a criterion for inclusion as a claimed variant, so long as such claimed variant is a suitable β-secretase substrate and the variant falls within a stated range of sequence identity to its original $APP_{695}$, $APP_{751}$ or $APP_{770}$ sequence. That is, for some embodiments, sequence identity of a variant must be at least 65 percent compared to the respective original $APP_{695}$, $APP_{751}$ or $APP_{770}$ sequence. In more preferred embodiments, sequence identity of a variant must be at least 85 percent compared to the respective original $APP_{695}$, $APP_{751}$ or $APP_{770}$ sequence. In yet more preferred embodiments, sequence identity of a variant must be at least 95 percent compared to the respective original $APP_{695}$, $APP_{751}$ or $APP_{770}$ sequence.

When a modified β-secretase substrate polypeptide is used in cell-based assays, such polypeptide will be anchored in an appropriate cellular membrane (e.g., the endoplasmic reticulum) either by the APP transmembrane sequences or by other sequences known in the art that can be incorporated into the polypeptide in order to direct the polypeptide to the appropriate membrane. The N-terminal portion of the modified substrate polypeptide will often include APP sequences further N-terminal than those shown above, optionally including the signal sequence at the N-terminus of APP. In cases, where the APP signal sequence is not used, another signal sequence may be incorporated in the fusion protein. Such other signal sequences are known in the art.

Expression vectors are generally used to express the modified β-secretase substrate polypeptide in the recombinant cells. An expression vector contains recombinant nucleic acid encoding a polypeptide (e.g., a modified β-secretase substrate polypeptide) along with regulatory elements for proper transcription and processing. Generally, the regulatory elements that are present in an expression vector include a transcriptional promoter, a ribosome binding site, a transcriptional terminator, and a polyadenylation signal. Other elements may include an origin of replication for autonomous replication in a host cell, a selectable marker, a limited number of useful restriction enzyme sites, and a potential for high copy number.

A variety of expression vectors are known in the art and can be used in the present invention. Commercially available expression vectors which are suitable include, but are not limited to, pMC1neo (Stratagene), pSG5 (Stratagene), pcDNAI and pcDNAIamp, pcDNA3, pcDNA3.1, pCR3.1 (Invitrogen, San Diego, Calif.), EBO-pSV2-neo (ATCC 37593), pBPV-1(8-2) (ATCC 37110), pdBPV-MMTneo (342-12) (ATCC 37224), pRSVgpt (ATCC 37199), pRSV-neo (ATCC 37198), pCI.neo (Promega), pTRE (Clontech, Palo Alto, Calif.), pV1Jneo, pIRESneo (Clontech, Palo Alto, Calif.), pCEP4 (Invitrogen, San Diego, Calif.), pSC11, and pSV2-dhfr (ATCC 37146). The choice of vector will depend upon the cell type in which it is desired to express the modified β-secretase substrate polypeptide, as well as on the level of expression desired, and the like.

The expression vectors can be used to transiently express or stably express the modified β-secretase substrate polypeptide. The transient expression or stable expression of transfected DNA is well known in the art. See, e.g., Ausubel et al., 1995, "Introduction of DNA into mammalian cells," in

*Current Protocols in Molecular Biology*, sections 9.5.1–9.5.6 (John Wiley & Sons, Inc.).

The recombinant cells that have been engineered to express a modified β-secretase substrate polypeptide are useful in methods of screening substances for the ability to inhibit β-secretase. In one embodiment, the methods of the present invention comprise adding a candidate inhibitory substance to a recombinant cell comprising a modified β-secretase substrate polypeptide and comparing the level of β-secretase activity in the presence and absence of the candidate substance, wherein the level of β-secretase activity on the modified β-secretase substrate polypeptide is lower when the candidate substance is present if the candidate substance is actually a β-secretase inhibitor. The level of β-secretase activity can be measured by any of several methods known in the art. When the modified β-secretase substrate comprises Aβ sequences, the production of Aβ can be used as a surrogate for β-secretase activity. Lower levels of Aβ derived from the modified β-secretase substrate produced by the recombinant cell in the presence of the substance indicates that the substance is likely to be a β-secretase inhibitor.

The candidate substance may be of any form suitable for entry into the cytoplasm of the recombinant cell or for contact with the cell's cytoplasmic membrane. Under appropriate conditions, the candidate substance may be allowed to freely diffuse into the cell, or the delivery of the substance may be facilitated by techniques and substances which enhance cell permeability, a wide variety of which are known in the art. Methods for increasing cell permeability include, without limitation, the use of organic solvents such as dimethylsulfoxide, liposomes, application of electrical current, and physical means such as substance-coated Teflon® pellets.

The present invention provides a method of identifying a substance that inhibits β-secretase comprising:
(a) providing a recombinant eukaryotic cell which expresses a polypeptide comprising a β-secretase cleavage site where the P2-P1-P1'-P2' amino acids are as follows:
  (i) P2 is selected from the group consisting of: N, K, and F;
  (ii) P1 is selected from the group consisting of: F, L, Y, T, and M;
  (iii) P1' is selected from the group consisting of: E, D, T, and A;
  (iv) P2' is selected from the group consisting of: V and A; with the proviso that P2, P1, P1', and P2' are not selected such that P2-P1-P1'-P2' is KMDA (SEQ.ID.NO.:1), NLDA (SEQ.ID.NO.:2), KYAA (SEQ.ID.NO.:22), or NFAV (SEQ.ID.NO.:23);
(b) measuring the level of β-secretase activity on the polypeptide in the cell in the absence of the substance;
(c) adding the substance to the cell and measuring the level of β-secretase activity in the cell in the presence of the substance;
where a decrease in the level of β-secretase activity in the presence as compared to the absence of the substance indicates that the substance inhibits β-secretase.

The manner in which the level of β-secretase activity is measured will be determined by the nature of the polypeptide and, often, the characteristics of the host cell.

For the sake of clarity, the above method is described in terms of "a" cell. In actual practice, the method will generally be carried on a large number of cells at one time. For example, the method will often be carried out in a well of a tissue culture plate, where, depending on the number of wells in the plate (and thus their size), there can be up to hundreds, thousands, or even several million cells. The step of "adding the substance to the cell" is generally carried out by simply adding the substance to the tissue culture medium in which the cells are present. Normally the cell culture system is appropriately buffered and the quantity of the substance added is so miniscule that such addition does not lead to a false positive due to adverse changes in pH, osmolality, and other parameters required for cell growth and health. Additionally, negative controls with the identical volume of vehicle are added to an adjoining well to further control for any changes to the cells that might arise only from the substance vehicle. In all cases if there is concern for the health of the cells, simple tests, such as visual inspection of cell morphology and the use of Alamar Blue to measure mitochondrial function, for cell toxicity can be easily performed.

After the substance is added to the cell, the cell and the substance are incubated for a period of time sufficient for the substance to inhibit β-secretase, if the substance is actually an inhibitor of β-secretase. This period is usually from about 15 minutes to 48 hours, but may be somewhat more in unusual cases.

A convenient way of carrying out the method is to grow a population of the recombinant eukaryotic cells and then split the population into a portion that will be exposed to the substance and a portion that will not be exposed to the substance.

The recombinant eukaryotic cell is generally produced by transfection of an expression vector encoding the modified β-secretase substrate polypeptide.

One skilled in the art would recognize that what is sought in terms of "a decrease in the level of β-secretase activity in the presence as compared to the absence of the substance" is a non-trivial decrease. For example, if in the method described above there is found a 1% decrease, this would not indicate that the substance is an inhibitor of β-secretase. Rather, one skilled in the art would attribute such a small decrease to normal experimental variation. What is looked for is a significant decrease. For the purposes of this invention, a significant decrease fulfills the usual requirements for a statistically valid measurement of a biological signal. For example, depending upon the details of the embodiment of the invention, a significant decrease might be a decrease of at least 10%, preferably at least 20%, more preferably at least 50%, and most preferably at least 90%.

In particular embodiments, the cell is a mammalian cell. In particular embodiments, the cell is a human cell.

In particular embodiments, the method is used to screen a library of more than 1,000 substances. In other embodiments, the method is used to screen a library of more than 50,000 substances at a rate of more than 1,000 substances per 24 hours.

The present invention also provides methods for identifying inhibitors of β-secretase where such methods can be carried out in a cell-free manner. Among such methods provided by the present invention is a method of identifying a substance that inhibits β-secretase comprising:
(a) providing a cell-free system comprising:
  (i) a polypeptide comprising a β-secretase cleavage site where the P2-P1-P1'-P2' amino acids are as follows:
    (i) P2 is selected from the group consisting of: N, K, and F;
    (ii) P1 is selected from the group consisting of: F, L, Y, and M;
    (iii) P1' is selected from the group consisting of: E, D, and A;

(iv) P2' is selected from the group consisting of: V and A; with the proviso that P2, P1, P1', and P2' are not selected such that P2-P1-P1'-P2' is KMDA (SEQ.ID.NO.:1), NLDA (SEQ.ID.NO.:2), KYAA (SEQ.ID.NO.:22), or NFAV (SEQ.ID.NO.:23); and (ii) a polypeptide comprising a β-secretase cleavage site, where the N-terminal or C-terminal was labeled with fluorophores such as coumarin or labeled with receptor ligand such as biotin was designed to facilitate monitoring the β-secretase activity. The P2-P1-P1'-P2' amino acids are as follows:

(i) P2 is selected from the group consisting of: N, K, and F;

(ii) P1 is selected from the group consisting of: F, L, Y, and M;

(iii) P1' is selected from the group consisting of: E, D, and A;

(iv) P2' is selected from the group consisting of: V and A; with the proviso that P2, P1, P1', and P2' are not selected such that P2-P1-P1'-P2' is KMDA (SEQ.ID.NO.:1), NLDA (SEQ.ID.NO.:2), KYAA (SEQ.ID.NO.:22), or NFAV (SEQ.ID.NO.:23); and (iii) a source of β-secretase activity;

(b) measuring the level of β-secretase activity in the cell-free system in the absence of the substance; and (c) adding the substance to the cell-free system and measuring the level of β-secretase activity in the cell-free system in the presence of the substance;

where a decrease in the level of β-secretase activity in the presence as compared to the absence of the substance indicates that the substance is a β-secretase inhibitor. While not being limited in scope of the claims appended hereto, one example of a high throughput cell free method of analysis using a modified β-secretase substrate of the present invention is provided in Example 7. Two examples of cell free method of analysis using labeled peptide substrate comprising NFEV β-secretase cleaving site of present invention are provided in Examples 8 and 9.

As discussed above, when the modified β-secretase substrate polypeptide contains a complete APP sequence or a substantial portion of the complete APP sequence, other positions of the polypeptide besides the β-secretase cleavage site may contain mutations that are known in the art. Of particular interest for certain embodiments are mutations that result in an increased proportion of Aβ being made in the form of Aβ1-42 rather than Aβ1-40. Such mutations are disclosed in the following publications (numbering is from the 770 amino acid version of APP):

Swedish (K670N, M671L): Mullan et al., 1992, Nature Genet. 1:345–347.

flemish (A692G): Hendriks et al., 1992, Nature Genet. 1:218–221; Cras et al., 1998, Acta Neuropathol. (Berlin) 96:253–260.

Dutch (E693Q): Levy et al., 1990, Science 248:1124–1126.

Arctic (E693G): Nilsberth et al., 2001, Nature Neuroscience 4: 887–893.

Austrian (T714I): Kumar-Singh et al., 2000, Hum. Mol. Genet. 9:2589–2598.

French (V715M): Ancolio et al., 1999, Proc. Natl. Acad. Sci. (USA) 96:4119–4124.

Florida (I716V): Eckman et al., 1997, Hum. Mol. Genet. 6:2087–2089.

V717F: Murrell et al., 1991, Science 254:97–99.

V717G: Chartier-Harlin et al., 1991, Nature 353:844–846.

London (V717I): Goate et al., 1991, Nature 349:704–706.

L723P: Kwok et al., 2000, Ann. Neurol. 47:249–253.

I716F (also called I45F, referring to the position relative to the β-secretase cleavage site):

This mutation in APP changes processing of Aβ almost exclusively to Aβ1-42.

Lichtenthaler et al., 1999, Proc. Natl. Acad. Sci. (USA) 96:3053–3058.

As with many proteins, it may be possible to modify many of the amino acids of the modified β-secretase substrate polypeptides described herein and still retain substantially the same biological activity in terms of β-secretase activity as for the original modified β-secretase substrate polypeptide. Thus, the present invention includes modified β-secretase substrate polypeptides which have amino acid deletions, additions, or substitutions but that still retain substantially the same properties with respect to β-secretase activity as the modified β-secretase substrate polypeptides described herein. It is generally accepted that single amino acid substitutions do not usually alter the biological activity of a protein (see, e.g., *Molecular Biology of the Gene*, Watson et al., 1987, Fourth Ed., The Benjamin/Cummings Publishing Co., Inc., page 226; and Cunningham & Wells, 1989, Science 244:1081–1085). Accordingly, the present invention includes modified β-secretase substrate polypeptides where one amino acid substitution has been made in the modified β-secretase substrate polypeptides described herein where the modified β-secretase substrate polypeptides still retain substantially the same properties with respect to β-secretase activity as the modified β-secretase substrate polypeptides described herein. The present invention also includes modified β-secretase substrate polypeptides where two or more amino acid substitutions have been made in the modified β-secretase substrate polypeptides described herein where the modified β-secretase substrate polypeptides still retain substantially the same properties with respect to β-secretase activity as the modified β-secretase substrate polypeptides described herein. In particular, the present invention includes embodiments where the substitutions are those that result in conservatively modified variants of the disclosed and claimed modified β-secretase substrate polypeptides. Examples of conservatively modified variants of a particular modified β-secretase substrate includes, but is not limited to: a deletion in the first 1–10 amino acids at the amino end of the molecule; a substitution of a conserved amino acid change such as a leucine for an isoleucine; an insertion of a defined antibody epitope such as myc in the amino terminus of the molecule; or truncation of the last 1–10 amino acids of the molecule.

Except where indicated, the numbering of the amino acids in APP used herein is based on the 695 amino acid version of APP described in Kang et al., 1987, Nature 325:733–736. There are two other major versions of APP, having 751 amino acids and 770 amino acids (see Ponte et al., 1988, Nature 331:525–527 for the 751 amino acid version and Kitaguchi et al., 1988, Nature 331:530–532 for the 770 amino acid version). One skilled in the art will understand how to translate the numbering used herein, based on the 695 amino acid version of APP, into the corresponding numbering for other versions of APP. For example, some of the modified β-secretase substrate polypeptides of the present invention contain the K612V mutation, based on the numbering of the 695 amino acid version. This mutation would correspond to a K668V mutation in the 751 amino acid version and a K687V mutation in the 770 amino acid version.

Therefore, when a "K612V" mutation is referred to herein, it will be understood that such reference also includes a K668V mutation of the 751 amino acid version of APP as well as a K687V mutation of the 770 amino acid version of APP.

Further to the point of modifications of any of these three amino acid versions of APP, all of the following modifications are also considered to fall within the definition of a modified β-secretase substrate. It is known that full length APP is encoded by a gene that is naturally differentially spliced to result in the three amino acid variants, or isoforms, of the protein: 695, 751, and 770 amino acids in length. A recombinant APP substrate can be generated by subcloning the cDNA encoding the APP isoform of interest in an expression vector containing appropriate promoters and stop signals. This vector containing the APP cDNA can then be expressed in a variety of organisms to generate the APP protein. By manipulating the cDNA subcloned into the expression vector, modified APP proteins can be recombinantly generated. Using the assay described, it can be determined if the newly modified APP protein is a substrate of BACE. For example, in this patent, we modify the APP substrate by altering the amino acids surrounding the cleavage site from KMDA to NFEV. This modified APP was verified as a substrate for BACE in a cellular assay. If insertion, deletion, or alteration of codons into the cDNA of the modified APP substrate resulted in an APP protein that could still be cleaved by BACE, then the newly modified APP would still be a BACE substrate. For example, by using restriction enzymes, PCR, or linker insertion/replacement to manipulate the modified APP cDNA, portions of the 5' end of the gene can be specifically deleted in-frame. These deletions can be as small as 3 codons, resulting in the removal of a single amino acid, and they can be as large as 1782 codons in the modified $APP_{695}$ gene, resulting in the removal of the entire N-terminus of the protein up to the modified BACE cleavage site. Although the removal of the entire N-terminus is an extreme example, the removal of 30 codons to delete 10 amino acids or 300 codons, resulting in the deletion of 100 amino acids, can result in fully functional BACE substrates. These newly derived modified APP proteins can all then be tested in the cellular system described to determine if they remain substrates of BACE. Similarly, molecular manipulations can be done downstream of the BACE cleavage site which might delete anywhere from 3 to 291 codons. This would result in the deletion of anywhere from 1 to 97 amino acids downstream of the modified BACE cleavage site. In the case of deleting amino acids downstream of the BACE cleavage site, the deletion does not necessarily have to remain in-frame. An in-frame deletion of codons will result in a protein that has specific amino acids removed. A deletion of codons that does not remain in-frame will result in a truncated protein. Again, in either the in-frame or the out-of-frame deletion, the resulting modified APP can be tested in the assay described to determine if the newly modified APP is a substrate of BACE.

Alternately, insertion of amino acids into APP with the modified BACE cleavage site can be done, using standard molecular biology techniques, such as linker/fragment insertion and PCR. After expression in an appropriate recombinant host, these manipulations will result in APP proteins that have been altered from the original modified APP. Insertions as small as 3 codons and as large as will be tolerated by the host of the recombinant vector can be made in-frame upstream and/or downstream of the modified BACE cleavage site. These modified APP genes can be tested in the cellular system described to determine if the newly modified APP protein is a substrate of BACE.

Finally, by using standard molecular biology techniques, any number of amino acids in the modified APP protein can be altered without changing the absolute number of amino acids in the protein. For example: the codon GTT encodes the amino acid valine. If this is altered by site directed mutagenesis to ATT, the codon would then encode the amino acid isoleucine. Although this is a relatively conservative change, the codon could also have been altered to AAT, which encodes asparagine, a non-conservative change. In any given protein, from one to multiple amino acid changes can be made in a similar manner. Depending on the location of the amino acid changes, the altered APP protein may or may not retain function as a substrate for BACE. The recombinant protein(s) generated from the altered APP cDNA(s) can be checked using the cellular assay described in this patent.

Thus, any of the above described deletions, insertions, and amino acid alterations made to an APP substrate that result in a biologically active protein that retains β-secretase activity, where the resulting protein also comprises a modified β-secretase cleavage site as disclosed herein (e.g., SEQ.ID.NO.:3 to SEQ.ID.NO.:23), is a β-secretase substrate. Basic molecular biology techniques to achieve such deletions, insertions, and amino acid alterations can be found in references such as the following: Ausubel, F. M., R. Brent, et al., Eds. (1992). *Short Protocols in Molecular Biology: A compendium of methods from Current Protocols in Molecular Biology*. Current Protocols in Molecular Biology. New York, N.Y., Green Publishing Associates and John Wiley & Sons;

Berger, S. L. and A. R. Kimmel, Eds. (1987); *Guide to Molecular Cloning Techniques*. Methods in Enzymology. Orlando, Fla., Academic Press, Inc.; and Innis, M. A., D. H. Gelfand, et al., Eds. (1990). *PCR Protocols: A Guide to Methods and Applications*. San Diego, Calif., Academic Press, Inc.

When β-secretase activity is measured by monitoring the production of Aβ, it will usually be desirable to further test inhibitors that are identified by the methods of the present invention to determine that such inhibitors actually act the step of β-secretase activity rather than at some other step in APP processing. Assays that are known to be specific for the various steps of APP processing can be used for this purpose. For example, the assay of Karlström et al., (Journal of Biological Chemistry papers in press, published on Dec. 13, 2001 as Manuscript C100649200) is only capable of detecting inhibitors of γ-secretase and cannot also detect inhibitors of other steps of APP processing such as, e.g., inhibitors of β-secretase. If an inhibitor identified by the methods of the present invention is found to also be an inhibitor when tested in the assay of Karlström et al., then that inhibitor is at least a γ-secretase inhibitor. It is still possible that that inhibitor could be a β-secretase inhibitor as well. Further tests known in the art can determine this.

Various constructs useful in the present invention can be made by use of the polymerase chain reaction (PCR) to amplify desired portions of DNA encoding APP and other DNA sequences, which can be then be cloned into expression vectors by methods well known in the art. Primers for PCR will generally include a small part of the DNA sequence it is desired to amplify as well as convenient cloning sites and/or linker peptide sequences. The PCR primers can be used to amplify the desired sequences from sources such as previously cloned DNA sequences, cDNA libraries, or genomic libraries. The amplified sequences can be cloned into suitable expression vectors. Methods of PCR and cloning are well known in the art and can be found in standard reference materials such as those listed below.

Standard techniques for cloning, DNA isolation, amplification and purification, for enzymatic reactions involving DNA ligase, DNA polymerase, restriction endonucleases and the like, and various separation techniques are known and commonly employed by those skilled in the art. A number of standard techniques are described in Sambrook et al. (1989) Molecular Cloning, Second Edition, Cold Spring Harbor Laboratory, Plainview, N.Y.; Maniatis et al. (1982) Molecular Cloning, Cold Spring Harbor Laboratory, Plainview, N.Y.; Wu (ed.) (1993) Meth. Enzymol. 218, Part I; Wu (ed.) (1979) Meth. Enzymol. 68; Wu et al. (eds.) (1983) Meth. Enzymol. 100 and 101; Grossman and Moldave (eds.) Meth. Enzymol. 65; Miller (ed.) (1972) Experiments in Molecular Genetics, Cold Spring Harbor Laboratory, Cold Spring Harbor, N.Y.; Old and Primrose (1981) Principles of Gene Manipulation, University of California Press, Berkeley; Schleif and Wensink (1982) Practical Methods in Molecular Biology; Glover (ed.) (1985) DNA Cloning Vol. I and II, IRL Press, Oxford, UK; Hames and Higgins (eds.) (1985) Nucleic Acid Hybridization, IRL Press, Oxford, UK; Setlow and Hollaender (1979) Genetic Engineering: Principles and Methods, Vols. 1–4, Plenum Press, New York, and Ausubel et al. (1992) Current Protocols in Molecular Biology, Greene/Wiley, New York, N.Y, Kornberg & Baker DNA Replication, W. H. Freeman, N.Y., $2^{nd}$ Ed., (1992).

PCR reactions can be carried out with a variety of thermostable enzymes including but not limited to AmpliTaq, AmpliTaq Gold, or Vent polymerase. For AmpliTaq, reactions can be carried out in 10 mM Tris-Cl, pH 8.3, 2.0 mM $MgCl_2$, 200 µM of each dNTP, 50 mM KCl, 0.2 µM of each primer, 10 ng of DNA template, 0.05 units/µl of AmpliTaq. The reactions are heated at 95° C. for 3 minutes and then cycled 35 times using suitable cycling parameters, including, but not limited to, 95° C., 20 seconds, 62° C., 20 seconds, 72° C., 3 minutes. In addition to these conditions, a variety of suitable PCR protocols can be found in PCR Primer, A Laboratory Manual, edited by C. W. Dieffenbach and G. S. Dveksler, 1995, Cold Spring Harbor Laboratory Press; or PCR Protocols: A Guide to Methods and Applications, Michael et al., eds., 1990, Academic Press.

It is desirable to sequence the DNA encoding the modified β-secretase substrate polypeptides, or at least the junction regions of the various portions of the polypeptides in order to verify that the desired portions have in fact been obtained, joined properly, and that no unexpected changes have been introduced into the sequences by the PCR reactions.

Although a wide variety of substances can be screened by the methods of the present invention, preferred substances for screening are libraries of low molecular weight organic compounds. Low molecular weight organic compounds are preferred because they are more readily absorbed after oral administration, have fewer potential antigenic determinants, and are more likely to cross the blood/brain barrier than larger molecules such as nucleic acids or proteins.

Once identified by the methods of the present invention, the low molecular weight organic compounds may then be produced in quantities sufficient for pharmaceutical testing and formulated in a pharmaceutically acceptable carrier (see, e.g., Remington's Pharmaceutical Sciences, Gennaro, A., ed., Mack Publishing, 1990, for suitable methods). The low molecular weight organic compounds may be administered to cell lines relevant to Alzheimer's disease, animal models of Alzheimer's disease, or Alzheimer's disease patients.

The methods of the present invention can be used to screen libraries of substances or other sources of substances to identify substances that are inhibitors of β-secretase. Such identified inhibitory substances can serve as "leads" for the development of pharmaceuticals that can be used to treat patients having Alzheimer's disease or in a prophylactic manner to prevent or delay the development of Alzheimer's disease. Such leads can be further developed into pharmaceuticals by, for example, subjecting the leads to sequential modifications, molecular modeling, and other routine procedures employed in the pharmaceutical industry. The β-secretase inhibitors identified by the present invention may also be tested in animal models of Alzheimer's disease such as the various transgenic mouse models that are known in the art.

The conditions under which substances are employed in the methods described herein are conditions that are typically used in the art for the study of protein-ligand interactions or enzyme inhibition studies: e.g., salt conditions such as those represented by such commonly used buffers as PBS or in tissue culture media; a temperature of about 4° C. to about 55° C.; incubation times of from several seconds to several hours or even up to 24 or 48 hours. A variety of reagents may be present, e.g., ATP, ATP analogs, salts, buffers, neutral proteins such as albumin, detergents, protease inhibitors, nuclease inhibitors, antimicrobial agents, etc. Screening for the identification of enzyme-specific inhibitors is a well-known procedure in the pharmaceutical arts and numerous conditions under which such screening has been done are available in the literature to guide the practitioner of the present invention.

Clinical symptoms of Alzheimer's disease include, for example, progressive disorientation, memory loss, and aphasia. Eventually, disablement, muteness, and immobility occur. Pathological indicators of Alzheimer's disease include, for example, the presence of neurofibrillary tangles, neuritic plaques, and amyloid angiopathy. Preventing the progression of Alzheimer's disease can mean preventing the onset or further development of clinical symptoms and/or pathological indicators of Alzheimer's disease. For example, an individual who does not have clinical symptoms or pathological indicators of Alzheimer's disease can be prevented from developing clinical symptoms or pathological indicators. Further, an individual who has a mild form of Alzheimer's disease can be prevented from developing a more severe form of Alzheimer's disease. Delaying the progression of Alzheimer's disease can mean delaying the time of onset of Alzheimer's disease-related symptoms and/or pathological indicators, or slowing the rate of progression of Alzheimer's disease, determined by the rate of development of clinical symptoms and pathological indicators. Reversing the progression of Alzheimer's disease can mean that the severity of an Alzheimer's disease condition has been lessened, i.e., the Alzheimer's disease condition of an individual has changed from severe to less severe as indicated by fewer clinical symptoms or pathological indicators.

An individual can choose to take a β-secretase inhibitor identified by the methods of the present invention as a preventative measure to avoid developing Alzheimer's disease. For example, an individual with a genetic predisposition to Alzheimer's disease can take a β-secretase inhibitor identified by the methods of the present invention to prevent or delay the development of Alzheimer's disease. A genetic predisposition can be determined based on known methods. For example, an individual can be considered to have a genetic predisposition to Alzheimer's disease if the individual has a family history of Alzheimer's disease. Genetic predisposition to Alzheimer's disease also can include point mutations in certain genes such as the APP gene, the presenilin-1 or presenilin-2 gene, or the apolipoprotein E gene. Such mutations can predispose individuals to early-onset familial Alzheimer's disease (FAD), increased risk of developing Alzheimer's disease, or decreased age at onset of Alzheimer's disease. Furthermore, an individual who has clinical symptoms of, or has been diagnosed with, Alzheimer's disease can take a β-secretase inhibitor identified by the methods of the present invention to prevent or delay further progression of Alzheimer's disease as well as to reverse the pathological condition of the disease.

Thus, aspects of this invention include the identification of inhibitors of various forms (whether related to genetic predisposition or later-identified factors) of Alzheimer's disease and other conditions related to the production βAPP, and the administration of appropriate forms and derivatives of such inhibitors to individuals. Such forms and derivatives of identified inhibitors may be taken in preventative doses (as may be estimated initially by means available), and in therapeutic doses. It is expected that the doses will differ depending on the form and stage of progression of the condition (e.g., pre-symptomatic state) or disease.

The present invention includes antibodies that have been raised against and/or recognize epitopes that are formed by the cleavage of the modified β-secretase β-secretase substrates of the present invention. An example of antibodies raised against variants of the sAPPβ and the CTFβ cleavage products of β-secretase activity on APP modified β-secretase substrates of the present invention is provided in Example 2. This example of antibody production is not meant to be limiting, as there are a number of methods known to those of ordinary skill in the art to produce polyclonal antibodies possessing the desired characteristics to be used in detection of various products and reactants of β-secretase activity.

Also, more generally the antibodies of the present invention can be monoclonal or polyclonal. Techniques for preparing monoclonal antibodies are well known in the art and, e.g., are described in Antibodies: A Laboratory Manual, Harlow and Lane, eds., Cold Spring Harbor Laboratory, 1988.

Example 2 also describes how the antibodies are utilized in the detection of sAPPβ cleavage products of β-secretase activity on modified β-secretase substrates of the present invention. This example of detection methodology is not meant to be limiting, as there are a number of methods known to those of ordinary skill in the art to measure the presence or concentration of breakdown products of β-secretase activity and to measure the decrease in concentration of the APP (whether wild type or modified) in test systems. For instance, and not meant to be limiting, two references for LC/MS, and two references regarding sandwich ELISA methods, are:

1) Methods in Molecular Biology, Volume 146, Mass Spectrometry of Proteins and Peptides, Ed, K. Chapman (2000) p 1–538
2) Mann, M. Hendrickson, R. C. and Pandey, A.; Analysis of Proteins and Proteomes by Mass Spectrometry in Annual Reviews in Biochemistry, V70, p 437–473 (2001)
3) The Elisa: Enzyme-Linked Immunosorbent Assay in Veterinary Research and Diagnosis, Wardley, R. C. and Crowther, J. R.; Norwell: Kluwer Academic Publishers, November 1982.
4) The ELISA Guidebook, J. R. Crowther, Humana Press, Totowa, N.J., 2001, 436 pp., Soft cover (Sigma Chemical Co, product E2027).

These and other methods, such as are found in the references already cited herein, may be employed by one of ordinary skill in the art to detect sAPPβ cleavage products of β-secretase activity on modified β-secretase substrates of the present invention.

In addition, it is recognized that the modified β-secretase substrates' CTFβ cleavage products also can be utilized to develop antibodies, and subsequent use of such antibodies can be utilized for detection purposes essentially as described herein for sAPPβ cleavage products. Methods such as those described and referred to above are employed to detect these modified β-secretase substrates' CTFβ cleavage products.

The present invention provides transgenic animals, e.g., transgenic mice, that are engineered to express one of the modified β-secretase substrates. Such transgenic mice are useful for screening collections of substances to identify inhibitors of β-secretase, particularly those substances identified by cell-based or cell free methods as potentially effective inhibitors of β-secretase activity. Such testing in transgenic animals, such as mice, also is used to elucidate specific effects of previously identified inhibitors in a living multi-cellular mammal model.

Transgenic mice are engineered so as to replace one or both copies of their APP genes with a recombinant β-secretase substrate that consists of the APP gene into which has been introduced one of the modified P2-P1-P1'-P2' sequences of the present invention.

Methods of making transgenic mice are known in the art. One approach is to make a DNA construct containing the modified β-secretase substrate and flanking sequences from APP. This DNA construct is transfected into pluripotent embryonic stem cells competent for recombination. The identical flanking sequences in the construct and APP on the mouse's chromosomes align with one another, and chromosomal recombination occurs in which the targeted APP sequence is replaced with the insert sequence containing the modified β-secretase substrate amino acids. See Bradley, A., Production and Analysis of Chimeric 2 0 Mice, in Teratocarcinomas and Embryonic Stem Cells-A Practical Approach, 1987, E. Roberson, Editor, IRC Press, pages 113–151 for a general description of this technique. The stem cells are injected into an embryo, which is then implanted into a female animal and allowed to be born. The animals may contain germ cells derived from the injected stem cells, and subsequent matings may produce animals heterozygous and homozygous for the APP gene containing the modified β-secretase substrate amino acids. Example 6 discloses two approaches to transgenic animal development that result in generation of a transgenic mammal possessing a modified β-secretase substrate of the present invention (e.g., any of SEQ.ID.NO.:3–23). A method of purifying β-secretase is disclosed in Vassar et al., 1999, Science 286:735–741. The method involves engineering a soluble, enzymatically active fusion protein of β-secretase and immunoglobulin G that contains amino acids 1–460 of β-secretase fused to human IgG1 at the carboxy terminus. The β-secretase/IgG fusion protein can be overexpressed in 293T cells and purified from conditioned media. The DNA codes for the rat and mouse β-secretase enzymes are available as follows:

rat β-secretase, GenBank accession no. AF190727 mouse β-secretase, GenBank accession no. AF190726.

The following non-limiting examples are presented to better illustrate the invention.

EXAMPLE 1

Polynucleotide sequences that code the mutants disclosed herein, and compared in Table 1 (shown in Example 4, below), were constructed as follows. All mutant polynucleotide constructs were derived from a plasmid designated pRBR899 or pRBR121. Both plasmids carry βAPP$_{695}$-derived cDNA (either wild type or with the K612V mutation) operatively linked to the CMV promoter. The plasmid pRBR121 was generated by site directed mutagenesis via PCR with an annealed oligonucleotide in which the codon for the K at position 612 (based on the 695 amino acid version of APP) was replaced by a codon for V.

Thereafter aliquots of both pRBR899 and pRBR121 separately underwent replacement of the 26 bp BglII-EcoRI fragment of βAPP$_{695}$ with an oligonucleotide that had been prepared to introduce a specific desired substitution of one or more of the four amino acids at the four positions flanking the β-secretase cleavage site (resulting in desired mutations of the APP in one or more of the four codons coding for amino acids 594, 595, 596 and 597 of the 695 variant of APP, also designated herein as P2-P1-P1'-P2'). Specify codon substitutions were made from the wild type APP695 K-M-D-A at the β-secretase P2-P1-P1'P2' cleavage site to the variants disclosed in this patent application.

In a representative ligation and annealing reaction, 2 ul of the plasmid was added (either pRBR899 (0.54 mg/ml)or pRBR121 (0.2 mg/ml)) in a solution with the restriction endonucleases BglII and EcoRI, along with: 2 ul 5×T4 DNA ligase buffer (Bethesda Research Laboratories); 1 ul of a 1 mg/ml. solution of the respective desired double stranded oligonucleotide, 1 ul of the 40,000 U/ml stock of T4 DNA ligase (New England Biochemicals); and 4 ul deionized water. The final volume of a typical reaction was 10 ul, thus the T4 DNA ligase buffer was at 1× concentration and the amount of ligase was 4U per ul.[1] This was incubated overnight at 14° C. Then the ligations were transformed into a competent strain of E. coli (HB101) and grown for minipreparation of DNA. 1 ul of DNA was incubated with 100 ul of Gibco/BRL competent HB101 cells on ice for 30 minutes. The DNA and cells were heat shocked at 42° C. for 45 seconds and placed back on ice for 2 minutes. 900 ul of SOC medium was added to the tube and the reaction was incubated for 1 hour at 37° C. while shaking at 225 rpm. Various volumes of the reaction were plated onto LBAmp agarose plates (25 ul, 100 ul and 300 ul). The plates were incubated at room temperature for 72 hours. Seven colonies from each sample were picked and grown in 2 ml of liquid LBAmp media. DNA mini preps were prepared from these samples. The protocol from the QIAprep Spin Miniprep Kit was followed. Basically, the pelleted bacterial cells were resuspended in 250 ul of Buffer P1. 250 ul of Buffer P2 was then added and the mixture was gently inverted 4–6 times to mix. 350 ul of Buffer N3 was added and the tube was immediately inverted 4–6 times to mix. The tube was centrifuged for 10 minutes and the supernatant was applied to the QIAprep column. The columns were centrifuged for 30–60 seconds and the flow through volume was discarded. The QIAprep spin column was washed by adding 0.5 ml of Buffer PB and centrifuging 30–60 seconds. Again, the flow through volume was discarded. The QIAprep spin column was washed by adding 0.75 ml of Buffer PE and centrifuging 30–60 seconds. After discarding the flow through solution and centrifuging for an additional 1 minute to remove the residual wash buffer, the QIAprep column was placed in a clean 1.5 ml microfuge tube to elute the DNA. After adding 50 ul of Buffer EB to the center of each QIAprep column, the column was incubated at room temperature for 1 minute and centrifuged for 1 minute. The eluate contained the DNA.

The DNA was then digested in the following manner to determine if any of the colonies contained the variant DNA of interest: 10 ul of DNA miniprep was aliquotted into each of the wells of two separate 96 well polypropylene non-treated plates. Controls (pR899 and PRBR121) were set up in each of the wells. Then 10 ul of respective "mastermix" was added to each of the wells. Plate 1 mastermix: EcoRI/PvuII digestion: 124 ul of 10× EcoRI buffer, 384 ul of dH2O, 12 ul of 100×BSA, 50 ul of PvuII, 50 ul of EcoRI. Plate2 mastermix: BglII/PvuII digestion: 124 ul of 10×NEB#3 buffer, 384 ul of dH2O, 12 ul 100× BSA, 50 ul of PvuII, 50 ul of BglII. Reactions were incubated at 37° C. for 45 minutes. 2 ul of loading buffer was added to each well. These reactions were stored overnight at 4° C. DNA gels were run the next morning. Plasmids containing the appropriate restriction digestion pattern were selected for further amplification.

EXAMPLE 2

Antibodies of the present invention were raised against and recognize epitopes (alternately referred to as "neo-epitopes") formed by the β-secretase cleavage of the modified β-secretase substrates of the present invention. Antibodies were raised against polypeptides mimicking the P1 free carboxylic acid end of a modified sAPPβ that is exposed following cleavage by β-secretase of the modified β-secretase substrates. Antibodies also were raised against polypeptides mimicking the P1'-free amino group end of a modified carboxyterminal fragment (CTFβ) that is exposed following cleavage by β-secretase of the modified β-secretase substrates. At a minimum the modification of modified sAPPβ and the modified CTFβ comprises modification of the amino acid sequences at the P2-P1-P1'-P2' β-secretase cleavage site. An example of an antibody raised to the P1 free carboxylic acid end of a modified sAPPβ, and an example of an antibody raised to the P1'-free amino group end of a modified carboxyterminal fragment (CTFβ), are provided below. In the examples below, each rabbit polyclonal antibody was raised against the indicated peptide, pooled, affinity purified and evaluated using standard practices known in the art.

For example, polyclonal rabbit antibodies were raised to the peptide sequence SEVNF-COOH (SEQ.ID.NO.:57). This penta-peptide, shown here with the carboxylic acid group that is part of the right-end amino acid, is at the carboxyl end of the modified sAPPβ formed from β-secretase cleavage of any of the modified substrates containing the following sequences at the β-secretase cleavage site: NFEV (SEQ.ID.NO.:3), NFDA (SEQ.ID.NO.:4), NFEA (SEQ.ID.NO.:5), NFDV (SEQ.ID.NO.:8), NFTV (SEQ.ID.NO.:9), and NFAA (SEQ.ID.NO.:16). This penta-peptide consists of the five C-terminal amino acids of the sAPPβ fragment created by cleavage of APP containing one of the above-mentioned modified beta-secretase cleavage sites. In preferred embodiments, polyclonal rabbit antibodies raised to the peptide sequence SEVNF-COOH (SEQ.ID.NO.:57) do not bind well to the same sequence which is part of a polypeptide sequence that does not have the free amino acid group at the end of phenylalanine ("F").

Similarly, polyclonal rabbit antibodies were raised to the peptide sequence NH$_2$-EVEFR (SEQ.ID.NO.:58) This is a penta-peptide at the amino-terminal end of the CTFβ portion of APP created by β-secretase cleavage of any of the modified substrates containing the following two sequences at the β-secretase cleavage site: NFEV (SEQ.ID.NO.:3), and FFEV (SEQ.ID.NO.:14). (As described above, CTFβ typically will form into Aβ after γ-secretase cleavage at the variable C-terminus). Two lots of the anti-sera were collected, pooled, and purified (such as by affinity purification) using standard techniques. Western blots comparing standard (wild type) 40 amino acid length Aβ with an equivalent length peptide having the EVEFR (SEQ.ID.NO.:58) at its amino end. The Western blots demonstrated that all pooled antibody bound the 40 amino acid length peptide bearing the EVEFR (SEQ.ID.NO.:58) amino end.

Antibody specificity also was evaluated for both lots. An ORIGEN Analyzer (described below) was utilized in a non-sandwich assay to compare the ability of related polypeptides to compete with the binding of ruthenylated anti-EVEFR antibodies to biotinylated EVEFR (SEQ. ID. NO. 58). Certain peptides and conjugated peptides were added as treatments over a broad concentration range, and competitive titrations were made. As shown in FIG. 3A, the antibodies prepared against EVEFR (SEQ.ID.NO.:58) are specific. At each concentration, the addition of non-biotinylated EVEFR (SEQ.ID.NO.:58) peptide competed with biotinylated EVEFR (SEQ.ID.NO.:58) for anti-EVEFR binding, while the addition of the wild type sequence, DAEFR, (SEQ.ID.NO.:61) was unable to compete for binding. This indicates that the antibody has greater specificity to EVEFR (SEQ.ID.NO.:58) and does not highly bind to DAEFR (SEQ. ID. NO.:61), the wild-type ending. The specificity is further demonstrated by the treatment of acetylated-EVEFR (SEQ. ID. NO.:62). The normal antigen is not acetylated. The inability of acetylated-EVERF (SEQ ID NO.:62) to compete with biotinylated EVEFR (SEQ ID NO.:58) for antibody binding indicates that the acetylated form does not bind well to the antibody. Also, a coumarin-bound deca-peptide including the EVEFR (SEQ.ID.NO.:58) sequence did not compete well. This further demonstrates the specificity of the polyclonal antibody preparation in that the antibody did not bind well to the EVEFR (SEQ.ID.NO.:58) sequence when the latter is part of a sequence blocking the amino end of the EVEFR (SEQ.ID.NO.:58) pentapeptide.

Additional treatments, shown in FIG. 3B, show slight competitive interference with +VEFR (SEQ.ID.NO.:59), and a somewhat higher level of interference (i.e., cross reactivity) in the +DVEFR (SEQ.ID.NO.:60) treatment. The significance of these competition assays to characterize the neo-epitope antibody is to demonstrate the exquisite specificity of the antibody. For example, the antibody did not cross react significantly with the VEFR (SEQ. ID. NO. 59) sequence indicating that if an amino peptidase were to cleave off the NH-terminus of the BACE cleavage product, the neo-epitope antibody against the EVEFR (SEQ.ID.NO.:58) sequence would not cross react with this modified product. Additionally, the specificity of the antibody raised against the EVEFR (SEQ.ID.NO.:58) sequence is tight enough that a conservative change in the epitope presented to the antibody, namely DVEFR(SEQ ID. NO. 60) where the NH-terminus E is conservatively changed to D, the antibody would only recognize the bona fide cleavage product. When measuring products in a cell-based environment, where thousands and perhaps millions of different proteins and epitopes are presented to the antibody, such specificity is required for the absolute measurement of the specific BACE cleavage product. Overall, the polyclonal rabbit antibodies raised against EVEFR (SEQ.ID.NO.:58) are shown to be sufficiently specific for use in detection analyses.

The effectiveness of antibody against the EVEFR (SEQ. ID.NO.:58) site was evaluated as follows in the ORIGEN Analyzer (see below). One lot of the antibody against EVEFR (SEQ.ID.NO.:58), identified as 2182, was ruthenylated for use after a second affinity purification. Then this antibody was added at three concentrations, 10 ug/ml, 20 ug/ml, and 30 ug/ml, to each of a negative control (25 ul H4 conditioned media) and two treatments (respectively: 25 ul 10 nM EV1-40 (a purified form of 'variant' Aβ molecule that has EVEFR (SEQ.ID.NO.:58) at its amino end); and 25 ul of media of H4 cells which were incubated for 24 hours with a plasmid expressing $APP_{695}$ with NFEV (SEQ.ID.NO.:3) at the P2-P1-P1'-P2' β-secretase cleavage site). The results, described above, are shown in FIGS. 4A and 4B. To summarize, these data indicate that the ruthenylated anti-EVEFR (SEQ.ID.NO.:58) #2182 antibody:

1) is not specifically immunoreactive with a protein or peptide in the negative control H4 conditioned media;
2) results in a linear increase in signal with increasing concentration in the two 'positive' treatments, indicating: this antibody is specifically immunoreactive with the target EVEFR (SEQ.ID.NO.:58) epitope; and these concentrations are within the appropriate range for use in testing; and
3) detects the EVEFR (SEQ.ID.NO.:58) epitope as the latter is exposed in cell culture medium by β-secretase cleavage of $APP_{695}$ with NFEV (SEQ.ID.NO.:3) (i.e., forming a 'variant' Aβ molecule with the EVEFR (SEQ.ID.NO.:58) epitope at the amino end).

Overall, these evaluations indicate the specificity and overall utility of polyclonal antibody produced by the methods disclosed herein to detect the rate of breakdown of modified β-secretase substrates of the present invention. The above antibodies, and other antibodies prepared as described above to epitopes that comprise the P2-P1 or the P1'-P2' amino acids of SEQ.ID.NO.:3 to SEQ.ID.NO.:23, inclusive, are useful in various systems to test the effect of one or more substances that are being considered as potential modulators (particularly for inhibition) of β-secretase activity.

Accordingly, based on the disclosure provided herein, and considering the level of skill in the art of preparing antigen and antibodies, antibodies to other end-peptide groups, which include the P2-P1 amino acids for binding to the carboxyl end of modified sAPPβ formed from β-secretase cleavage of any of the modified substrates, are readily prepared without undue experimentation. Likewise, antibodies to other end-peptide groups, which include the P1'-P2' amino acids for binding to the modified carboxyterminal fragment (CTFβ) formed from β-secretase cleavage of any of the modified substrates, are readily prepared.

Such antibodies recognize at least one epitope that is formed by β-secretase cleavage of one of the modified β-secretase substrates of the present invention. In certain embodiments, the antibodies do not also recognize epitopes that are formed by β-secretase cleavage of wild-type APP. In other embodiments, the antibodies recognize an epitope that is formed by β-secretase cleavage of one of the modified β-secretase substrates of the present invention as well as an epitope that is formed by β-secretase cleavage of wild-type APP. As noted, the antibodies of the present invention can be used for monitoring β-secretase activity and β-secretase inhibitor screening. Also, once identified, any of these antibodies are produced by any means known to those of skill in the art, including, but not limited to, polyclonal and monoclonal production methods for whole antibody and immunologically active fragments thereof.

Description of use of Antibodies in the ORIGEN Analyzer

In certain embodiments the antibodies of the present invention are used in an electrochemiluminescence (ECL) detection method known in the art as "Origen" technology (Yang et al., 1994, Bio/Technology 12:193–194; Khorkova et al., 1998. Journal of Neuroscience Methods 82:159–166), and an Origen 1.5 Analyzer (Igen Inc., Gaithersburg, Md.). In embodiments using this ECL-based ORIGEN technology, each purified antibody lot is derivatized to a ruthenium tris-bipyridyl compound. The following provides one example of one of such embodiments.

This example is for the detection of a modified sAPPβ molecule that has the HA/myc/flag epitopes spliced between amino acid 289 and 290 based on the 695 amino acid length APP variant. This sandwich assay that detects levels of this cleavage product, which indicates the level of β-secretase activity (and of the decrease in such activity due to the effect of a putative inhibitor) in a test system, employs a first antibody to capture the cleavage peptide and a second antibody to detect the presence of the cleavage peptide.

The first antibody is prepared or obtained such that it is biotinylated (typically on its Fc portion) and it immunologically binds to the introduced HA/myc/FLAG epitopes (tags) on the modified sAPPβ. The second antibody is the ruthenylated polyclonal antibody described above that immunologically binds to the penta-peptide sequence SEVNF-COOH (SEQ.ID.NO.:57). Thus, the analyte, the modified sAPPβ, is bound by both the first and the second antibodies.

The assay measures the levels of modified sAPPβ present in the cell medium of cells transfected with the recombinant plasmids coding for modified β-secretase substrates having the following P2-P1-P1'-P2' sequences: NFEV (SEQ ID NO:3); NFDA (SEQ ID NO:4); NFEA (SEQ ID NO:5); and NLDV (SEQ ID NO:7). A control with GFP, APPwt (SEQ ID NO:45), and APPsw (SEQ ID NO:46) also were transfected into the same cell lines as the modified β-secretase substrate plasmids. After transfection, the cells were maintained in culture at 37° C. for 48–72 hours.

Thereafter, for the assay, a 50 ul aliquot of well-shaken cell medium from each replicate was added to an analyzer tube. 25 ul of each solution of the first antibody and the second antibody also were added. The tubes were covered and incubated at room temperature for between 3 and about 14 hours (overnight). Then to each tube 25 ul of a 200 ug streptavidin beads/ml solution, diluted in BSA diluent, was added. After 30 minutes reaction time with shaking, 150 ul of "Origen" assay buffer was added, and the enhanced chemiluminescence reading was taken in a model 1.5 Origen Analyzer.

The analysis is based on the second antibody being attracted to the streptavidin coated magnetic bead due to its biotin moiety. The second antibody also binds to the HA/myc/flag epitopes of the modified sAPPβ. The first antibody also binds, and thus sandwiches, the modified sAPPβ because it was raised to immunologically bind to the penta-peptide end of the carboxy terminal end of the modified sAPPβ. The ruthinylation of the first antibody is critical to the measurement of the chemiluminescence, which is measured when the magnetic beads have been concentrated to a position for such measurement by a transient magnetic field.

It is appreciated that in other embodiments using the Origen-based immuno-sandwich assay, the second antibody can be the one that is attracted to the penta-peptide end of the carboxy terminal end of the modified sAPPβ. In this case, this is biotinylated. In such case the first antibody, which immunologically binds to the epitope tag introduced on the modified sAPPβ molecule, is ruthenylated.

A second example, similar to the methods disclosed above for EVEFR (SEQ.ID.NO.:58), established that an antibody used in the above ECL method is specific to the products of the β-secretase cleavage of mutants having the penta-peptide SEVNF-COOH (SEQ.ID.NO.:57) at the carboxyl end of the sAPPβ polypeptide. As noted above, the 4-mer sequences for such mutants (e.g., all modified B-secretase substrates bearing these 4-mers) are: NFEV (SEQ.ID.NO.:3), NFDA (SEQ.ID.NO.:4), NFEA (SEQ.ID.NO.:5), NFDV (SEQ.ID.NO.:8), NFTV (SEQ.ID.NO.:9), and NFAA (SEQ.ID.NO.:16).

Having described a specific method for detection, it is appreciated that the β-secretase peptide substrates disclosed herein can be employed in a number of different types of assays that measure production of cleavage products. In general, cleavage of β-secretase substrates can be measured by detecting formation of the N- or C-terminal cleavage products of any of the herein disclosed peptide substrates. The presence of either of these products can be measured using techniques such as those employing antibodies and radioactive, electrochemiluminescent or fluorescent labels. Alternatively, biotinylated antibodies can be judiciously employed to form tertiary complexes with avidin and streptavidin conjugated reporter enzymes, including but not limited to, alkaline phosphatase, CAT, HRP, luciferase, and beta-lactamase. If needed or desirable, a purification step enriching the different products may be employed. Examples of purification steps include the use of antibodies, separation gels, and columns.

In addition, an APP backbone with a modified β-secretase cleavage site can be constructed with fusion partners either at its N-terminal or C-terminals. As examples, the approximate relative locations of maltose-binding protein (SEQ.ID.NO.:68) and a biotinylation sequence site ("BSS") (SEQ.ID.NO.:66) are graphically depicted in FIG. 1D. Such modifications facilitate the purification of recombinant modified β-secretase substrates and allow the measurement of β-secretase cleaved modified β-secretase substrate N-terminal or C-terminal products without using any antibodies against the APP backbone itself (other than the penta-peptide end that remains from the β-secretase cleavage site, where this is used in part of the assay). Other fusion proteins include, for example, APP fused to GFP and it derivatives for the detection of and tracking of protein trafficking.

EXAMPLE 3

The following provides an example, not meant to be limiting, of a cell-based assay that uses modified APP substrate and measures rate of enzymatic break-down of such substrate by detection of a secreted fragment (sAPP$_\beta$) of such modified APP substrate.

A stable cell line has been generated by transfecting APP695 containing the HA-myc-FLAG epitope in the amino portion of the protein, the K612V (APP695 numbering) mutation altering the alpha-cleavage site, and the modified NFEV BACE cleavage site into HEK293T cells. Standard cell biology protocols were used to generate the cell line. (Ref: Jakoby, W. B. and I. H. Pastan, Eds. (1979). *Cell Culture*. Methods in Enzymology. San Diego, Calif., Academic Press, Inc.) A polyclonal antibody that recognizes the COOH-terminus of the BACE cleavage product of the NFEV-variant of APP has also been generated. This antibody, called 2081/anti-NF IgG, was generated against the SEVNF peptide and recognizes the cleaved NF-COOH terminus generated by BACE proteolytic cleavage. As has been previously reported in the literature, the sAPP$_\beta$ fragment is secreted into the conditioned media of tissue culture cells expressing the substrate. The modified sAPP$_\beta$ fragment is similarly secreted into the conditioned media and with an appropriate assay can be detected and quantified. The following outlines the experiments performed to verify that the reagents generated to measure the secreted sAPP$_\beta$ (NFEV) are sufficiently sensitive and specific for high throughput detection of the secreted fragment; and a protocol that is used to detect and quantify the fragment in a high-throughput/robotized format.

To determine the sensitivity of the 2081 antibody, a titration using a biotinylated-SEVNF peptide was done. In this experiment, 2081 was used at 50 ng/100 ul and the biotinylated-SEVNF peptide was tested at 100 uM, 10 uM, 1 uM, 0.1 uM, 10 nM, 1 nM, and 0.1 nM. The negative controls were 0 nM biotinylated-SEVNF plus 50 ng/100 ul 2081 antibody and 100 nM biotinylated-SEVNF plus 0 ng/100 ul 2081 antibody. Each sample was set up in triplicate. All reactions were incubated at room temperature with shaking overnight. 5 ug of magnetic streptavidin beads were added to each reaction in the morning. The reaction was further incubated at room temperature for 30 minutes with shaking. 150 ul of Origen assay buffer was then added to each sample and the reactions were analyzed by ECL as previously described in the *Description of use of antibodies in the ORIGEN Analyzer*. Results of this experiment show that there is a peptide-dependent dose response of signal seen only in the presence of the 2081 antibody. This indicates that the 2081 antibody can recognize the biotinylated-SEVNF peptide and the signal to noise ratio is sufficient for detection of the cleaved product secreted into the conditioned media of the 293T/NFEV cells.

To determine the specificity of the 2081 antibody, competition experiments against the biotinylated-SEVNF with the following peptides were performed: SEVNF, SEVN, SEVNFE, SEVNL, and SEVNLD. The experiment was performed similar to the experiment outlined in Example 2 to determine the specificity of antibody 2081. The results indicate that SEVNF could compete for the biotinylated-SEVNF peptide but the SEVN, SEVNFE, and SEVNLD peptides could not compete with the binding of the 2081 antibody. The SEVNL peptide showed a limited amount of competition, 100-fold less effective than SEVNF. Thus, the 2081 antibody had the highest binding affinity for the SEVNF-COOH peptide.

Although the ORIGEN Analyzer has the advantage of sensitivity, the format is not amenable for high-throughput robotics. Accordingly, the assay was adapted to the Alpha Screen format (Perkin Elmer). Optimization of the amount of conditioned media, the concentration of the FLAG and 2081 antibodies, the concentration of the donor beads, and the concentration of the acceptor beads was done by titrating each variable and selecting for the best signal to noise ratio. A representative reaction with optimized conditions is described as follows.

HEK293T/NFEV cells are seeded into a 96-well tissue culture plate at $2.5 \times 10^4$ cells per well in 0.1 ml DMEM media containing 10% FBS and 5 ug/ml puromycin. Cells are incubated at 37° C. with 5% $CO_2$ for 4 hours. Media are then removed and replaced with fresh media containing 1% DMSO (control) or substance in 1% DMSO. Cells are incubated for an additional 20 hours at 37° C. with 5% $CO_2$. Media will be transferred to a separate plate for the Alpha screen assay.

To summarize, the following provides dilution steps and materials summaries:

Total assay volume=50 ul:
   30 ul CM+10 ul BioFLAG-IgG/Donor beads+10 ul anti-NF-IgG/Acceptor beads
1) Dilute Bio-Flag IgG to 15 nM from 16 uM in Alpha buffer
   =>final 3 nM
2) Dilute SA-coated Donor beads to 0.1 mg/ml from 5 mg/ml into Bio-Flag (15 nM dilution);
   =>after preincubation use 10 ul of Donor bead/Bio-FLAG IgG mixture per well.
   =>20 ug/ml final Donor bead concentration.
3) Dilute anti-NF IgG to 5 nM in Alpha buffer
   =>final 1 nM.
4) Dilute Protein-A Acceptor beads to 0.1 mg/ml from 5 mg/ml into anti-NF IgG (5 nM dilution);
   =>use 10 ul of Acceptor beads/anti-NF IgG mixture per well.
   =>20 ug/ml final Acceptor bead concentration.
5) Dilute the samples:
   HEK 293T/NFEV CM with substance titrations=>use 15 ul of media diluted with HEK 293T CM to yield a total of 30 ul sample;
   (−) control 1: 30 ul HEK 293T CM per well
   (+) control 2: 15 ul of HEK 293T/NFEV CM treated with 1% DMSO (no substance) diluted to 30 ul total volume with HEK 293T CM
   (+) control 3: 3 nM final MBPsAPP -NFEV-HA/Myc/Flag
6) Combine: 30 ul of CM dilutions in 384 well plate+10 ul Acceptor beads/anti-NF IgG per well
7) Preincubate two mixtures (CM+anti-NF-IgG/Acceptor beads and BioFLAG-IgG/Donor beads) in the dark at RT for ~1–2 hr.
8) Add 10 ul of Donor beads/Bio-Flag mix to each well with Acceptor beads/anti-NF IgG/CM.
9) Incubate in the dark at RT over night.

Materials:

Alpha Buffer:
   50 mM HEPES (HEPES Buffer Solution, 1M, from Gibco by Invitrogen Corp., #15630–080)
   150 mM NaCl (Sodium Chloride from FisherChemicals by Fisher Scientific, #S671-3)
   0.1% BSA (Albumin, Bovine, Fraction V, from Sigma, #A-4503)
   0.1% Tween-20 (Tween-20 from PlusOne by Pharmacia Biotech, #17-1316-01) dH$_2$O Bio-Flag IgG:
   Anti-Flag BioM2, 2.4 mg/ml, from Sigma, # F-9291

AlphaScreen General IgG (Protein A) Detection Kit
   Perkin Elmer Life Sciences;
   500 pts (Part Number 6760617C) or 10,000 pts (Part Number: 6760617M)

OptiPlate-384 NEW, White
   Perkin Elmer Life Sciences;
   50 plates (Part Number: 6007290) or 200 plates (Part Number: 6007299)

EXAMPLE 4

In order to assess the relative suitability of modified β-secretase substrates as substrates that are more reactive than the wild type KMDA cleavage site, plasmid DNA constructs were made expressing 21 different modified β-secretase cleavage site sequences. Table 1, below, summarizes data obtained from most of these modified β-secretase substrates in HEK293T cells. The HEK293T cells were transfected with plasmids containing the genetic sequences for the APP$_{695}$ polypeptides that contain each of these beta-site substitutions. These plasmids were prepared using the method described above in Example 1. Transient transfection was performed using LipofectaminePlus reagent (Gibco/BRL, Rockville, Md.) according to the instructions of the manufacturer. Media was harvested 48 hrs post transfection. Then Western blot analysis was used to determine levels of sAPP and IP/Western to determine levels of Aβ. Several volumes of conditioned media, 20 μl, 10 μl, 5 μl, 2.5 μl, from the transiently transfected cells were run on 10% SDS-PAGE gels and transferred to PVDF for the measurement of sAPP. Each blot contained a titration of wild type APP transfected conditioned media to normalize for any experimental variations derived from transferring of the gels and western blot detection. The blots were then probed with the antibody LN27 (Zymed, Calif.) to detect the secreted APP, sAPP. Densitometry of each western blot determined the relative amount of total APP expressed in each transfection.

To determine the levels of Aβ, each of the conditioned media was immuno-precipitated and analyzed via the following method. 5 μg of monoclonal antibody G2-10 (a monoclonal antibody that immunologically binds to the carboxyl end of Aβ40, licensed from University of Heidelberg) was added to 1 ml of each conditioned media. The mixture was rotated overnight at 4° C. for 16 hours. 25 μl of a 50% slurry of Protein A sepharose Fast flow beads (Amersham, N.J.) was added and incubation continued, rotating, for 2 hours at 4° C. The beads were pelleted and the supernatant was removed. The beads were washed once with 1 ml PBS. This material was then run on SDS-Tricine gels for analysis. 20 μl of 2×tricine loading buffer was added to the pellet and the mixture was heated at 95° C. for 5 minutes. A pipette tip was used to mix and load the whole mixture (beads included) onto a Bio-Rad 10–20% Tricine gel. The gels were electrophoresed at 125 Volts for 2 hours and 15 minutes and then transferred onto 0.2 μm nitrocellulose backed by a 0.1 μm nitrocellulose membrane for 75 minutes at 100V constant. Blots were then washed in PBS and boiled in PBS for 5 minutes before blocking in PBS plus 0.05% Tween-20 (PBST) with 5% non-fat milk for 60 minutes at room temperature. The milk was washed off twice with PBST and the blots were incubated overnight at 4° C. with G2-10 in PBST (1:1000 dilution). Blots were washed five times for 5 minutes each with large volumes of PBST and the secondary antibody of Goat anti-mouse IgG2b-HRP (Southern Biotechnology Associates, Inc., Birmingham, Ala.) was added at 1:5000 in PBST-5% milk and incubated, rocking, for 1 hour at room temperature. The blots were again washed, five times for 10 minutes each in large volumes of PBST. The substrate Pico ECL (Pierce) was added for 5 minutes and the blots were exposed to Kodak BioMax film. After western analysis was complete, the bands were quantitated by densitometry. For both the sAPP and the Aβ, the GFP control plasmid transfection serves as the background reference level (1×).

The effects of the modified β-secretase cleavage site sequences on Aβ production in cells are shown in Table 1 below. One sequence, NFEV (SEQ.ID.NO.:3), when introduced by the insertion of DNA corresponding to SEQ.ID.NO.24, produced high levels of Aβ, comparable to that generated by the APP Swedish mutant (NLDA (SEQ.ID.NO.:2) similarly introduced by the insertion of DNA corresponding to SEQ.ID.NO.46 (an APP$_{695}$-derived polypeptide modified with NLDA (SEQ.ID.NO.:2) at the β-secretase cleavage site. Another treatment, comprising an APP$_{695}$-derived polypeptide (SEQ.ID.NO.: 28) having the modified sequence, NLDV (SEQ.ID.NO.: 7), demonstrated production of Aβ in the HEK293T cells that was lower than APP$_{695}$-derived polypeptide, SEQ.ID.NO.:46, having the Swedish mutant (NLDA (SEQ.ID.NO.:2), but over three times the level of wild type APP$_{695}$, (SEQ.ID.NO.:45), which contains KMDA (SEQ.ID.NO.: 1).

Separate treatments of DNA molecules that each contained one of the following modified β-secretase cleavage sites also were transfected into 293T cells; however, the levels of APP expressed resulted in sAPP and Aβ that were below the limit of detection for the protocols employed: KYAA (SEQ.ID.NO.:43), in the APP$_{695}$-derived polypeptide SEQ.ID.NO.:43, NFAV (SEQ.ID.NO.:23) in the APP$_{695}$-derived polypeptide SEQ.ID.NO.:44, FFAV (SEQ.ID.NO.:13) in the APP$_{695}$-derived polypeptide SEQ.ID.NO.:34, NYAA (SEQ.ID.NO.:17) in the APP$_{695}$-derived polypeptide SEQ.ID.NO.:38, KFAA (SEQ.ID.NO.: 18) in the APP$_{695}$-derived polypeptide SEQ.ID.NO.:39, NFDV (SEQ.ID.NO.:8) in the APP$_{695}$-derived polypeptide SEQ.ID.NO.:29, NFTV (SEQ.ID.NO.:9) in the APP$_{695}$-derived polypeptide SEQ.ID.NO.:30, NYEA (SEQ.ID.NO.: 11) in the APP$_{695}$-derived polypeptide SEQ.ID.NO.:32, NYDV (SEQ.ID.NO.:12) in the APP$_{695}$-derived polypeptide SEQ.ID.NO.:33, and NFEA (SEQ.ID.NO.:5) in the APP$_{695}$-derived polypeptide SEQ.ID.NO.:26.

When APP-derived polypeptides comprising modified β-secretase cleavage site sequences, such as NFEV (SEQ.ID.NO.:3), NFEA (SEQ.ID.NO.:5), and NLDV (SEQ.ID.NO.:7), were transfected into immortalized β-secretase-/-mouse fibroblast cells (obtained under license from Johns Hopkins University), no production of Aβ was observed. Production of Aβ in β-secretase-/-cells could be rescued by co-transfection of the APP-derived polypeptides comprising modified β-secretase cleavage site sequences with human β-secretase. These data demonstrate that β-secretase is responsible for the cleavage of these modified β-secretase cleavage site sequences.

TABLE 1

| Aβ Level produced by APP β-site mutants in HEK293T cells | | | |
|---|---|---|---|
| High | Medium | | Low |
| 15–20X | 10–15X | 5–10X | 1–5X GFP control = 1X) |
| NFEV | NLDV | KLDA | FFEV |
| NLDA (Swedish) | | NLEA | NFAA |
| | | | KMAA |
| | | | KFEA |
| | | | KFDA |
| | | | NLAA |
| | | | KMDV |
| | | | NYDA |
| | | | KYDA |
| | | | NFDA |
| | | | KMDA (WT) |

EXAMPLE 5

Validation and Screening Studies

Inhibition studies can be performed to demonstrate that the β-secretase activity is catalyzed by a bona fide APP processing enzyme in cells and is not simply due to a spurious proteolytic activity. The studies may examine the effects of various peptide substrates from Table 2 on cleavage at the β-secretase scissile bond of the substrates in in vitro assays using any known inhibitor of β-secretase.

The effect of a β-secretase inhibitor on β-secretase activity is, for example, measured using HEK293T cells or H4 cells that stably express any one of the peptide substrates of the invention. HEK293T cells or H4 cells expressing the invention peptides are grown in a suitable medium under appropriate growth conditions, exemplified by 90% DMEM, 10% fetal bovine serum, 2 mM glutamine, 100 μg/ml each of penicillin and streptomycin, and 2–5 μg puromycin. . The cells are seeded in 96-well dishes at $2\times10^4$ cells/well. Cleavage product formation may be detected using antibodies specific for at least one cleavage product of the reference peptide substrate that is used to transfect the HEK293T or H4 cells.

Treatment of HEK293T or H4 cells expressing the invention peptides with a known β-secretase inhibitor is expected to block cleavage products from being secreted from such cells in a dose-dependent manner with $IC_{50}$ values for suppression of such products that are similar to values reported in the literature.

Similarly, a β-secretase inhibitor is expected to inhibit "solubilized β-secretase" mediated processing of any of the invention peptide substrate sequences shown in Table 1 that eventually result in the generation of the cleavage related products.

Initial data on a number of substances that are candidate inhibitors has been conducted, showing that the subject invention does operate in the manner intended as disclosed above.

EXAMPLE 6

This example pertains to generation of transgenic animals containing APP substrates of the present invention.

It is known that human APP gene consists of 16 exons spanning over 290 kb genomic regions. A search of existing human genome data revealed no bacterial artificial chromosome (BAC) clones that contain this gene. The average size of DNA inserts on BAC clones is approximately 150 kb, and it is likely that a gene of 290 kb in size is too big for a BAC to carry. The yeast artificial chromosome (YAC) can carry a DNA insert of a few hundred kb up to 1 Mb in size, and more than one human APP YAC transgenic mouse lines have been reported previously. However, to introduce further modifications to the APP gene which, due to the documented genetic instability of YAC clones, may lead to unpredictable complications. The following two approaches are used to more reliably, consistently and predictably generate a transgenic mouse strain expressing a modified human APP (e.g., a modified β-secretase substrate of the present invention).

1. Expressing a modified human APP from the mouse ROSA26 locus (targeted transgenic approach). The ROSA26 locus was initially identified in a gene-trap assay and has been since used extensively for targeting transgenes for predictable and ubiquitous expression under the control of the endogenous ROSA26 promoter. In this approach, a ROSA26 targeting construct is generated, which carries a human APP cDNA containing the desired modifications, as indicated above, at the P2-P1-P1'-P2' amino acid sites surrounding the β-secretase cleavage site. Other modifications, useful for detection by analytical means described herein (insertion of nucleic acid coding for Myc/flag, etc.) are additionally inserted in certain embodiments. Homologous recombination is carried out in mouse embryonic stem (ES) cells to target the modified human APP cDNA into the mouse ROSA26 locus, and correctly targeted ES cells are used to produce transgenic mice.

2. Modifying the endogenous mouse APP gene (gene 'knock-in' approach). Mouse and human APP share a high degree of similarity, especially in and around the Aβ region. In vitro biochemical data also suggest that the two proteins can substitute each other as BACE1 substrates. In this approach, the desired humanizing modifications are introduced into the endogenous mouse APP gene through homologous recombination in ES cells. This partially humanized mouse APP protein serves as a substrate for both mouse and human BACE1, making it possible to measure the activity of the enzyme and its inhibition.

It will be quickly recognized that APP cleaved by BACE1 in these transgenic animals can be readily detected by the unique and novel antibodies of the present invention. These antibodies in principle, should allow one to distinguish inhibition of the humanized form of APP, compared to the murine, if used in combination with an antibody which only recognizes the epitope of the humanized APP. It should be apparent to one skilled in the art that any of the means of sandwich immuno-assay detection described in the present disclosure can be used on brain extracts, cerebrospinal fluid and blood plasma samples from animals created with the novel BACE substrates.

Finally, these animals are useful for the in vivo screening and identification of potential BACE inhibitors after administration through standards means. Animals, which when treated with potent BACE1 inhibitors show depressed levels of BACE cleaved neo-epitopes, thus identify and measure in vivo efficacy of potential BACE inhibitors.

It will be apparent that the invention disclosed in the above example is equally applicable to transgenic rats and other transgenic animal models. Thus, at a minimum, the above example is applicable to laboratory rodents that include rats and mice.

EXAMPLE 7

One example of a cell free system for testing the relative effectiveness of potential modulators of β-secretase activity is provided herein. This method uses one purified β-secretase cleavable substrate of the present invention; any of the other β-secretase cleavable substrate of the present invention may be used without undue experimentation. The assay utilizes high-throughput Alpha-Screen technology (from Perkin-Elmer, Inc.), and in the example herein the testing is with purified NFEV substrate (SEQ.ID.NO.:24). The purified substrate contains maltose binding protein (MBP) fused to biotinylation sequence site ("BSS") sequence to facilitate intracellular biotinylation of the expressed protein, fused to APP(NFEV). The position of this MBP-BSS sequence in relation to the basic APP backbone is depicted in FIG. 1D. The MBP-BSS-APP(NFEV) (SEQ.ID.NO.:63) protein expression vector was produced using standard molecular biology techniques as described in Example 1 and the protein was produced using standard protein purification techniques familiar to those skilled in the art. The detailed steps of the method are as follows:

1. Purified BACE protein is diluted to 25 nM in enzyme buffer (25 mM NaOAc, 150 mM NaCl, 0.1% BSA, 0.05% CHAPS, PI cocktail, pH 4.5).
2. MBP-BSS-APP(NFEV)(SEQ.ID.NO.:63) is diluted to 30 μM in substrate buffer (25 mM NaOAc, 150 mM NaCl, 0.1% BSA, 0.05% CHAPS, PI cocktail, pH 6).
3. 4 μL BACE is dispensed into all columns of a 384-well plate.

4. 60 nL substance (at 500 µM in DMSO) is dispensed into columns 3–22 of the plate, and 60 nL DMSO is dispensed into columns 1, 2, 23, and 24 of the plate.
5. 1 µL MBP-BSS-APP(NFEV)(SEQ.ID.NO.:63) is dispensed into columns 1–23 of the plate.
6. The plate is incubated at 37C for 1 hour.
7. Affinity purified NF antisera (as described in Example 2 and references therein, below) is diluted to 10 nM in Quench Buffer (125 mM Tris, 150 mM NaCl, 0.1% BSA, pH 8).
8. 2.5 µL of the diluted NF-antisera is added to all columns of the plate.
9. The plate is incubated at room temperature for 3 minutes.
10. Protein A-labeled acceptor Beads and streptavidin-labeled donor beads are diluted to 80 µg/mL in Quench buffer.
11. 2.5 µL of a solution of protein A-acceptor beads and streptavidin-donor beads is added to all columns of the plate.
12. The plate is incubated for 3 hours at room temperature.
13. The plate is then read with the AlphaQuest plate reader.

The final assay conditions are:
20 nM BACE
400 nM MBP-BSS-APP(NFEV)(SEQ.ID.NO.:63)
2.5 nM NF Ab
20 ug/ml Protein A beads
20 ug/ml SA beads
0.9% DMSO
5 uM substance 14. Substances selected for follow-up are re-tested in triplicate as above.
15. Substances are tested for detection artifacts by the following method:
   4 µL Enzyme dilution buffer are dispensed into all columns of a 384-well plate.
   60 nL substance (at 500 µM in DMSO) is dispensed into columns 3–22 of the plate, and 60 nL DMSO is dispensed into columns 1, 2, 23, and 24 of the plate.
   1 µL MBP-BSS-APP(NF-COOH) (SEQ.ID.NO.:64) BACE cleavage product, constructed and purified using molecular biology techniques and protein purification techniques familiar to those skilled in the art is dispensed into columns 1–23 of the plate
   The plate is incubated at 37C. for 1 hour.
   Affinity purified NF antisera (as described in Example 2) is diluted to 10 nM in Quench Buffer (125 mM Tris, 150 mM NaCl, 0.1% BSA, pH 8).
   2.5 µL of the diluted NF-antisera is added to all columns of the plate.
   The plate is incubated at room temperature for 3 minutes.
   Protein A-labeled acceptor Beads and streptavidin-labeled donor beads are diluted to 80 µg/mL in Quench buffer.
   2.5 µL of a solution of protein A-acceptor beads and streptavidin-donor beads is added to all columns of the plate.
   The plate is incubated for 3 hours at room temperature.
   The plate is then read with the AlphaQuest plate reader
   Substances that inhibit detection of the MBP-BSS-APP (NF-COOH) (SEQ.ID.NO.:64) BACE cleavage product will be rejected for further development as BACE inhibitors.

The methods shown above in this example have been utilized with some candidate substances (i.e., possible BACE inhibitors) and the methods were shown to be reliable. Further, it is appreciated by those skilled in the art that proteins and/or polypeptides and/or peptides other than MBP are fusable to an APP backbone that comprises a modified β-secretase substrate of the present invention. Such proteins and/or polypeptides and/or peptides include reporter genes and epitope tags, which typically include linker sequences (as does "MBP" above), and in preferred embodiments two or more such proteins and/or polypeptides and/or peptides, are fused to an APP backbone that comprises a modified β-secretase substrate of the present invention.

EXAMPLE 8

A homogeneous end point HPLC assay is employed with the substrate (coumarin-CO-REVNFEVEFR), which is cleaved by BACE 1 to release the N-terminal fragment attached with coumarin. The Km of the substrate is greater than 100 µM and cannot be determined due to the limit of solubility of the substrate. A typical reaction contains 2 nM enzyme, 1.0 µM of the substrate, and buffer (50 mM NaOAc, pH 4.5, 0.1 mg/ml BSA, 0.2% CHAPS, 15 mM EDTA and 1 mM deferoxamine) in a total reaction volume of 100 µL. The reaction is proceeded for 30 min and the reaction is stopped by the addition of 25 µL of 1 M Tris-HCl, pH 8.0. The resulting reaction mixture was loaded on the HPLC and the product was separated from substrate with 5 min linear gradient. Under these conditions, less than 10% of substrate is processed by BACE 1. The enzyme used in these studies was soluble (transmembrane domain and cytoplasmic extension excluded) human protein produced in a baculovirus expression system. To measure the inhibitory potency for compounds, solutions of inhibitor in DMSO (12 concentrations of the inhibitors were prepared ) were included in the reaction mixture (final DMSO concentration is 10%). All experiments were conducted at room temperature using the standard reaction conditions described above. To determine the IC50 of the compound, four parameters equation is employed for curve fitting. The errors in reproducing the dissociation constants are typically less than two-fold.

Another highly sensitive homogeneous electrochemiluminescence assay for monitoring β-secretase activity in the presence or absence of compound is developed, using biotinylated substrate (Biotin-spacer-KTEEISEVNF, the spacer is hexanoic acid). The Origen technology is employed for the signal detection. A typical reaction contains 100 pM enzyme, 0.5 µM of the substrate, and buffer (50 mM NaOAc, pH 4.5, 0.1 mg/ml BSA, 0.2% CHAPS, 15 mM EDTA and 1 mM deferoxamine) in a total reaction volume of 100 µL. The reaction is proceeded for 30 min and the reaction is stopped by the addition of 25 µL of 1 M Tris-HCl, pH 8.0. Ruthenylated NF antibody (25 µL, 1.5 µg/mL) was added to capture NF terminal of product followed by the addition of streptavidin coated magnetic beads. The resulting mixture is incubated for overnight before measurement. All experiments were conducted at room temperature using the standard reaction conditions described above. To determine the IC50 of the compound, four parameters equation is employed for curve fitting. The errors in reproducing the dissociation constants are typically less than two-fold.

EXAMPLE 9

A second example of a cell free system for testing the relative effectiveness of potential modulators of β-secretase activity is provided herein. This method uses one purified β-secretase cleavable substrate of the present invention; any of the other β-secretase cleavable substrate of the present invention may be used without undue experimentation. The assay utilizes Alpha-Screen technology (from Perkin-Elmer, Inc.), and in the example herein the testing is with purified MBP-BSS-APP(NFEV)(SEQ.ID.NO.:63) protein. The detailed steps of the method are as follows:

Materials for BACE Assay (1–8) and AlphaScreen (9–12)
1. Recombinant substrate: MBP-BSS-APP(NFEV)(SEQ.ID.NO.:63)
2. Recombinant human BACE: BACE
3. 10×PI (1 protease inhibitor cocktail tablet(Cat# 1836153, Roche) in 1 ml dH2O)
4. 10×BSA solution(1 mg/ml)
5. 5% CHAPS in $H_2O$
6. 200 mM Sodium Acetate, pH 4.5
7. 1 M TrisCl, pH 8.0
8. Affinity purified antibody 2191
9. AlphaScreen IgG (Protein A) detection kit (Cat#6760617C, PerkinElmer)
10. AlphaScreen assay plate
11. 1×AlphaScreen assay buffer: 0.1% BSA in PBS, pH 7.2

| BACE assay (100 ul) | |
| --- | --- |
| 200 mM Sodium Acetate, pH 4.5 | 25 ul |
| 10 X PI | 10 ul |
| 10 X BSA solution | 10 ul |
| 5% CHAPS | 4 ul |
| MBP-BSS-APP(NFEV)(SEQ. ID. NO.:63) (see below) | 4 ul |
| BACE (see below) | 2 ul |
| DMSO | 1 ul |
| dH2O | 44 ul |

In a substrate concentration optimization experiment, the final concentration of MBP-BSS-APP(NFEV)(SEQ.ID.NO.:63) in the assay was varied between 100 and 800 nM, with the final concentration of BACE held constant at 20 nM (See FIG. 5). In an enzyme concentration optimization experiment, the final concentration of BACE in the assay was titrated between 2.5 and 160 nM with the final concentration of MBP-BSS-APP(NFEV)(SEQ.ID.NO.:63) held constant at 400 nM (See FIG. 5).

The BACE reaction was incubated at 37 C. for 60 minute.
7 ul of 1 M TrisCl, pH 8.0 was added to quench the reaction and neutralize pH.

| AlphaScreen assay (50 ul, 96 well plate) | |
| --- | --- |
| 1. AlphaScreen mix: | |
| Streptavidin donor beads (100 ug/ml) | 10.0 ul |
| Protein A acceptor beads (100 ug/ml) | 10.0 ul |
| Affinity purified antibody 2191 (5 nM) | 5.0 ul |
| 2. Assay: | |
| 1 X AlphaScreen assay buffer | 21.0 ul |
| BACE assay sample | 4.0 ul |
| AlphaScreen mix | 25.0 ul |

Incubated at room temperature for 3 hours and read on α-Fusion.

Results:
An increase in AlphaScreen signal was observed with an increasing concentration of MBP-BSS-APP(NFEV)(SEQ.ID.NO.:63) through the highest concentration tested (800 nM); however, the increase in signal remained linear only through 400 nM, thus this concentration was chosen for the use of this assay in screening potential BACE inhibitors (FIG. 5).

An increase in AlphaScreen signal was observed with an increasing concentration of BACE, and the signal increased linearly from 10 nM to 160 nM BACE (FIG. 6).

EXAMPLE 10

The following example describes an additional cell-free assay for BACE cleavage of APP(NFEV) using HTRF for detection of the cleavage event. This assay was carried out in two steps. In the first step, BACE cleaves the MBP-BSS-APP(NFEV)(SEQ.ID.NO.:63) substrate:

50 μL of BACE1 assay buffer (50 mM sodium acetate, pH 4.5, 1×Protease Inhibitor Cocktail (Roche), 0.2% CHAPS, and 0.1 mg/mL BSA)

Recombinant BACE1 (titration or final concentration of 20 nM in the assay)

MBP-BSS-APP(NFEV)(SEQ.ID.NO.:63) (titration or final concentration of 400 nM in the assay)

2 μL of DMSO Brought to a final volume of 100 μL with water

The assay was incubated at 37C for 90 minutes, and quenched with 7 μL of 1M Tris-HCL, pH 8.0.

The second step of the assay was the detection of the cleaved sAPPbeta(NF) fragment using HTRF.

Preparation of the HTRF assay mixture:

| | |
| --- | --- |
| HTRF buffer (25 mM HEPES, 0.1% BSA, 0.5 mM EDTA) | 800 μL |
| KF (2 M in HTRF buffer) | 200 μL |
| 2191 (affinity purified -NF antisera, 2.9 μM stock) | 1.38 μL (4 nM final) |
| $Eu^{3+}$-Protein G (2.41 μM stock) | 1.66 μL (4 nM final) |

This mixture was incubated at room temperature for 1 hour. After the incubation, 20.4 μL XL-anti-Flag Antibody (250 μg/mL stock) was added for a final concentration of 5 μg/mL.

The HTRF assay was carried out by combining 50 μL of the quenched BACE1 assay mixture with 50 μL of HTRF assay mixture. The mixture was incubated at room temperature for 2 hours and time resolved fluorescence was quantified using a LJL analyst (excitation-330-80 and emission 665).

RESULTS
The signal to noise ratio (expressed as S/N in FIGS. 7 and 8) increased with BACE concentration up to 20 nM as shown in FIG. 7. The signal to noise ratio increased with MBP-BSS-APP(NFEV) (SEQ.ID.NO.:63) concentration up to 400 nM as shown in FIG. 8.

Further in regard to the above disclosure and examples, those of skill in the relevant arts will appreciate that the invention is defined by the claims appended hereto, and further includes more specific combinations of limitations summarized as follows:

A method for detecting human β-secretase cleavage of a polypeptide substrate comprising:
providing a reaction system including human β-secretase, and a polypeptide substrate comprising a modified β-secretase cleavage site of β-amyloid precursor protein (APP) under conditions which permit β-secretase cleavage of the polypeptide substrate into carboxyl terminal and amino terminal β-secretase cleavage fragments; and detecting the amount of at least one of the β-secretase cleavage fragments produced as a result of β-secretase cleavage of the substrate relative to a control by binding the amino terminus of the carboxyl terminal fragment with an antibody specific for said end, wherein the presence of the peptide is detected by reaction of the specimen with a binding substance specific for an epitope at the amino terminus of the carboxyl terminal fragment.

A method for detecting human β-secretase cleavage of a polypeptide substrate, said method comprising:

providing a reaction system including human β-secretase, and a polypeptide substrate comprising a modified β-secretase cleavage site of β-amyloid precursor protein (APP) under conditions which permit β-secretase cleavage of the polypeptide substrate into carboxyl terminal and amino terminal β-secretase cleavage fragments; and detecting the amount of at least one of the β-secretase cleavage fragments produced as a result of β-secretase cleavage of the substrate relative to a control by binding the carboxy terminus of the amino terminal fragment of the polypeptide substrate with an antibody specific for said end, wherein the presence of the peptide is detected by reaction of the specimen with a binding substance specific for an epitope at the carboxy terminus of the amino terminal fragment.

An in vitro method of identifying a substance that inhibits β-secretase comprising:

(a) providing a plurality of replicates of a cell-free system, each of said plurality of replicates comprising:

(i) a polypeptide comprising a β-secretase cleavage site comprising an amino acid sequence selected from the group consisting of SEQ.ID.NO.:1 to SEQ.ID.NO.:23; and (ii) a source of β-secretase activity;

(b) measuring in one or more of said replicates of the cell-free system the level of β-secretase activity in the absence of the substance; and (c) measuring in one or more of said replicates of the cell-free system the level of β-secretase activity in the presence of the substance;

wherein a decrease in the level of β-secretase activity in the presence as compared to the absence of the substance identifies the substance as a β-secretase inhibitor, wherein said polypeptide additionally comprises a biotinylation sequence site, and additionally comprising capturing said biotinylated polypeptide in a sandwich type ELISA assay, or wherein said measuring is conducted by electrochemiluminescence.

A substantially pure polypeptide comprising an amino acid sequence as set forth in one of SEQ.ID.NO.:24–44 and variants thereof, wherein said variant is at least 95 percent identical in amino acid sequence to any of SEQ.ID.NO.: 24–44 with an identical P2-P1-P1'-P2' β-secretase cleavage site, and is a substrate of β-secretase.

A protein having any of SEQ.ID.NO.:24–44 and variants thereof that are at least 85 percent identical in amino acid sequence to any of SEQ.ID.NO.:24–44 with an identical P2-P1-P1'-P2' β-secretase cleavage site, and is a substrate of β-secretase.

A protein having any of SEQ.ID.NO.:24–44 and variants thereof that are at least 65 percent identical in amino acid sequence to any of SEQ.ID.NO.:24–44 with an identical P2-P1-P1'-P2' β-secretase cleavage site, and is a substrate of β-secretase.

With regard to novel sequences disclosed in International Application No. PCT/US/02/15590, filed May 17, 2002, and provisional applications to which the instant application claims priority, it is noted that 8-mer sequences disclosed in said priority applications have different sequence numbering than the sequence numbering used herein. Despite such numbering differences, the modified β-secretase substrates disclosed and claimed herein include some of the modified β-secretase substrates disclosed in such prior applications. For instance, without being limiting, the following table provides a cross-index to certain sequences in the present application that include the specific 8-mer sequences disclosed in the previous applications:

| $APP_{695}$ SEQ ID NO in present application | SEQ ID NO of 8-mer in 20886PV2, found in respective $APP_{695}$ |
|---|---|
| 46 | 257 |
| 24 | 262 |
| 26 | 260 |
| 34 | 92 |
| 35 | 116 |
| 36 | 258 |
| 37 | 259 |
| 44 | 261 |

All patents, patent applications, publications, texts and references discussed or cited herein are incorporated by reference to the same extent as if each individual publication or patent application was specifically and individually set forth in its entirety. Nothing herein is to be construed as an admission that the invention is not entitled to antedate such disclosures by virtue of prior invention. In addition, all terms not specifically defined are first taken to have the meaning given through usage in this disclosure, and if no such meaning is inferable, their normal meaning. Where a limitation is described but not given a specific term, a term corresponding to such limitation may be taken from any references, patents, applications, and other documents cited herein, or, for an application claiming priority to this application, additionally from an Invention Disclosure Statement, Examiner's Summary of Cited References, or a paper otherwise entered into the file history of this application.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims. Thus, for the above variations and in other regards, it should be understood that the examples and embodiments described herein are for illustrative purposes only and that various modifications or changes in light thereof will be suggested to persons skilled in the relevant arts and are to be included within the spirit and purview of this application and the scope of the appended claims.

What is claimed is:

1. An APP molecule selected from the group consisting of APP695, APP751, and APP770, or a biologically active fragment thereof, having a modified β-secretase cleavage site comprising an amino acid sequence of NFEV (SEQ.ID.NO:3) and located at positions corresponding to positions 595-596-597-598 of APP695.

2. An APP molecule of claim 1 further comprising a single amino acid substitution comprising a valine for lysine at an amino acid position corresponding to position 612 in APP695.

3. An APP molecule of claim 1 wherein the β-secretase cleavage site corresponds to positions 595-596-597-598 of APP695, positions 651-652-653-654 of APP751 and positions 670-671-672-673 APP770.

4. An APP molecule of claim 3 further comprising a marker or label attached to one of a carboxyl or amino terminus of the polypeptide.

5. An APP molecule of claim 4 wherein said marker further comprises a reporter protein amino acid attached to one of a carboxyl or amino terminus of the β-secretase cleavage site.

* * * * *

SEQUENCE LISTING

<160> NUMBER OF SEQ ID NOS: 75

<210> SEQ ID NO 1
<211> LENGTH: 4
<212> TYPE: PRT
<213> ORGANISM: Homo sapiens

<400> SEQUENCE: 1

Lys Met Asp Ala
1

<210> SEQ ID NO 2
<211> LENGTH: 4
<212> TYPE: PRT
<213> ORGANISM: Homo sapiens

<400> SEQUENCE: 2

Asn Leu Asp Ala
1

<210> SEQ ID NO 3
<211> LENGTH: 4
<212> TYPE: PRT
<213> ORGANISM: Artificial
<220> FEATURE:
<223> OTHER INFORMATION: novel sequence of known enzyme cleavage site

<400> SEQUENCE: 3

Asn Phe Glu Val
1

<210> SEQ ID NO 4
<211> LENGTH: 4
<212> TYPE: PRT
<213> ORGANISM: Artificial
<220> FEATURE:
<223> OTHER INFORMATION: novel sequence of known enzyme cleavage site

<400> SEQUENCE: 4

Asn Phe Asp Ala
1

<210> SEQ ID NO 5
<211> LENGTH: 4
<212> TYPE: PRT
<213> ORGANISM: Artificial
<220> FEATURE:
<223> OTHER INFORMATION: novel sequence of known enzyme cleavage site

<400> SEQUENCE: 5

Asn Phe Glu Ala
1

<210> SEQ ID NO 6
<211> LENGTH: 4
<212> TYPE: PRT
<213> ORGANISM: Artificial
<220> FEATURE:
<223> OTHER INFORMATION: novel sequence of known enzyme cleavage site

<400> SEQUENCE: 6

Asn Leu Glu Ala
1

```
<210> SEQ ID NO 7
<211> LENGTH: 4
<212> TYPE: PRT
<213> ORGANISM: Artificial
<220> FEATURE:
<223> OTHER INFORMATION: novel sequence of known enzyme cleavage site

<400> SEQUENCE: 7

Asn Leu Asp Val
1

<210> SEQ ID NO 8
<211> LENGTH: 4
<212> TYPE: PRT
<213> ORGANISM: Artificial
<220> FEATURE:
<223> OTHER INFORMATION: novel sequence of known enzyme cleavage site

<400> SEQUENCE: 8

Asn Phe Asp Val
1

<210> SEQ ID NO 9
<211> LENGTH: 4
<212> TYPE: PRT
<213> ORGANISM: Artificial
<220> FEATURE:
<223> OTHER INFORMATION: novel sequence of known enzyme cleavage site

<400> SEQUENCE: 9

Asn Phe Thr Val
1

<210> SEQ ID NO 10
<211> LENGTH: 4
<212> TYPE: PRT
<213> ORGANISM: Artificial
<220> FEATURE:
<223> OTHER INFORMATION: novel sequence of known enzyme cleavage site

<400> SEQUENCE: 10

Asn Tyr Asp Ala
1

<210> SEQ ID NO 11
<211> LENGTH: 4
<212> TYPE: PRT
<213> ORGANISM: Artificial
<220> FEATURE:
<223> OTHER INFORMATION: novel sequence of known enzyme cleavage site

<400> SEQUENCE: 11

Asn Tyr Glu Ala
1

<210> SEQ ID NO 12
<211> LENGTH: 4
<212> TYPE: PRT
<213> ORGANISM: Artificial
<220> FEATURE:
<223> OTHER INFORMATION: novel sequence of known enzyme cleavage site

<400> SEQUENCE: 12

Asn Tyr Asp Val
1

<210> SEQ ID NO 13
```

```
<211> LENGTH: 4
<212> TYPE: PRT
<213> ORGANISM: Artificial
<220> FEATURE:
<223> OTHER INFORMATION: novel sequence of known enzyme cleavage site

<400> SEQUENCE: 13

Phe Phe Ala Val
1

<210> SEQ ID NO 14
<211> LENGTH: 4
<212> TYPE: PRT
<213> ORGANISM: Artificial
<220> FEATURE:
<223> OTHER INFORMATION: novel sequence of known enzyme cleavage site

<400> SEQUENCE: 14

Phe Phe Glu Val
1

<210> SEQ ID NO 15
<211> LENGTH: 4
<212> TYPE: PRT
<213> ORGANISM: Artificial
<220> FEATURE:
<223> OTHER INFORMATION: novel sequence of known enzyme cleavage site

<400> SEQUENCE: 15

Asn Leu Ala Ala
1

<210> SEQ ID NO 16
<211> LENGTH: 4
<212> TYPE: PRT
<213> ORGANISM: Artificial
<220> FEATURE:
<223> OTHER INFORMATION: novel sequence of known enzyme cleavage site

<400> SEQUENCE: 16

Asn Phe Ala Ala
1

<210> SEQ ID NO 17
<211> LENGTH: 4
<212> TYPE: PRT
<213> ORGANISM: Artificial
<220> FEATURE:
<223> OTHER INFORMATION: novel sequence of known enzyme cleavage site

<400> SEQUENCE: 17

Asn Tyr Ala Ala
1

<210> SEQ ID NO 18
<211> LENGTH: 4
<212> TYPE: PRT
<213> ORGANISM: Artificial
<220> FEATURE:
<223> OTHER INFORMATION: novel sequence of known enzyme cleavage site

<400> SEQUENCE: 18

Lys Phe Ala Ala
1

<210> SEQ ID NO 19
<211> LENGTH: 4
```

```
<212> TYPE: PRT
<213> ORGANISM: Artificial
<220> FEATURE:
<223> OTHER INFORMATION: novel sequence of known enzyme cleavage site

<400> SEQUENCE: 19

Lys Met Ala Ala
1

<210> SEQ ID NO 20
<211> LENGTH: 4
<212> TYPE: PRT
<213> ORGANISM: Artificial
<220> FEATURE:
<223> OTHER INFORMATION: novel sequence of known enzyme cleavage site

<400> SEQUENCE: 20

Lys Met Asp Val
1

<210> SEQ ID NO 21
<211> LENGTH: 4
<212> TYPE: PRT
<213> ORGANISM: Artificial
<220> FEATURE:
<223> OTHER INFORMATION: novel sequence of known enzyme cleavage site

<400> SEQUENCE: 21

Lys Phe Glu Ala
1

<210> SEQ ID NO 22
<211> LENGTH: 4
<212> TYPE: PRT
<213> ORGANISM: Artificial
<220> FEATURE:
<223> OTHER INFORMATION: novel sequence of known enzyme cleavage site

<400> SEQUENCE: 22

Lys Tyr Ala Ala
1

<210> SEQ ID NO 23
<211> LENGTH: 4
<212> TYPE: PRT
<213> ORGANISM: Artificial
<220> FEATURE:
<223> OTHER INFORMATION: novel sequence of known enzyme cleavage site

<400> SEQUENCE: 23

Asn Phe Ala Val
1

<210> SEQ ID NO 24
<211> LENGTH: 695
<212> TYPE: PRT
<213> ORGANISM: Artificial
<220> FEATURE:
<223> OTHER INFORMATION: polypeptide containing novel sequence at known
      enzyme cleavage site

<400> SEQUENCE: 24

Met Leu Pro Gly Leu Ala Leu Leu Leu Ala Ala Trp Thr Ala Arg
1               5                   10                  15

Ala Leu Glu Val Pro Thr Asp Gly Asn Ala Gly Leu Leu Ala Glu Pro
            20                  25                  30
```

-continued

```
Gln Ile Ala Met Phe Cys Gly Arg Leu Asn Met His Met Asn Val Gln
             35                  40                  45

Asn Gly Lys Trp Asp Ser Asp Pro Ser Gly Thr Lys Thr Cys Ile Asp
     50                  55                  60

Thr Lys Glu Gly Ile Leu Gln Tyr Cys Gln Glu Val Tyr Pro Glu Leu
 65                  70                  75                  80

Gln Ile Thr Asn Val Val Glu Ala Asn Gln Pro Val Thr Ile Gln Asn
                 85                  90                  95

Trp Cys Lys Arg Gly Arg Lys Gln Cys Lys Thr His Pro His Phe Val
            100                 105                 110

Ile Pro Tyr Arg Cys Leu Val Gly Glu Phe Val Ser Asp Ala Leu Leu
            115                 120                 125

Val Pro Asp Lys Cys Lys Phe Leu His Gln Glu Arg Met Asp Val Cys
130                 135                 140

Glu Thr His Leu His Trp His Thr Val Ala Lys Glu Thr Cys Ser Glu
145                 150                 155                 160

Lys Ser Thr Asn Leu His Asp Tyr Gly Met Leu Leu Pro Cys Gly Ile
                165                 170                 175

Asp Lys Phe Arg Gly Val Glu Phe Val Cys Cys Pro Leu Ala Glu Glu
            180                 185                 190

Ser Asp Asn Val Asp Ser Ala Asp Ala Glu Glu Asp Asp Ser Asp Val
            195                 200                 205

Trp Trp Gly Gly Ala Asp Thr Asp Tyr Ala Asp Gly Ser Glu Asp Lys
210                 215                 220

Val Val Glu Val Ala Glu Glu Glu Val Ala Glu Val Glu Glu Glu
225                 230                 235                 240

Glu Ala Asp Asp Asp Glu Asp Asp Glu Asp Gly Asp Glu Val Glu Glu
            245                 250                 255

Glu Ala Glu Glu Pro Tyr Glu Glu Ala Thr Glu Arg Thr Thr Ser Ile
            260                 265                 270

Ala Thr Thr Thr Thr Thr Thr Glu Ser Val Glu Glu Val Val Arg
            275                 280                 285

Val Pro Thr Thr Ala Ala Ser Thr Pro Asp Ala Val Asp Lys Tyr Leu
            290                 295                 300

Glu Thr Pro Gly Asp Glu Asn Glu His Ala His Phe Gln Lys Ala Lys
305                 310                 315                 320

Glu Arg Leu Glu Ala Lys His Arg Glu Arg Met Ser Gln Val Met Arg
                325                 330                 335

Glu Trp Glu Glu Ala Glu Arg Gln Ala Lys Asn Leu Pro Lys Ala Asp
            340                 345                 350

Lys Lys Ala Val Ile Gln His Phe Gln Glu Lys Val Glu Ser Leu Glu
            355                 360                 365

Gln Glu Ala Ala Asn Glu Arg Gln Gln Leu Val Glu Thr His Met Ala
            370                 375                 380

Arg Val Glu Ala Met Leu Asn Asp Arg Arg Arg Leu Ala Leu Glu Asn
385                 390                 395                 400

Tyr Ile Thr Ala Leu Gln Ala Val Pro Pro Arg Pro Arg His Val Phe
                405                 410                 415

Asn Met Leu Lys Lys Tyr Val Arg Ala Glu Gln Lys Asp Arg Gln His
            420                 425                 430

Thr Leu Lys His Phe Glu His Val Arg Met Val Asp Pro Lys Lys Ala
            435                 440                 445

Ala Gln Ile Arg Ser Gln Val Met Thr His Leu Arg Val Ile Tyr Glu
```

```
              450               455               460
Arg Met Asn Gln Ser Leu Ser Leu Leu Tyr Asn Val Pro Ala Val Ala
465                 470                 475                 480

Glu Glu Ile Gln Asp Glu Val Asp Glu Leu Leu Gln Lys Glu Gln Asn
                485                 490                 495

Tyr Ser Asp Asp Val Leu Ala Asn Met Ile Ser Glu Pro Arg Ile Ser
                500                 505                 510

Tyr Gly Asn Asp Ala Leu Met Pro Ser Leu Thr Glu Thr Lys Thr Thr
            515                 520                 525

Val Glu Leu Leu Pro Val Asn Gly Glu Phe Ser Leu Asp Asp Leu Gln
530                 535                 540

Pro Trp His Ser Phe Gly Ala Asp Ser Val Pro Ala Asn Thr Glu Asn
545                 550                 555                 560

Glu Val Glu Pro Val Asp Ala Arg Pro Ala Ala Asp Arg Gly Leu Thr
                565                 570                 575

Thr Arg Pro Gly Ser Gly Leu Thr Asn Ile Lys Thr Glu Glu Ile Ser
            580                 585                 590

Glu Val Asn Phe Glu Val Glu Phe Arg His Asp Ser Gly Tyr Glu Val
            595                 600                 605

His His Gln Lys Leu Val Phe Phe Ala Glu Asp Val Gly Ser Asn Lys
        610                 615                 620

Gly Ala Ile Ile Gly Leu Met Val Gly Gly Val Val Ile Ala Thr Val
625                 630                 635                 640

Ile Val Ile Thr Leu Val Met Leu Lys Lys Lys Gln Tyr Thr Ser Ile
                645                 650                 655

His His Gly Val Val Glu Val Asp Ala Ala Val Thr Pro Glu Glu Arg
            660                 665                 670

His Leu Ser Lys Met Gln Gln Asn Gly Tyr Glu Asn Pro Thr Tyr Lys
            675                 680                 685

Phe Phe Glu Gln Met Gln Asn
        690                 695

<210> SEQ ID NO 25
<211> LENGTH: 695
<212> TYPE: PRT
<213> ORGANISM: Artificial
<220> FEATURE:
<223> OTHER INFORMATION: polypeptide containing novel sequence at known
      enzyme cleavage site

<400> SEQUENCE: 25

Met Leu Pro Gly Leu Ala Leu Leu Leu Leu Ala Ala Trp Thr Ala Arg
1               5                   10                  15

Ala Leu Glu Val Pro Thr Asp Gly Asn Ala Gly Leu Leu Ala Glu Pro
                20                  25                  30

Gln Ile Ala Met Phe Cys Gly Arg Leu Asn Met His Met Asn Val Gln
            35                  40                  45

Asn Gly Lys Trp Asp Ser Asp Pro Ser Gly Thr Lys Thr Cys Ile Asp
50                  55                  60

Thr Lys Glu Gly Ile Leu Gln Tyr Cys Gln Glu Val Tyr Pro Glu Leu
65                  70                  75                  80

Gln Ile Thr Asn Val Val Glu Ala Asn Gln Pro Val Thr Ile Gln Asn
                85                  90                  95

Trp Cys Lys Arg Gly Arg Lys Gln Cys Lys Thr His Pro His Phe Val
            100                 105                 110
```

-continued

```
Ile Pro Tyr Arg Cys Leu Val Gly Glu Phe Val Ser Asp Ala Leu Leu
    115                 120                 125

Val Pro Asp Lys Cys Lys Phe Leu His Gln Glu Arg Met Asp Val Cys
130                 135                 140

Glu Thr His Leu His Trp His Thr Val Ala Lys Glu Thr Cys Ser Glu
145                 150                 155                 160

Lys Ser Thr Asn Leu His Asp Tyr Gly Met Leu Leu Pro Cys Gly Ile
                165                 170                 175

Asp Lys Phe Arg Gly Val Glu Phe Val Cys Cys Pro Leu Ala Glu Glu
            180                 185                 190

Ser Asp Asn Val Asp Ser Ala Asp Ala Glu Glu Asp Asp Ser Asp Val
            195                 200                 205

Trp Trp Gly Gly Ala Asp Thr Asp Tyr Ala Asp Gly Ser Glu Asp Lys
210                 215                 220

Val Val Glu Val Ala Glu Glu Glu Val Ala Glu Val Glu Glu Glu Glu
225                 230                 235                 240

Glu Ala Asp Asp Asp Glu Asp Asp Glu Asp Gly Asp Glu Val Glu Glu
                245                 250                 255

Glu Ala Glu Glu Pro Tyr Glu Glu Ala Thr Glu Arg Thr Thr Ser Ile
            260                 265                 270

Ala Thr Thr Thr Thr Thr Thr Glu Ser Val Glu Glu Val Val Arg
        275                 280                 285

Val Pro Thr Thr Ala Ala Ser Thr Pro Asp Ala Val Asp Lys Tyr Leu
    290                 295                 300

Glu Thr Pro Gly Asp Glu Asn Glu His Ala His Phe Gln Lys Ala Lys
305                 310                 315                 320

Glu Arg Leu Glu Ala Lys His Arg Glu Arg Met Ser Gln Val Met Arg
                325                 330                 335

Glu Trp Glu Glu Ala Glu Arg Gln Ala Lys Asn Leu Pro Lys Ala Asp
            340                 345                 350

Lys Lys Ala Val Ile Gln His Phe Gln Glu Lys Val Glu Ser Leu Glu
        355                 360                 365

Gln Glu Ala Ala Asn Glu Arg Gln Gln Leu Val Glu Thr His Met Ala
    370                 375                 380

Arg Val Glu Ala Met Leu Asn Asp Arg Arg Arg Leu Ala Leu Glu Asn
385                 390                 395                 400

Tyr Ile Thr Ala Leu Gln Ala Val Pro Pro Arg Pro Arg His Val Phe
                405                 410                 415

Asn Met Leu Lys Lys Tyr Val Arg Ala Glu Gln Lys Asp Arg Gln His
            420                 425                 430

Thr Leu Lys His Phe Glu His Val Arg Met Val Asp Pro Lys Lys Ala
        435                 440                 445

Ala Gln Ile Arg Ser Gln Val Met Thr His Leu Arg Val Ile Tyr Glu
    450                 455                 460

Arg Met Asn Gln Ser Leu Ser Leu Leu Tyr Asn Val Pro Ala Val Ala
465                 470                 475                 480

Glu Glu Ile Gln Asp Glu Val Asp Glu Leu Leu Gln Lys Glu Gln Asn
                485                 490                 495

Tyr Ser Asp Asp Val Leu Ala Asn Met Ile Ser Glu Pro Arg Ile Ser
            500                 505                 510

Tyr Gly Asn Asp Ala Leu Met Pro Ser Leu Thr Glu Thr Lys Thr Thr
        515                 520                 525

Val Glu Leu Leu Pro Val Asn Gly Glu Phe Ser Leu Asp Asp Leu Gln
```

-continued

```
                530                 535                 540
Pro Trp His Ser Phe Gly Ala Asp Ser Val Pro Ala Asn Thr Glu Asn
545                 550                 555                 560

Glu Val Glu Pro Val Asp Ala Arg Pro Ala Asp Arg Gly Leu Thr
                565                 570                 575

Thr Arg Pro Gly Ser Gly Leu Thr Asn Ile Lys Thr Glu Glu Ile Ser
                580                 585                 590

Glu Val Asn Phe Asp Ala Glu Phe Arg His Asp Ser Gly Tyr Glu Val
                595                 600                 605

His His Gln Lys Leu Val Phe Phe Ala Glu Asp Val Gly Ser Asn Lys
                610                 615                 620

Gly Ala Ile Ile Gly Leu Met Val Gly Val Val Ile Ala Thr Val
625                 630                 635                 640

Ile Val Ile Thr Leu Val Met Leu Lys Lys Lys Gln Tyr Thr Ser Ile
                645                 650                 655

His His Gly Val Val Glu Val Asp Ala Ala Val Thr Pro Glu Glu Arg
                660                 665                 670

His Leu Ser Lys Met Gln Gln Asn Gly Tyr Glu Asn Pro Thr Tyr Lys
                675                 680                 685

Phe Phe Glu Gln Met Gln Asn
    690                 695

<210> SEQ ID NO 26
<211> LENGTH: 695
<212> TYPE: PRT
<213> ORGANISM: Artificial
<220> FEATURE:
<223> OTHER INFORMATION: polypeptide containing novel sequence at known
      enzyme cleavage site

<400> SEQUENCE: 26

Met Leu Pro Gly Leu Ala Leu Leu Leu Ala Ala Trp Thr Ala Arg
1               5                   10                  15

Ala Leu Glu Val Pro Thr Asp Gly Asn Ala Gly Leu Leu Ala Glu Pro
                20                  25                  30

Gln Ile Ala Met Phe Cys Gly Arg Leu Asn Met His Met Asn Val Gln
            35                  40                  45

Asn Gly Lys Trp Asp Ser Asp Pro Ser Gly Thr Lys Thr Cys Ile Asp
        50                  55                  60

Thr Lys Glu Gly Ile Leu Gln Tyr Cys Gln Glu Val Tyr Pro Glu Leu
65              70                  75                  80

Gln Ile Thr Asn Val Val Glu Ala Asn Gln Pro Val Thr Ile Gln Asn
                85                  90                  95

Trp Cys Lys Arg Gly Arg Lys Gln Cys Lys Thr His Pro His Phe Val
            100                 105                 110

Ile Pro Tyr Arg Cys Leu Val Gly Glu Phe Val Ser Asp Ala Leu Leu
        115                 120                 125

Val Pro Asp Lys Cys Lys Phe Leu His Gln Glu Arg Met Asp Val Cys
130                 135                 140

Glu Thr His Leu His Trp His Thr Val Ala Lys Glu Thr Cys Ser Glu
145                 150                 155                 160

Lys Ser Thr Asn Leu His Asp Tyr Gly Met Leu Leu Pro Cys Gly Ile
                165                 170                 175

Asp Lys Phe Arg Gly Val Glu Phe Val Cys Cys Pro Leu Ala Glu Glu
            180                 185                 190
```

-continued

```
Ser Asp Asn Val Asp Ser Ala Asp Ala Glu Glu Asp Asp Ser Asp Val
        195                 200                 205

Trp Trp Gly Gly Ala Asp Thr Asp Tyr Ala Asp Gly Ser Glu Asp Lys
        210                 215                 220

Val Val Glu Val Ala Glu Glu Glu Val Ala Glu Val Glu Glu Glu
225                 230                 235                 240

Glu Ala Asp Asp Asp Glu Asp Asp Glu Asp Gly Asp Glu Val Glu Glu
                245                 250                 255

Glu Ala Glu Glu Pro Tyr Glu Glu Ala Thr Glu Arg Thr Thr Ser Ile
                260                 265                 270

Ala Thr Thr Thr Thr Thr Thr Glu Ser Val Glu Glu Val Val Arg
        275                 280                 285

Val Pro Thr Thr Ala Ala Ser Thr Pro Asp Ala Val Asp Lys Tyr Leu
        290                 295                 300

Glu Thr Pro Gly Asp Glu Asn Glu His Ala His Phe Gln Lys Ala Lys
305                 310                 315                 320

Glu Arg Leu Glu Ala Lys His Arg Glu Arg Met Ser Gln Val Met Arg
                325                 330                 335

Glu Trp Glu Glu Ala Glu Arg Gln Ala Lys Asn Leu Pro Lys Ala Asp
                340                 345                 350

Lys Lys Ala Val Ile Gln His Phe Gln Glu Lys Val Glu Ser Leu Glu
        355                 360                 365

Gln Glu Ala Ala Asn Glu Arg Gln Gln Leu Val Glu Thr His Met Ala
        370                 375                 380

Arg Val Glu Ala Met Leu Asn Asp Arg Arg Arg Leu Ala Leu Glu Asn
385                 390                 395                 400

Tyr Ile Thr Ala Leu Gln Ala Val Pro Pro Arg Pro Arg His Val Phe
                405                 410                 415

Asn Met Leu Lys Lys Tyr Val Arg Ala Glu Gln Lys Asp Arg Gln His
                420                 425                 430

Thr Leu Lys His Phe Glu His Val Arg Met Val Asp Pro Lys Lys Ala
        435                 440                 445

Ala Gln Ile Arg Ser Gln Val Met Thr His Leu Arg Val Ile Tyr Glu
        450                 455                 460

Arg Met Asn Gln Ser Leu Ser Leu Leu Tyr Asn Val Pro Ala Val Ala
465                 470                 475                 480

Glu Glu Ile Gln Asp Glu Val Asp Glu Leu Leu Gln Lys Glu Gln Asn
                485                 490                 495

Tyr Ser Asp Asp Val Leu Ala Asn Met Ile Ser Glu Pro Arg Ile Ser
                500                 505                 510

Tyr Gly Asn Asp Ala Leu Met Pro Ser Leu Thr Glu Thr Lys Thr Thr
        515                 520                 525

Val Glu Leu Leu Pro Val Asn Gly Glu Phe Ser Leu Asp Asp Leu Gln
        530                 535                 540

Pro Trp His Ser Phe Gly Ala Asp Ser Val Pro Ala Asn Thr Glu Asn
545                 550                 555                 560

Glu Val Glu Pro Val Asp Ala Arg Pro Ala Asp Arg Gly Leu Thr
                565                 570                 575

Thr Arg Pro Gly Ser Gly Leu Thr Asn Ile Lys Thr Glu Glu Ile Ser
                580                 585                 590

Glu Val Asn Phe Glu Ala Glu Phe Arg His Asp Ser Gly Tyr Glu Val
        595                 600                 605

His His Gln Lys Leu Val Phe Phe Ala Glu Asp Val Gly Ser Asn Lys
```

```
             610                 615                 620
Gly Ala Ile Ile Gly Leu Met Val Gly Val Val Ile Ala Thr Val
625                 630                 635                 640

Ile Val Ile Thr Leu Val Met Leu Lys Lys Gln Tyr Thr Ser Ile
                645                 650                 655

His His Gly Val Val Glu Val Asp Ala Ala Val Thr Pro Glu Glu Arg
            660                 665                 670

His Leu Ser Lys Met Gln Gln Asn Gly Tyr Glu Asn Pro Thr Tyr Lys
            675                 680                 685

Phe Phe Glu Gln Met Gln Asn
        690                 695

<210> SEQ ID NO 27
<211> LENGTH: 695
<212> TYPE: PRT
<213> ORGANISM: Artificial
<220> FEATURE:
<223> OTHER INFORMATION: polypeptide containing novel sequence at known
      enzyme cleavage site

<400> SEQUENCE: 27

Met Leu Pro Gly Leu Ala Leu Leu Leu Leu Ala Ala Trp Thr Ala Arg
1               5                   10                  15

Ala Leu Glu Val Pro Thr Asp Gly Asn Ala Gly Leu Leu Ala Glu Pro
                20                  25                  30

Gln Ile Ala Met Phe Cys Gly Arg Leu Asn Met His Met Asn Val Gln
            35                  40                  45

Asn Gly Lys Trp Asp Ser Asp Pro Ser Gly Thr Lys Thr Cys Ile Asp
50                  55                  60

Thr Lys Glu Gly Ile Leu Gln Tyr Cys Gln Glu Val Tyr Pro Glu Leu
65                  70                  75                  80

Gln Ile Thr Asn Val Val Glu Ala Asn Gln Pro Val Thr Ile Gln Asn
                85                  90                  95

Trp Cys Lys Arg Gly Arg Lys Gln Cys Lys Thr His Pro His Phe Val
            100                 105                 110

Ile Pro Tyr Arg Cys Leu Val Gly Glu Phe Val Ser Asp Ala Leu Leu
            115                 120                 125

Val Pro Asp Lys Cys Lys Phe Leu His Gln Glu Arg Met Asp Val Cys
            130                 135                 140

Glu Thr His Leu His Trp His Thr Val Ala Lys Glu Thr Cys Ser Glu
145                 150                 155                 160

Lys Ser Thr Asn Leu His Asp Tyr Gly Met Leu Leu Pro Cys Gly Ile
                165                 170                 175

Asp Lys Phe Arg Gly Val Glu Phe Val Cys Cys Pro Leu Ala Glu Glu
            180                 185                 190

Ser Asp Asn Val Asp Ser Ala Asp Ala Glu Glu Asp Asp Ser Asp Val
            195                 200                 205

Trp Trp Gly Gly Ala Asp Thr Asp Tyr Ala Asp Gly Ser Glu Asp Lys
        210                 215                 220

Val Val Glu Val Ala Glu Glu Glu Val Ala Glu Val Glu Glu Glu
225                 230                 235                 240

Glu Ala Asp Asp Asp Glu Asp Asp Glu Asp Gly Asp Glu Val Glu Glu
            245                 250                 255

Glu Ala Glu Glu Pro Tyr Glu Glu Ala Thr Glu Arg Thr Thr Ser Ile
            260                 265                 270
```

-continued

```
Ala Thr Thr Thr Thr Thr Thr Glu Ser Val Glu Val Val Arg
        275                 280             285

Val Pro Thr Thr Ala Ala Ser Thr Pro Asp Ala Val Asp Lys Tyr Leu
290         295                 300

Glu Thr Pro Gly Asp Glu Asn Glu His Ala His Phe Gln Lys Ala Lys
305                 310                 315                 320

Glu Arg Leu Glu Ala Lys His Arg Glu Arg Met Ser Gln Val Met Arg
                325                 330                 335

Glu Trp Glu Glu Ala Glu Arg Gln Ala Lys Asn Leu Pro Lys Ala Asp
            340                 345                 350

Lys Lys Ala Val Ile Gln His Phe Gln Glu Lys Val Glu Ser Leu Glu
        355                 360                 365

Gln Glu Ala Ala Asn Glu Arg Gln Gln Leu Val Glu Thr His Met Ala
370                 375                 380

Arg Val Glu Ala Met Leu Asn Asp Arg Arg Leu Ala Leu Glu Asn
385                 390                 395                 400

Tyr Ile Thr Ala Leu Gln Ala Val Pro Pro Arg Pro Arg His Val Phe
                405                 410                 415

Asn Met Leu Lys Lys Tyr Val Arg Ala Glu Gln Lys Asp Arg Gln His
            420                 425                 430

Thr Leu Lys His Phe Glu His Val Arg Met Val Asp Pro Lys Lys Ala
        435                 440                 445

Ala Gln Ile Arg Ser Gln Val Met Thr His Leu Arg Val Ile Tyr Glu
450                 455                 460

Arg Met Asn Gln Ser Leu Ser Leu Leu Tyr Asn Val Pro Ala Val Ala
465                 470                 475                 480

Glu Glu Ile Gln Asp Glu Val Asp Glu Leu Leu Gln Lys Glu Gln Asn
                485                 490                 495

Tyr Ser Asp Asp Val Leu Ala Asn Met Ile Ser Glu Pro Arg Ile Ser
            500                 505                 510

Tyr Gly Asn Asp Ala Leu Met Pro Ser Leu Thr Glu Thr Lys Thr Thr
        515                 520                 525

Val Glu Leu Leu Pro Val Asn Gly Glu Phe Ser Leu Asp Asp Leu Gln
530                 535                 540

Pro Trp His Ser Phe Gly Ala Asp Ser Val Pro Ala Asn Thr Glu Asn
545                 550                 555                 560

Glu Val Glu Pro Val Asp Ala Arg Pro Ala Ala Asp Arg Gly Leu Thr
                565                 570                 575

Thr Arg Pro Gly Ser Gly Leu Thr Asn Ile Lys Thr Glu Glu Ile Ser
            580                 585                 590

Glu Val Asn Leu Glu Ala Glu Phe Arg His Asp Ser Gly Tyr Glu Val
        595                 600                 605

His His Gln Lys Leu Val Phe Phe Ala Glu Asp Val Gly Ser Asn Lys
610                 615                 620

Gly Ala Ile Ile Gly Leu Met Val Gly Gly Val Val Ile Ala Thr Val
625                 630                 635                 640

Ile Val Ile Thr Leu Val Met Leu Lys Lys Lys Gln Tyr Thr Ser Ile
                645                 650                 655

His His Gly Val Val Glu Val Asp Ala Ala Val Thr Pro Glu Glu Arg
            660                 665                 670

His Leu Ser Lys Met Gln Gln Asn Gly Tyr Glu Asn Pro Thr Tyr Lys
        675                 680                 685

Phe Phe Glu Gln Met Gln Asn
```

<210> SEQ ID NO 28
<211> LENGTH: 695
<212> TYPE: PRT
<213> ORGANISM: Artificial
<220> FEATURE:
<223> OTHER INFORMATION: polypeptide containing novel sequence at known enzyme cleavage site

<400> SEQUENCE: 28

```
Met Leu Pro Gly Leu Ala Leu Leu Leu Ala Ala Trp Thr Ala Arg
1               5                   10                  15

Ala Leu Glu Val Pro Thr Asp Gly Asn Ala Gly Leu Leu Ala Glu Pro
            20                  25                  30

Gln Ile Ala Met Phe Cys Gly Arg Leu Asn Met His Met Asn Val Gln
        35                  40                  45

Asn Gly Lys Trp Asp Ser Asp Pro Ser Gly Thr Lys Thr Cys Ile Asp
50                  55                  60

Thr Lys Glu Gly Ile Leu Gln Tyr Cys Gln Glu Val Tyr Pro Glu Leu
65                  70                  75                  80

Gln Ile Thr Asn Val Val Glu Ala Asn Gln Pro Val Thr Ile Gln Asn
                85                  90                  95

Trp Cys Lys Arg Gly Arg Lys Gln Cys Lys Thr His Pro His Phe Val
            100                 105                 110

Ile Pro Tyr Arg Cys Leu Val Gly Glu Phe Val Ser Asp Ala Leu Leu
        115                 120                 125

Val Pro Asp Lys Cys Lys Phe Leu His Gln Glu Arg Met Asp Val Cys
    130                 135                 140

Glu Thr His Leu His Trp His Thr Val Ala Lys Glu Thr Cys Ser Glu
145                 150                 155                 160

Lys Ser Thr Asn Leu His Asp Tyr Gly Met Leu Leu Pro Cys Gly Ile
                165                 170                 175

Asp Lys Phe Arg Gly Val Glu Phe Val Cys Cys Pro Leu Ala Glu Glu
            180                 185                 190

Ser Asp Asn Val Asp Ser Ala Asp Ala Glu Glu Asp Asp Ser Asp Val
        195                 200                 205

Trp Trp Gly Gly Ala Asp Thr Asp Tyr Ala Asp Gly Ser Glu Asp Lys
    210                 215                 220

Val Val Glu Val Ala Glu Glu Glu Val Ala Glu Val Glu Glu Glu
225                 230                 235                 240

Glu Ala Asp Asp Asp Glu Asp Asp Glu Asp Gly Asp Glu Val Glu Glu
                245                 250                 255

Glu Ala Glu Glu Pro Tyr Glu Glu Ala Thr Glu Arg Thr Thr Ser Ile
            260                 265                 270

Ala Thr Thr Thr Thr Thr Thr Glu Ser Val Glu Glu Val Val Arg
        275                 280                 285

Val Pro Thr Thr Ala Ala Ser Thr Pro Asp Ala Val Asp Lys Tyr Leu
    290                 295                 300

Glu Thr Pro Gly Asp Glu Asn Glu His Ala His Phe Gln Lys Ala Lys
305                 310                 315                 320

Glu Arg Leu Glu Ala Lys His Arg Glu Arg Met Ser Gln Val Met Arg
                325                 330                 335

Glu Trp Glu Glu Ala Glu Arg Gln Ala Lys Asn Leu Pro Lys Ala Asp
            340                 345                 350
```

```
Lys Lys Ala Val Ile Gln His Phe Gln Glu Lys Val Glu Ser Leu Glu
        355                 360                 365

Gln Glu Ala Ala Asn Glu Arg Gln Gln Leu Val Glu Thr His Met Ala
    370                 375                 380

Arg Val Glu Ala Met Leu Asn Asp Arg Arg Leu Ala Leu Glu Asn
385                 390                 395                 400

Tyr Ile Thr Ala Leu Gln Ala Val Pro Pro Arg Pro His Val Phe
                405                 410                 415

Asn Met Leu Lys Lys Tyr Val Arg Ala Glu Gln Lys Asp Arg Gln His
                420                 425                 430

Thr Leu Lys His Phe Glu His Val Arg Met Val Asp Pro Lys Lys Ala
            435                 440                 445

Ala Gln Ile Arg Ser Gln Val Met Thr His Leu Arg Val Ile Tyr Glu
        450                 455                 460

Arg Met Asn Gln Ser Leu Ser Leu Leu Tyr Asn Val Pro Ala Val Ala
465                 470                 475                 480

Glu Glu Ile Gln Asp Glu Val Asp Glu Leu Leu Gln Lys Glu Gln Asn
                485                 490                 495

Tyr Ser Asp Asp Val Leu Ala Asn Met Ile Ser Glu Pro Arg Ile Ser
                500                 505                 510

Tyr Gly Asn Asp Ala Leu Met Pro Ser Leu Thr Glu Thr Lys Thr Thr
            515                 520                 525

Val Glu Leu Leu Pro Val Asn Gly Glu Phe Ser Leu Asp Asp Leu Gln
        530                 535                 540

Pro Trp His Ser Phe Gly Ala Asp Ser Val Pro Ala Asn Thr Glu Asn
545                 550                 555                 560

Glu Val Glu Pro Val Asp Ala Arg Pro Ala Ala Asp Arg Gly Leu Thr
                565                 570                 575

Thr Arg Pro Gly Ser Gly Leu Thr Asn Ile Lys Thr Glu Glu Ile Ser
            580                 585                 590

Glu Val Asn Leu Asp Val Glu Phe Arg His Asp Ser Gly Tyr Glu Val
        595                 600                 605

His His Gln Lys Leu Val Phe Phe Ala Glu Asp Val Gly Ser Asn Lys
    610                 615                 620

Gly Ala Ile Ile Gly Leu Met Val Gly Gly Val Val Ile Ala Thr Val
625                 630                 635                 640

Ile Val Ile Thr Leu Val Met Leu Lys Lys Lys Gln Tyr Thr Ser Ile
                645                 650                 655

His His Gly Val Val Glu Val Asp Ala Ala Val Thr Pro Glu Glu Arg
            660                 665                 670

His Leu Ser Lys Met Gln Gln Asn Gly Tyr Glu Asn Pro Thr Tyr Lys
        675                 680                 685

Phe Phe Glu Gln Met Gln Asn
    690                 695

<210> SEQ ID NO 29
<211> LENGTH: 695
<212> TYPE: PRT
<213> ORGANISM: Artificial
<220> FEATURE:
<223> OTHER INFORMATION: polypeptide containing novel sequence at known
      enzyme cleavage site

<400> SEQUENCE: 29

Met Leu Pro Gly Leu Ala Leu Leu Leu Leu Ala Ala Trp Thr Ala Arg
1               5                   10                  15
```

-continued

```
Ala Leu Glu Val Pro Thr Asp Gly Asn Ala Gly Leu Leu Ala Glu Pro
            20                  25                  30

Gln Ile Ala Met Phe Cys Gly Arg Leu Asn Met His Met Asn Val Gln
            35                  40                  45

Asn Gly Lys Trp Asp Ser Asp Pro Ser Gly Thr Lys Thr Cys Ile Asp
            50                  55                  60

Thr Lys Glu Gly Ile Leu Gln Tyr Cys Gln Val Tyr Pro Glu Leu
 65                  70                  75                  80

Gln Ile Thr Asn Val Val Glu Ala Asn Gln Pro Val Thr Ile Gln Asn
                    85                  90                  95

Trp Cys Lys Arg Gly Arg Lys Gln Cys Lys Thr His Pro His Phe Val
                100                 105                 110

Ile Pro Tyr Arg Cys Leu Val Gly Glu Phe Val Ser Asp Ala Leu Leu
            115                 120                 125

Val Pro Asp Lys Cys Lys Phe Leu His Gln Glu Arg Met Asp Val Cys
130                 135                 140

Glu Thr His Leu His Trp His Thr Val Ala Lys Glu Thr Cys Ser Glu
145                 150                 155                 160

Lys Ser Thr Asn Leu His Asp Tyr Gly Met Leu Leu Pro Cys Gly Ile
                165                 170                 175

Asp Lys Phe Arg Gly Val Glu Phe Val Cys Cys Pro Leu Ala Glu Glu
            180                 185                 190

Ser Asp Asn Val Asp Ser Ala Asp Ala Glu Glu Asp Asp Ser Asp Val
            195                 200                 205

Trp Trp Gly Gly Ala Asp Thr Asp Tyr Ala Asp Gly Ser Glu Asp Lys
210                 215                 220

Val Val Glu Val Ala Glu Glu Glu Val Ala Glu Val Glu Glu Glu
225                 230                 235                 240

Glu Ala Asp Asp Asp Glu Asp Asp Glu Asp Gly Asp Glu Val Glu Glu
            245                 250                 255

Glu Ala Glu Glu Pro Tyr Glu Glu Ala Thr Glu Arg Thr Thr Ser Ile
            260                 265                 270

Ala Thr Thr Thr Thr Thr Thr Glu Ser Val Glu Glu Val Val Arg
    275                 280                 285

Val Pro Thr Thr Ala Ala Ser Thr Pro Asp Ala Val Asp Lys Tyr Leu
            290                 295                 300

Glu Thr Pro Gly Asp Glu Asn Glu His Ala His Phe Gln Lys Ala Lys
305                 310                 315                 320

Glu Arg Leu Glu Ala Lys His Arg Glu Arg Met Ser Gln Val Met Arg
                325                 330                 335

Glu Trp Glu Glu Ala Glu Arg Gln Ala Lys Asn Leu Pro Lys Ala Asp
            340                 345                 350

Lys Lys Ala Val Ile Gln His Phe Gln Glu Lys Val Glu Ser Leu Glu
            355                 360                 365

Gln Glu Ala Ala Asn Glu Arg Gln Gln Leu Val Glu Thr His Met Ala
370                 375                 380

Arg Val Glu Ala Met Leu Asn Asp Arg Arg Arg Leu Ala Leu Glu Asn
385                 390                 395                 400

Tyr Ile Thr Ala Leu Gln Ala Val Pro Pro Arg Pro Arg His Val Phe
                405                 410                 415

Asn Met Leu Lys Lys Tyr Val Arg Ala Glu Gln Lys Asp Arg Gln His
            420                 425                 430
```

```
Thr Leu Lys His Phe Glu His Val Arg Met Val Asp Pro Lys Lys Ala
        435                 440                 445

Ala Gln Ile Arg Ser Gln Val Met Thr His Leu Arg Val Ile Tyr Glu
    450                 455                 460

Arg Met Asn Gln Ser Leu Ser Leu Leu Tyr Asn Val Pro Ala Val Ala
465                 470                 475                 480

Glu Glu Ile Gln Asp Glu Val Asp Leu Leu Gln Lys Glu Gln Asn
                485                 490                 495

Tyr Ser Asp Asp Val Leu Ala Asn Met Ile Ser Glu Pro Arg Ile Ser
            500                 505                 510

Tyr Gly Asn Asp Ala Leu Met Pro Ser Leu Thr Glu Thr Lys Thr Thr
            515                 520                 525

Val Glu Leu Leu Pro Val Asn Gly Glu Phe Ser Leu Asp Asp Leu Gln
        530                 535                 540

Pro Trp His Ser Phe Gly Ala Asp Ser Val Pro Ala Asn Thr Glu Asn
545                 550                 555                 560

Glu Val Glu Pro Val Asp Ala Arg Pro Ala Ala Asp Arg Gly Leu Thr
                565                 570                 575

Thr Arg Pro Gly Ser Gly Leu Thr Asn Ile Lys Thr Glu Glu Ile Ser
            580                 585                 590

Glu Val Asn Phe Asp Val Glu Phe Arg His Asp Ser Gly Tyr Glu Val
        595                 600                 605

His His Gln Lys Leu Val Phe Phe Ala Glu Asp Val Gly Ser Asn Lys
610                 615                 620

Gly Ala Ile Ile Gly Leu Met Val Gly Gly Val Val Ile Ala Thr Val
625                 630                 635                 640

Ile Val Ile Thr Leu Val Met Leu Lys Lys Lys Gln Tyr Thr Ser Ile
                645                 650                 655

His His Gly Val Val Glu Val Asp Ala Ala Val Thr Pro Glu Glu Arg
            660                 665                 670

His Leu Ser Lys Met Gln Gln Asn Gly Tyr Glu Asn Pro Thr Tyr Lys
            675                 680                 685

Phe Phe Glu Gln Met Gln Asn
        690                 695

<210> SEQ ID NO 30
<211> LENGTH: 695
<212> TYPE: PRT
<213> ORGANISM: Artificial
<220> FEATURE:
<223> OTHER INFORMATION: polypeptide containing novel sequence at known
      enzyme cleavage site

<400> SEQUENCE: 30

Met Leu Pro Gly Leu Ala Leu Leu Leu Ala Ala Trp Thr Ala Arg
1               5                   10                  15

Ala Leu Glu Val Pro Thr Asp Gly Asn Ala Gly Leu Leu Ala Glu Pro
            20                  25                  30

Gln Ile Ala Met Phe Cys Gly Arg Leu Asn Met His Met Asn Val Gln
        35                  40                  45

Asn Gly Lys Trp Asp Ser Asp Pro Ser Gly Thr Lys Thr Cys Ile Asp
    50                  55                  60

Thr Lys Glu Gly Ile Leu Gln Tyr Cys Gln Glu Val Tyr Pro Glu Leu
65                  70                  75                  80

Gln Ile Thr Asn Val Val Glu Ala Asn Gln Pro Val Thr Ile Gln Asn
                85                  90                  95
```

-continued

```
Trp Cys Lys Arg Gly Arg Lys Gln Cys Lys Thr His Pro His Phe Val
            100                 105                 110

Ile Pro Tyr Arg Cys Leu Val Gly Glu Phe Val Ser Asp Ala Leu Leu
            115                 120                 125

Val Pro Asp Lys Cys Lys Phe Leu His Gln Glu Arg Met Asp Val Cys
            130                 135                 140

Glu Thr His Leu His Trp His Thr Val Ala Lys Glu Thr Cys Ser Glu
145                 150                 155                 160

Lys Ser Thr Asn Leu His Asp Tyr Gly Met Leu Leu Pro Cys Gly Ile
                165                 170                 175

Asp Lys Phe Arg Gly Val Glu Phe Val Cys Cys Pro Leu Ala Glu Glu
            180                 185                 190

Ser Asp Asn Val Asp Ser Ala Asp Ala Glu Glu Asp Asp Ser Asp Val
            195                 200                 205

Trp Trp Gly Gly Ala Asp Thr Asp Tyr Ala Asp Gly Ser Glu Asp Lys
210                 215                 220

Val Val Glu Val Ala Glu Glu Glu Val Ala Glu Val Glu Glu Glu
225                 230                 235                 240

Glu Ala Asp Asp Asp Glu Asp Asp Glu Asp Gly Asp Glu Val Glu Glu
            245                 250                 255

Glu Ala Glu Glu Pro Tyr Glu Glu Ala Thr Glu Arg Thr Thr Ser Ile
            260                 265                 270

Ala Thr Thr Thr Thr Thr Thr Thr Glu Ser Val Glu Glu Val Val Arg
            275                 280                 285

Val Pro Thr Thr Ala Ala Ser Thr Pro Asp Ala Val Asp Lys Tyr Leu
            290                 295                 300

Glu Thr Pro Gly Asp Glu Asn Glu His Ala His Phe Gln Lys Ala Lys
305                 310                 315                 320

Glu Arg Leu Glu Ala Lys His Arg Glu Arg Met Ser Gln Val Met Arg
                325                 330                 335

Glu Trp Glu Glu Ala Glu Arg Gln Ala Lys Asn Leu Pro Lys Ala Asp
            340                 345                 350

Lys Lys Ala Val Ile Gln His Phe Gln Glu Lys Val Glu Ser Leu Glu
            355                 360                 365

Gln Glu Ala Ala Asn Glu Arg Gln Gln Leu Val Glu Thr His Met Ala
            370                 375                 380

Arg Val Glu Ala Met Leu Asn Asp Arg Arg Arg Leu Ala Leu Glu Asn
385                 390                 395                 400

Tyr Ile Thr Ala Leu Gln Ala Val Pro Pro Arg Pro Arg His Val Phe
                405                 410                 415

Asn Met Leu Lys Lys Tyr Val Arg Ala Glu Gln Lys Asp Arg Gln His
            420                 425                 430

Thr Leu Lys His Phe Glu His Val Arg Met Val Asp Pro Lys Lys Ala
            435                 440                 445

Ala Gln Ile Arg Ser Gln Val Met Thr His Leu Arg Val Ile Tyr Glu
450                 455                 460

Arg Met Asn Gln Ser Leu Ser Leu Leu Tyr Asn Val Pro Ala Val Ala
465                 470                 475                 480

Glu Glu Ile Gln Asp Glu Val Asp Glu Leu Leu Gln Lys Glu Gln Asn
                485                 490                 495

Tyr Ser Asp Asp Val Leu Ala Asn Met Ile Ser Glu Pro Arg Ile Ser
            500                 505                 510
```

```
Tyr Gly Asn Asp Ala Leu Met Pro Ser Leu Thr Glu Thr Lys Thr Thr
        515                 520                 525

Val Glu Leu Leu Pro Val Asn Gly Glu Phe Ser Leu Asp Asp Leu Gln
        530                 535                 540

Pro Trp His Ser Phe Gly Ala Asp Ser Val Pro Ala Asn Thr Glu Asn
545                 550                 555                 560

Glu Val Glu Pro Val Asp Ala Arg Pro Ala Asp Arg Gly Leu Thr
                565                 570                 575

Thr Arg Pro Gly Ser Gly Leu Thr Asn Ile Lys Thr Glu Glu Ile Ser
                580                 585                 590

Glu Val Asn Phe Thr Val Glu Phe Arg His Asp Ser Gly Tyr Glu Val
            595                 600                 605

His His Gln Lys Leu Val Phe Phe Ala Glu Asp Val Gly Ser Asn Lys
        610                 615                 620

Gly Ala Ile Ile Gly Leu Met Val Gly Gly Val Val Ile Ala Thr Val
625                 630                 635                 640

Ile Val Ile Thr Leu Val Met Leu Lys Lys Lys Gln Tyr Thr Ser Ile
                645                 650                 655

His His Gly Val Val Glu Val Asp Ala Ala Val Thr Pro Glu Glu Arg
            660                 665                 670

His Leu Ser Lys Met Gln Gln Asn Gly Tyr Glu Asn Pro Thr Tyr Lys
        675                 680                 685

Phe Phe Glu Gln Met Gln Asn
    690                 695

<210> SEQ ID NO 31
<211> LENGTH: 695
<212> TYPE: PRT
<213> ORGANISM: Artificial
<220> FEATURE:
<223> OTHER INFORMATION: polypeptide containing novel sequence at known
      enzyme cleavage site

<400> SEQUENCE: 31

Met Leu Pro Gly Leu Ala Leu Leu Leu Leu Ala Ala Trp Thr Ala Arg
1               5                   10                  15

Ala Leu Glu Val Pro Thr Asp Gly Asn Ala Gly Leu Leu Ala Glu Pro
            20                  25                  30

Gln Ile Ala Met Phe Cys Gly Arg Leu Asn Met His Met Asn Val Gln
        35                  40                  45

Asn Gly Lys Trp Asp Ser Asp Pro Ser Gly Thr Lys Thr Cys Ile Asp
    50                  55                  60

Thr Lys Glu Gly Ile Leu Gln Tyr Cys Gln Glu Val Tyr Pro Glu Leu
65                  70                  75                  80

Gln Ile Thr Asn Val Val Glu Ala Asn Gln Pro Val Thr Ile Gln Asn
                85                  90                  95

Trp Cys Lys Arg Gly Arg Lys Gln Cys Lys Thr His Pro His Phe Val
            100                 105                 110

Ile Pro Tyr Arg Cys Leu Val Gly Glu Phe Val Ser Asp Ala Leu Leu
        115                 120                 125

Val Pro Asp Lys Cys Lys Phe Leu His Gln Glu Arg Met Asp Val Cys
    130                 135                 140

Glu Thr His Leu His Trp His Thr Val Ala Lys Glu Thr Cys Ser Glu
145                 150                 155                 160

Lys Ser Thr Asn Leu His Asp Tyr Gly Met Leu Leu Pro Cys Gly Ile
                165                 170                 175
```

```
Asp Lys Phe Arg Gly Val Glu Phe Val Cys Cys Pro Leu Ala Glu Glu
            180                 185                 190

Ser Asp Asn Val Asp Ser Ala Asp Glu Glu Asp Ser Asp Val
        195                 200                 205

Trp Trp Gly Gly Ala Asp Thr Asp Tyr Ala Asp Gly Ser Glu Asp Lys
            210                 215                 220

Val Val Glu Val Ala Glu Glu Glu Val Ala Glu Val Glu Glu Glu
225                 230                 235                 240

Glu Ala Asp Asp Asp Glu Asp Asp Glu Asp Gly Asp Glu Val Glu Glu
                245                 250                 255

Glu Ala Glu Glu Pro Tyr Glu Glu Ala Thr Glu Arg Thr Thr Ser Ile
            260                 265                 270

Ala Thr Thr Thr Thr Thr Thr Glu Ser Val Glu Glu Val Val Arg
            275                 280                 285

Val Pro Thr Thr Ala Ala Ser Thr Pro Asp Ala Val Asp Lys Tyr Leu
            290                 295                 300

Glu Thr Pro Gly Asp Glu Asn Glu His Ala His Phe Gln Lys Ala Lys
305                 310                 315                 320

Glu Arg Leu Glu Ala Lys His Arg Glu Arg Met Ser Gln Val Met Arg
                325                 330                 335

Glu Trp Glu Glu Ala Glu Arg Gln Ala Lys Asn Leu Pro Lys Ala Asp
            340                 345                 350

Lys Lys Ala Val Ile Gln His Phe Gln Glu Lys Val Glu Ser Leu Glu
            355                 360                 365

Gln Glu Ala Ala Asn Glu Arg Gln Gln Leu Val Glu Thr His Met Ala
    370                 375                 380

Arg Val Glu Ala Met Leu Asn Asp Arg Arg Arg Leu Ala Leu Glu Asn
385                 390                 395                 400

Tyr Ile Thr Ala Leu Gln Ala Val Pro Pro Arg Pro Arg His Val Phe
            405                 410                 415

Asn Met Leu Lys Lys Tyr Val Arg Ala Glu Gln Lys Asp Arg Gln His
            420                 425                 430

Thr Leu Lys His Phe Glu His Val Arg Met Val Asp Pro Lys Lys Ala
            435                 440                 445

Ala Gln Ile Arg Ser Gln Val Met Thr His Leu Arg Val Ile Tyr Glu
    450                 455                 460

Arg Met Asn Gln Ser Leu Ser Leu Leu Tyr Asn Val Pro Ala Val Ala
465                 470                 475                 480

Glu Glu Ile Gln Asp Glu Val Asp Glu Leu Leu Gln Lys Glu Gln Asn
            485                 490                 495

Tyr Ser Asp Asp Val Leu Ala Asn Met Ile Ser Glu Pro Arg Ile Ser
            500                 505                 510

Tyr Gly Asn Asp Ala Leu Met Pro Ser Leu Thr Glu Thr Lys Thr Thr
            515                 520                 525

Val Glu Leu Leu Pro Val Asn Gly Glu Phe Ser Leu Asp Asp Leu Gln
            530                 535                 540

Pro Trp His Ser Phe Gly Ala Asp Ser Val Pro Ala Asn Thr Glu Asn
545                 550                 555                 560

Glu Val Glu Pro Val Asp Ala Arg Pro Ala Ala Asp Arg Gly Leu Thr
                565                 570                 575

Thr Arg Pro Gly Ser Gly Leu Thr Asn Ile Lys Thr Glu Glu Ile Ser
            580                 585                 590
```

-continued

Glu Val Asn Tyr Asp Ala Glu Phe Arg His Asp Ser Gly Tyr Glu Val
            595                 600                 605

His His Gln Lys Leu Val Phe Phe Ala Glu Asp Val Gly Ser Asn Lys
        610                 615                 620

Gly Ala Ile Ile Gly Leu Met Val Gly Gly Val Val Ile Ala Thr Val
625                 630                 635                 640

Ile Val Ile Thr Leu Val Met Leu Lys Lys Lys Gln Tyr Thr Ser Ile
                645                 650                 655

His His Gly Val Val Glu Val Asp Ala Ala Val Thr Pro Glu Glu Arg
        660                 665                 670

His Leu Ser Lys Met Gln Gln Asn Gly Tyr Glu Asn Pro Thr Tyr Lys
        675                 680                 685

Phe Phe Glu Gln Met Gln Asn
        690                 695

<210> SEQ ID NO 32
<211> LENGTH: 695
<212> TYPE: PRT
<213> ORGANISM: Artificial
<220> FEATURE:
<223> OTHER INFORMATION: polypeptide containing novel sequence at known
      enzyme cleavage site

<400> SEQUENCE: 32

Met Leu Pro Gly Leu Ala Leu Leu Leu Ala Ala Trp Thr Ala Arg
1               5                   10                  15

Ala Leu Glu Val Pro Thr Asp Gly Asn Ala Gly Leu Leu Ala Glu Pro
            20                  25                  30

Gln Ile Ala Met Phe Cys Gly Arg Leu Asn Met His Met Asn Val Gln
        35                  40                  45

Asn Gly Lys Trp Asp Ser Asp Pro Ser Gly Thr Lys Thr Cys Ile Asp
    50                  55                  60

Thr Lys Glu Gly Ile Leu Gln Tyr Cys Gln Glu Val Tyr Pro Glu Leu
65                  70                  75                  80

Gln Ile Thr Asn Val Val Glu Ala Asn Gln Pro Val Thr Ile Gln Asn
                85                  90                  95

Trp Cys Lys Arg Gly Arg Lys Gln Cys Lys Thr His Pro His Phe Val
            100                 105                 110

Ile Pro Tyr Arg Cys Leu Val Gly Glu Phe Val Ser Asp Ala Leu Leu
        115                 120                 125

Val Pro Asp Lys Cys Lys Phe Leu His Gln Glu Arg Met Asp Val Cys
    130                 135                 140

Glu Thr His Leu His Trp His Thr Val Ala Lys Glu Thr Cys Ser Glu
145                 150                 155                 160

Lys Ser Thr Asn Leu His Asp Tyr Gly Met Leu Leu Pro Cys Gly Ile
                165                 170                 175

Asp Lys Phe Arg Gly Val Glu Phe Val Cys Cys Pro Leu Ala Glu Glu
            180                 185                 190

Ser Asp Asn Val Asp Ser Ala Asp Ala Glu Glu Asp Asp Ser Asp Val
        195                 200                 205

Trp Trp Gly Gly Ala Asp Thr Asp Tyr Ala Asp Gly Ser Glu Asp Lys
    210                 215                 220

Val Val Glu Val Ala Glu Glu Glu Val Ala Glu Val Glu Glu Glu
225                 230                 235                 240

Glu Ala Asp Asp Asp Glu Asp Asp Glu Asp Gly Asp Glu Val Glu Glu
                245                 250                 255

```
Glu Ala Glu Glu Pro Tyr Glu Glu Ala Thr Glu Arg Thr Thr Ser Ile
                260                 265                 270
Ala Thr Thr Thr Thr Thr Thr Thr Glu Ser Val Glu Val Val Arg
    275                 280                 285
Val Pro Thr Thr Ala Ala Ser Thr Pro Asp Ala Val Asp Lys Tyr Leu
    290                 295                 300
Glu Thr Pro Gly Asp Glu Asn Glu His Ala His Phe Gln Lys Ala Lys
305                 310                 315                 320
Glu Arg Leu Glu Ala Lys His Arg Glu Arg Met Ser Gln Val Met Arg
                325                 330                 335
Glu Trp Glu Glu Ala Glu Arg Gln Ala Lys Asn Leu Pro Lys Ala Asp
                340                 345                 350
Lys Lys Ala Val Ile Gln His Phe Gln Glu Lys Val Glu Ser Leu Glu
                355                 360                 365
Gln Glu Ala Ala Asn Glu Arg Gln Gln Leu Val Glu Thr His Met Ala
            370                 375                 380
Arg Val Glu Ala Met Leu Asn Asp Arg Arg Arg Leu Ala Leu Glu Asn
385                 390                 395                 400
Tyr Ile Thr Ala Leu Gln Ala Val Pro Pro Arg Pro Arg His Val Phe
                405                 410                 415
Asn Met Leu Lys Lys Tyr Val Arg Ala Glu Gln Lys Asp Arg Gln His
                420                 425                 430
Thr Leu Lys His Phe Glu His Val Arg Met Val Asp Pro Lys Lys Ala
                435                 440                 445
Ala Gln Ile Arg Ser Gln Val Met Thr His Leu Arg Val Ile Tyr Glu
            450                 455                 460
Arg Met Asn Gln Ser Leu Ser Leu Leu Tyr Asn Val Pro Ala Val Ala
465                 470                 475                 480
Glu Glu Ile Gln Asp Glu Val Asp Glu Leu Leu Gln Lys Glu Gln Asn
                485                 490                 495
Tyr Ser Asp Asp Val Leu Ala Asn Met Ile Ser Glu Pro Arg Ile Ser
                500                 505                 510
Tyr Gly Asn Asp Ala Leu Met Pro Ser Leu Thr Glu Thr Lys Thr Thr
                515                 520                 525
Val Glu Leu Leu Pro Val Asn Gly Glu Phe Ser Leu Asp Asp Leu Gln
            530                 535                 540
Pro Trp His Ser Phe Gly Ala Asp Ser Val Pro Ala Asn Thr Glu Asn
545                 550                 555                 560
Glu Val Glu Pro Val Asp Ala Arg Pro Ala Ala Asp Arg Gly Leu Thr
                565                 570                 575
Thr Arg Pro Gly Ser Gly Leu Thr Asn Ile Lys Thr Glu Glu Ile Ser
                580                 585                 590
Glu Val Asn Tyr Glu Ala Glu Phe Arg His Asp Ser Gly Tyr Glu Val
                595                 600                 605
His His Gln Lys Leu Val Phe Phe Ala Glu Asp Val Gly Ser Asn Lys
            610                 615                 620
Gly Ala Ile Ile Gly Leu Met Val Gly Gly Val Val Ile Ala Thr Val
625                 630                 635                 640
Ile Val Ile Thr Leu Val Met Leu Lys Lys Lys Gln Tyr Thr Ser Ile
                645                 650                 655
His His Gly Val Val Glu Val Asp Ala Ala Val Thr Pro Glu Glu Arg
                660                 665                 670
```

```
His Leu Ser Lys Met Gln Gln Asn Gly Tyr Glu Asn Pro Thr Tyr Lys
        675                 680                 685

Phe Phe Glu Gln Met Gln Asn
        690                 695

<210> SEQ ID NO 33
<211> LENGTH: 695
<212> TYPE: PRT
<213> ORGANISM: Artificial
<220> FEATURE:
<223> OTHER INFORMATION: polypeptide containing novel sequence at known
      enzyme cleavage site

<400> SEQUENCE: 33

Met Leu Pro Gly Leu Ala Leu Leu Leu Ala Ala Trp Thr Ala Arg
1               5                   10                  15

Ala Leu Glu Val Pro Thr Asp Gly Asn Ala Gly Leu Leu Ala Glu Pro
                20                  25                  30

Gln Ile Ala Met Phe Cys Gly Arg Leu Asn Met His Met Asn Val Gln
            35                  40                  45

Asn Gly Lys Trp Asp Ser Asp Pro Ser Gly Thr Lys Thr Cys Ile Asp
        50                  55                  60

Thr Lys Glu Gly Ile Leu Gln Tyr Cys Gln Glu Val Tyr Pro Glu Leu
65                  70                  75                  80

Gln Ile Thr Asn Val Val Glu Ala Asn Gln Pro Val Thr Ile Gln Asn
                85                  90                  95

Trp Cys Lys Arg Gly Arg Lys Gln Cys Lys Thr His Pro His Phe Val
            100                 105                 110

Ile Pro Tyr Arg Cys Leu Val Gly Glu Phe Val Ser Asp Ala Leu Leu
        115                 120                 125

Val Pro Asp Lys Cys Lys Phe Leu His Gln Glu Arg Met Asp Val Cys
130                 135                 140

Glu Thr His Leu His Trp His Thr Val Ala Lys Glu Thr Cys Ser Glu
145                 150                 155                 160

Lys Ser Thr Asn Leu His Asp Tyr Gly Met Leu Leu Pro Cys Gly Ile
                165                 170                 175

Asp Lys Phe Arg Gly Val Glu Phe Val Cys Cys Pro Leu Ala Glu Glu
            180                 185                 190

Ser Asp Asn Val Asp Ser Ala Asp Ala Glu Glu Asp Asp Ser Asp Val
        195                 200                 205

Trp Trp Gly Gly Ala Asp Thr Asp Tyr Ala Asp Gly Ser Glu Asp Lys
    210                 215                 220

Val Val Glu Val Ala Glu Glu Glu Val Ala Glu Val Glu Glu Glu
225                 230                 235                 240

Glu Ala Asp Asp Asp Glu Asp Asp Glu Asp Gly Asp Glu Val Glu Glu
                245                 250                 255

Glu Ala Glu Glu Pro Tyr Glu Glu Ala Thr Glu Arg Thr Thr Ser Ile
            260                 265                 270

Ala Thr Thr Thr Thr Thr Thr Thr Glu Ser Val Glu Glu Val Val Arg
        275                 280                 285

Val Pro Thr Thr Ala Ala Ser Thr Pro Asp Ala Val Asp Lys Tyr Leu
    290                 295                 300

Glu Thr Pro Gly Asp Glu Asn Glu His Ala His Phe Gln Lys Ala Lys
305                 310                 315                 320

Glu Arg Leu Glu Ala Lys His Arg Glu Arg Met Ser Gln Val Met Arg
                325                 330                 335
```

```
Glu Trp Glu Glu Ala Glu Arg Gln Ala Lys Asn Leu Pro Lys Ala Asp
            340                 345                 350

Lys Lys Ala Val Ile Gln His Phe Gln Glu Lys Val Glu Ser Leu Glu
            355                 360                 365

Gln Glu Ala Ala Asn Glu Arg Gln Gln Leu Val Glu Thr His Met Ala
            370                 375                 380

Arg Val Glu Ala Met Leu Asn Asp Arg Arg Leu Ala Leu Glu Asn
385                 390                 395                 400

Tyr Ile Thr Ala Leu Gln Ala Val Pro Pro Arg Pro His Val Phe
                405                 410                 415

Asn Met Leu Lys Lys Tyr Val Arg Ala Glu Gln Lys Asp Arg Gln His
                420                 425                 430

Thr Leu Lys His Phe Glu His Val Arg Met Val Asp Pro Lys Lys Ala
            435                 440                 445

Ala Gln Ile Arg Ser Gln Val Met Thr His Leu Arg Val Ile Tyr Glu
450                 455                 460

Arg Met Asn Gln Ser Leu Ser Leu Leu Tyr Asn Val Pro Ala Val Ala
465                 470                 475                 480

Glu Glu Ile Gln Asp Glu Val Asp Glu Leu Leu Gln Lys Glu Gln Asn
                485                 490                 495

Tyr Ser Asp Asp Val Leu Ala Asn Met Ile Ser Glu Pro Arg Ile Ser
                500                 505                 510

Tyr Gly Asn Asp Ala Leu Met Pro Ser Leu Thr Glu Thr Lys Thr Thr
                515                 520                 525

Val Glu Leu Leu Pro Val Asn Gly Glu Phe Ser Leu Asp Asp Leu Gln
            530                 535                 540

Pro Trp His Ser Phe Gly Ala Asp Ser Val Pro Ala Asn Thr Glu Asn
545                 550                 555                 560

Glu Val Glu Pro Val Asp Ala Arg Pro Ala Ala Asp Arg Gly Leu Thr
                565                 570                 575

Thr Arg Pro Gly Ser Gly Leu Thr Asn Ile Lys Thr Glu Glu Ile Ser
            580                 585                 590

Glu Val Asn Tyr Asp Val Glu Phe Arg His Asp Ser Gly Tyr Glu Val
            595                 600                 605

His His Gln Lys Leu Val Phe Phe Ala Glu Asp Val Gly Ser Asn Lys
            610                 615                 620

Gly Ala Ile Ile Gly Leu Met Val Gly Gly Val Val Ile Ala Thr Val
625                 630                 635                 640

Ile Val Ile Thr Leu Val Met Leu Lys Lys Lys Gln Tyr Thr Ser Ile
                645                 650                 655

His His Gly Val Val Glu Val Asp Ala Ala Val Thr Pro Glu Glu Arg
                660                 665                 670

His Leu Ser Lys Met Gln Gln Asn Gly Tyr Glu Asn Pro Thr Tyr Lys
            675                 680                 685

Phe Phe Glu Gln Met Gln Asn
            690                 695

<210> SEQ ID NO 34
<211> LENGTH: 695
<212> TYPE: PRT
<213> ORGANISM: Artificial
<220> FEATURE:
<223> OTHER INFORMATION: polypeptide containing novel sequence at known
      enzyme cleavage site
```

<400> SEQUENCE: 34

```
Met Leu Pro Gly Leu Ala Leu Leu Leu Ala Ala Trp Thr Ala Arg
1               5                   10                  15

Ala Leu Glu Val Pro Thr Asp Gly Asn Ala Gly Leu Leu Ala Glu Pro
            20                  25                  30

Gln Ile Ala Met Phe Cys Gly Arg Leu Asn Met His Met Asn Val Gln
        35                  40                  45

Asn Gly Lys Trp Asp Ser Asp Pro Ser Gly Thr Lys Thr Cys Ile Asp
    50                  55                  60

Thr Lys Glu Gly Ile Leu Gln Tyr Cys Gln Glu Val Tyr Pro Glu Leu
65                  70                  75                  80

Gln Ile Thr Asn Val Val Glu Ala Asn Gln Pro Val Thr Ile Gln Asn
                85                  90                  95

Trp Cys Lys Arg Gly Arg Lys Gln Cys Lys Thr His Pro His Phe Val
            100                 105                 110

Ile Pro Tyr Arg Cys Leu Val Gly Glu Phe Val Ser Asp Ala Leu Leu
        115                 120                 125

Val Pro Asp Lys Cys Lys Phe Leu His Gln Glu Arg Met Asp Val Cys
130                 135                 140

Glu Thr His Leu His Trp His Thr Val Ala Lys Glu Thr Cys Ser Glu
145                 150                 155                 160

Lys Ser Thr Asn Leu His Asp Tyr Gly Met Leu Leu Pro Cys Gly Ile
                165                 170                 175

Asp Lys Phe Arg Gly Val Glu Phe Val Cys Cys Pro Leu Ala Glu Glu
            180                 185                 190

Ser Asp Asn Val Asp Ser Ala Asp Ala Glu Glu Asp Asp Ser Asp Val
        195                 200                 205

Trp Trp Gly Gly Ala Asp Thr Asp Tyr Ala Asp Gly Ser Glu Asp Lys
    210                 215                 220

Val Val Glu Val Ala Glu Glu Glu Val Ala Glu Val Glu Glu Glu Glu
225                 230                 235                 240

Glu Ala Asp Asp Asp Glu Asp Asp Glu Asp Gly Asp Glu Val Glu Glu
                245                 250                 255

Glu Ala Glu Glu Pro Tyr Glu Glu Ala Thr Glu Arg Thr Thr Ser Ile
            260                 265                 270

Ala Thr Thr Thr Thr Thr Thr Glu Ser Val Glu Glu Val Val Arg
        275                 280                 285

Val Pro Thr Thr Ala Ala Ser Thr Pro Asp Ala Val Asp Lys Tyr Leu
        290                 295                 300

Glu Thr Pro Gly Asp Glu Asn Glu His Ala His Phe Gln Lys Ala Lys
305                 310                 315                 320

Glu Arg Leu Glu Ala Lys His Arg Glu Arg Met Ser Gln Val Met Arg
                325                 330                 335

Glu Trp Glu Glu Ala Glu Arg Gln Ala Lys Asn Leu Pro Lys Ala Asp
            340                 345                 350

Lys Lys Ala Val Ile Gln His Phe Gln Glu Lys Val Glu Ser Leu Glu
        355                 360                 365

Gln Glu Ala Ala Asn Glu Arg Gln Gln Leu Val Glu Thr His Met Ala
    370                 375                 380

Arg Val Glu Ala Met Leu Asn Asp Arg Arg Arg Leu Ala Leu Glu Asn
385                 390                 395                 400

Tyr Ile Thr Ala Leu Gln Ala Val Pro Pro Arg Pro Arg His Val Phe
                405                 410                 415
```

```
Asn Met Leu Lys Lys Tyr Val Arg Ala Glu Gln Lys Asp Arg Gln His
            420                 425                 430

Thr Leu Lys His Phe Glu His Val Arg Met Val Asp Pro Lys Lys Ala
            435                 440                 445

Ala Gln Ile Arg Ser Gln Val Met Thr His Leu Arg Val Ile Tyr Glu
            450                 455                 460

Arg Met Asn Gln Ser Leu Ser Leu Leu Tyr Asn Val Pro Ala Val Ala
465                 470                 475                 480

Glu Glu Ile Gln Asp Glu Val Asp Leu Leu Gln Lys Glu Gln Asn
                485                 490                 495

Tyr Ser Asp Asp Val Leu Ala Asn Met Ile Ser Glu Pro Arg Ile Ser
            500                 505                 510

Tyr Gly Asn Asp Ala Leu Met Pro Ser Leu Thr Glu Thr Lys Thr Thr
            515                 520                 525

Val Glu Leu Leu Pro Val Asn Gly Glu Phe Ser Leu Asp Asp Leu Gln
            530                 535                 540

Pro Trp His Ser Phe Gly Ala Asp Ser Val Pro Ala Asn Thr Glu Asn
545                 550                 555                 560

Glu Val Glu Pro Val Asp Ala Arg Pro Ala Ala Asp Arg Gly Leu Thr
                565                 570                 575

Thr Arg Pro Gly Ser Gly Leu Thr Asn Ile Lys Thr Glu Glu Ile Ser
            580                 585                 590

Glu Val Phe Phe Ala Val Glu Phe Arg His Asp Ser Gly Tyr Glu Val
            595                 600                 605

His His Gln Lys Leu Val Phe Phe Ala Glu Asp Val Gly Ser Asn Lys
            610                 615                 620

Gly Ala Ile Ile Gly Leu Met Val Gly Gly Val Val Ile Ala Thr Val
625                 630                 635                 640

Ile Val Ile Thr Leu Val Met Leu Lys Lys Lys Gln Tyr Thr Ser Ile
                645                 650                 655

His His Gly Val Val Glu Val Asp Ala Ala Val Thr Pro Glu Glu Arg
            660                 665                 670

His Leu Ser Lys Met Gln Gln Asn Gly Tyr Glu Asn Pro Thr Tyr Lys
            675                 680                 685

Phe Phe Glu Gln Met Gln Asn
            690                 695

<210> SEQ ID NO 35
<211> LENGTH: 695
<212> TYPE: PRT
<213> ORGANISM: Artificial
<220> FEATURE:
<223> OTHER INFORMATION: polypeptide containing novel sequence at known
      enzyme cleavage site

<400> SEQUENCE: 35

Met Leu Pro Gly Leu Ala Leu Leu Leu Ala Ala Trp Thr Ala Arg
1               5                   10                  15

Ala Leu Glu Val Pro Thr Asp Gly Asn Ala Gly Leu Leu Ala Glu Pro
                20                  25                  30

Gln Ile Ala Met Phe Cys Gly Arg Leu Asn Met His Met Asn Val Gln
            35                  40                  45

Asn Gly Lys Trp Asp Ser Asp Pro Ser Gly Thr Lys Thr Cys Ile Asp
        50                  55                  60

Thr Lys Glu Gly Ile Leu Gln Tyr Cys Gln Glu Val Tyr Pro Glu Leu
```

```
            65                  70                  75                  80
Gln Ile Thr Asn Val Val Glu Ala Asn Gln Pro Val Thr Ile Gln Asn
                    85                  90                  95
Trp Cys Lys Arg Gly Arg Lys Gln Cys Lys Thr His Pro His Phe Val
                100                 105                 110
Ile Pro Tyr Arg Cys Leu Val Gly Glu Phe Val Ser Asp Ala Leu Leu
                115                 120                 125
Val Pro Asp Lys Cys Lys Phe Leu His Gln Glu Arg Met Asp Val Cys
            130                 135                 140
Glu Thr His Leu His Trp His Thr Val Ala Lys Glu Thr Cys Ser Glu
145                 150                 155                 160
Lys Ser Thr Asn Leu His Asp Tyr Gly Met Leu Leu Pro Cys Gly Ile
                165                 170                 175
Asp Lys Phe Arg Gly Val Glu Phe Val Cys Cys Pro Leu Ala Glu Glu
                180                 185                 190
Ser Asp Asn Val Asp Ser Ala Asp Ala Glu Glu Asp Asp Ser Asp Val
                195                 200                 205
Trp Trp Gly Gly Ala Asp Thr Asp Tyr Ala Asp Gly Ser Glu Asp Lys
            210                 215                 220
Val Val Glu Val Ala Glu Glu Glu Val Ala Glu Val Glu Glu Glu
225                 230                 235                 240
Glu Ala Asp Asp Asp Glu Asp Asp Glu Asp Gly Asp Glu Val Glu Glu
                245                 250                 255
Glu Ala Glu Glu Pro Tyr Glu Glu Ala Thr Glu Arg Thr Thr Ser Ile
                260                 265                 270
Ala Thr Thr Thr Thr Thr Thr Glu Ser Val Glu Glu Val Val Arg
            275                 280                 285
Val Pro Thr Thr Ala Ala Ser Thr Pro Asp Ala Val Asp Lys Tyr Leu
            290                 295                 300
Glu Thr Pro Gly Asp Glu Asn Glu His Ala His Phe Gln Lys Ala Lys
305                 310                 315                 320
Glu Arg Leu Glu Ala Lys His Arg Glu Arg Met Ser Gln Val Met Arg
                325                 330                 335
Glu Trp Glu Glu Ala Glu Arg Gln Ala Lys Asn Leu Pro Lys Ala Asp
            340                 345                 350
Lys Lys Ala Val Ile Gln His Phe Gln Glu Lys Val Glu Ser Leu Glu
            355                 360                 365
Gln Glu Ala Ala Asn Glu Arg Gln Gln Leu Val Glu Thr His Met Ala
            370                 375                 380
Arg Val Glu Ala Met Leu Asn Asp Arg Arg Arg Leu Ala Leu Glu Asn
385                 390                 395                 400
Tyr Ile Thr Ala Leu Gln Ala Val Pro Pro Arg Pro Arg His Val Phe
                405                 410                 415
Asn Met Leu Lys Lys Tyr Val Arg Ala Glu Gln Lys Asp Arg Gln His
                420                 425                 430
Thr Leu Lys His Phe Glu His Val Arg Met Val Asp Pro Lys Lys Ala
            435                 440                 445
Ala Gln Ile Arg Ser Gln Val Met Thr His Leu Arg Val Ile Tyr Glu
            450                 455                 460
Arg Met Asn Gln Ser Leu Ser Leu Leu Tyr Asn Val Pro Ala Val Ala
465                 470                 475                 480
Glu Glu Ile Gln Asp Glu Val Asp Glu Leu Leu Gln Lys Glu Gln Asn
                485                 490                 495
```

```
Tyr Ser Asp Asp Val Leu Ala Asn Met Ile Ser Glu Pro Arg Ile Ser
            500                 505                 510

Tyr Gly Asn Asp Ala Leu Met Pro Ser Leu Thr Glu Thr Lys Thr Thr
        515                 520                 525

Val Glu Leu Leu Pro Val Asn Gly Glu Phe Ser Leu Asp Asp Leu Gln
    530                 535                 540

Pro Trp His Ser Phe Gly Ala Asp Ser Val Pro Ala Asn Thr Glu Asn
545                 550                 555                 560

Glu Val Glu Pro Val Asp Ala Arg Pro Ala Asp Arg Gly Leu Thr
                565                 570                 575

Thr Arg Pro Gly Ser Gly Leu Thr Asn Ile Lys Thr Glu Glu Ile Ser
                580                 585                 590

Glu Val Phe Phe Glu Val Glu Phe Arg His Asp Ser Gly Tyr Glu Val
            595                 600                 605

His His Gln Lys Leu Val Phe Phe Ala Glu Asp Val Gly Ser Asn Lys
        610                 615                 620

Gly Ala Ile Ile Gly Leu Met Val Gly Gly Val Val Ile Ala Thr Val
625                 630                 635                 640

Ile Val Ile Thr Leu Val Met Leu Lys Lys Lys Gln Tyr Thr Ser Ile
                645                 650                 655

His His Gly Val Val Glu Val Asp Ala Ala Val Thr Pro Glu Glu Arg
            660                 665                 670

His Leu Ser Lys Met Gln Gln Asn Gly Tyr Glu Asn Pro Thr Tyr Lys
        675                 680                 685

Phe Phe Glu Gln Met Gln Asn
    690                 695

<210> SEQ ID NO 36
<211> LENGTH: 695
<212> TYPE: PRT
<213> ORGANISM: Artificial
<220> FEATURE:
<223> OTHER INFORMATION: polypeptide containing novel sequence at known
      enzyme cleavage site

<400> SEQUENCE: 36

Met Leu Pro Gly Leu Ala Leu Leu Leu Ala Ala Trp Thr Ala Arg
1               5                   10                  15

Ala Leu Glu Val Pro Thr Asp Gly Asn Ala Gly Leu Leu Ala Glu Pro
            20                  25                  30

Gln Ile Ala Met Phe Cys Gly Arg Leu Asn Met His Met Asn Val Gln
        35                  40                  45

Asn Gly Lys Trp Asp Ser Asp Pro Ser Gly Thr Lys Thr Cys Ile Asp
    50                  55                  60

Thr Lys Glu Gly Ile Leu Gln Tyr Cys Gln Glu Val Tyr Pro Glu Leu
65                  70                  75                  80

Gln Ile Thr Asn Val Val Glu Ala Asn Gln Pro Val Thr Ile Gln Asn
                85                  90                  95

Trp Cys Lys Arg Gly Arg Lys Gln Cys Lys Thr His Pro His Phe Val
            100                 105                 110

Ile Pro Tyr Arg Cys Leu Val Gly Glu Phe Val Ser Asp Ala Leu Leu
        115                 120                 125

Val Pro Asp Lys Cys Lys Phe Leu His Gln Glu Arg Met Asp Val Cys
    130                 135                 140

Glu Thr His Leu His Trp His Thr Val Ala Lys Glu Thr Cys Ser Glu
```

-continued

```
            145                 150                 155                 160
        Lys Ser Thr Asn Leu His Asp Tyr Gly Met Leu Leu Pro Cys Gly Ile
                        165                 170                 175

Asp Lys Phe Arg Gly Val Glu Phe Val Cys Cys Pro Leu Ala Glu Glu
                        180                 185                 190

Ser Asp Asn Val Asp Ser Ala Asp Glu Glu Asp Ser Asp Val
                        195                 200                 205

Trp Trp Gly Gly Ala Asp Thr Asp Tyr Ala Asp Gly Ser Glu Asp Lys
            210                 215                 220

Val Val Glu Val Ala Glu Glu Glu Val Ala Glu Val Glu Glu Glu
        225                 230                 235                 240

Glu Ala Asp Asp Asp Glu Asp Asp Glu Asp Gly Asp Glu Val Glu Glu
                        245                 250                 255

Glu Ala Glu Glu Pro Tyr Glu Glu Ala Thr Glu Arg Thr Thr Ser Ile
                        260                 265                 270

Ala Thr Thr Thr Thr Thr Thr Glu Ser Val Glu Val Val Arg
                        275                 280                 285

Val Pro Thr Thr Ala Ala Ser Thr Pro Asp Ala Val Asp Lys Tyr Leu
                        290                 295                 300

Glu Thr Pro Gly Asp Glu Asn Glu His Ala His Phe Gln Lys Ala Lys
        305                 310                 315                 320

Glu Arg Leu Glu Ala Lys His Arg Glu Arg Met Ser Gln Val Met Arg
                        325                 330                 335

Glu Trp Glu Glu Ala Glu Arg Gln Ala Lys Asn Leu Pro Lys Ala Asp
                        340                 345                 350

Lys Lys Ala Val Ile Gln His Phe Gln Glu Lys Val Glu Ser Leu Glu
                        355                 360                 365

Gln Glu Ala Ala Asn Glu Arg Gln Gln Leu Val Glu Thr His Met Ala
                        370                 375                 380

Arg Val Glu Ala Met Leu Asn Asp Arg Arg Arg Leu Ala Leu Glu Asn
        385                 390                 395                 400

Tyr Ile Thr Ala Leu Gln Ala Val Pro Pro Arg Pro Arg His Val Phe
                        405                 410                 415

Asn Met Leu Lys Lys Tyr Val Arg Ala Glu Gln Lys Asp Arg Gln His
                        420                 425                 430

Thr Leu Lys His Phe Glu His Val Arg Met Val Asp Pro Lys Lys Ala
                        435                 440                 445

Ala Gln Ile Arg Ser Gln Val Met Thr His Leu Arg Val Ile Tyr Glu
                        450                 455                 460

Arg Met Asn Gln Ser Leu Ser Leu Leu Tyr Asn Val Pro Ala Val Ala
        465                 470                 475                 480

Glu Glu Ile Gln Asp Glu Val Asp Glu Leu Leu Gln Lys Glu Gln Asn
                        485                 490                 495

Tyr Ser Asp Asp Val Leu Ala Asn Met Ile Ser Glu Pro Arg Ile Ser
                        500                 505                 510

Tyr Gly Asn Asp Ala Leu Met Pro Ser Leu Thr Glu Lys Thr Thr
                        515                 520                 525

Val Glu Leu Leu Pro Val Asn Gly Glu Phe Ser Leu Asp Asp Leu Gln
                        530                 535                 540

Pro Trp His Ser Phe Gly Ala Asp Ser Val Pro Ala Asn Thr Glu Asn
        545                 550                 555                 560

Glu Val Glu Pro Val Asp Ala Arg Pro Ala Ala Asp Arg Gly Leu Thr
                        565                 570                 575
```

Thr Arg Pro Gly Ser Gly Leu Thr Asn Ile Lys Thr Glu Glu Ile Ser
            580                 585                 590

Glu Val Asn Leu Ala Ala Glu Phe Arg His Asp Ser Gly Tyr Glu Val
            595                 600                 605

His His Gln Lys Leu Val Phe Phe Ala Glu Asp Val Gly Ser Asn Lys
            610                 615                 620

Gly Ala Ile Ile Gly Leu Met Val Gly Val Val Ile Ala Thr Val
625                 630                 635                 640

Ile Val Ile Thr Leu Val Met Leu Lys Lys Lys Gln Tyr Thr Ser Ile
            645                 650                 655

His His Gly Val Val Glu Val Asp Ala Ala Val Thr Pro Glu Glu Arg
            660                 665                 670

His Leu Ser Lys Met Gln Gln Asn Gly Tyr Glu Asn Pro Thr Tyr Lys
            675                 680                 685

Phe Phe Glu Gln Met Gln Asn
            690                 695

<210> SEQ ID NO 37
<211> LENGTH: 695
<212> TYPE: PRT
<213> ORGANISM: Artificial
<220> FEATURE:
<223> OTHER INFORMATION: polypeptide containing novel sequence at known
      enzyme cleavage site

<400> SEQUENCE: 37

Met Leu Pro Gly Leu Ala Leu Leu Leu Ala Ala Trp Thr Ala Arg
1               5                   10                  15

Ala Leu Glu Val Pro Thr Asp Gly Asn Ala Gly Leu Leu Ala Glu Pro
            20                  25                  30

Gln Ile Ala Met Phe Cys Gly Arg Leu Asn Met His Met Asn Val Gln
            35                  40                  45

Asn Gly Lys Trp Asp Ser Asp Pro Ser Gly Thr Lys Thr Cys Ile Asp
50                  55                  60

Thr Lys Glu Gly Ile Leu Gln Tyr Cys Gln Glu Val Tyr Pro Glu Leu
65                  70                  75                  80

Gln Ile Thr Asn Val Val Glu Ala Asn Gln Pro Val Thr Ile Gln Asn
            85                  90                  95

Trp Cys Lys Arg Gly Arg Lys Gln Cys Lys Thr His Pro His Phe Val
            100                 105                 110

Ile Pro Tyr Arg Cys Leu Val Gly Glu Phe Val Ser Asp Ala Leu Leu
            115                 120                 125

Val Pro Asp Lys Cys Lys Phe Leu His Gln Glu Arg Met Asp Val Cys
            130                 135                 140

Glu Thr His Leu His Trp His Thr Val Ala Lys Glu Thr Cys Ser Glu
145                 150                 155                 160

Lys Ser Thr Asn Leu His Asp Tyr Gly Met Leu Leu Pro Cys Gly Ile
            165                 170                 175

Asp Lys Phe Arg Gly Val Glu Phe Val Cys Cys Pro Leu Ala Glu Glu
            180                 185                 190

Ser Asp Asn Val Asp Ser Ala Asp Ala Glu Glu Asp Ser Asp Val
            195                 200                 205

Trp Trp Gly Gly Ala Asp Thr Asp Tyr Ala Asp Gly Ser Glu Asp Lys
            210                 215                 220

Val Val Glu Val Ala Glu Glu Glu Glu Val Ala Glu Val Glu Glu Glu

-continued

```
            225                 230                 235                 240

Glu Ala Asp Asp Asp Glu Asp Asp Glu Asp Gly Asp Glu Val Glu Glu
                245                 250                 255

Glu Ala Glu Glu Pro Tyr Glu Glu Ala Thr Glu Arg Thr Thr Ser Ile
            260                 265                 270

Ala Thr Thr Thr Thr Thr Thr Thr Glu Ser Val Glu Glu Val Val Arg
        275                 280                 285

Val Pro Thr Thr Ala Ala Ser Thr Pro Asp Ala Val Asp Lys Tyr Leu
        290                 295                 300

Glu Thr Pro Gly Asp Glu Asn Glu His Ala His Phe Gln Lys Ala Lys
305                 310                 315                 320

Glu Arg Leu Glu Ala Lys His Arg Glu Arg Met Ser Gln Val Met Arg
                325                 330                 335

Glu Trp Glu Glu Ala Glu Arg Gln Ala Lys Asn Leu Pro Lys Ala Asp
                340                 345                 350

Lys Lys Ala Val Ile Gln His Phe Gln Glu Lys Val Glu Ser Leu Glu
                355                 360                 365

Gln Glu Ala Ala Asn Glu Arg Gln Gln Leu Val Glu Thr His Met Ala
            370                 375                 380

Arg Val Glu Ala Met Leu Asn Asp Arg Arg Arg Leu Ala Leu Glu Asn
385                 390                 395                 400

Tyr Ile Thr Ala Leu Gln Ala Val Pro Pro Arg Pro Arg His Val Phe
                405                 410                 415

Asn Met Leu Lys Lys Tyr Val Arg Ala Glu Gln Lys Asp Arg Gln His
                420                 425                 430

Thr Leu Lys His Phe Glu His Val Arg Met Val Asp Pro Lys Lys Ala
            435                 440                 445

Ala Gln Ile Arg Ser Gln Val Met Thr His Leu Arg Val Ile Tyr Glu
450                 455                 460

Arg Met Asn Gln Ser Leu Ser Leu Leu Tyr Asn Val Pro Ala Val Ala
465                 470                 475                 480

Glu Glu Ile Gln Asp Glu Val Asp Glu Leu Leu Gln Lys Glu Gln Asn
                485                 490                 495

Tyr Ser Asp Asp Val Leu Ala Asn Met Ile Ser Glu Pro Arg Ile Ser
            500                 505                 510

Tyr Gly Asn Asp Ala Leu Met Pro Ser Leu Thr Glu Thr Lys Thr Thr
        515                 520                 525

Val Glu Leu Leu Pro Val Asn Gly Glu Phe Ser Leu Asp Asp Leu Gln
        530                 535                 540

Pro Trp His Ser Phe Gly Ala Asp Ser Val Pro Ala Asn Thr Glu Asn
545                 550                 555                 560

Glu Val Glu Pro Val Asp Ala Arg Pro Ala Ala Asp Arg Gly Leu Thr
                565                 570                 575

Thr Arg Pro Gly Ser Gly Leu Thr Asn Ile Lys Thr Glu Glu Ile Ser
            580                 585                 590

Glu Val Asn Phe Ala Ala Glu Phe Arg His Asp Ser Gly Tyr Glu Val
            595                 600                 605

His His Gln Lys Leu Val Phe Phe Ala Glu Asp Val Gly Ser Asn Lys
        610                 615                 620

Gly Ala Ile Ile Gly Leu Met Val Gly Gly Val Val Ile Ala Thr Val
625                 630                 635                 640

Ile Val Ile Thr Leu Val Met Leu Lys Lys Lys Gln Tyr Thr Ser Ile
                645                 650                 655
```

```
His His Gly Val Val Glu Val Asp Ala Ala Val Thr Pro Glu Glu Arg
            660                 665                 670

His Leu Ser Lys Met Gln Gln Asn Gly Tyr Glu Asn Pro Thr Tyr Lys
        675                 680                 685

Phe Phe Glu Gln Met Gln Asn
    690                 695

<210> SEQ ID NO 38
<211> LENGTH: 695
<212> TYPE: PRT
<213> ORGANISM: Artificial
<220> FEATURE:
<223> OTHER INFORMATION: polypeptide containing novel sequence at known
      enzyme cleavage site

<400> SEQUENCE: 38

Met Leu Pro Gly Leu Ala Leu Leu Leu Ala Ala Trp Thr Ala Arg
1               5                   10                  15

Ala Leu Glu Val Pro Thr Asp Gly Asn Ala Gly Leu Leu Ala Glu Pro
            20                  25                  30

Gln Ile Ala Met Phe Cys Gly Arg Leu Asn Met His Met Asn Val Gln
        35                  40                  45

Asn Gly Lys Trp Asp Ser Asp Pro Ser Gly Thr Lys Thr Cys Ile Asp
    50                  55                  60

Thr Lys Glu Gly Ile Leu Gln Tyr Cys Gln Glu Val Tyr Pro Glu Leu
65                  70                  75                  80

Gln Ile Thr Asn Val Val Glu Ala Asn Gln Pro Val Thr Ile Gln Asn
            85                  90                  95

Trp Cys Lys Arg Gly Arg Lys Gln Cys Lys Thr His Pro His Phe Val
            100                 105                 110

Ile Pro Tyr Arg Cys Leu Val Gly Glu Phe Val Ser Asp Ala Leu Leu
        115                 120                 125

Val Pro Asp Lys Cys Lys Phe Leu His Gln Glu Arg Met Asp Val Cys
    130                 135                 140

Glu Thr His Leu His Trp His Thr Val Ala Lys Glu Thr Cys Ser Glu
145                 150                 155                 160

Lys Ser Thr Asn Leu His Asp Tyr Gly Met Leu Leu Pro Cys Gly Ile
            165                 170                 175

Asp Lys Phe Arg Gly Val Glu Phe Val Cys Cys Pro Leu Ala Glu Glu
        180                 185                 190

Ser Asp Asn Val Asp Ser Ala Asp Ala Glu Glu Asp Asp Ser Asp Val
    195                 200                 205

Trp Trp Gly Gly Ala Asp Thr Asp Tyr Ala Asp Gly Ser Glu Asp Lys
    210                 215                 220

Val Val Glu Val Ala Glu Glu Glu Val Ala Glu Val Glu Glu Glu
225                 230                 235                 240

Glu Ala Asp Asp Asp Glu Asp Asp Glu Asp Gly Asp Glu Val Glu Glu
            245                 250                 255

Glu Ala Glu Glu Pro Tyr Glu Glu Ala Thr Glu Arg Thr Thr Ser Ile
            260                 265                 270

Ala Thr Thr Thr Thr Thr Thr Thr Glu Ser Val Glu Glu Val Val Arg
        275                 280                 285

Val Pro Thr Thr Ala Ala Ser Thr Pro Asp Ala Val Asp Lys Tyr Leu
    290                 295                 300

Glu Thr Pro Gly Asp Glu Asn Glu His Ala His Phe Gln Lys Ala Lys
```

```
             305                 310                 315                 320
    Glu Arg Leu Glu Ala Lys His Arg Glu Arg Met Ser Gln Val Met Arg
                    325                 330                 335
    Glu Trp Glu Glu Ala Glu Arg Gln Ala Lys Asn Leu Pro Lys Ala Asp
                340                 345                 350
    Lys Lys Ala Val Ile Gln His Phe Gln Glu Lys Val Glu Ser Leu Glu
                355                 360                 365
    Gln Glu Ala Ala Asn Glu Arg Gln Gln Leu Val Glu Thr His Met Ala
            370                 375                 380
    Arg Val Glu Ala Met Leu Asn Asp Arg Arg Leu Ala Leu Glu Asn
    385                 390                 395                 400
    Tyr Ile Thr Ala Leu Gln Ala Val Pro Pro Arg Pro Arg His Val Phe
                    405                 410                 415
    Asn Met Leu Lys Lys Tyr Val Arg Ala Glu Gln Lys Asp Arg Gln His
                420                 425                 430
    Thr Leu Lys His Phe Glu His Val Arg Met Val Asp Pro Lys Lys Ala
                435                 440                 445
    Ala Gln Ile Arg Ser Gln Val Met Thr His Leu Arg Val Ile Tyr Glu
        450                 455                 460
    Arg Met Asn Gln Ser Leu Ser Leu Leu Tyr Asn Val Pro Ala Val Ala
    465                 470                 475                 480
    Glu Glu Ile Gln Asp Glu Val Asp Glu Leu Leu Gln Lys Glu Gln Asn
                    485                 490                 495
    Tyr Ser Asp Asp Val Leu Ala Asn Met Ile Ser Glu Pro Arg Ile Ser
                500                 505                 510
    Tyr Gly Asn Asp Ala Leu Met Pro Ser Leu Thr Glu Thr Lys Thr Thr
                515                 520                 525
    Val Glu Leu Leu Pro Val Asn Gly Glu Phe Ser Leu Asp Asp Leu Gln
        530                 535                 540
    Pro Trp His Ser Phe Gly Ala Asp Ser Val Pro Ala Asn Thr Glu Asn
    545                 550                 555                 560
    Glu Val Glu Pro Val Asp Ala Arg Pro Ala Ala Asp Arg Gly Leu Thr
                    565                 570                 575
    Thr Arg Pro Gly Ser Gly Leu Thr Asn Ile Lys Thr Glu Glu Ile Ser
                580                 585                 590
    Glu Val Asn Tyr Ala Ala Glu Phe Arg His Asp Ser Gly Tyr Glu Val
                595                 600                 605
    His His Gln Lys Leu Val Phe Phe Ala Glu Asp Val Gly Ser Asn Lys
            610                 615                 620
    Gly Ala Ile Ile Gly Leu Met Val Gly Gly Val Val Ile Ala Thr Val
    625                 630                 635                 640
    Ile Val Ile Thr Leu Val Met Leu Lys Lys Lys Gln Tyr Thr Ser Ile
                    645                 650                 655
    His His Gly Val Val Glu Val Asp Ala Ala Val Thr Pro Glu Glu Arg
                660                 665                 670
    His Leu Ser Lys Met Gln Gln Asn Gly Tyr Glu Asn Pro Thr Tyr Lys
                675                 680                 685
    Phe Phe Glu Gln Met Gln Asn
        690                 695

<210> SEQ ID NO 39
<211> LENGTH: 695
<212> TYPE: PRT
<213> ORGANISM: Artificial
```

<220> FEATURE:
<223> OTHER INFORMATION: polypeptide containing novel sequence at known enzyme cleavage site

<400> SEQUENCE: 39

```

```
                385                 390                 395                 400
Tyr Ile Thr Ala Leu Gln Ala Val Pro Pro Arg Pro Arg His Val Phe
                405                 410                 415
Asn Met Leu Lys Lys Tyr Val Arg Ala Glu Gln Lys Asp Arg Gln His
            420                 425                 430
Thr Leu Lys His Phe Glu His Val Arg Met Val Asp Pro Lys Lys Ala
        435                 440                 445
Ala Gln Ile Arg Ser Gln Val Met Thr His Leu Arg Val Ile Tyr Glu
    450                 455                 460
Arg Met Asn Gln Ser Leu Ser Leu Leu Tyr Asn Val Pro Ala Val Ala
465                 470                 475                 480
Glu Glu Ile Gln Asp Glu Val Asp Leu Leu Gln Lys Glu Gln Asn
                485                 490                 495
Tyr Ser Asp Asp Val Leu Ala Asn Met Ile Ser Glu Pro Arg Ile Ser
                500                 505                 510
Tyr Gly Asn Asp Ala Leu Met Pro Ser Leu Thr Glu Thr Lys Thr Thr
            515                 520                 525
Val Glu Leu Leu Pro Val Asn Gly Glu Phe Ser Leu Asp Asp Leu Gln
        530                 535                 540
Pro Trp His Ser Phe Gly Ala Asp Ser Val Pro Ala Asn Thr Glu Asn
545                 550                 555                 560
Glu Val Glu Pro Val Asp Ala Arg Pro Ala Ala Asp Arg Gly Leu Thr
                565                 570                 575
Thr Arg Pro Gly Ser Gly Leu Thr Asn Ile Lys Thr Glu Glu Ile Ser
            580                 585                 590
Glu Val Lys Phe Ala Ala Glu Phe Arg His Asp Ser Gly Tyr Glu Val
        595                 600                 605
His His Gln Lys Leu Val Phe Phe Ala Glu Asp Val Gly Ser Asn Lys
    610                 615                 620
Gly Ala Ile Ile Gly Leu Met Val Gly Gly Val Val Ile Ala Thr Val
625                 630                 635                 640
Ile Val Ile Thr Leu Val Met Leu Lys Lys Lys Gln Tyr Thr Ser Ile
                645                 650                 655
His His Gly Val Val Glu Val Asp Ala Ala Val Thr Pro Glu Glu Arg
            660                 665                 670
His Leu Ser Lys Met Gln Gln Asn Gly Tyr Glu Asn Pro Thr Tyr Lys
        675                 680                 685
Phe Phe Glu Gln Met Gln Asn
    690                 695

<210> SEQ ID NO 40
<211> LENGTH: 695
<212> TYPE: PRT
<213> ORGANISM: Artificial
<220> FEATURE:
<223> OTHER INFORMATION: polypeptide containing novel sequence at known
      enzyme cleavage site

<400> SEQUENCE: 40

Met Leu Pro Gly Leu Ala Leu Leu Leu Ala Ala Trp Thr Ala Arg
1               5                   10                  15
Ala Leu Glu Val Pro Thr Asp Gly Asn Ala Gly Leu Leu Ala Glu Pro
                20                  25                  30
Gln Ile Ala Met Phe Cys Gly Arg Leu Asn Met His Met Asn Val Gln
            35                  40                  45
```

-continued

```
Asn Gly Lys Trp Asp Ser Asp Pro Ser Gly Thr Lys Thr Cys Ile Asp
        50                  55                  60

Thr Lys Glu Gly Ile Leu Gln Tyr Cys Gln Glu Val Tyr Pro Glu Leu
 65                  70                  75                  80

Gln Ile Thr Asn Val Val Glu Ala Asn Gln Pro Val Thr Ile Gln Asn
                    85                  90                  95

Trp Cys Lys Arg Gly Arg Lys Gln Cys Lys Thr His Pro His Phe Val
                100                 105                 110

Ile Pro Tyr Arg Cys Leu Val Gly Glu Phe Val Ser Asp Ala Leu Leu
                115                 120                 125

Val Pro Asp Lys Cys Lys Phe Leu His Gln Glu Arg Met Asp Val Cys
130                 135                 140

Glu Thr His Leu His Trp His Thr Val Ala Lys Glu Thr Cys Ser Glu
145                 150                 155                 160

Lys Ser Thr Asn Leu His Asp Tyr Gly Met Leu Leu Pro Cys Gly Ile
                165                 170                 175

Asp Lys Phe Arg Gly Val Glu Phe Val Cys Cys Pro Leu Ala Glu Glu
                180                 185                 190

Ser Asp Asn Val Asp Ser Ala Asp Ala Glu Glu Asp Asp Ser Asp Val
                195                 200                 205

Trp Trp Gly Gly Ala Asp Thr Asp Tyr Ala Asp Gly Ser Glu Asp Lys
210                 215                 220

Val Val Glu Val Ala Glu Glu Glu Val Ala Glu Val Glu Glu Glu
225                 230                 235                 240

Glu Ala Asp Asp Asp Glu Asp Asp Glu Asp Gly Asp Glu Val Glu Glu
                245                 250                 255

Glu Ala Glu Glu Pro Tyr Glu Glu Ala Thr Glu Arg Thr Thr Ser Ile
                260                 265                 270

Ala Thr Thr Thr Thr Thr Thr Glu Ser Val Glu Glu Val Val Arg
                275                 280                 285

Val Pro Thr Thr Ala Ala Ser Thr Pro Asp Ala Val Asp Lys Tyr Leu
                290                 295                 300

Glu Thr Pro Gly Asp Glu Asn Glu His Ala His Phe Gln Lys Ala Lys
305                 310                 315                 320

Glu Arg Leu Glu Ala Lys His Arg Glu Arg Met Ser Gln Val Met Arg
                325                 330                 335

Glu Trp Glu Glu Ala Glu Arg Gln Ala Lys Asn Leu Pro Lys Ala Asp
                340                 345                 350

Lys Lys Ala Val Ile Gln His Phe Gln Glu Lys Val Glu Ser Leu Glu
                355                 360                 365

Gln Glu Ala Ala Asn Glu Arg Gln Gln Leu Val Glu Thr His Met Ala
                370                 375                 380

Arg Val Glu Ala Met Leu Asn Asp Arg Arg Arg Leu Ala Leu Glu Asn
385                 390                 395                 400

Tyr Ile Thr Ala Leu Gln Ala Val Pro Pro Arg Pro Arg His Val Phe
                405                 410                 415

Asn Met Leu Lys Lys Tyr Val Arg Ala Glu Gln Lys Asp Arg Gln His
                420                 425                 430

Thr Leu Lys His Phe Glu His Val Arg Met Val Asp Pro Lys Lys Ala
                435                 440                 445

Ala Gln Ile Arg Ser Gln Val Met Thr His Leu Arg Val Ile Tyr Glu
450                 455                 460

Arg Met Asn Gln Ser Leu Ser Leu Leu Tyr Asn Val Pro Ala Val Ala
```

```
                    465                 470                 475                 480
Glu Glu Ile Gln Asp Glu Val Asp Glu Leu Leu Gln Lys Glu Gln Asn
                        485                 490                 495

Tyr Ser Asp Asp Val Leu Ala Asn Met Ile Ser Glu Pro Arg Ile Ser
            500                 505                 510

Tyr Gly Asn Asp Ala Leu Met Pro Ser Leu Thr Glu Thr Lys Thr Thr
        515                 520                 525

Val Glu Leu Leu Pro Val Asn Gly Glu Phe Ser Leu Asp Asp Leu Gln
    530                 535                 540

Pro Trp His Ser Phe Gly Ala Asp Ser Val Pro Ala Asn Thr Glu Asn
545                 550                 555                 560

Glu Val Glu Pro Val Asp Ala Arg Pro Ala Asp Arg Gly Leu Thr
                565                 570                 575

Thr Arg Pro Gly Ser Gly Leu Thr Asn Ile Lys Thr Glu Glu Ile Ser
                580                 585                 590

Glu Val Lys Met Ala Ala Glu Phe Arg His Asp Ser Gly Tyr Glu Val
                595                 600                 605

His His Gln Lys Leu Val Phe Phe Ala Glu Asp Val Gly Ser Asn Lys
        610                 615                 620

Gly Ala Ile Ile Gly Leu Met Val Gly Gly Val Val Ile Ala Thr Val
625                 630                 635                 640

Ile Val Ile Thr Leu Val Met Leu Lys Lys Lys Gln Tyr Thr Ser Ile
                645                 650                 655

His His Gly Val Val Glu Val Asp Ala Ala Val Thr Pro Glu Glu Arg
            660                 665                 670

His Leu Ser Lys Met Gln Gln Asn Gly Tyr Glu Asn Pro Thr Tyr Lys
        675                 680                 685

Phe Phe Glu Gln Met Gln Asn
690                 695

<210> SEQ ID NO 41
<211> LENGTH: 695
<212> TYPE: PRT
<213> ORGANISM: Artificial
<220> FEATURE:
<223> OTHER INFORMATION: polypeptide containing novel sequence at known
      enzyme cleavage site

<400> SEQUENCE: 41

Met Leu Pro Gly Leu Ala Leu Leu Leu Leu Ala Ala Trp Thr Ala Arg
1               5                   10                  15

Ala Leu Glu Val Pro Thr Asp Gly Asn Ala Gly Leu Leu Ala Glu Pro
                20                  25                  30

Gln Ile Ala Met Phe Cys Gly Arg Leu Asn Met His Met Asn Val Gln
            35                  40                  45

Asn Gly Lys Trp Asp Ser Asp Pro Ser Gly Thr Lys Thr Cys Ile Asp
        50                  55                  60

Thr Lys Glu Gly Ile Leu Gln Tyr Cys Gln Glu Val Tyr Pro Glu Leu
65                  70                  75                  80

Gln Ile Thr Asn Val Val Glu Ala Asn Gln Pro Val Thr Ile Gln Asn
                85                  90                  95

Trp Cys Lys Arg Gly Arg Lys Gln Cys Lys Thr His Pro His Phe Val
            100                 105                 110

Ile Pro Tyr Arg Cys Leu Val Gly Glu Phe Val Ser Asp Ala Leu Leu
        115                 120                 125
```

-continued

```
Val Pro Asp Lys Cys Lys Phe Leu His Gln Glu Arg Met Asp Val Cys
    130                 135                 140
Glu Thr His Leu His Trp His Thr Val Ala Lys Glu Thr Cys Ser Glu
145                 150                 155                 160
Lys Ser Thr Asn Leu His Asp Tyr Gly Met Leu Leu Pro Cys Gly Ile
                165                 170                 175
Asp Lys Phe Arg Gly Val Glu Phe Val Cys Cys Pro Leu Ala Glu Glu
            180                 185                 190
Ser Asp Asn Val Asp Ser Ala Asp Ala Glu Glu Asp Asp Ser Asp Val
        195                 200                 205
Trp Trp Gly Gly Ala Asp Thr Asp Tyr Ala Asp Gly Ser Glu Asp Lys
    210                 215                 220
Val Val Glu Val Ala Glu Glu Glu Val Ala Glu Val Glu Glu Glu
225                 230                 235                 240
Glu Ala Asp Asp Asp Glu Asp Asp Glu Asp Gly Asp Glu Val Glu Glu
                245                 250                 255
Glu Ala Glu Glu Pro Tyr Glu Glu Ala Thr Glu Arg Thr Thr Ser Ile
            260                 265                 270
Ala Thr Thr Thr Thr Thr Thr Glu Ser Val Glu Glu Val Val Arg
        275                 280                 285
Val Pro Thr Thr Ala Ala Ser Thr Pro Asp Ala Val Asp Lys Tyr Leu
    290                 295                 300
Glu Thr Pro Gly Asp Glu Asn Glu His Ala His Phe Gln Lys Ala Lys
305                 310                 315                 320
Glu Arg Leu Glu Ala Lys His Arg Glu Arg Met Ser Gln Val Met Arg
                325                 330                 335
Glu Trp Glu Glu Ala Glu Arg Gln Ala Lys Asn Leu Pro Lys Ala Asp
            340                 345                 350
Lys Lys Ala Val Ile Gln His Phe Gln Glu Lys Val Glu Ser Leu Glu
        355                 360                 365
Gln Glu Ala Ala Asn Glu Arg Gln Gln Leu Val Glu Thr His Met Ala
    370                 375                 380
Arg Val Glu Ala Met Leu Asn Asp Arg Arg Arg Leu Ala Leu Glu Asn
385                 390                 395                 400
Tyr Ile Thr Ala Leu Gln Ala Val Pro Pro Arg Pro Arg His Val Phe
                405                 410                 415
Asn Met Leu Lys Lys Tyr Val Arg Ala Glu Gln Lys Asp Arg Gln His
            420                 425                 430
Thr Leu Lys His Phe Glu His Val Arg Met Val Asp Pro Lys Lys Ala
        435                 440                 445
Ala Gln Ile Arg Ser Gln Val Met Thr His Leu Arg Val Ile Tyr Glu
    450                 455                 460
Arg Met Asn Gln Ser Leu Ser Leu Leu Tyr Asn Val Pro Ala Val Ala
465                 470                 475                 480
Glu Glu Ile Gln Asp Glu Val Asp Glu Leu Leu Gln Lys Glu Gln Asn
                485                 490                 495
Tyr Ser Asp Asp Val Leu Ala Asn Met Ile Ser Glu Pro Arg Ile Ser
            500                 505                 510
Tyr Gly Asn Asp Ala Leu Met Pro Ser Leu Thr Glu Thr Lys Thr Thr
        515                 520                 525
Val Glu Leu Leu Pro Val Asn Gly Glu Phe Ser Leu Asp Asp Leu Gln
    530                 535                 540
Pro Trp His Ser Phe Gly Ala Asp Ser Val Pro Ala Asn Thr Glu Asn
```

```
                545                 550                 555                 560
Glu Val Glu Pro Val Asp Ala Arg Pro Ala Asp Arg Gly Leu Thr
            565                 570                 575
Thr Arg Pro Gly Ser Gly Leu Thr Asn Ile Lys Thr Glu Glu Ile Ser
        580                 585                 590
Glu Val Lys Met Asp Val Glu Phe Arg His Asp Ser Gly Tyr Glu Val
            595                 600                 605
His His Gln Lys Leu Val Phe Phe Ala Glu Asp Val Gly Ser Asn Lys
        610                 615                 620
Gly Ala Ile Ile Gly Leu Met Val Gly Val Val Ile Ala Thr Val
625                 630                 635                 640
Ile Val Ile Thr Leu Val Met Leu Lys Lys Lys Gln Tyr Thr Ser Ile
            645                 650                 655
His His Gly Val Val Glu Val Asp Ala Ala Val Thr Pro Glu Glu Arg
        660                 665                 670
His Leu Ser Lys Met Gln Gln Asn Gly Tyr Glu Asn Pro Thr Tyr Lys
            675                 680                 685
Phe Phe Glu Gln Met Gln Asn
        690                 695

<210> SEQ ID NO 42
<211> LENGTH: 695
<212> TYPE: PRT
<213> ORGANISM: Artificial
<220> FEATURE:
<223> OTHER INFORMATION: polypeptide containing novel sequence at known
      enzyme cleavage site

<400> SEQUENCE: 42

Met Leu Pro Gly Leu Ala Leu Leu Leu Leu Ala Ala Trp Thr Ala Arg
1               5                   10                  15
Ala Leu Glu Val Pro Thr Asp Gly Asn Ala Gly Leu Leu Ala Glu Pro
            20                  25                  30
Gln Ile Ala Met Phe Cys Gly Arg Leu Asn Met His Met Asn Val Gln
        35                  40                  45
Asn Gly Lys Trp Asp Ser Asp Pro Ser Gly Thr Lys Thr Cys Ile Asp
    50                  55                  60
Thr Lys Glu Gly Ile Leu Gln Tyr Cys Gln Glu Val Tyr Pro Glu Leu
65                  70                  75                  80
Gln Ile Thr Asn Val Val Glu Ala Asn Gln Pro Val Thr Ile Gln Asn
            85                  90                  95
Trp Cys Lys Arg Gly Arg Lys Gln Cys Lys Thr His Pro His Phe Val
        100                 105                 110
Ile Pro Tyr Arg Cys Leu Val Gly Glu Phe Val Ser Asp Ala Leu Leu
    115                 120                 125
Val Pro Asp Lys Cys Lys Phe Leu His Gln Glu Arg Met Asp Val Cys
130                 135                 140
Glu Thr His Leu His Trp His Thr Val Ala Lys Glu Thr Cys Ser Glu
145                 150                 155                 160
Lys Ser Thr Asn Leu His Asp Tyr Gly Met Leu Leu Pro Cys Gly Ile
            165                 170                 175
Asp Lys Phe Arg Gly Val Glu Phe Val Cys Cys Pro Leu Ala Glu Glu
        180                 185                 190
Ser Asp Asn Val Asp Ser Ala Asp Ala Glu Glu Asp Asp Ser Asp Val
    195                 200                 205
```

-continued

```
Trp Trp Gly Gly Ala Asp Thr Asp Tyr Ala Asp Gly Ser Glu Asp Lys
210                 215                 220
Val Val Glu Val Ala Glu Glu Glu Val Ala Glu Val Glu Glu Glu
225                 230                 235                 240
Glu Ala Asp Asp Asp Glu Asp Asp Glu Asp Gly Asp Glu Val Glu Glu
                245                 250                 255
Glu Ala Glu Glu Pro Tyr Glu Glu Ala Thr Glu Arg Thr Thr Ser Ile
            260                 265                 270
Ala Thr Thr Thr Thr Thr Thr Glu Ser Val Glu Glu Val Val Arg
                275                 280                 285
Val Pro Thr Thr Ala Ala Ser Thr Pro Asp Ala Val Asp Lys Tyr Leu
290                 295                 300
Glu Thr Pro Gly Asp Glu Asn Glu His Ala His Phe Gln Lys Ala Lys
305                 310                 315                 320
Glu Arg Leu Glu Ala Lys His Arg Glu Arg Met Ser Gln Val Met Arg
                325                 330                 335
Glu Trp Glu Glu Ala Glu Arg Gln Ala Lys Asn Leu Pro Lys Ala Asp
                340                 345                 350
Lys Lys Ala Val Ile Gln His Phe Gln Glu Lys Val Glu Ser Leu Glu
            355                 360                 365
Gln Glu Ala Ala Asn Glu Arg Gln Gln Leu Val Glu Thr His Met Ala
370                 375                 380
Arg Val Glu Ala Met Leu Asn Asp Arg Arg Arg Leu Ala Leu Glu Asn
385                 390                 395                 400
Tyr Ile Thr Ala Leu Gln Ala Val Pro Pro Arg Pro Arg His Val Phe
            405                 410                 415
Asn Met Leu Lys Lys Tyr Val Arg Ala Glu Gln Lys Asp Arg Gln His
                420                 425                 430
Thr Leu Lys His Phe Glu His Val Arg Met Val Asp Pro Lys Lys Ala
            435                 440                 445
Ala Gln Ile Arg Ser Gln Val Met Thr His Leu Arg Val Ile Tyr Glu
450                 455                 460
Arg Met Asn Gln Ser Leu Ser Leu Leu Tyr Asn Val Pro Ala Val Ala
465                 470                 475                 480
Glu Glu Ile Gln Asp Glu Val Asp Glu Leu Leu Gln Lys Glu Gln Asn
                485                 490                 495
Tyr Ser Asp Asp Val Leu Ala Asn Met Ile Ser Glu Pro Arg Ile Ser
                500                 505                 510
Tyr Gly Asn Asp Ala Leu Met Pro Ser Leu Thr Glu Thr Lys Thr Thr
            515                 520                 525
Val Glu Leu Leu Pro Val Asn Gly Glu Phe Ser Leu Asp Asp Leu Gln
530                 535                 540
Pro Trp His Ser Phe Gly Ala Asp Ser Val Pro Ala Asn Thr Glu Asn
545                 550                 555                 560
Glu Val Glu Pro Val Asp Ala Arg Pro Ala Ala Asp Arg Gly Leu Thr
                565                 570                 575
Thr Arg Pro Gly Ser Gly Leu Thr Asn Ile Lys Thr Glu Glu Ile Ser
            580                 585                 590
Glu Val Lys Phe Glu Ala Glu Phe Arg His Asp Ser Gly Tyr Glu Val
            595                 600                 605
His His Gln Lys Leu Val Phe Phe Ala Glu Asp Val Gly Ser Asn Lys
610                 615                 620
Gly Ala Ile Ile Gly Leu Met Val Gly Gly Val Val Ile Ala Thr Val
```

```
                    625                 630                 635                 640
Ile Val Ile Thr Leu Val Met Leu Lys Lys Gln Tyr Thr Ser Ile
                645                 650                 655

His His Gly Val Val Glu Val Asp Ala Ala Val Thr Pro Glu Glu Arg
            660                 665                 670

His Leu Ser Lys Met Gln Gln Asn Gly Tyr Glu Asn Pro Thr Tyr Lys
            675                 680                 685

Phe Phe Glu Gln Met Gln Asn
        690                 695

<210> SEQ ID NO 43
<211> LENGTH: 695
<212> TYPE: PRT
<213> ORGANISM: Artificial
<220> FEATURE:
<223> OTHER INFORMATION: polypeptide containing novel sequence at known
      enzyme cleavage site

<400> SEQUENCE: 43

Met Leu Pro Gly Leu Ala Leu Leu Leu Ala Ala Trp Thr Ala Arg
1               5                   10                  15

Ala Leu Glu Val Pro Thr Asp Gly Asn Ala Gly Leu Leu Ala Glu Pro
                20                  25                  30

Gln Ile Ala Met Phe Cys Gly Arg Leu Asn Met His Met Asn Val Gln
            35                  40                  45

Asn Gly Lys Trp Asp Ser Asp Pro Ser Gly Thr Lys Thr Cys Ile Asp
        50                  55                  60

Thr Lys Glu Gly Ile Leu Gln Tyr Cys Gln Glu Val Tyr Pro Glu Leu
65                  70                  75                  80

Gln Ile Thr Asn Val Val Glu Ala Asn Gln Pro Val Thr Ile Gln Asn
                85                  90                  95

Trp Cys Lys Arg Gly Arg Lys Gln Cys Lys Thr His Pro His Phe Val
            100                 105                 110

Ile Pro Tyr Arg Cys Leu Val Gly Glu Phe Val Ser Asp Ala Leu Leu
        115                 120                 125

Val Pro Asp Lys Cys Lys Phe Leu His Gln Glu Arg Met Asp Val Cys
    130                 135                 140

Glu Thr His Leu His Trp His Thr Val Ala Lys Glu Thr Cys Ser Glu
145                 150                 155                 160

Lys Ser Thr Asn Leu His Asp Tyr Gly Met Leu Leu Pro Cys Gly Ile
                165                 170                 175

Asp Lys Phe Arg Gly Val Glu Phe Val Cys Cys Pro Leu Ala Glu Glu
            180                 185                 190

Ser Asp Asn Val Asp Ser Ala Asp Ala Glu Glu Asp Asp Ser Asp Val
        195                 200                 205

Trp Trp Gly Gly Ala Asp Thr Asp Tyr Ala Asp Gly Ser Glu Asp Lys
    210                 215                 220

Val Val Glu Val Ala Glu Glu Glu Val Ala Glu Val Glu Glu Glu Glu
225                 230                 235                 240

Glu Ala Asp Asp Asp Glu Asp Asp Glu Asp Gly Asp Glu Val Glu Glu
                245                 250                 255

Glu Ala Glu Glu Pro Tyr Glu Glu Ala Thr Glu Arg Thr Thr Ser Ile
            260                 265                 270

Ala Thr Thr Thr Thr Thr Thr Thr Glu Ser Val Glu Glu Val Val Arg
        275                 280                 285
```

```
Val Pro Thr Thr Ala Ala Ser Thr Pro Asp Ala Val Asp Lys Tyr Leu
    290                 295                 300
Glu Thr Pro Gly Asp Glu Asn Glu His Ala His Phe Gln Lys Ala Lys
305                 310                 315                 320
Glu Arg Leu Glu Ala Lys His Arg Glu Arg Met Ser Gln Val Met Arg
                325                 330                 335
Glu Trp Glu Glu Ala Glu Arg Gln Ala Lys Asn Leu Pro Lys Ala Asp
            340                 345                 350
Lys Lys Ala Val Ile Gln His Phe Gln Glu Lys Val Glu Ser Leu Glu
        355                 360                 365
Gln Glu Ala Ala Asn Glu Arg Gln Gln Leu Val Glu Thr His Met Ala
    370                 375                 380
Arg Val Glu Ala Met Leu Asn Asp Arg Arg Arg Leu Ala Leu Glu Asn
385                 390                 395                 400
Tyr Ile Thr Ala Leu Gln Ala Val Pro Pro Arg Pro Arg His Val Phe
                405                 410                 415
Asn Met Leu Lys Lys Tyr Val Arg Ala Glu Gln Lys Asp Arg Gln His
            420                 425                 430
Thr Leu Lys His Phe Glu His Val Arg Met Val Asp Pro Lys Lys Ala
        435                 440                 445
Ala Gln Ile Arg Ser Gln Val Met Thr His Leu Arg Val Ile Tyr Glu
    450                 455                 460
Arg Met Asn Gln Ser Leu Ser Leu Leu Tyr Asn Val Pro Ala Val Ala
465                 470                 475                 480
Glu Glu Ile Gln Asp Glu Val Asp Glu Leu Leu Gln Lys Glu Gln Asn
                485                 490                 495
Tyr Ser Asp Asp Val Leu Ala Asn Met Ile Ser Glu Pro Arg Ile Ser
            500                 505                 510
Tyr Gly Asn Asp Ala Leu Met Pro Ser Leu Thr Glu Thr Lys Thr Thr
        515                 520                 525
Val Glu Leu Leu Pro Val Asn Gly Glu Phe Ser Leu Asp Asp Leu Gln
    530                 535                 540
Pro Trp His Ser Phe Gly Ala Asp Ser Val Pro Ala Asn Thr Glu Asn
545                 550                 555                 560
Glu Val Glu Pro Val Asp Ala Arg Pro Ala Ala Asp Arg Gly Leu Thr
                565                 570                 575
Thr Arg Pro Gly Ser Gly Leu Thr Asn Ile Lys Thr Glu Glu Ile Ser
            580                 585                 590
Glu Val Lys Tyr Ala Ala Glu Phe Arg His Asp Ser Gly Tyr Glu Val
        595                 600                 605
His His Gln Lys Leu Val Phe Phe Ala Glu Asp Val Gly Ser Asn Lys
    610                 615                 620
Gly Ala Ile Ile Gly Leu Met Val Gly Gly Val Val Ile Ala Thr Val
625                 630                 635                 640
Ile Val Ile Thr Leu Val Met Leu Lys Lys Lys Gln Tyr Thr Ser Ile
                645                 650                 655
His His Gly Val Val Glu Val Asp Ala Ala Val Thr Pro Glu Glu Arg
            660                 665                 670
His Leu Ser Lys Met Gln Gln Asn Gly Tyr Glu Asn Pro Thr Tyr Lys
        675                 680                 685
Phe Phe Glu Gln Met Gln Asn
    690                 695
```

-continued

```
<210> SEQ ID NO 44
<211> LENGTH: 695
<212> TYPE: PRT
<213> ORGANISM: Artificial
<220> FEATURE:
<223> OTHER INFORMATION: polypeptide containing novel sequence at known
      enzyme cleavage site

<400> SEQUENCE: 44

Met Leu Pro Gly Leu Ala Leu Leu Leu Ala Ala Trp Thr Ala Arg
1               5                   10                  15

Ala Leu Glu Val Pro Thr Asp Gly Asn Ala Gly Leu Leu Ala Glu Pro
                20                  25                  30

Gln Ile Ala Met Phe Cys Gly Arg Leu Asn Met His Met Asn Val Gln
            35                  40                  45

Asn Gly Lys Trp Asp Ser Asp Pro Ser Gly Thr Lys Thr Cys Ile Asp
        50                  55                  60

Thr Lys Glu Gly Ile Leu Gln Tyr Cys Gln Glu Val Tyr Pro Glu Leu
65                  70                  75                  80

Gln Ile Thr Asn Val Val Glu Ala Asn Gln Pro Val Thr Ile Gln Asn
                85                  90                  95

Trp Cys Lys Arg Gly Arg Lys Gln Cys Lys Thr His Pro His Phe Val
            100                 105                 110

Ile Pro Tyr Arg Cys Leu Val Gly Glu Phe Val Ser Asp Ala Leu Leu
        115                 120                 125

Val Pro Asp Lys Cys Lys Phe Leu His Gln Glu Arg Met Asp Val Cys
130                 135                 140

Glu Thr His Leu His Trp His Thr Val Ala Lys Glu Thr Cys Ser Glu
145                 150                 155                 160

Lys Ser Thr Asn Leu His Asp Tyr Gly Met Leu Leu Pro Cys Gly Ile
                165                 170                 175

Asp Lys Phe Arg Gly Val Glu Phe Val Cys Cys Pro Leu Ala Glu Glu
            180                 185                 190

Ser Asp Asn Val Asp Ser Ala Asp Ala Glu Glu Asp Asp Ser Asp Val
        195                 200                 205

Trp Trp Gly Gly Ala Asp Thr Asp Tyr Ala Asp Gly Ser Glu Asp Lys
210                 215                 220

Val Val Glu Val Ala Glu Glu Glu Val Ala Glu Val Glu Glu Glu
225                 230                 235                 240

Glu Ala Asp Asp Asp Glu Asp Asp Glu Asp Gly Asp Glu Val Glu Glu
                245                 250                 255

Glu Ala Glu Glu Pro Tyr Glu Glu Ala Thr Glu Arg Thr Thr Ser Ile
            260                 265                 270

Ala Thr Thr Thr Thr Thr Thr Glu Ser Val Glu Glu Val Val Arg
        275                 280                 285

Val Pro Thr Thr Ala Ala Ser Thr Pro Asp Ala Val Asp Lys Tyr Leu
290                 295                 300

Glu Thr Pro Gly Asp Glu Asn Glu His Ala His Phe Gln Lys Ala Lys
305                 310                 315                 320

Glu Arg Leu Glu Ala Lys His Arg Glu Arg Met Ser Gln Val Met Arg
                325                 330                 335

Glu Trp Glu Glu Ala Glu Arg Gln Ala Lys Asn Leu Pro Lys Ala Asp
            340                 345                 350

Lys Lys Ala Val Ile Gln His Phe Gln Glu Lys Val Glu Ser Leu Glu
        355                 360                 365
```

-continued

```
Gln Glu Ala Ala Asn Glu Arg Gln Gln Leu Val Glu Thr His Met Ala
    370                 375                 380

Arg Val Glu Ala Met Leu Asn Asp Arg Arg Leu Ala Leu Glu Asn
385                 390                 395                 400

Tyr Ile Thr Ala Leu Gln Ala Val Pro Pro Arg Pro Arg His Val Phe
                405                 410                 415

Asn Met Leu Lys Lys Tyr Val Arg Ala Glu Gln Lys Asp Arg Gln His
            420                 425                 430

Thr Leu Lys His Phe Glu His Val Arg Met Val Asp Pro Lys Lys Ala
        435                 440                 445

Ala Gln Ile Arg Ser Gln Val Met Thr His Leu Arg Val Ile Tyr Glu
    450                 455                 460

Arg Met Asn Gln Ser Leu Ser Leu Leu Tyr Asn Val Pro Ala Val Ala
465                 470                 475                 480

Glu Glu Ile Gln Asp Glu Val Asp Glu Leu Leu Gln Lys Glu Gln Asn
                485                 490                 495

Tyr Ser Asp Asp Val Leu Ala Asn Met Ile Ser Glu Pro Arg Ile Ser
            500                 505                 510

Tyr Gly Asn Asp Ala Leu Met Pro Ser Leu Thr Glu Thr Lys Thr Thr
        515                 520                 525

Val Glu Leu Leu Pro Val Asn Gly Glu Phe Ser Leu Asp Asp Leu Gln
    530                 535                 540

Pro Trp His Ser Phe Gly Ala Asp Ser Val Pro Ala Asn Thr Glu Asn
545                 550                 555                 560

Glu Val Glu Pro Val Asp Ala Arg Pro Ala Ala Asp Arg Gly Leu Thr
                565                 570                 575

Thr Arg Pro Gly Ser Gly Leu Thr Asn Ile Lys Thr Glu Glu Ile Ser
            580                 585                 590

Glu Val Asn Phe Ala Val Glu Phe Arg His Asp Ser Gly Tyr Glu Val
        595                 600                 605

His His Gln Lys Leu Val Phe Phe Ala Glu Asp Val Gly Ser Asn Lys
    610                 615                 620

Gly Ala Ile Ile Gly Leu Met Val Gly Gly Val Val Ile Ala Thr Val
625                 630                 635                 640

Ile Val Ile Thr Leu Val Met Leu Lys Lys Lys Gln Tyr Thr Ser Ile
                645                 650                 655

His His Gly Val Val Glu Val Asp Ala Ala Val Thr Pro Glu Glu Arg
            660                 665                 670

His Leu Ser Lys Met Gln Gln Asn Gly Tyr Glu Asn Pro Thr Tyr Lys
        675                 680                 685

Phe Phe Glu Gln Met Gln Asn
    690                 695

<210> SEQ ID NO 45
<211> LENGTH: 695
<212> TYPE: PRT
<213> ORGANISM: Homo sapiens

<400> SEQUENCE: 45

Met Leu Pro Gly Leu Ala Leu Leu Leu Leu Ala Ala Trp Thr Ala Arg
1               5                   10                  15

Ala Leu Glu Val Pro Thr Asp Gly Asn Ala Gly Leu Leu Ala Glu Pro
                20                  25                  30

Gln Ile Ala Met Phe Cys Gly Arg Leu Asn Met His Met Asn Val Gln
            35                  40                  45
```

-continued

```
Asn Gly Lys Trp Asp Ser Asp Pro Ser Gly Thr Lys Thr Cys Ile Asp
     50                  55                  60
Thr Lys Glu Gly Ile Leu Gln Tyr Cys Gln Glu Val Tyr Pro Glu Leu
 65                  70                  75                  80
Gln Ile Thr Asn Val Val Glu Ala Asn Gln Pro Val Thr Ile Gln Asn
                 85                  90                  95
Trp Cys Lys Arg Gly Arg Lys Gln Cys Lys Thr His Pro His Phe Val
             100                 105                 110
Ile Pro Tyr Arg Cys Leu Val Gly Glu Phe Val Ser Asp Ala Leu Leu
         115                 120                 125
Val Pro Asp Lys Cys Lys Phe Leu His Gln Glu Arg Met Asp Val Cys
130                 135                 140
Glu Thr His Leu His Trp His Thr Val Ala Lys Glu Thr Cys Ser Glu
145                 150                 155                 160
Lys Ser Thr Asn Leu His Asp Tyr Gly Met Leu Leu Pro Cys Gly Ile
             165                 170                 175
Asp Lys Phe Arg Gly Val Glu Phe Val Cys Cys Pro Leu Ala Glu Glu
         180                 185                 190
Ser Asp Asn Val Asp Ser Ala Asp Ala Glu Glu Asp Asp Ser Asp Val
     195                 200                 205
Trp Trp Gly Gly Ala Asp Thr Asp Tyr Ala Asp Gly Ser Glu Asp Lys
210                 215                 220
Val Val Glu Val Ala Glu Glu Glu Val Ala Glu Val Glu Glu Glu
225                 230                 235                 240
Glu Ala Asp Asp Asp Glu Asp Asp Glu Asp Gly Asp Glu Val Glu Glu
             245                 250                 255
Glu Ala Glu Glu Pro Tyr Glu Glu Ala Thr Glu Arg Thr Thr Ser Ile
         260                 265                 270
Ala Thr Thr Thr Thr Thr Thr Thr Glu Ser Val Glu Glu Val Val Arg
         275                 280                 285
Val Pro Thr Thr Ala Ala Ser Thr Pro Asp Ala Val Asp Lys Tyr Leu
    290                 295                 300
Glu Thr Pro Gly Asp Glu Asn Glu His Ala His Phe Gln Lys Ala Lys
305                 310                 315                 320
Glu Arg Leu Glu Ala Lys His Arg Glu Arg Met Ser Gln Val Met Arg
             325                 330                 335
Glu Trp Glu Glu Ala Glu Arg Gln Ala Lys Asn Leu Pro Lys Ala Asp
         340                 345                 350
Lys Lys Ala Val Ile Gln His Phe Gln Glu Lys Val Glu Ser Leu Glu
         355                 360                 365
Gln Glu Ala Ala Asn Glu Arg Gln Gln Leu Val Glu Thr His Met Ala
    370                 375                 380
Arg Val Glu Ala Met Leu Asn Asp Arg Arg Arg Leu Ala Leu Glu Asn
385                 390                 395                 400
Tyr Ile Thr Ala Leu Gln Ala Val Pro Pro Arg Pro His Val Phe
             405                 410                 415
Asn Met Leu Lys Lys Tyr Val Arg Ala Glu Gln Lys Asp Arg Gln His
         420                 425                 430
Thr Leu Lys His Phe Glu His Val Arg Met Val Asp Pro Lys Lys Ala
         435                 440                 445
Ala Gln Ile Arg Ser Gln Val Met Thr His Leu Arg Val Ile Tyr Glu
    450                 455                 460
```

```
Arg Met Asn Gln Ser Leu Ser Leu Leu Tyr Asn Val Pro Ala Val Ala
465                 470                 475                 480

Glu Glu Ile Gln Asp Glu Val Asp Glu Leu Leu Gln Lys Glu Gln Asn
            485                 490                 495

Tyr Ser Asp Asp Val Leu Ala Asn Met Ile Ser Glu Pro Arg Ile Ser
        500                 505                 510

Tyr Gly Asn Asp Ala Leu Met Pro Ser Leu Thr Glu Thr Lys Thr Thr
    515                 520                 525

Val Glu Leu Leu Pro Val Asn Gly Glu Phe Ser Leu Asp Asp Leu Gln
530                 535                 540

Pro Trp His Ser Phe Gly Ala Asp Ser Val Pro Ala Asn Thr Glu Asn
545                 550                 555                 560

Glu Val Glu Pro Val Asp Ala Arg Pro Ala Asp Arg Gly Leu Thr
                565                 570                 575

Thr Arg Pro Gly Ser Gly Leu Thr Asn Ile Lys Thr Glu Glu Ile Ser
            580                 585                 590

Glu Val Lys Met Asp Ala Glu Phe Arg His Asp Ser Gly Tyr Glu Val
        595                 600                 605

His His Gln Lys Leu Val Phe Phe Ala Glu Asp Val Gly Ser Asn Lys
        610                 615                 620

Gly Ala Ile Ile Gly Leu Met Val Gly Gly Val Val Ile Ala Thr Val
625                 630                 635                 640

Ile Val Ile Thr Leu Val Met Leu Lys Lys Lys Gln Tyr Thr Ser Ile
            645                 650                 655

His His Gly Val Val Glu Val Asp Ala Ala Val Thr Pro Glu Glu Arg
            660                 665                 670

His Leu Ser Lys Met Gln Gln Asn Gly Tyr Glu Asn Pro Thr Tyr Lys
            675                 680                 685

Phe Phe Glu Gln Met Gln Asn
690                 695

<210> SEQ ID NO 46
<211> LENGTH: 695
<212> TYPE: PRT
<213> ORGANISM: Homo sapiens

<400> SEQUENCE: 46

Met Leu Pro Gly Leu Ala Leu Leu Leu Leu Ala Ala Trp Thr Ala Arg
1               5                   10                  15

Ala Leu Glu Val Pro Thr Asp Gly Asn Ala Gly Leu Leu Ala Glu Pro
            20                  25                  30

Gln Ile Ala Met Phe Cys Gly Arg Leu Asn Met His Met Asn Val Gln
        35                  40                  45

Asn Gly Lys Trp Asp Ser Asp Pro Ser Gly Thr Lys Thr Cys Ile Asp
    50                  55                  60

Thr Lys Glu Gly Ile Leu Gln Tyr Cys Gln Glu Val Tyr Pro Glu Leu
65                  70                  75                  80

Gln Ile Thr Asn Val Val Glu Ala Asn Gln Pro Val Thr Ile Gln Asn
                85                  90                  95

Trp Cys Lys Arg Gly Arg Lys Gln Cys Lys Thr His Pro His Phe Val
            100                 105                 110

Ile Pro Tyr Arg Cys Leu Val Gly Glu Phe Val Ser Asp Ala Leu Leu
        115                 120                 125

Val Pro Asp Lys Cys Lys Phe Leu His Gln Glu Arg Met Asp Val Cys
130                 135                 140
```

-continued

```
Glu Thr His Leu His Trp His Thr Val Ala Lys Glu Thr Cys Ser Glu
145                 150                 155                 160

Lys Ser Thr Asn Leu His Asp Tyr Gly Met Leu Leu Pro Cys Gly Ile
            165                 170                 175

Asp Lys Phe Arg Gly Val Glu Phe Val Cys Cys Pro Leu Ala Glu Glu
        180                 185                 190

Ser Asp Asn Val Asp Ser Ala Asp Ala Glu Glu Asp Asp Ser Asp Val
    195                 200                 205

Trp Trp Gly Gly Ala Asp Thr Asp Tyr Ala Asp Gly Ser Glu Asp Lys
210                 215                 220

Val Val Glu Val Ala Glu Glu Glu Val Ala Glu Val Glu Glu Glu
225                 230                 235                 240

Glu Ala Asp Asp Glu Asp Asp Glu Asp Gly Asp Glu Val Glu Glu Glu
                245                 250                 255

Glu Ala Glu Glu Pro Tyr Glu Glu Ala Thr Glu Arg Thr Thr Ser Ile
            260                 265                 270

Ala Thr Thr Thr Thr Thr Thr Thr Glu Ser Val Glu Glu Val Val Arg
        275                 280                 285

Val Pro Thr Thr Ala Ala Ser Thr Pro Asp Ala Val Asp Lys Tyr Leu
    290                 295                 300

Glu Thr Pro Gly Asp Glu Asn Glu His Ala His Phe Gln Lys Ala Lys
305                 310                 315                 320

Glu Arg Leu Glu Ala Lys His Arg Glu Arg Met Ser Gln Val Met Arg
                325                 330                 335

Glu Trp Glu Glu Ala Glu Arg Gln Ala Lys Asn Leu Pro Lys Ala Asp
            340                 345                 350

Lys Lys Ala Val Ile Gln His Phe Gln Glu Lys Val Glu Ser Leu Glu
        355                 360                 365

Gln Glu Ala Ala Asn Glu Arg Gln Gln Leu Val Glu Thr His Met Ala
    370                 375                 380

Arg Val Glu Ala Met Leu Asn Asp Arg Arg Arg Leu Ala Leu Glu Asn
385                 390                 395                 400

Tyr Ile Thr Ala Leu Gln Ala Val Pro Pro Arg Pro Arg His Val Phe
                405                 410                 415

Asn Met Leu Lys Lys Tyr Val Arg Ala Glu Gln Lys Asp Arg Gln His
            420                 425                 430

Thr Leu Lys His Phe Glu His Val Arg Met Val Asp Pro Lys Lys Ala
        435                 440                 445

Ala Gln Ile Arg Ser Gln Val Met Thr His Leu Arg Val Ile Tyr Glu
    450                 455                 460

Arg Met Asn Gln Ser Leu Ser Leu Leu Tyr Asn Val Pro Ala Val Ala
465                 470                 475                 480

Glu Glu Ile Gln Asp Glu Val Asp Glu Leu Leu Gln Lys Glu Gln Asn
                485                 490                 495

Tyr Ser Asp Asp Val Leu Ala Asn Met Ile Ser Glu Pro Arg Ile Ser
            500                 505                 510

Tyr Gly Asn Asp Ala Leu Met Pro Ser Leu Thr Glu Thr Lys Thr Thr
        515                 520                 525

Val Glu Leu Leu Pro Val Asn Gly Glu Phe Ser Leu Asp Asp Leu Gln
    530                 535                 540

Pro Trp His Ser Phe Gly Ala Asp Ser Val Pro Ala Asn Thr Glu Asn
545                 550                 555                 560
```

```
Glu Val Glu Pro Val Asp Ala Arg Pro Ala Ala Asp Arg Gly Leu Thr
            565                 570                 575

Thr Arg Pro Gly Ser Gly Leu Thr Asn Ile Lys Thr Glu Glu Ile Ser
            580                 585                 590

Glu Val Asn Leu Asp Ala Glu Phe Arg His Asp Ser Gly Tyr Glu Val
            595                 600                 605

His His Gln Lys Leu Val Phe Phe Ala Glu Asp Val Gly Ser Asn Lys
            610                 615                 620

Gly Ala Ile Ile Gly Leu Met Val Gly Gly Val Val Ile Ala Thr Val
625                 630                 635                 640

Ile Val Ile Thr Leu Val Met Leu Lys Lys Lys Gln Tyr Thr Ser Ile
            645                 650                 655

His His Gly Val Val Glu Val Asp Ala Ala Val Thr Pro Glu Glu Arg
            660                 665                 670

His Leu Ser Lys Met Gln Gln Asn Gly Tyr Glu Asn Pro Thr Tyr Lys
            675                 680                 685

Phe Phe Glu Gln Met Gln Asn
690                 695

<210> SEQ ID NO 47
<211> LENGTH: 4
<212> TYPE: PRT
<213> ORGANISM: Artificial
<220> FEATURE:
<223> OTHER INFORMATION: synthetic sequence for known enzyme cleavage
      site

<400> SEQUENCE: 47

Lys Met Glu Ala
1

<210> SEQ ID NO 48
<211> LENGTH: 4
<212> TYPE: PRT
<213> ORGANISM: Artificial
<220> FEATURE:
<223> OTHER INFORMATION: synthetic sequence for known enzyme cleavage
      site

<400> SEQUENCE: 48

Lys Phe Asp Ala
1

<210> SEQ ID NO 49
<211> LENGTH: 4
<212> TYPE: PRT
<213> ORGANISM: Artificial
<220> FEATURE:
<223> OTHER INFORMATION: synthetic sequence for known enzyme cleavage
      site

<400> SEQUENCE: 49

Lys Leu Asp Ala
1

<210> SEQ ID NO 50
<211> LENGTH: 4
<212> TYPE: PRT
<213> ORGANISM: Artificial
<220> FEATURE:
<223> OTHER INFORMATION: synthetic sequence for known enzyme cleavage
      site

<400> SEQUENCE: 50
```

Lys Tyr Asp Ala
1

<210> SEQ ID NO 51
<211> LENGTH: 4
<212> TYPE: PRT
<213> ORGANISM: Artificial
<220> FEATURE:
<223> OTHER INFORMATION: synthetic sequence for known enzyme cleavage
      site

<400> SEQUENCE: 51

Asn Met Asp Ala
1

<210> SEQ ID NO 52
<211> LENGTH: 8
<212> TYPE: PRT
<213> ORGANISM: Homo sapiens

<400> SEQUENCE: 52

Glu Val Lys Met Asp Ala Glu Phe
1               5

<210> SEQ ID NO 53
<211> LENGTH: 10
<212> TYPE: PRT
<213> ORGANISM: Homo sapiens

<400> SEQUENCE: 53

Ser Glu Val Lys Met Asp Ala Glu Phe Arg
1               5                   10

<210> SEQ ID NO 54
<211> LENGTH: 12
<212> TYPE: PRT
<213> ORGANISM: Homo sapiens

<400> SEQUENCE: 54

Ile Ser Glu Val Lys Met Asp Ala Glu Phe Arg His
1               5                   10

<210> SEQ ID NO 55
<211> LENGTH: 14
<212> TYPE: PRT
<213> ORGANISM: Homo sapiens

<400> SEQUENCE: 55

Glu Ile Ser Glu Val Lys Met Asp Ala Glu Phe Arg His Asp
1               5                   10

<210> SEQ ID NO 56
<211> LENGTH: 16
<212> TYPE: PRT
<213> ORGANISM: Homo sapiens

<400> SEQUENCE: 56

Glu Glu Ile Ser Glu Val Lys Met Asp Ala Glu Phe Arg His Asp Ser
1               5                   10                  15

<210> SEQ ID NO 57
<211> LENGTH: 5
<212> TYPE: PRT
<213> ORGANISM: Artificial
<220> FEATURE:

```
<223> OTHER INFORMATION: peptide for use in antibody specificity
      evaluation

<400> SEQUENCE: 57

Ser Glu Val Asn Phe
1               5

<210> SEQ ID NO 58
<211> LENGTH: 5
<212> TYPE: PRT
<213> ORGANISM: Artificial
<220> FEATURE:
<223> OTHER INFORMATION: peptide simulating cleaved portion from carboxy
      side of novel sequence at known enzyme cleavage site

<400> SEQUENCE: 58

Glu Val Glu Phe Arg
1               5

<210> SEQ ID NO 59
<211> LENGTH: 4
<212> TYPE: PRT
<213> ORGANISM: Artificial
<220> FEATURE:
<223> OTHER INFORMATION: peptide simulating cleaved portion from carboxy
      side of novel sequence at known enzyme cleavage site, lacking end
      amino acid

<400> SEQUENCE: 59

Val Glu Phe Arg
1

<210> SEQ ID NO 60
<211> LENGTH: 5
<212> TYPE: PRT
<213> ORGANISM: Artificial
<220> FEATURE:
<223> OTHER INFORMATION: peptide for use in antibody specificity
      evaluation

<400> SEQUENCE: 60

Asp Val Glu Phe Arg
1               5

<210> SEQ ID NO 61
<211> LENGTH: 5
<212> TYPE: PRT
<213> ORGANISM: Artificial
<220> FEATURE:
<223> OTHER INFORMATION: peptide for use in antibody specificity
      evaluation

<400> SEQUENCE: 61

Asp Ala Glu Phe Arg
1               5

<210> SEQ ID NO 62
<211> LENGTH: 5
<212> TYPE: PRT
<213> ORGANISM: Artificial
<220> FEATURE:
<223> OTHER INFORMATION: peptide for use in antibody specificity
      evaluation
<220> FEATURE:
<221> NAME/KEY: MOD_RES
<222> LOCATION: (1)..(1)
<223> OTHER INFORMATION: ACETYLATION

<400> SEQUENCE: 62
```

```
Glu Val Glu Phe Arg
1               5

<210> SEQ ID NO 63
<211> LENGTH: 1149
<212> TYPE: PRT
<213> ORGANISM: Artificial
<220> FEATURE:
<223> OTHER INFORMATION: fused polypeptide, with linkers, containing
      novel sequence at known enzyme cleavage site

<400> SEQUENCE: 63

Met Gly Ile Glu Glu Gly Lys Leu Val Ile Trp Ile Asn Gly Asp Lys
1               5                   10                  15

Gly Tyr Asn Gly Leu Ala Glu Val Gly Lys Lys Phe Glu Lys Asp Thr
                20                  25                  30

Gly Ile Lys Val Thr Val Glu His Pro Asp Lys Leu Glu Glu Lys Phe
            35                  40                  45

Pro Gln Val Ala Ala Thr Gly Asp Gly Pro Asp Ile Ile Phe Trp Ala
    50                  55                  60

His Asp Arg Phe Gly Gly Tyr Ala Gln Ser Gly Leu Leu Ala Glu Ile
65                  70                  75                  80

Thr Pro Asp Lys Ala Phe Gln Asp Lys Leu Tyr Pro Phe Thr Trp Asp
                85                  90                  95

Ala Val Arg Tyr Asn Gly Lys Leu Ile Ala Tyr Pro Ile Ala Val Glu
            100                 105                 110

Ala Leu Ser Leu Ile Tyr Asn Lys Asp Leu Leu Pro Asn Pro Pro Lys
        115                 120                 125

Thr Trp Glu Glu Ile Pro Ala Leu Asp Lys Glu Leu Lys Ala Lys Gly
    130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ala Gly Ala Lys Ala Gly
            180                 185                 190

Leu Thr Phe Leu Val Asp Leu Ile Lys Asn Lys His Met Asn Ala Asp
        195                 200                 205

Thr Asp Tyr Ser Ile Ala Glu Ala Ala Phe Asn Lys Gly Glu Thr Ala
    210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                245                 250                 255

Lys Pro Phe Val Gly Val Leu Ser Ala Gly Ile Asn Ala Ala Ser Pro
            260                 265                 270

Asn Lys Glu Leu Ala Lys Glu Phe Leu Glu Asn Tyr Leu Leu Thr Asp
        275                 280                 285

Glu Gly Leu Glu Ala Val Asn Lys Asp Lys Pro Leu Gly Ala Val Ala
    290                 295                 300

Leu Lys Ser Tyr Glu Glu Glu Leu Ala Lys Asp Pro Arg Ile Ala Ala
305                 310                 315                 320

Thr Met Glu Asn Ala Gln Lys Gly Glu Ile Met Pro Asn Ile Pro Gln
                325                 330                 335

Met Ser Ala Phe Trp Tyr Ala Val Arg Thr Ala Val Ile Asn Ala Ala
```

-continued

```
            340                 345                 350
Ser Gly Arg Gln Thr Val Asp Glu Ala Leu Lys Asp Ala Gln Thr Asn
        355                 360                 365
Ser Ser Ser Asn Asn Asn Asn Asn Asn Asn Asn Asn Leu Gly Ser
370                 375                 380
Ser Gly Leu Val Pro Arg Gly Ser His Met Ser Gly Leu Asn Asp Ile
385                 390                 395                 400
Phe Glu Ala Gln Lys Ile Glu Trp His Glu Gly Ala Pro Leu Pro Gly
                405                 410                 415
Leu Ala Leu Leu Leu Ala Ala Trp Thr Ala Arg Ala Leu Glu Val
            420                 425                 430
Pro Thr Asp Gly Asn Ala Gly Leu Leu Ala Glu Pro Gln Ile Ala Met
        435                 440                 445
Phe Cys Gly Arg Leu Asn Met His Met Asn Val Gln Asn Gly Lys Trp
450                 455                 460
Asp Ser Asp Pro Ser Gly Thr Lys Thr Cys Ile Asp Thr Lys Glu Gly
465                 470                 475                 480
Ile Leu Gln Tyr Cys Gln Glu Val Tyr Pro Glu Leu Gln Ile Thr Asn
                485                 490                 495
Val Val Glu Ala Asn Gln Pro Val Thr Ile Gln Asn Trp Cys Lys Arg
            500                 505                 510
Gly Arg Lys Gln Cys Lys Thr His Pro His Phe Val Ile Pro Tyr Arg
        515                 520                 525
Cys Leu Val Gly Glu Phe Val Ser Asp Ala Leu Leu Val Pro Asp Lys
530                 535                 540
Cys Lys Phe Leu His Gln Glu Arg Met Asp Val Cys Glu Thr His Leu
545                 550                 555                 560
His Trp His Thr Val Ala Lys Glu Thr Cys Ser Glu Lys Ser Thr Asn
                565                 570                 575
Leu His Asp Tyr Gly Met Leu Leu Pro Cys Gly Ile Asp Lys Phe Arg
            580                 585                 590
Gly Val Glu Phe Val Cys Cys Pro Leu Ala Glu Glu Ser Asp Asn Val
        595                 600                 605
Asp Ser Ala Asp Ala Glu Glu Asp Asp Ser Asp Val Trp Trp Gly Gly
610                 615                 620
Ala Asp Thr Asp Tyr Ala Asp Gly Ser Glu Asp Lys Val Val Glu Val
625                 630                 635                 640
Ala Glu Glu Glu Val Ala Glu Val Glu Glu Glu Ala Asp Asp
                645                 650                 655
Asp Glu Asp Asp Glu Asp Gly Asp Glu Val Glu Glu Glu Ala Glu Glu
            660                 665                 670
Pro Tyr Glu Glu Ala Thr Glu Arg Thr Thr Ser Ile Ala Thr Thr Thr
        675                 680                 685
Thr Thr Thr Thr Glu Ser Val Glu Val Val Arg Val Ser Lys Tyr
            690                 695                 700
Pro Tyr Asp Val Pro Asp Tyr Ala Ala Ala Ala Ala Ala Ala
705                 710                 715                 720
Ser Glu Gln Lys Leu Ile Ser Glu Glu Asp Leu Gly Ala Asp Tyr Lys
                725                 730                 735
Asp Asp Asp Asp Lys Ala Ala Pro Thr Thr Ala Ala Ser Thr Pro Asp
            740                 745                 750
Ala Val Asp Lys Tyr Leu Glu Thr Pro Gly Asp Glu Asn Glu His Ala
        755                 760                 765
```

```
His Phe Gln Lys Ala Lys Glu Arg Leu Glu Ala Lys His Arg Glu Arg
    770                 775                 780

Met Ser Gln Val Met Arg Glu Trp Glu Glu Ala Glu Arg Gln Ala Lys
785                 790                 795                 800

Asn Leu Pro Lys Ala Asp Lys Lys Ala Val Ile Gln His Phe Gln Glu
                805                 810                 815

Lys Val Glu Ser Leu Glu Gln Glu Ala Ala Asn Glu Arg Gln Gln Leu
            820                 825                 830

Val Glu Thr His Met Ala Arg Val Glu Ala Met Leu Asn Asp Arg Arg
        835                 840                 845

Arg Leu Ala Leu Glu Asn Tyr Ile Thr Ala Leu Gln Ala Val Pro Pro
    850                 855                 860

Arg Pro Arg His Val Phe Asn Met Leu Lys Lys Tyr Val Arg Ala Glu
865                 870                 875                 880

Gln Lys Asp Arg Gln His Thr Leu Lys His Phe Glu His Val Arg Met
                885                 890                 895

Val Asp Pro Lys Lys Ala Ala Gln Ile Arg Ser Gln Val Met Thr His
            900                 905                 910

Leu Arg Val Ile Tyr Glu Arg Met Asn Gln Ser Leu Ser Leu Leu Tyr
        915                 920                 925

Asn Val Pro Ala Val Ala Glu Glu Ile Gln Asp Glu Val Asp Glu Leu
    930                 935                 940

Leu Gln Lys Glu Gln Asn Tyr Ser Asp Asp Val Leu Ala Asn Met Ile
945                 950                 955                 960

Ser Glu Pro Arg Ile Ser Tyr Gly Asn Asp Ala Leu Met Pro Ser Leu
                965                 970                 975

Thr Glu Thr Lys Thr Thr Val Glu Leu Leu Pro Val Asn Gly Glu Phe
            980                 985                 990

Ser Leu Asp Asp Leu Gln Pro Trp His Ser Phe Gly Ala Asp Ser Val
        995                 1000                1005

Pro Ala Asn Thr Glu Asn Glu Val Glu Pro Val Asp Ala Arg Pro
    1010                1015                1020

Ala Ala Asp Arg Gly Leu Thr Thr Arg Pro Gly Ser Gly Leu Thr
    1025                1030                1035

Asn Ile Lys Thr Glu Glu Ile Ser Glu Val Asn Phe Glu Val Glu
    1040                1045                1050

Phe Arg His Asp Ser Gly Tyr Glu Val His His Gln Val Leu Val
    1055                1060                1065

Phe Phe Ala Glu Asp Val Gly Ser Asn Lys Gly Ala Ile Ile Gly
    1070                1075                1080

Leu Met Val Gly Gly Val Val Ile Ala Thr Val Ile Val Ile Thr
    1085                1090                1095

Leu Val Met Leu Lys Lys Lys Gln Tyr Thr Ser Ile His His Gly
    1100                1105                1110

Val Val Glu Val Asp Ala Ala Val Thr Pro Glu Glu Arg His Leu
    1115                1120                1125

Ser Lys Met Gln Gln Asn Gly Tyr Glu Asn Pro Thr Tyr Lys Phe
    1130                1135                1140

Phe Glu Gln Met Gln Asn
    1145

<210> SEQ ID NO 64
<211> LENGTH: 1050
```

<212> TYPE: PRT
<213> ORGANISM: Artificial
<220> FEATURE:
<223> OTHER INFORMATION: fused polypeptide, with linkers, containing
novel sequence at known enzyme cleavage site

<400> SEQUENCE: 64

```
Met Gly Ile Glu Glu Gly Lys Leu Val Ile Trp Ile Asn Gly Asp Lys
1               5                   10                  15

Gly Tyr Asn Gly Leu Ala Glu Val Gly Lys Lys Phe Glu Lys Asp Thr
            20                  25                  30

Gly Ile Lys Val Thr Val Glu His Pro Asp Lys Leu Glu Glu Lys Phe
        35                  40                  45

Pro Gln Val Ala Ala Thr Gly Asp Gly Pro Asp Ile Ile Phe Trp Ala
50                  55                  60

His Asp Arg Phe Gly Gly Tyr Ala Gln Ser Gly Leu Leu Ala Glu Ile
65                  70                  75                  80

Thr Pro Asp Lys Ala Phe Gln Asp Lys Leu Tyr Pro Phe Thr Trp Asp
                85                  90                  95

Ala Val Arg Tyr Asn Gly Lys Leu Ile Ala Tyr Pro Ile Ala Val Glu
            100                 105                 110

Ala Leu Ser Leu Ile Tyr Asn Lys Asp Leu Leu Pro Asn Pro Pro Lys
        115                 120                 125

Thr Trp Glu Glu Ile Pro Ala Leu Asp Lys Glu Leu Lys Ala Lys Gly
130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ala Gly Ala Lys Ala Gly
            180                 185                 190

Leu Thr Phe Leu Val Asp Leu Ile Lys Asn Lys His Met Asn Ala Asp
        195                 200                 205

Thr Asp Tyr Ser Ile Ala Glu Ala Ala Phe Asn Lys Gly Glu Thr Ala
210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                245                 250                 255

Lys Pro Phe Val Gly Val Leu Ser Ala Gly Ile Asn Ala Ala Ser Pro
            260                 265                 270

Asn Lys Glu Leu Ala Lys Glu Phe Leu Glu Asn Tyr Leu Leu Thr Asp
        275                 280                 285

Glu Gly Leu Glu Ala Val Asn Lys Asp Lys Pro Leu Gly Ala Val Ala
290                 295                 300

Leu Lys Ser Tyr Glu Glu Leu Ala Lys Asp Pro Arg Ile Ala Ala
305                 310                 315                 320

Thr Met Glu Asn Ala Gln Lys Gly Glu Ile Met Pro Asn Ile Pro Gln
                325                 330                 335

Met Ser Ala Phe Trp Tyr Ala Val Arg Thr Ala Val Ile Asn Ala Ala
            340                 345                 350

Ser Gly Arg Gln Thr Val Asp Glu Ala Leu Lys Asp Ala Gln Thr Asn
        355                 360                 365

Ser Ser Ser Asn Asn Asn Asn Asn Asn Asn Asn Asn Asn Leu Gly Ser
370                 375                 380
```

-continued

```
Ser Gly Leu Val Pro Arg Gly Ser His Met Ser Gly Leu Asn Asp Ile
385                 390                 395                 400

Phe Glu Ala Gln Lys Ile Glu Trp His Glu Gly Ala Pro Leu Pro Gly
                405                 410                 415

Leu Ala Leu Leu Leu Leu Ala Ala Trp Thr Ala Arg Ala Leu Glu Val
            420                 425                 430

Pro Thr Asp Gly Asn Ala Gly Leu Leu Ala Glu Pro Gln Ile Ala Met
        435                 440                 445

Phe Cys Gly Arg Leu Asn Met His Met Asn Val Gln Asn Gly Lys Trp
    450                 455                 460

Asp Ser Asp Pro Ser Gly Thr Lys Thr Cys Ile Asp Thr Lys Glu Gly
465                 470                 475                 480

Ile Leu Gln Tyr Cys Gln Glu Val Tyr Pro Glu Leu Gln Ile Thr Asn
                485                 490                 495

Val Val Glu Ala Asn Gln Pro Val Thr Ile Gln Asn Trp Cys Lys Arg
            500                 505                 510

Gly Arg Lys Gln Cys Lys Thr His Pro His Phe Val Ile Pro Tyr Arg
        515                 520                 525

Cys Leu Val Gly Glu Phe Val Ser Asp Ala Leu Leu Val Pro Asp Lys
    530                 535                 540

Cys Lys Phe Leu His Gln Glu Arg Met Asp Val Cys Glu Thr His Leu
545                 550                 555                 560

His Trp His Thr Val Ala Lys Glu Thr Cys Ser Glu Lys Ser Thr Asn
                565                 570                 575

Leu His Asp Tyr Gly Met Leu Leu Pro Cys Gly Ile Asp Lys Phe Arg
            580                 585                 590

Gly Val Glu Phe Val Cys Cys Pro Leu Ala Glu Glu Ser Asp Asn Val
        595                 600                 605

Asp Ser Ala Asp Ala Glu Glu Asp Asp Ser Asp Val Trp Trp Gly Gly
610                 615                 620

Ala Asp Thr Asp Tyr Ala Asp Gly Ser Glu Asp Lys Val Val Glu Val
625                 630                 635                 640

Ala Glu Glu Glu Glu Val Ala Glu Val Glu Glu Glu Ala Asp Asp Asp
                645                 650                 655

Asp Glu Asp Asp Glu Asp Gly Asp Glu Val Glu Glu Glu Ala Glu Glu
            660                 665                 670

Pro Tyr Glu Glu Ala Thr Glu Arg Thr Thr Ser Ile Ala Thr Thr Thr
        675                 680                 685

Thr Thr Thr Thr Glu Ser Val Glu Glu Val Val Arg Val Ser Lys Tyr
    690                 695                 700

Pro Tyr Asp Val Pro Asp Tyr Ala Ala Ala Ala Ala Ala Ala Ala Ala
705                 710                 715                 720

Ser Glu Gln Lys Leu Ile Ser Glu Glu Asp Leu Gly Ala Asp Tyr Lys
                725                 730                 735

Asp Asp Asp Asp Lys Ala Ala Pro Thr Thr Ala Ala Ser Thr Pro Asp
            740                 745                 750

Ala Val Asp Lys Tyr Leu Glu Thr Pro Gly Asp Glu Asn Glu His Ala
        755                 760                 765

His Phe Gln Lys Ala Lys Glu Arg Leu Glu Ala Lys His Arg Glu Arg
    770                 775                 780

Met Ser Gln Val Met Arg Glu Trp Glu Glu Ala Glu Arg Gln Ala Lys
785                 790                 795                 800
```

-continued

```
Asn Leu Pro Lys Ala Asp Lys Lys Ala Val Ile Gln His Phe Gln Glu
            805                 810                 815

Lys Val Glu Ser Leu Glu Gln Glu Ala Ala Asn Glu Arg Gln Gln Leu
            820                 825                 830

Val Glu Thr His Met Ala Arg Val Glu Ala Met Leu Asn Asp Arg Arg
            835                 840                 845

Arg Leu Ala Leu Glu Asn Tyr Ile Thr Ala Leu Gln Ala Val Pro Pro
            850                 855                 860

Arg Pro Arg His Val Phe Asn Met Leu Lys Lys Tyr Val Arg Ala Glu
865                 870                 875                 880

Gln Lys Asp Arg Gln His Thr Leu Lys His Phe Glu His Val Arg Met
                885                 890                 895

Val Asp Pro Lys Lys Ala Ala Gln Ile Arg Ser Gln Val Met Thr His
            900                 905                 910

Leu Arg Val Ile Tyr Glu Arg Met Asn Gln Ser Leu Ser Leu Leu Tyr
            915                 920                 925

Asn Val Pro Ala Val Ala Glu Glu Ile Gln Asp Glu Val Asp Glu Leu
            930                 935                 940

Leu Gln Lys Glu Gln Asn Tyr Ser Asp Asp Val Leu Ala Asn Met Ile
945                 950                 955                 960

Ser Glu Pro Arg Ile Ser Tyr Gly Asn Asp Ala Leu Met Pro Ser Leu
                965                 970                 975

Thr Glu Thr Lys Thr Thr Val Glu Leu Leu Pro Val Asn Gly Glu Phe
            980                 985                 990

Ser Leu Asp Asp Leu Gln Pro Trp His Ser Phe Gly Ala Asp Ser Val
            995                 1000                1005

Pro Ala Asn Thr Glu Asn Glu Val Glu Pro Val Asp Ala Arg Pro
            1010                1015                1020

Ala Ala Asp Arg Gly Leu Thr Thr Arg Pro Gly Ser Gly Leu Thr
            1025                1030                1035

Asn Ile Lys Thr Glu Glu Ile Ser Glu Val Asn Phe
            1040                1045                1050
```

<210> SEQ ID NO 65
<211> LENGTH: 20
<212> TYPE: PRT
<213> ORGANISM: Artificial
<220> FEATURE:
<223> OTHER INFORMATION: fusable polypeptide: myc, flag, with linkers

<400> SEQUENCE: 65

```
Glu Gln Lys Leu Ile Ser Glu Glu Asp Leu Gly Ala Asp Tyr Lys Asp
1               5                   10                  15

Asp Asp Asp Lys
            20
```

<210> SEQ ID NO 66
<211> LENGTH: 15
<212> TYPE: PRT
<213> ORGANISM: Artificial
<220> FEATURE:
<223> OTHER INFORMATION: fusable polypeptide, biotinylation site

<400> SEQUENCE: 66

```
Gly Leu Asn Asp Ile Phe Glu Ala Gln Lys Ile Glu Trp His Glu
1               5                   10                  15
```

<210> SEQ ID NO 67

```
<211> LENGTH: 14
<212> TYPE: PRT
<213> ORGANISM: Artificial
<220> FEATURE:
<223> OTHER INFORMATION: fusable polypeptide: V5

<400> SEQUENCE: 67

Gly Lys Pro Ile Pro Asn Pro Leu Leu Gly Leu Asp Ser Thr
1               5                   10

<210> SEQ ID NO 68
<211> LENGTH: 395
<212> TYPE: PRT
<213> ORGANISM: Artificial
<220> FEATURE:
<223> OTHER INFORMATION: fusable polypeptide: MBP, BSS, with linkers

<400> SEQUENCE: 68

Met Gly Ile Glu Glu Gly Lys Leu Val Ile Trp Ile Asn Gly Asp Lys
1               5                   10                  15

Gly Tyr Asn Gly Leu Ala Glu Val Gly Lys Lys Phe Glu Lys Asp Thr
            20                  25                  30

Gly Ile Lys Val Thr Val Glu His Pro Asp Lys Leu Glu Glu Lys Phe
        35                  40                  45

Pro Gln Val Ala Ala Thr Gly Asp Gly Pro Asp Ile Ile Phe Trp Ala
    50                  55                  60

His Asp Arg Phe Gly Gly Tyr Ala Gln Ser Gly Leu Leu Ala Glu Ile
65                  70                  75                  80

Thr Pro Asp Lys Ala Phe Gln Asp Lys Leu Tyr Pro Phe Thr Trp Asp
                85                  90                  95

Ala Val Arg Tyr Asn Gly Lys Leu Ile Ala Tyr Pro Ile Ala Val Glu
            100                 105                 110

Ala Leu Ser Leu Ile Tyr Asn Lys Asp Leu Leu Pro Asn Pro Pro Lys
        115                 120                 125

Thr Trp Glu Glu Ile Pro Ala Leu Asp Lys Glu Leu Lys Ala Lys Gly
    130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ala Gly Ala Lys Ala Gly
            180                 185                 190

Leu Thr Phe Leu Val Asp Leu Ile Lys Asn Lys His Met Asn Ala Asp
        195                 200                 205

Thr Asp Tyr Ser Ile Ala Glu Ala Ala Phe Asn Lys Gly Glu Thr Ala
    210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                245                 250                 255

Lys Pro Phe Val Gly Val Leu Ser Ala Gly Ile Asn Ala Ala Ser Pro
            260                 265                 270

Asn Lys Glu Leu Ala Lys Glu Phe Leu Glu Asn Tyr Leu Leu Thr Asp
        275                 280                 285

Glu Gly Leu Glu Ala Val Asn Lys Asp Lys Pro Leu Gly Ala Val Ala
    290                 295                 300

Leu Lys Ser Tyr Glu Glu Glu Leu Ala Lys Asp Pro Arg Ile Ala Ala
```

```
                305                 310                 315                 320
Thr Met Glu Asn Ala Gln Lys Gly Glu Ile Met Pro Asn Ile Pro Gln
                    325                 330                 335

Met Ser Ala Phe Trp Tyr Ala Val Arg Thr Ala Val Ile Asn Ala Ala
            340                 345                 350

Ser Gly Arg Gln Thr Val Asp Glu Ala Leu Lys Asp Ala Gln Thr Asn
        355                 360                 365

Ser Ser Ser Asn Asn Asn Asn Asn Asn Asn Asn Asn Leu Gly Ser
    370                 375                 380

Ser Gly Leu Val Pro Arg Gly Ser His Met Ser
385                 390                 395

<210> SEQ ID NO 69
<211> LENGTH: 42
<212> TYPE: PRT
<213> ORGANISM: Artificial
<220> FEATURE:
<223> OTHER INFORMATION: fusable polypeptide: HA, myc, flag, with
      linkers

<400> SEQUENCE: 69

Ser Lys Tyr Pro Tyr Asp Val Pro Asp Tyr Ala Ala Ala Ala Ala Ala
1               5                   10                  15

Ala Ala Ala Ser Glu Gln Lys Leu Ile Ser Glu Glu Asp Leu Gly Ala
            20                  25                  30

Asp Tyr Lys Asp Asp Asp Asp Lys Ala Ala
        35                  40

<210> SEQ ID NO 70
<211> LENGTH: 32
<212> TYPE: PRT
<213> ORGANISM: Artificial
<220> FEATURE:
<223> OTHER INFORMATION: fusable polypeptide: HA, myc, with linkers

<400> SEQUENCE: 70

Ser Lys Tyr Pro Tyr Asp Val Pro Asp Tyr Ala Ala Ala Ala Ala Ala
1               5                   10                  15

Ala Ala Ala Ser Glu Gln Lys Leu Ile Ser Glu Glu Asp Leu Gly Ala
            20                  25                  30

<210> SEQ ID NO 71
<211> LENGTH: 9
<212> TYPE: PRT
<213> ORGANISM: Artificial
<220> FEATURE:
<223> OTHER INFORMATION: fusable polypeptide: HA

<400> SEQUENCE: 71

Tyr Pro Tyr Asp Val Pro Asp Tyr Ala
1               5

<210> SEQ ID NO 72
<211> LENGTH: 10
<212> TYPE: PRT
<213> ORGANISM: Artificial
<220> FEATURE:
<223> OTHER INFORMATION: fusable polypeptide: myc

<400> SEQUENCE: 72

Glu Gln Lys Leu Ile Ser Glu Glu Asp Leu
1               5                   10
```

<210> SEQ ID NO 73
<211> LENGTH: 8
<212> TYPE: PRT
<213> ORGANISM: Artificial
<220> FEATURE:
<223> OTHER INFORMATION: fusable polypeptide: flag

<400> SEQUENCE: 73

Asp Tyr Lys Asp Asp Asp Asp Lys
1               5

<210> SEQ ID NO 74
<211> LENGTH: 751
<212> TYPE: PRT
<213> ORGANISM: Homo sapiens

<400> SEQUENCE: 74

Met Leu Pro Gly Leu Ala Leu Leu Leu Leu Ala Ala Trp Thr Ala Arg
1               5                   10                  15

Ala Leu Glu Val Pro Thr Asp Gly Asn Ala Gly Leu Leu Ala Glu Pro
            20                  25                  30

Gln Ile Ala Met Phe Cys Gly Arg Leu Asn Met His Met Asn Val Gln
        35                  40                  45

Asn Gly Lys Trp Asp Ser Asp Pro Ser Gly Thr Lys Thr Cys Ile Asp
    50                  55                  60

Thr Lys Glu Gly Ile Leu Gln Tyr Cys Gln Glu Val Tyr Pro Glu Leu
65                  70                  75                  80

Gln Ile Thr Asn Val Val Glu Ala Asn Gln Pro Val Thr Ile Gln Asn
                85                  90                  95

Trp Cys Lys Arg Gly Arg Lys Gln Cys Lys Thr His Pro His Phe Val
            100                 105                 110

Ile Pro Tyr Arg Cys Leu Val Gly Glu Phe Val Ser Asp Ala Leu Leu
        115                 120                 125

Val Pro Asp Lys Cys Lys Phe Leu His Gln Glu Arg Met Asp Val Cys
    130                 135                 140

Glu Thr His Leu His Trp His Thr Val Ala Lys Glu Thr Cys Ser Glu
145                 150                 155                 160

Lys Ser Thr Asn Leu His Asp Tyr Gly Met Leu Leu Pro Cys Gly Ile
                165                 170                 175

Asp Lys Phe Arg Gly Val Glu Phe Val Cys Cys Pro Leu Ala Glu Glu
            180                 185                 190

Ser Asp Asn Val Asp Ser Ala Asp Ala Glu Glu Asp Asp Ser Asp Val
        195                 200                 205

Trp Trp Gly Gly Ala Asp Thr Asp Tyr Ala Asp Gly Ser Glu Asp Lys
    210                 215                 220

Val Val Glu Val Ala Glu Glu Glu Val Ala Glu Val Glu Glu Glu Glu
225                 230                 235                 240

Glu Ala Asp Asp Asp Glu Asp Asp Glu Asp Gly Asp Glu Val Glu Glu
                245                 250                 255

Glu Ala Glu Glu Pro Tyr Glu Glu Ala Thr Glu Arg Thr Thr Ser Ile
            260                 265                 270

Ala Thr Thr Thr Thr Thr Thr Thr Glu Ser Val Glu Glu Val Val Arg
        275                 280                 285

Glu Val Cys Ser Glu Gln Ala Glu Thr Gly Pro Cys Arg Ala Met Ile
    290                 295                 300

Ser Arg Trp Tyr Phe Asp Val Thr Glu Gly Lys Cys Ala Pro Phe Phe

-continued

```
           305                 310                 315                 320
     Tyr Gly Gly Cys Gly Gly Asn Arg Asn Asn Phe Asp Thr Glu Glu Tyr
                     325                 330                 335

Cys Met Ala Val Cys Gly Ser Ala Ile Pro Thr Thr Ala Ala Ser Thr
                     340                 345                 350

Pro Asp Ala Val Asp Lys Tyr Leu Glu Thr Pro Gly Asp Glu Asn Glu
                     355                 360                 365

His Ala His Phe Gln Lys Ala Lys Glu Arg Leu Glu Ala Lys His Arg
                     370                 375                 380

Glu Arg Met Ser Gln Val Met Arg Glu Trp Glu Glu Ala Glu Arg Gln
     385                 390                 395                 400

Ala Lys Asn Leu Pro Lys Ala Asp Lys Lys Ala Val Ile Gln His Phe
                     405                 410                 415

Gln Glu Lys Val Glu Ser Leu Glu Gln Glu Ala Ala Asn Glu Arg Gln
                     420                 425                 430

Gln Leu Val Glu Thr His Met Ala Arg Val Glu Ala Met Leu Asn Asp
                     435                 440                 445

Arg Arg Arg Leu Ala Leu Glu Asn Tyr Ile Thr Ala Leu Gln Ala Val
     450                 455                 460

Pro Pro Arg Pro Arg His Val Phe Asn Met Leu Lys Lys Tyr Val Arg
     465                 470                 475                 480

Ala Glu Gln Lys Asp Arg Gln His Thr Leu Lys His Phe Glu His Val
                     485                 490                 495

Arg Met Val Asp Pro Lys Lys Ala Ala Gln Ile Arg Ser Gln Val Met
                     500                 505                 510

Thr His Leu Arg Val Ile Tyr Glu Arg Met Asn Gln Ser Leu Ser Leu
                     515                 520                 525

Leu Tyr Asn Val Pro Ala Val Ala Glu Glu Ile Gln Asp Glu Val Asp
                     530                 535                 540

Glu Leu Leu Gln Lys Glu Gln Asn Tyr Ser Asp Asp Val Leu Ala Asn
     545                 550                 555                 560

Met Ile Ser Glu Pro Arg Ile Ser Tyr Gly Asn Asp Ala Leu Met Pro
                     565                 570                 575

Ser Leu Thr Glu Thr Lys Thr Thr Val Glu Leu Leu Pro Val Asn Gly
                     580                 585                 590

Glu Phe Ser Leu Asp Asp Leu Gln Pro Trp His Ser Phe Gly Ala Asp
                     595                 600                 605

Ser Val Pro Ala Asn Thr Glu Asn Glu Val Glu Pro Val Asp Ala Arg
                     610                 615                 620

Pro Ala Ala Asp Arg Gly Leu Thr Thr Arg Pro Gly Ser Gly Leu Thr
     625                 630                 635                 640

Asn Ile Lys Thr Glu Glu Ile Ser Glu Val Lys Met Asp Ala Glu Phe
                     645                 650                 655

Arg His Asp Ser Gly Tyr Glu Val His His Gln Lys Leu Val Phe Phe
                     660                 665                 670

Ala Glu Asp Val Gly Ser Asn Lys Gly Ala Ile Ile Gly Leu Met Val
                     675                 680                 685

Gly Gly Val Val Ile Ala Thr Val Ile Val Ile Thr Leu Val Met Leu
                     690                 695                 700

Lys Lys Lys Gln Tyr Thr Ser Ile His His Gly Val Val Glu Val Asp
     705                 710                 715                 720

Ala Ala Val Thr Pro Glu Glu Arg His Leu Ser Lys Met Gln Gln Asn
                     725                 730                 735
```

-continued

```
Gly Tyr Glu Asn Pro Thr Tyr Lys Phe Phe Glu Gln Met Gln Asn
            740                 745                 750

<210> SEQ ID NO 75
<211> LENGTH: 770
<212> TYPE: PRT
<213> ORGANISM: Homo sapiens

<400> SEQUENCE: 75

Met Leu Pro Gly Leu Ala Leu Leu Leu Ala Ala Trp Thr Ala Arg
1               5                   10                  15

Ala Leu Glu Val Pro Thr Asp Gly Asn Ala Gly Leu Leu Ala Glu Pro
            20                  25                  30

Gln Ile Ala Met Phe Cys Gly Arg Leu Asn Met His Met Asn Val Gln
            35                  40                  45

Asn Gly Lys Trp Asp Ser Asp Pro Ser Gly Thr Lys Thr Cys Ile Asp
        50                  55                  60

Thr Lys Glu Gly Ile Leu Gln Tyr Cys Gln Glu Val Tyr Pro Glu Leu
65                  70                  75                  80

Gln Ile Thr Asn Val Val Glu Ala Asn Gln Pro Val Thr Ile Gln Asn
                85                  90                  95

Trp Cys Lys Arg Gly Arg Lys Gln Cys Lys Thr His Pro His Phe Val
            100                 105                 110

Ile Pro Tyr Arg Cys Leu Val Gly Glu Phe Val Ser Asp Ala Leu Leu
            115                 120                 125

Val Pro Asp Lys Cys Lys Phe Leu His Gln Glu Arg Met Asp Val Cys
            130                 135                 140

Glu Thr His Leu His Trp His Thr Val Ala Lys Glu Thr Cys Ser Glu
145                 150                 155                 160

Lys Ser Thr Asn Leu His Asp Tyr Gly Met Leu Leu Pro Cys Gly Ile
                165                 170                 175

Asp Lys Phe Arg Gly Val Glu Phe Val Cys Cys Pro Leu Ala Glu Glu
            180                 185                 190

Ser Asp Asn Val Asp Ser Ala Asp Ala Glu Glu Asp Asp Ser Asp Val
            195                 200                 205

Trp Trp Gly Gly Ala Asp Thr Asp Tyr Ala Asp Gly Ser Glu Asp Lys
        210                 215                 220

Val Val Glu Val Ala Glu Glu Glu Val Ala Glu Val Glu Glu Glu
225                 230                 235                 240

Glu Ala Asp Asp Asp Glu Asp Asp Glu Asp Gly Asp Glu Val Glu Glu
            245                 250                 255

Glu Ala Glu Glu Pro Tyr Glu Glu Ala Thr Glu Arg Thr Thr Ser Ile
            260                 265                 270

Ala Thr Thr Thr Thr Thr Thr Glu Ser Val Glu Glu Val Val Arg
            275                 280                 285

Glu Val Cys Ser Glu Gln Ala Glu Thr Gly Pro Cys Arg Ala Met Ile
            290                 295                 300

Ser Arg Trp Tyr Phe Asp Val Thr Glu Gly Lys Cys Ala Pro Phe Phe
305                 310                 315                 320

Tyr Gly Gly Cys Gly Gly Asn Arg Asn Asn Phe Asp Thr Glu Glu Tyr
            325                 330                 335

Cys Met Ala Val Cys Gly Ser Ala Met Ser Gln Ser Leu Leu Lys Thr
            340                 345                 350

Thr Gln Glu Pro Leu Ala Arg Asp Pro Val Lys Leu Pro Thr Thr Ala
```

-continued

```
              355                 360                 365
Ala Ser Thr Pro Asp Ala Val Asp Lys Tyr Leu Glu Thr Pro Gly Asp
    370                 375                 380
Glu Asn Glu His Ala His Phe Gln Lys Ala Lys Glu Arg Leu Glu Ala
385                 390                 395                 400
Lys His Arg Glu Arg Met Ser Gln Val Met Arg Glu Trp Glu Ala
                405                 410                 415
Glu Arg Gln Ala Lys Asn Leu Pro Lys Ala Asp Lys Lys Ala Val Ile
            420                 425                 430
Gln His Phe Gln Glu Lys Val Glu Ser Leu Glu Gln Glu Ala Ala Asn
        435                 440                 445
Glu Arg Gln Gln Leu Val Glu Thr His Met Ala Arg Val Glu Ala Met
    450                 455                 460
Leu Asn Asp Arg Arg Arg Leu Ala Leu Glu Asn Tyr Ile Thr Ala Leu
465                 470                 475                 480
Gln Ala Val Pro Pro Arg Pro Arg His Val Phe Asn Met Leu Lys Lys
                485                 490                 495
Tyr Val Arg Ala Glu Gln Lys Asp Arg Gln His Thr Leu Lys His Phe
            500                 505                 510
Glu His Val Arg Met Val Asp Pro Lys Lys Ala Ala Gln Ile Arg Ser
        515                 520                 525
Gln Val Met Thr His Leu Arg Val Ile Tyr Glu Arg Met Asn Gln Ser
    530                 535                 540
Leu Ser Leu Leu Tyr Asn Val Pro Ala Val Ala Glu Glu Ile Gln Asp
545                 550                 555                 560
Glu Val Asp Glu Leu Leu Gln Lys Glu Gln Asn Tyr Ser Asp Asp Val
                565                 570                 575
Leu Ala Asn Met Ile Ser Glu Pro Arg Ile Ser Tyr Gly Asn Asp Ala
            580                 585                 590
Leu Met Pro Ser Leu Thr Glu Thr Lys Thr Thr Val Glu Leu Leu Pro
        595                 600                 605
Val Asn Gly Glu Phe Ser Leu Asp Asp Leu Gln Pro Trp His Ser Phe
    610                 615                 620
Gly Ala Asp Ser Val Pro Ala Asn Thr Glu Asn Glu Val Glu Pro Val
625                 630                 635                 640
Asp Ala Arg Pro Ala Ala Asp Arg Gly Leu Thr Thr Arg Pro Gly Ser
                645                 650                 655
Gly Leu Thr Asn Ile Lys Thr Glu Glu Ile Ser Glu Val Lys Met Asp
            660                 665                 670
Ala Glu Phe Arg His Asp Ser Gly Tyr Glu Val His His Gln Lys Leu
        675                 680                 685
Val Phe Phe Ala Glu Asp Val Gly Ser Asn Lys Gly Ala Ile Ile Gly
    690                 695                 700
Leu Met Val Gly Gly Val Val Ile Ala Thr Val Ile Val Ile Thr Leu
705                 710                 715                 720
Val Met Leu Lys Lys Lys Gln Tyr Thr Ser Ile His His Gly Val Val
                725                 730                 735
Glu Val Asp Ala Ala Val Thr Pro Glu Glu Arg His Leu Ser Lys Met
            740                 745                 750
```

```
Gln Gln Asn Gly Tyr Glu Asn Pro Thr Tyr Lys Phe Phe Glu Gln Met
        755                 760             765
Gln Asn
    770
```